US012559540B2

(12) United States Patent
Hla et al.

(10) Patent No.: US 12,559,540 B2
(45) Date of Patent: *Feb. 24, 2026

(54) APOM-FC FUSION PROTEINS AND USES THEREOF

(71) Applicant: Children's Medical Center Corporation, Boston, MA (US)

(72) Inventors: Timothy T. Hla, Wellesley, MA (US); Steven L. Swendeman, Cambridge, MA (US); Lois Smith, West Newton, MA (US)

(73) Assignee: Children's Medical Center Corporation, Boston, MA (US)

( * ) Notice: Subject to any disclaimer, the term of this patent is extended or adjusted under 35 U.S.C. 154(b) by 367 days.

This patent is subject to a terminal disclaimer.

(21) Appl. No.: 16/639,445

(22) PCT Filed: Aug. 15, 2018

(86) PCT No.: PCT/US2018/000202
§ 371 (c)(1),
(2) Date: Feb. 14, 2020

(87) PCT Pub. No.: WO2019/035931
PCT Pub. Date: Feb. 21, 2019

(65) Prior Publication Data
US 2021/0032310 A1 Feb. 4, 2021

Related U.S. Application Data

(60) Provisional application No. 62/545,629, filed on Aug. 15, 2017.

(51) Int. Cl.
| | |
|---|---|
| C07K 14/775 | (2006.01) |
| A61K 31/713 | (2006.01) |
| A61P 19/02 | (2006.01) |
| A61P 35/04 | (2006.01) |
| C12N 5/10 | (2006.01) |
| C12N 15/62 | (2006.01) |

(52) U.S. Cl.
CPC .......... *C07K 14/775* (2013.01); *A61K 31/713* (2013.01); *A61P 19/02* (2018.01); *A61P 35/04* (2018.01); *C12N 5/10* (2013.01); *C12N 15/62* (2013.01); *C07K 2319/02* (2013.01); *C07K 2319/30* (2013.01)

(58) Field of Classification Search
None
See application file for complete search history.

(56) References Cited

U.S. PATENT DOCUMENTS

| | | |
|---|---|---|
| 10,870,689 B2 | 12/2020 | Hla et al. |
| 2011/0178029 A1 | 7/2011 | Knudsen et al. |
| 2013/0195849 A1 | 8/2013 | Von Spreter et al. |
| 2013/0324701 A1 | 12/2013 | Williams et al. |
| 2014/0303086 A1 | 10/2014 | Hla et al. |
| 2016/0184458 A1 | 6/2016 | Heartlein |
| 2017/0360749 A1 | 12/2017 | Harijith et al. |
| 2019/0185545 A1 | 6/2019 | Hla et al. |
| 2021/0380665 A1 | 12/2021 | Hla et al. |

FOREIGN PATENT DOCUMENTS

| | | |
|---|---|---|
| CN | 1556409 A | 12/2004 |
| CN | 101557817 A | 10/2009 |
| CN | 102858985 A | 1/2013 |
| CN | 105175553 A | 12/2015 |
| JP | 2020-531010 A | 11/2020 |
| WO | WO 2006/000448 A2 | 1/2006 |
| WO | WO 2010/049103 A1 | 5/2010 |
| WO | WO 2012/162392 A1 | 11/2012 |
| WO | WO 2017/031353 A1 | 2/2017 |
| WO | WO 2018/052615 A1 | 3/2018 |
| WO | WO 2019/035931 A1 | 2/2019 |

OTHER PUBLICATIONS

UniProt Database, Accession No. P01857, 20 pages (first available 1986) (Year: 1986).*
NCBI Protein Blast Sequence Comparison, 1 page (performed on Apr. 8, 2022) (Year: 2022).*
"Artificial", Cambridge English Dictionary, available online at https://dictionary.cambridge.org/us/dictionary/english/artificial, 7 pages (accessed on Dec. 19, 2022) (Year: 2022).*
Chen et al., Proc. Natl. Acad. Sci. 106:21783-21788 (2009) (Year: 2009).*
Sioud et al., Molec. Ther. Methods Clin. Development 2:1-10 (2015) (Year: 2015).*
Burg et al., Sphingosine 1-Phosphate Receptor 1 Signaling Maintains Endothelial Cell Barrier Function and Protects Against Immune Complex-Induced Vascular Injury. Arthritis Rheumatol. Nov. 2018;70(11):1879-1889.
Christoffersen et al., Endothelium-protective sphingosine-1-phosphate provided by HDL-associated apolipoprotein M. Proc Natl Acad Sci U S A. Jun. 7, 2011;108(23):9613-8.
Kaplan et al., Trail (Apo2 ligand) and Tweak (Apo3 ligand) mediate CD4+ T cell killing of antigen-presenting macrophages. J Immunol. Mar. 15, 2000;164(6):2897-904.
Snoek et al., Sphingolipids in Congenital Diaphragmatic Hernia; Results from an International Multicenter Study. PLoS One. May 9, 2016;11(5).

(Continued)

*Primary Examiner* — Thea D' Ambrosio
(74) *Attorney, Agent, or Firm* — Wolf, Greenfield & Sacks, P.C.

(57) ABSTRACT

Provided herein are engineered fusion proteins comprising ApoM (e.g., human or murine ApoM) fused to a constant region (Fc) of a immunoglobulin G (IgG, e.g., human IgG or murine IgG). In some embodiments, the ApoM-Fc fusion protein further comprises a signal peptide (e.g., IL-2 signal peptide) fused to the ApoM, allowing the fusion protein to be secreted once expressed recombinantly. Methods of using the ApoM-Fc fusion protein or the sponge variants in the treatment of various diseases or disorders are provided.

8 Claims, 6 Drawing Sheets

Specification includes a Sequence Listing.

(56) References Cited

OTHER PUBLICATIONS

Swendemen et al., An engineered S1P chaperone attenuates hypertension and ischemic injury. Sci Signal. Aug. 15, 2017;10(492).

Wang et al., Immunoglobulin Fc domain fusion to Trail significantly prolongs its plasma half-life and enhances its antitumor activity. Mol Cancer Ther. Mar. 2014;13(3):643-50.

Wu et al., Pharmacokinetics of Peptide-Fc fusion proteins. J Pharm Sci. Jan. 2014;103(1):53-64. doi: 10.1002/jps.23783. Epub Nov. 27, 2013.

Yu et al., Immunoglobulin Fc domain fusion to apolipoprotein (a) kringle V significantly prolongs plasma half-life without affecting its anti-angiogenic activity. Protein Eng Des Sel. Jun. 2013;26(6):425-32.

Zauner et al., Glycoproteomic analysis of antibodies. Mol Cell Proteomics. Apr. 2013;12 (4):856-65.

[No Author Listed] GenBank Accession No. NP_061974.2. Apolipoprotein M Isoform 1. *Homo sapiens*. Accessed on Mar. 25, 2022. 3 pages.

[No Author Listed] GenBank Accession No. NP_061286.1. Apolipoprotein M Precursor. *Mus musculus*. Accessed on Mar. 25, 2022. 3 pages.

Burg et al., Sphingosine-1 Phosphate Receptor-1-Mediated Endothelial Cell Barrier Function Protects Against Immune Complex-Induced Vascular Injury: A Potential Novel Therapeutic Target for SLE. Abstract 1790. 2017 ACR/ARHP Annual Meeting. Sep. 18, 2017.

Christoffersen et al., The signal peptide anchors apolipoprotein M in plasma lipoproteins and prevents rapid clearance of apolipoprotein M from plasma. J Biol Chem. Jul. 4, 2008;283(27):18765-72.

Andersson-Sjoland et al., ROS-induced endothelial stress contributes to pulmonary fibrosis through pericytes and Wnt signaling. Lab Invest. Feb. 2016;96(2):206-17. doi: 10.1038/labinvest.2015.100. Epub Sep. 14, 2015.

Green et al., The role of the endothelium in asthma and chronic obstructive pulmonary disease (COPD). Respir Res. Jan. 18, 2017;18(1):20. doi:10.1186/s12931-017-0505-1.

Zhaorigetu et al., Perturbations in Endothelial Dysfunction-Associated Pathways in the Nitrofen-Induced Congenital Diaphragmatic Hernia Model. J Vasc Res. 2018;55(1):26-34. doi: 10.1159/000484087. Epub Dec. 8, 2017.

Zhaorigetu et al., Perturbations in Endothelial Dysfunction-Associated Pathways in the Nitrofen-Induced Congenital Diaphragmatic Hernia Model. J Vasc Res. 2018;55(1):26-34. doi: 10.1159/000484087. Epub Dec. 8, 2017. Abstract Only.

Chen et al., The sphingosine kinase 1/sphingosine-1-phosphate pathway in pulmonary arterial hypertension. Am J Respir Crit Care Med. Nov. 1, 2014;190(9):1032-43. doi: 10.1164/rccm.201401-0121OC.

Gorshkova et al., Inhibition of serine palmitoyltransferase delays the onset of radiation-induced pulmonary fibrosis through the negative regulation of sphingosine kinase-1 expression. J Lipid Res. Aug. 2012;53(8):1553-68. doi: 10.1194/jlr.M026039. Epub May 21, 2012.

Harijith et al., Sphingosine kinase 1 deficiency confers protection against hyperoxia-induced bronchopulmonary dysplasia in a murine model: role of S1P signaling and Nox proteins. Am J Pathol. Oct. 2013;183(4):1169-1182. doi: 10.1016/j.ajpath.2013.06.018. Epub Aug. 8, 2013.

[No Author Listed], Conditions and Diseases: Bronchopulmonary Dysplasia from Johns Hopkins Medicine [online]. Accessed Jul. 12, 2024. www.hopkinsmedicine.org/health/conditions-and-diseases/bronchopulmonary-dysplasia. 7 pages.

[No Author Listed], Conditions and Diseases: Congenital Diaphragmatic Hernia (CDH) from Johns Hopkins Medicine [online]. Accessed Jul. 12, 2024. www.hopkinsmedicine.org/health/conditions-and-diseases/congenital-diaphragmatic-hernia. 14 pages.

Kho et al., Identification of dedifferentiation and redevelopment phases during postpneumonectomy lung growth. Am J Physiol Lung Cell Mol Physiol. Oct. 15, 2013;305(8):L542-54. doi: 10.1152/ajplung.00403.2012. Epub Aug. 30, 2013.

Notice of Allowance for U.S. Appl. No. 17/284,299 mailed May 20, 2025 and allowed claims as of May 20, 2025.

* cited by examiner

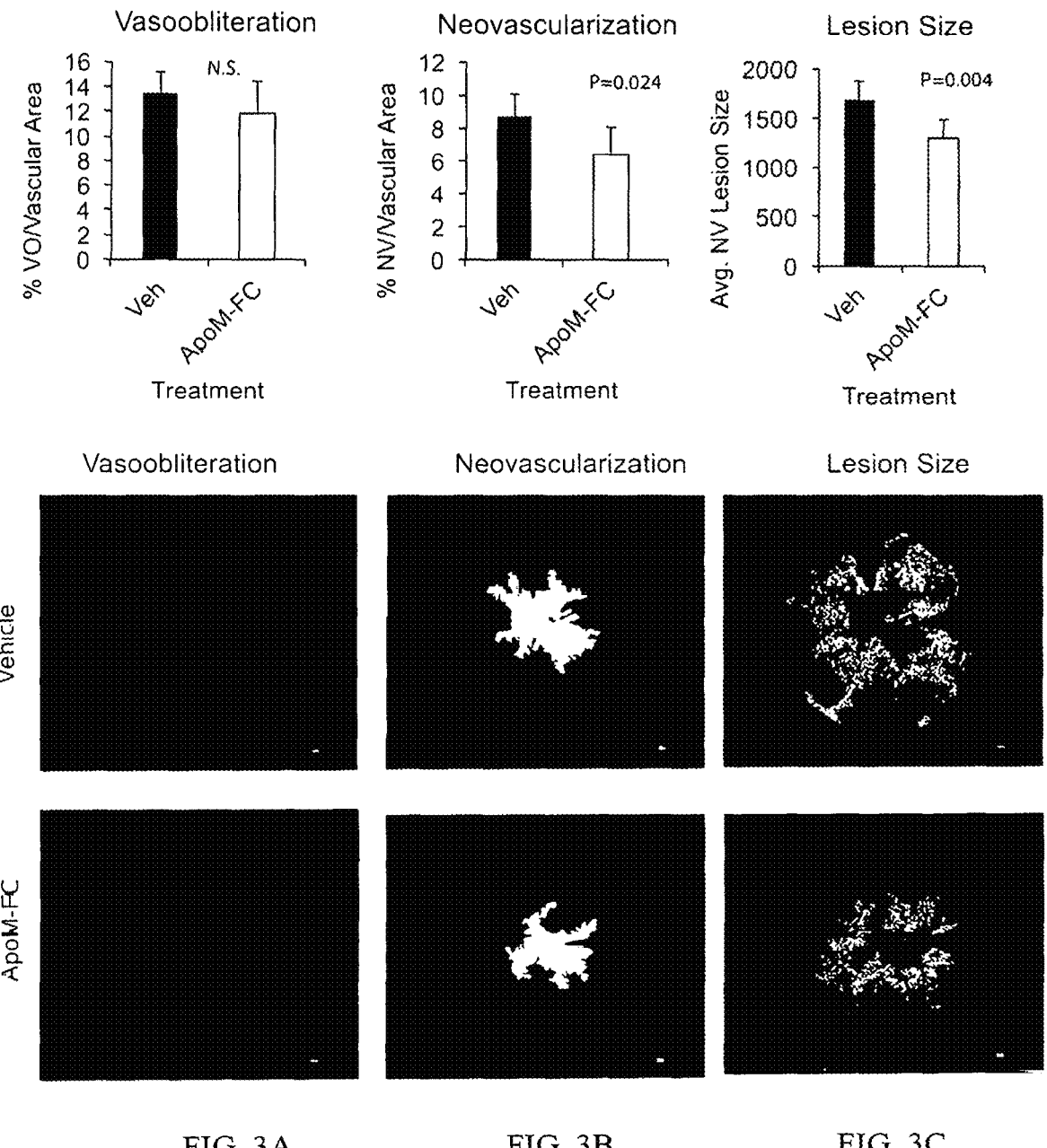
FIG. 3A                    FIG. 3B                    FIG. 3C

SEQUENCE LISTING

```
<160> NUMBER OF SEQ ID NOS: 93

<210> SEQ ID NO 1
<211> LENGTH: 523
<212> TYPE: PRT
<213> ORGANISM: Artificial Sequence
<220> FEATURE:
<223> OTHER INFORMATION: Synthetic polypeptide

<400> SEQUENCE: 1

Met Tyr Arg Met Gln Leu Leu Ser Cys Ile Ala Leu Ser Leu Ala Leu
1               5                   10                  15

Val Thr Asn Ser Ile Ser Arg Val Tyr Gln Cys Pro Glu His Ser Gln
            20                  25                  30

Leu Thr Thr Leu Gly Val Asp Gly Lys Glu Phe Pro Glu Val His Leu
        35                  40                  45

Gly Gln Trp Tyr Phe Ile Ala Gly Ala Ala Pro Thr Lys Glu Glu Leu
    50                  55                  60

Ala Thr Phe Asp Pro Val Asp Asn Ile Val Phe Asn Met Ala Ala Gly
65                  70                  75                  80

Ser Ala Pro Met Gln Leu His Leu Arg Ala Thr Ile Arg Met Lys Asp
                85                  90                  95

Gly Leu Cys Val Pro Arg Lys Trp Ile Tyr His Leu Thr Glu Gly Ser
            100                 105                 110

Thr Asp Leu Arg Thr Glu Gly Arg Pro Asp Met Lys Thr Glu Leu Phe
        115                 120                 125

Ser Ser Ser Cys Pro Gly Gly Ile Met Leu Asn Glu Thr Gly Gln Gly
    130                 135                 140

Tyr Gln Arg Phe Leu Leu Tyr Asn Arg Ser Pro His Pro Pro Glu Lys
145                 150                 155                 160

Cys Val Glu Glu Phe Lys Ser Leu Thr Ser Cys Leu Asp Ser Lys Ala
                165                 170                 175

Phe Leu Leu Thr Pro Arg Asn Gln Glu Ala Cys Glu Leu Ser Asn Asn
            180                 185                 190

Trp Ala Ser Thr Lys Gly Pro Ser Val Phe Pro Leu Ala Pro Ser Ser
        195                 200                 205

Lys Ser Thr Ser Gly Gly Thr Ala Ala Leu Gly Cys Leu Val Lys Asp
    210                 215                 220

Tyr Phe Pro Glu Pro Val Thr Val Ser Trp Asn Ser Gly Ala Leu Thr
225                 230                 235                 240
```

```
Ser Gly Val His Thr Phe Pro Ala Val Leu Gln Ser Ser Gly Leu Tyr
            245                 250                 255

Ser Leu Ser Ser Val Val Thr Val Pro Ser Ser Ser Leu Gly Thr Gln
            260                 265                 270

Thr Tyr Ile Cys Asn Val Asn His Lys Pro Ser Asn Thr Lys Val Asp
            275                 280                 285

Lys Lys Val Glu Pro Lys Ser Cys Asp Lys Thr His Thr Cys Pro Pro
        290                 295                 300

Cys Pro Ala Pro Glu Leu Leu Gly Gly Pro Ser Val Phe Leu Phe Pro
305                 310                 315                 320

Pro Lys Pro Lys Asp Thr Leu Met Ile Ser Arg Thr Pro Glu Val Thr
                325                 330                 335

Cys Val Val Val Asp Val Ser His Glu Asp Pro Glu Val Lys Phe Asn
            340                 345                 350

Trp Tyr Val Asp Gly Val Glu Val His Asn Ala Lys Thr Lys Pro Arg
            355                 360                 365

Glu Glu Gln Tyr Asn Ser Thr Tyr Arg Val Val Ser Val Leu Thr Val
        370                 375                 380

Leu His Gln Asp Trp Leu Asn Gly Lys Glu Tyr Lys Cys Lys Val Ser
385                 390                 395                 400

Asn Lys Ala Leu Pro Ala Pro Ile Glu Lys Thr Ile Ser Lys Ala Lys
                405                 410                 415

Gly Gln Pro Arg Glu Pro Gln Val Tyr Thr Leu Pro Pro Ser Arg Glu
                420                 425                 430

Glu Met Thr Lys Asn Gln Val Ser Leu Thr Cys Leu Val Lys Gly Phe
            435                 440                 445

Tyr Pro Ser Asp Ile Ala Val Glu Trp Glu Ser Asn Gly Gln Pro Glu
        450                 455                 460

Asn Asn Tyr Lys Thr Thr Pro Pro Val Leu Asp Ser Asp Gly Ser Phe
465                 470                 475                 480

Phe Leu Tyr Ser Lys Leu Thr Val Asp Lys Ser Arg Trp Gln Gln Gly
                485                 490                 495

Asn Val Phe Ser Cys Ser Val Met His Glu Ala Leu His Asn His Tyr
            500                 505                 510

Thr Gln Lys Ser Leu Ser Leu Ser Pro Gly Lys
        515                 520
```

```
<210> SEQ ID NO 2
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 2
```

```
Met Tyr Arg Met Gln Leu Leu Ser Cys Ile Ala Leu Ser Leu Ala Leu
1               5                   10                  15

Val Thr Asn Ser Asn Gln Cys Pro Glu His Ser Gln Leu Thr Ala Leu
            20                  25                  30

Gly Met Asp Asp Thr Glu Thr Pro Glu Pro His Leu Gly Leu Trp Tyr
            35                  40                  45

Phe Ile Ala Gly Ala Ala Pro Thr Thr Glu Glu Leu Ala Thr Phe Asp
        50                  55                  60

Pro Val Asp Asn Ile Val Phe Asn Met Ala Ala Gly Ser Ala Pro Arg
65                  70                  75                  80
```

-continued

```
Gln Leu Gln Leu Arg Ala Thr Ile Arg Thr Lys Ser Gly Val Cys Val
            85                  90                  95

Pro Arg Lys Trp Thr Tyr Arg Leu Thr Glu Gly Lys Gly Asn Met Glu
            100                 105                 110

Leu Arg Thr Glu Gly Arg Pro Asp Met Lys Thr Asp Leu Phe Ser Ser
            115                 120                 125

Ser Cys Pro Gly Gly Ile Met Leu Lys Glu Thr Gly Gln Gly Tyr Gln
    130                 135                 140

Arg Phe Leu Leu Tyr Asn Arg Ser Pro His Pro Pro Glu Lys Cys Val
145                 150                 155                 160

Glu Glu Phe Lys Ser Leu Thr Ser Cys Leu Asp Phe Lys Ala Phe Leu
                165                 170                 175

Val Thr Pro Arg Asn Gln Glu Ala Cys Pro Leu Ser Ser Lys Trp Ile
                180                 185                 190

Ser Ser Ala Ser Ser Ala Lys Thr Thr Pro Pro Ser Val Tyr Pro Leu
            195                 200                 205

Ala Pro Gly Ser Ala Ala Gln Thr Asn Ser Met Val Thr Leu Gly Cys
    210                 215                 220

Leu Val Lys Gly Tyr Phe Pro Glu Pro Val Thr Val Thr Trp Asn Ser
225                 230                 235                 240

Gly Ser Leu Ser Ser Gly Val His Thr Phe Pro Ala Val Leu Gln Ser
                245                 250                 255

Asp Leu Tyr Thr Leu Ser Ser Ser Val Thr Val Pro Ser Ser Thr Trp
            260                 265                 270

Pro Ser Glu Thr Val Thr Cys Asn Val Ala His Pro Ala Ser Ser Thr
            275                 280                 285

Lys Val Asp Lys Lys Ile Val Pro Arg Asp Cys Gly Cys Lys Pro Cys
    290                 295                 300

Ile Cys Thr Val Pro Glu Val Ser Ser Val Phe Ile Phe Pro Pro Lys
305                 310                 315                 320

Pro Lys Asp Val Leu Thr Ile Thr Leu Thr Pro Lys Val Thr Cys Val
                325                 330                 335

Val Val Asp Ile Ser Lys Asp Asp Pro Glu Val Gln Phe Ser Trp Phe
            340                 345                 350

Val Asp Asp Val Glu Val His Thr Ala Gln Thr Gln Pro Arg Glu Glu
            355                 360                 365

Gln Phe Asn Ser Thr Phe Arg Ser Val Ser Glu Leu Pro Ile Met His
    370                 375                 380

Gln Asp Trp Leu Asn Gly Lys Glu Phe Lys Cys Arg Val Asn Ser Ala
385                 390                 395                 400

Ala Phe Pro Ala Pro Ile Glu Lys Thr Ile Ser Lys Thr Lys Gly Arg
                405                 410                 415

Pro Lys Ala Pro Gln Val Tyr Thr Ile Pro Pro Pro Lys Glu Gln Met
            420                 425                 430

Ala Lys Asp Lys Val Ser Leu Thr Cys Met Ile Thr Asp Phe Phe Pro
            435                 440                 445

Glu Asp Ile Thr Val Glu Trp Gln Trp Asn Gly Gln Pro Ala Glu Asn
    450                 455                 460

Tyr Lys Asn Thr Gln Pro Ile Met Asp Thr Asp Gly Ser Tyr Phe Val
465                 470                 475                 480

Tyr Ser Lys Leu Asn Val Gln Lys Ser Asn Trp Glu Ala Gly Asn Thr
                485                 490                 495
```

-continued

```
Phe Thr Cys Ser Val Leu His Glu Gly Leu His Asn His His Thr Glu
            500                 505                 510

Lys Ser Leu Ser His Ser Pro Gly Lys
        515                 520

<210> SEQ ID NO 3
<211> LENGTH: 523
<212> TYPE: PRT
<213> ORGANISM: Artificial Sequence
<220> FEATURE:
<223> OTHER INFORMATION: Synthetic polypeptide

<400> SEQUENCE: 3

Met Tyr Arg Met Gln Leu Leu Ser Cys Ile Ala Leu Ser Leu Ala Leu
1               5                   10                  15

Val Thr Asn Ser Ile Ser Arg Val Tyr Gln Cys Pro Glu His Ser Gln
            20                  25                  30

Leu Thr Thr Leu Gly Val Asp Gly Lys Glu Phe Pro Glu Val His Leu
        35                  40                  45

Gly Gln Trp Tyr Phe Ile Ala Gly Ala Ala Pro Thr Lys Glu Glu Leu
    50                  55                  60

Ala Thr Phe Asp Pro Val Asp Asn Ile Val Phe Asn Met Ala Ala Gly
65                  70                  75                  80

Ser Ala Pro Met Gln Leu His Leu Arg Ala Thr Ile Arg Met Lys Asp
                85                  90                  95

Gly Leu Cys Val Pro Arg Lys Trp Ile Tyr His Leu Thr Glu Gly Ser
            100                 105                 110

Thr Asp Leu Arg Thr Glu Gly Arg Pro Asp Met Lys Thr Glu Leu Phe
        115                 120                 125

Ser Ser Ser Cys Pro Gly Gly Ile Met Leu Asn Glu Thr Gly Gln Gly
    130                 135                 140

Tyr Gln Arg Phe Leu Leu Tyr Asn Arg Ser Pro His Pro Pro Glu Lys
145                 150                 155                 160

Cys Val Glu Glu Phe Lys Ser Leu Thr Ser Cys Leu Asp Ser Lys Ala
                165                 170                 175

Phe Leu Leu Thr Pro Arg Asn Gln Glu Ala Cys Glu Leu Ser Asn Asn
            180                 185                 190

Trp Ile Ser Ser Ala Ser Ser Ala Lys Thr Thr Pro Pro Ser Val Tyr
        195                 200                 205

Pro Leu Ala Pro Gly Ser Ala Ala Gln Thr Asn Ser Met Val Thr Leu
    210                 215                 220

Gly Cys Leu Val Lys Gly Tyr Phe Pro Glu Pro Val Thr Val Thr Trp
225                 230                 235                 240

Asn Ser Gly Ser Leu Ser Ser Gly Val His Thr Phe Pro Ala Val Leu
                245                 250                 255

Gln Ser Asp Leu Tyr Thr Leu Ser Ser Ser Val Thr Val Pro Ser Ser
            260                 265                 270

Thr Trp Pro Ser Glu Thr Val Thr Cys Asn Val Ala His Pro Ala Ser
        275                 280                 285

Ser Thr Lys Val Asp Lys Lys Ile Val Pro Arg Asp Cys Gly Cys Lys
    290                 295                 300

Pro Cys Ile Cys Thr Val Pro Glu Val Ser Ser Val Phe Ile Phe Pro
305                 310                 315                 320

Pro Lys Pro Lys Asp Val Leu Thr Ile Thr Leu Thr Pro Lys Val Thr
                325                 330                 335
```

-continued

```
Cys Val Val Val Asp Ile Ser Lys Asp Asp Pro Glu Val Gln Phe Ser
            340             345             350

Trp Phe Val Asp Asp Val Glu Val His Thr Ala Gln Thr Gln Pro Arg
            355             360             365

Glu Glu Gln Phe Asn Ser Thr Phe Arg Ser Val Ser Glu Leu Pro Ile
    370             375             380

Met His Gln Asp Trp Leu Asn Gly Lys Glu Phe Lys Cys Arg Val Asn
385             390             395             400

Ser Ala Ala Phe Pro Ala Pro Ile Glu Lys Thr Ile Ser Lys Thr Lys
                405             410             415

Gly Arg Pro Lys Ala Pro Gln Val Tyr Thr Ile Pro Pro Lys Glu
            420             425             430

Gln Met Ala Lys Asp Lys Val Ser Leu Thr Cys Met Ile Thr Asp Phe
            435             440             445

Phe Pro Glu Asp Ile Thr Val Glu Trp Gln Trp Asn Gly Gln Pro Ala
    450             455             460

Glu Asn Tyr Lys Asn Thr Gln Pro Ile Met Asp Thr Asp Gly Ser Tyr
465             470             475             480

Phe Val Tyr Ser Lys Leu Asn Val Gln Lys Ser Asn Trp Glu Ala Gly
            485             490             495

Asn Thr Phe Thr Cys Ser Val Leu His Glu Gly Leu His Asn His His
            500             505             510

Thr Glu Lys Ser Leu Ser His Ser Pro Gly Lys
            515             520
```

```
<210> SEQ ID NO 4
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 4
```

```
Met Tyr Arg Met Gln Leu Leu Ser Cys Ile Ala Leu Ser Leu Ala Leu
1               5               10              15

Val Thr Asn Ser Asn Gln Cys Pro Glu His Ser Gln Leu Thr Ala Leu
            20              25              30

Gly Met Asp Asp Thr Glu Thr Pro Glu Pro His Leu Gly Leu Trp Tyr
            35              40              45

Phe Ile Ala Gly Ala Ala Pro Thr Thr Glu Glu Leu Ala Thr Phe Asp
    50              55              60

Pro Val Asp Asn Ile Val Phe Asn Met Ala Ala Gly Ser Ala Pro Arg
65              70              75              80

Gln Leu Gln Leu Arg Ala Thr Ile Arg Thr Lys Ser Gly Val Cys Val
            85              90              95

Pro Arg Lys Trp Thr Tyr Arg Leu Thr Glu Gly Lys Gly Asn Met Glu
            100             105             110

Leu Arg Thr Glu Gly Arg Pro Asp Met Lys Thr Asp Leu Phe Ser Ser
            115             120             125

Ser Cys Pro Gly Gly Ile Met Leu Lys Glu Thr Gly Gln Gly Tyr Gln
    130             135             140

Arg Phe Leu Leu Tyr Asn Arg Ser Pro His Pro Pro Glu Lys Cys Val
145             150             155             160

Glu Glu Phe Lys Ser Leu Thr Ser Cys Leu Asp Phe Lys Ala Phe Leu
            165             170             175
```

```
Val Thr Pro Arg Asn Gln Glu Ala Cys Pro Leu Ser Ser Lys Trp Ala
            180                 185                 190

Ser Thr Lys Gly Pro Ser Val Phe Pro Leu Ala Pro Ser Ser Lys Ser
            195                 200                 205

Thr Ser Gly Gly Thr Ala Ala Leu Gly Cys Leu Val Lys Asp Tyr Phe
            210                 215                 220

Pro Glu Pro Val Thr Val Ser Trp Asn Ser Gly Ala Leu Thr Ser Gly
225                 230                 235                 240

Val His Thr Phe Pro Ala Val Leu Gln Ser Ser Gly Leu Tyr Ser Leu
                245                 250                 255

Ser Ser Val Val Thr Val Pro Ser Ser Ser Leu Gly Thr Gln Thr Tyr
            260                 265                 270

Ile Cys Asn Val Asn His Lys Pro Ser Asn Thr Lys Val Asp Lys Lys
            275                 280                 285

Val Glu Pro Lys Ser Cys Asp Lys Thr His Thr Cys Pro Pro Cys Pro
            290                 295                 300

Ala Pro Glu Leu Leu Gly Gly Pro Ser Val Phe Leu Phe Pro Pro Lys
305                 310                 315                 320

Pro Lys Asp Thr Leu Met Ile Ser Arg Thr Pro Glu Val Thr Cys Val
                325                 330                 335

Val Val Asp Val Ser His Glu Asp Pro Glu Val Lys Phe Asn Trp Tyr
                340                 345                 350

Val Asp Gly Val Glu Val His Asn Ala Lys Thr Lys Pro Arg Glu Glu
                355                 360                 365

Gln Tyr Asn Ser Thr Tyr Arg Val Val Ser Val Leu Thr Val Leu His
            370                 375                 380

Gln Asp Trp Leu Asn Gly Lys Glu Tyr Lys Cys Lys Val Ser Asn Lys
385                 390                 395                 400

Ala Leu Pro Ala Pro Ile Glu Lys Thr Ile Ser Lys Ala Lys Gly Gln
                405                 410                 415

Pro Arg Glu Pro Gln Val Tyr Thr Leu Pro Pro Ser Arg Glu Glu Met
                420                 425                 430

Thr Lys Asn Gln Val Ser Leu Thr Cys Leu Val Lys Gly Phe Tyr Pro
            435                 440                 445

Ser Asp Ile Ala Val Glu Trp Glu Ser Asn Gly Gln Pro Glu Asn Asn
            450                 455                 460

Tyr Lys Thr Thr Pro Pro Val Leu Asp Ser Asp Gly Ser Phe Phe Leu
465                 470                 475                 480

Tyr Ser Lys Leu Thr Val Asp Lys Ser Arg Trp Gln Gln Gly Asn Val
                485                 490                 495

Phe Ser Cys Ser Val Met His Glu Ala Leu His Asn His Tyr Thr Gln
                500                 505                 510

Lys Ser Leu Ser Leu Ser Pro Gly Lys
            515                 520
```

<210> SEQ ID NO 5
<211> LENGTH: 168
<212> TYPE: PRT
<213> ORGANISM: Homo sapiens

<400> SEQUENCE: 5

```
Tyr Gln Cys Pro Glu His Ser Gln Leu Thr Thr Leu Gly Val Asp Gly
1               5                   10                  15

Lys Glu Phe Pro Glu Val His Leu Gly Gln Trp Tyr Phe Ile Ala Gly
            20                  25                  30
```

-continued

```
Ala Ala Pro Thr Lys Glu Glu Leu Ala Thr Phe Asp Pro Val Asp Asn
        35              40              45

Ile Val Phe Asn Met Ala Ala Gly Ser Ala Pro Met Gln Leu His Leu
    50              55              60

Arg Ala Thr Ile Arg Met Lys Asp Gly Leu Cys Val Pro Arg Lys Trp
65              70              75              80

Ile Tyr His Leu Thr Glu Gly Ser Thr Asp Leu Arg Thr Glu Gly Arg
            85              90              95

Pro Asp Met Lys Thr Glu Leu Phe Ser Ser Ser Cys Pro Gly Gly Ile
            100             105             110

Met Leu Asn Glu Thr Gly Gln Gly Tyr Gln Arg Phe Leu Leu Tyr Asn
            115             120             125

Arg Ser Pro His Pro Pro Glu Lys Cys Val Glu Glu Phe Lys Ser Leu
    130             135             140

Thr Ser Cys Leu Asp Ser Lys Ala Phe Leu Leu Thr Pro Arg Asn Gln
145             150             155             160

Glu Ala Cys Glu Leu Ser Asn Asn
            165
```

<210> SEQ ID NO 6
<211> LENGTH: 170
<212> TYPE: PRT
<213> ORGANISM: Mus musculus

<400> SEQUENCE: 6

```
Asn Gln Cys Pro Glu His Ser Gln Leu Thr Ala Leu Gly Met Asp Asp
1               5               10              15

Thr Glu Thr Pro Glu Pro His Leu Gly Leu Trp Tyr Phe Ile Ala Gly
            20              25              30

Ala Ala Pro Thr Thr Glu Glu Leu Ala Thr Phe Asp Pro Val Asp Asn
        35              40              45

Ile Val Phe Asn Met Ala Ala Gly Ser Ala Pro Arg Gln Leu Gln Leu
    50              55              60

Arg Ala Thr Ile Arg Thr Lys Ser Gly Val Cys Val Pro Arg Lys Trp
65              70              75              80

Thr Tyr Arg Leu Thr Glu Gly Lys Gly Asn Met Glu Leu Arg Thr Glu
            85              90              95

Gly Arg Pro Asp Met Lys Thr Asp Leu Phe Ser Ser Ser Cys Pro Gly
            100             105             110

Gly Ile Met Leu Lys Glu Thr Gly Gln Gly Tyr Gln Arg Phe Leu Leu
            115             120             125

Tyr Asn Arg Ser Pro His Pro Pro Glu Lys Cys Val Glu Glu Phe Lys
    130             135             140

Ser Leu Thr Ser Cys Leu Asp Phe Lys Ala Phe Leu Val Thr Pro Arg
145             150             155             160

Asn Gln Glu Ala Cys Pro Leu Ser Ser Lys
            165             170
```

<210> SEQ ID NO 7
<211> LENGTH: 331
<212> TYPE: PRT
<213> ORGANISM: Homo sapiens

<400> SEQUENCE: 7

```
Trp Ala Ser Thr Lys Gly Pro Ser Val Phe Pro Leu Ala Pro Ser Ser
1               5               10              15
```

```
Lys Ser Thr Ser Gly Gly Thr Ala Ala Leu Gly Cys Leu Val Lys Asp
        20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
                180                 185                 190

Leu His Gln Asp Trp Leu Asn Gly Lys Glu Tyr Lys Cys Lys Val Ser
            195                 200                 205

Asn Lys Ala Leu Pro Ala Pro Ile Glu Lys Thr Ile Ser Lys Ala Lys
        210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 8
<211> LENGTH: 331
<212> TYPE: PRT
<213> ORGANISM: Mus musculus

<400> SEQUENCE: 8

Trp Ile Ser Ser Ala Ser Ser Ala Lys Thr Thr Pro Pro Ser Val Tyr
1               5                   10                  15

Pro Leu Ala Pro Gly Ser Ala Ala Gln Thr Asn Ser Met Val Thr Leu
        20                  25                  30

Gly Cys Leu Val Lys Gly Tyr Phe Pro Glu Pro Val Thr Val Thr Trp
        35                  40                  45

Asn Ser Gly Ser Leu Ser Ser Gly Val His Thr Phe Pro Ala Val Leu
```

-continued

```
              50                  55                  60

Gln Ser Asp Leu Tyr Thr Leu Ser Ser Ser Val Thr Val Pro Ser Ser
65                  70                  75                  80

Thr Trp Pro Ser Glu Thr Val Thr Cys Asn Val Ala His Pro Ala Ser
                85                  90                  95

Ser Thr Lys Val Asp Lys Lys Ile Val Pro Arg Asp Cys Gly Cys Lys
                100                 105                 110

Pro Cys Ile Cys Thr Val Pro Glu Val Ser Ser Val Phe Ile Phe Pro
                115                 120                 125

Pro Lys Pro Lys Asp Val Leu Thr Ile Thr Leu Thr Pro Lys Val Thr
                130                 135                 140

Cys Val Val Val Asp Ile Ser Lys Asp Asp Pro Glu Val Gln Phe Ser
145                 150                 155                 160

Trp Phe Val Asp Asp Val Glu Val His Thr Ala Gln Thr Gln Pro Arg
                165                 170                 175

Glu Glu Gln Phe Asn Ser Thr Phe Arg Ser Val Ser Glu Leu Pro Ile
                180                 185                 190

Met His Gln Asp Trp Leu Asn Gly Lys Glu Phe Lys Cys Arg Val Asn
                195                 200                 205

Ser Ala Ala Phe Pro Ala Pro Ile Glu Lys Thr Ile Ser Lys Thr Lys
                210                 215                 220

Gly Arg Pro Lys Ala Pro Gln Val Tyr Thr Ile Pro Pro Pro Lys Glu
225                 230                 235                 240

Gln Met Ala Lys Asp Lys Val Ser Leu Thr Cys Met Ile Thr Asp Phe
                245                 250                 255

Phe Pro Glu Asp Ile Thr Val Glu Trp Gln Trp Asn Gly Gln Pro Ala
                260                 265                 270

Glu Asn Tyr Lys Asn Thr Gln Pro Ile Met Asp Thr Asp Gly Ser Tyr
                275                 280                 285

Phe Val Tyr Ser Lys Leu Asn Val Gln Lys Ser Asn Trp Glu Ala Gly
                290                 295                 300

Asn Thr Phe Thr Cys Ser Val Leu His Glu Gly Leu His Asn His His
305                 310                 315                 320

Thr Glu Lys Ser Leu Ser His Ser Pro Gly Lys
                325                 330

<210> SEQ ID NO 9
<211> LENGTH: 168
<212> TYPE: PRT
<213> ORGANISM: Artificial Sequence
<220> FEATURE:
<223> OTHER INFORMATION: Synthetic polypeptide

<400> SEQUENCE: 9

Tyr Gln Cys Pro Glu His Ser Gln Leu Thr Thr Leu Gly Val Asp Gly
1                   5                   10                  15

Lys Glu Phe Pro Glu Val His Leu Gly Gln Trp Tyr Phe Ile Ala Gly
                20                  25                  30

Ala Ala Pro Thr Lys Glu Glu Leu Ala Asn Phe Asp Pro Val Asp Asn
                35                  40                  45

Ile Val Phe Asn Met Ala Ala Gly Ser Ala Pro Met Gln Leu His Leu
                50                  55                  60

Arg Ala Thr Ile Arg Met Lys Asp Gly Leu Cys Val Pro Arg Lys Trp
65                  70                  75                  80

Ile Tyr His Leu Thr Glu Gly Ser Thr Asp Leu Arg Thr Glu Gly Arg
```

-continued

```
                     85              90              95

Pro Asp Met Lys Thr Glu Leu Phe Ser Ser Ser Cys Pro Gly Gly Ile
            100             105             110

Met Leu Asn Glu Thr Gly Gln Gly Tyr Gln Arg Phe Leu Leu Tyr Asn
        115             120             125

Arg Ser Pro His Pro Pro Glu Lys Cys Val Glu Glu Phe Lys Ser Leu
    130             135             140

Thr Ser Cys Leu Asp Ser Lys Ala Phe Leu Leu Thr Pro Arg Asn Gln
145             150             155             160

Glu Ala Cys Glu Leu Ser Asn Asn
            165

<210> SEQ ID NO 10
<211> LENGTH: 168
<212> TYPE: PRT
<213> ORGANISM: Artificial Sequence
<220> FEATURE:
<223> OTHER INFORMATION: Synthetic polypeptide

<400> SEQUENCE: 10

Tyr Gln Cys Pro Glu His Ser Gln Leu Thr Thr Leu Gly Val Asp Gly
1               5               10              15

Lys Glu Phe Pro Glu Val His Leu Gly Gln Trp Tyr Phe Ile Ala Gly
            20              25              30

Ala Ala Pro Thr Lys Glu Glu Leu Ala Thr Phe Asp Pro Lys Asp Asn
        35              40              45

Ile Val Phe Asn Met Ala Ala Gly Ser Ala Pro Met Gln Leu His Leu
    50              55              60

Arg Ala Thr Ile Arg Met Lys Asp Gly Leu Cys Val Pro Arg Lys Trp
65              70              75              80

Ile Tyr His Leu Thr Glu Gly Ser Thr Asp Leu Arg Thr Glu Gly Arg
            85              90              95

Pro Asp Met Lys Thr Glu Leu Phe Ser Ser Ser Cys Pro Gly Gly Ile
            100             105             110

Met Leu Asn Glu Thr Gly Gln Gly Tyr Gln Arg Phe Leu Leu Tyr Asn
        115             120             125

Arg Ser Pro His Pro Pro Glu Lys Cys Val Glu Glu Phe Lys Ser Leu
    130             135             140

Thr Ser Cys Leu Asp Ser Lys Ala Phe Leu Leu Thr Pro Arg Asn Gln
145             150             155             160

Glu Ala Cys Glu Leu Ser Asn Asn
            165

<210> SEQ ID NO 11
<211> LENGTH: 168
<212> TYPE: PRT
<213> ORGANISM: Artificial Sequence
<220> FEATURE:
<223> OTHER INFORMATION: Synthetic polypeptide

<400> SEQUENCE: 11

Tyr Gln Cys Pro Glu His Ser Gln Leu Thr Thr Leu Gly Val Asp Gly
1               5               10              15

Lys Glu Phe Pro Glu Val His Leu Gly Gln Trp Tyr Phe Ile Ala Gly
            20              25              30

Ala Ala Pro Thr Lys Glu Glu Leu Ala Thr Phe Asp Pro Asn Asp Asn
        35              40              45
```

-continued

```
Ile Val Phe Asn Met Ala Ala Gly Ser Ala Pro Met Gln Leu His Leu
    50                  55                  60

Arg Ala Thr Ile Arg Met Lys Asp Gly Leu Cys Val Pro Arg Lys Trp
65                  70                  75                  80

Ile Tyr His Leu Thr Glu Gly Ser Thr Asp Leu Arg Thr Glu Gly Arg
                85                  90                  95

Pro Asp Met Lys Thr Glu Leu Phe Ser Ser Ser Cys Pro Gly Gly Ile
                100                 105                 110

Met Leu Asn Glu Thr Gly Gln Gly Tyr Gln Arg Phe Leu Leu Tyr Asn
                115                 120                 125

Arg Ser Pro His Pro Pro Glu Lys Cys Val Glu Glu Phe Lys Ser Leu
    130                 135                 140

Thr Ser Cys Leu Asp Ser Lys Ala Phe Leu Leu Thr Pro Arg Asn Gln
145                 150                 155                 160

Glu Ala Cys Glu Leu Ser Asn Asn
                165
```

<210> SEQ ID NO 12
<211> LENGTH: 168
<212> TYPE: PRT
<213> ORGANISM: Artificial Sequence
<220> FEATURE:
<223> OTHER INFORMATION: Synthetic polypeptide

<400> SEQUENCE: 12

```
Tyr Gln Cys Pro Glu His Ser Gln Leu Thr Thr Leu Gly Val Asp Gly
1               5                   10                  15

Lys Glu Phe Pro Glu Val His Leu Gly Gln Trp Tyr Phe Ile Ala Gly
                20                  25                  30

Ala Ala Pro Thr Lys Glu Glu Leu Ala Thr Phe Asp Pro Gln Asp Asn
        35                  40                  45

Ile Val Phe Asn Met Ala Ala Gly Ser Ala Pro Met Gln Leu His Leu
    50                  55                  60

Arg Ala Thr Ile Arg Met Lys Asp Gly Leu Cys Val Pro Arg Lys Trp
65                  70                  75                  80

Ile Tyr His Leu Thr Glu Gly Ser Thr Asp Leu Arg Thr Glu Gly Arg
                85                  90                  95

Pro Asp Met Lys Thr Glu Leu Phe Ser Ser Ser Cys Pro Gly Gly Ile
                100                 105                 110

Met Leu Asn Glu Thr Gly Gln Gly Tyr Gln Arg Phe Leu Leu Tyr Asn
                115                 120                 125

Arg Ser Pro His Pro Pro Glu Lys Cys Val Glu Glu Phe Lys Ser Leu
    130                 135                 140

Thr Ser Cys Leu Asp Ser Lys Ala Phe Leu Leu Thr Pro Arg Asn Gln
145                 150                 155                 160

Glu Ala Cys Glu Leu Ser Asn Asn
                165
```

<210> SEQ ID NO 13
<211> LENGTH: 168
<212> TYPE: PRT
<213> ORGANISM: Artificial Sequence
<220> FEATURE:
<223> OTHER INFORMATION: Synthetic polypeptide

<400> SEQUENCE: 13

```
Tyr Gln Cys Pro Glu His Ser Gln Leu Thr Thr Leu Gly Val Asp Gly
1               5                   10                  15
```

-continued

```
Lys Glu Phe Pro Glu Val His Leu Gly Gln Trp Tyr Phe Ile Ala Gly
          20                  25                  30

Ala Ala Pro Thr Lys Glu Glu Leu Ala Thr Phe Asp Pro Val Asp Asn
          35                  40                  45

Ile Val Phe Asn Met Ala Ala Gly Ser Ala Pro Met Gln Leu His Leu
      50                  55                  60

Arg Ala Thr Lys Arg Met Lys Asp Gly Leu Cys Val Pro Arg Lys Trp
65                  70                  75                  80

Ile Tyr His Leu Thr Glu Gly Ser Thr Asp Leu Arg Thr Glu Gly Arg
              85                  90                  95

Pro Asp Met Lys Thr Glu Leu Phe Ser Ser Ser Cys Pro Gly Gly Ile
          100                 105                 110

Met Leu Asn Glu Thr Gly Gln Gly Tyr Gln Arg Phe Leu Leu Tyr Asn
          115                 120                 125

Arg Ser Pro His Pro Pro Glu Lys Cys Val Glu Glu Phe Lys Ser Leu
      130                 135                 140

Thr Ser Cys Leu Asp Ser Lys Ala Phe Leu Leu Thr Pro Arg Asn Gln
145                 150                 155                 160

Glu Ala Cys Glu Leu Ser Asn Asn
              165
```

```
<210> SEQ ID NO 14
<211> LENGTH: 168
<212> TYPE: PRT
<213> ORGANISM: Artificial Sequence
<220> FEATURE:
<223> OTHER INFORMATION: Synthetic polypeptide

<400> SEQUENCE: 14
```

```
Tyr Gln Cys Pro Glu His Ser Gln Leu Thr Thr Leu Gly Val Asp Gly
1               5                   10                  15

Lys Glu Phe Pro Glu Val His Leu Gly Gln Trp Tyr Phe Ile Ala Gly
          20                  25                  30

Ala Ala Pro Thr Lys Glu Glu Leu Ala Thr Phe Asp Pro Val Asp Asn
          35                  40                  45

Ile Val Phe Asn Met Ala Ala Gly Ser Ala Pro Met Gln Leu His Leu
      50                  55                  60

Arg Ala Thr Asn Arg Met Lys Asp Gly Leu Cys Val Pro Arg Lys Trp
65                  70                  75                  80

Ile Tyr His Leu Thr Glu Gly Ser Thr Asp Leu Arg Thr Glu Gly Arg
              85                  90                  95

Pro Asp Met Lys Thr Glu Leu Phe Ser Ser Ser Cys Pro Gly Gly Ile
          100                 105                 110

Met Leu Asn Glu Thr Gly Gln Gly Tyr Gln Arg Phe Leu Leu Tyr Asn
          115                 120                 125

Arg Ser Pro His Pro Pro Glu Lys Cys Val Glu Glu Phe Lys Ser Leu
      130                 135                 140

Thr Ser Cys Leu Asp Ser Lys Ala Phe Leu Leu Thr Pro Arg Asn Gln
145                 150                 155                 160

Glu Ala Cys Glu Leu Ser Asn Asn
              165
```

```
<210> SEQ ID NO 15
<211> LENGTH: 168
<212> TYPE: PRT
<213> ORGANISM: Artificial Sequence
```

```
<220> FEATURE:
<223> OTHER INFORMATION: Synthetic polypeptide

<400> SEQUENCE: 15

Tyr Gln Cys Pro Glu His Ser Gln Leu Thr Thr Leu Gly Val Asp Gly
1               5                   10                  15

Lys Glu Phe Pro Glu Val His Leu Gly Gln Trp Tyr Phe Ile Ala Gly
                20                  25                  30

Ala Ala Pro Thr Lys Glu Glu Leu Ala Thr Phe Asp Pro Val Asp Asn
            35                  40                  45

Ile Val Phe Asn Met Ala Ala Gly Ser Ala Pro Met Gln Leu His Leu
        50                  55                  60

Arg Ala Thr Ile Arg Tyr Lys Asp Gly Leu Cys Val Pro Arg Lys Trp
65                  70                  75                  80

Ile Tyr His Leu Thr Glu Gly Ser Thr Asp Leu Arg Thr Glu Gly Arg
                85                  90                  95

Pro Asp Met Lys Thr Glu Leu Phe Ser Ser Ser Cys Pro Gly Gly Ile
            100                 105                 110

Met Leu Asn Glu Thr Gly Gln Gly Tyr Gln Arg Phe Leu Leu Tyr Asn
            115                 120                 125

Arg Ser Pro His Pro Pro Glu Lys Cys Val Glu Glu Phe Lys Ser Leu
        130                 135                 140

Thr Ser Cys Leu Asp Ser Lys Ala Phe Leu Leu Thr Pro Arg Asn Gln
145                 150                 155                 160

Glu Ala Cys Glu Leu Ser Asn Asn
                165

<210> SEQ ID NO 16
<211> LENGTH: 170
<212> TYPE: PRT
<213> ORGANISM: Artificial Sequence
<220> FEATURE:
<223> OTHER INFORMATION: Synthetic polypeptide

<400> SEQUENCE: 16

Asn Gln Cys Pro Glu His Ser Gln Leu Thr Ala Leu Gly Met Asp Asp
1               5                   10                  15

Thr Glu Thr Pro Glu Pro His Leu Gly Leu Trp Tyr Phe Ile Ala Gly
                20                  25                  30

Ala Ala Pro Thr Thr Glu Glu Leu Ala Asn Phe Asp Pro Val Asp Asn
            35                  40                  45

Ile Val Phe Asn Met Ala Ala Gly Ser Ala Pro Arg Gln Leu Gln Leu
        50                  55                  60

Arg Ala Thr Ile Arg Thr Lys Ser Gly Val Cys Val Pro Arg Lys Trp
65                  70                  75                  80

Thr Tyr Arg Leu Thr Glu Gly Lys Gly Asn Met Glu Leu Arg Thr Glu
                85                  90                  95

Gly Arg Pro Asp Met Lys Thr Asp Leu Phe Ser Ser Ser Cys Pro Gly
            100                 105                 110

Gly Ile Met Leu Lys Glu Thr Gly Gln Gly Tyr Gln Arg Phe Leu Leu
            115                 120                 125

Tyr Asn Arg Ser Pro His Pro Pro Glu Lys Cys Val Glu Glu Phe Lys
        130                 135                 140

Ser Leu Thr Ser Cys Leu Asp Phe Lys Ala Phe Leu Val Thr Pro Arg
145                 150                 155                 160

Asn Gln Glu Ala Cys Pro Leu Ser Ser Lys
```

-continued

```
                 165                 170

<210> SEQ ID NO 17
<211> LENGTH: 170
<212> TYPE: PRT
<213> ORGANISM: Artificial Sequence
<220> FEATURE:
<223> OTHER INFORMATION: Synthetic polypeptide

<400> SEQUENCE: 17

Asn Gln Cys Pro Glu His Ser Gln Leu Thr Ala Leu Gly Met Asp Asp
1               5                   10                  15

Thr Glu Thr Pro Glu Pro His Leu Gly Leu Trp Tyr Phe Ile Ala Gly
            20                  25                  30

Ala Ala Pro Thr Thr Glu Glu Leu Ala Thr Phe Asp Pro Lys Asp Asn
        35                  40                  45

Ile Val Phe Asn Met Ala Ala Gly Ser Ala Pro Arg Gln Leu Gln Leu
    50                  55                  60

Arg Ala Thr Ile Arg Thr Lys Ser Gly Val Cys Val Pro Arg Lys Trp
65                  70                  75                  80

Thr Tyr Arg Leu Thr Glu Gly Lys Gly Asn Met Glu Leu Arg Thr Glu
                85                  90                  95

Gly Arg Pro Asp Met Lys Thr Asp Leu Phe Ser Ser Ser Cys Pro Gly
            100                 105                 110

Gly Ile Met Leu Lys Glu Thr Gly Gln Gly Tyr Gln Arg Phe Leu Leu
        115                 120                 125

Tyr Asn Arg Ser Pro His Pro Pro Glu Lys Cys Val Glu Glu Phe Lys
    130                 135                 140

Ser Leu Thr Ser Cys Leu Asp Phe Lys Ala Phe Leu Val Thr Pro Arg
145                 150                 155                 160

Asn Gln Glu Ala Cys Pro Leu Ser Ser Lys
                165                 170

<210> SEQ ID NO 18
<211> LENGTH: 170
<212> TYPE: PRT
<213> ORGANISM: Artificial Sequence
<220> FEATURE:
<223> OTHER INFORMATION: Synthetic polypeptide

<400> SEQUENCE: 18

Asn Gln Cys Pro Glu His Ser Gln Leu Thr Ala Leu Gly Met Asp Asp
1               5                   10                  15

Thr Glu Thr Pro Glu Pro His Leu Gly Leu Trp Tyr Phe Ile Ala Gly
            20                  25                  30

Ala Ala Pro Thr Thr Glu Glu Leu Ala Thr Phe Asp Pro Asn Asp Asn
        35                  40                  45

Ile Val Phe Asn Met Ala Ala Gly Ser Ala Pro Arg Gln Leu Gln Leu
    50                  55                  60

Arg Ala Thr Ile Arg Thr Lys Ser Gly Val Cys Val Pro Arg Lys Trp
65                  70                  75                  80

Thr Tyr Arg Leu Thr Glu Gly Lys Gly Asn Met Glu Leu Arg Thr Glu
                85                  90                  95

Gly Arg Pro Asp Met Lys Thr Asp Leu Phe Ser Ser Ser Cys Pro Gly
            100                 105                 110

Gly Ile Met Leu Lys Glu Thr Gly Gln Gly Tyr Gln Arg Phe Leu Leu
        115                 120                 125
```

```
Tyr Asn Arg Ser Pro His Pro Pro Glu Lys Cys Val Glu Glu Phe Lys
    130             135             140

Ser Leu Thr Ser Cys Leu Asp Phe Lys Ala Phe Leu Val Thr Pro Arg
145             150             155             160

Asn Gln Glu Ala Cys Pro Leu Ser Ser Lys
                165             170

<210> SEQ ID NO 19
<211> LENGTH: 170
<212> TYPE: PRT
<213> ORGANISM: Artificial Sequence
<220> FEATURE:
<223> OTHER INFORMATION: Synthetic polypeptide

<400> SEQUENCE: 19

Asn Gln Cys Pro Glu His Ser Gln Leu Thr Ala Leu Gly Met Asp Asp
1               5               10              15

Thr Glu Thr Pro Glu Pro His Leu Gly Leu Trp Tyr Phe Ile Ala Gly
            20              25              30

Ala Ala Pro Thr Thr Glu Glu Leu Ala Thr Phe Asp Pro Gln Asp Asn
        35              40              45

Ile Val Phe Asn Met Ala Ala Gly Ser Ala Pro Arg Gln Leu Gln Leu
    50              55              60

Arg Ala Thr Ile Arg Thr Lys Ser Gly Val Cys Val Pro Arg Lys Trp
65              70              75              80

Thr Tyr Arg Leu Thr Glu Gly Lys Gly Asn Met Glu Leu Arg Thr Glu
            85              90              95

Gly Arg Pro Asp Met Lys Thr Asp Leu Phe Ser Ser Ser Cys Pro Gly
            100             105             110

Gly Ile Met Leu Lys Glu Thr Gly Gln Gly Tyr Gln Arg Phe Leu Leu
        115             120             125

Tyr Asn Arg Ser Pro His Pro Pro Glu Lys Cys Val Glu Glu Phe Lys
    130             135             140

Ser Leu Thr Ser Cys Leu Asp Phe Lys Ala Phe Leu Val Thr Pro Arg
145             150             155             160

Asn Gln Glu Ala Cys Pro Leu Ser Ser Lys
                165             170

<210> SEQ ID NO 20
<211> LENGTH: 170
<212> TYPE: PRT
<213> ORGANISM: Artificial Sequence
<220> FEATURE:
<223> OTHER INFORMATION: Synthetic polypeptide

<400> SEQUENCE: 20

Asn Gln Cys Pro Glu His Ser Gln Leu Thr Ala Leu Gly Met Asp Asp
1               5               10              15

Thr Glu Thr Pro Glu Pro His Leu Gly Leu Trp Tyr Phe Ile Ala Gly
            20              25              30

Ala Ala Pro Thr Thr Glu Glu Leu Ala Thr Phe Asp Pro Val Asp Asn
        35              40              45

Ile Val Phe Asn Met Ala Ala Gly Ser Ala Pro Arg Gln Leu Gln Leu
    50              55              60

Arg Ala Thr Lys Arg Thr Lys Ser Gly Val Cys Val Pro Arg Lys Trp
65              70              75              80

Thr Tyr Arg Leu Thr Glu Gly Lys Gly Asn Met Glu Leu Arg Thr Glu
            85              90              95
```

```
Gly Arg Pro Asp Met Lys Thr Asp Leu Phe Ser Ser Ser Cys Pro Gly
            100             105             110

Gly Ile Met Leu Lys Glu Thr Gly Gln Gly Tyr Gln Arg Phe Leu Leu
            115             120             125

Tyr Asn Arg Ser Pro His Pro Pro Glu Lys Cys Val Glu Glu Phe Lys
            130             135             140

Ser Leu Thr Ser Cys Leu Asp Phe Lys Ala Phe Leu Val Thr Pro Arg
145             150             155             160

Asn Gln Glu Ala Cys Pro Leu Ser Ser Lys
            165             170

<210> SEQ ID NO 21
<211> LENGTH: 170
<212> TYPE: PRT
<213> ORGANISM: Artificial Sequence
<220> FEATURE:
<223> OTHER INFORMATION: Synthetic polypeptide

<400> SEQUENCE: 21

Asn Gln Cys Pro Glu His Ser Gln Leu Thr Ala Leu Gly Met Asp Asp
1               5               10              15

Thr Glu Thr Pro Glu Pro His Leu Gly Leu Trp Tyr Phe Ile Ala Gly
            20              25              30

Ala Ala Pro Thr Thr Glu Glu Leu Ala Thr Phe Asp Pro Val Asp Asn
            35              40              45

Ile Val Phe Asn Met Ala Ala Gly Ser Ala Pro Arg Gln Leu Gln Leu
            50              55              60

Arg Ala Thr Asn Arg Thr Lys Ser Gly Val Cys Val Pro Arg Lys Trp
65              70              75              80

Thr Tyr Arg Leu Thr Glu Gly Lys Gly Asn Met Glu Leu Arg Thr Glu
            85              90              95

Gly Arg Pro Asp Met Lys Thr Asp Leu Phe Ser Ser Ser Cys Pro Gly
            100             105             110

Gly Ile Met Leu Lys Glu Thr Gly Gln Gly Tyr Gln Arg Phe Leu Leu
            115             120             125

Tyr Asn Arg Ser Pro His Pro Pro Glu Lys Cys Val Glu Glu Phe Lys
            130             135             140

Ser Leu Thr Ser Cys Leu Asp Phe Lys Ala Phe Leu Val Thr Pro Arg
145             150             155             160

Asn Gln Glu Ala Cys Pro Leu Ser Ser Lys
            165             170

<210> SEQ ID NO 22
<211> LENGTH: 170
<212> TYPE: PRT
<213> ORGANISM: Artificial Sequence
<220> FEATURE:
<223> OTHER INFORMATION: Synthetic polypeptide

<400> SEQUENCE: 22

Asn Gln Cys Pro Glu His Ser Gln Leu Thr Ala Leu Gly Met Asp Asp
1               5               10              15

Thr Glu Thr Pro Glu Pro His Leu Gly Leu Trp Tyr Phe Ile Ala Gly
            20              25              30

Ala Ala Pro Thr Thr Glu Glu Leu Ala Thr Phe Asp Pro Val Asp Asn
            35              40              45

Ile Val Phe Asn Met Ala Ala Gly Ser Ala Pro Arg Gln Leu Gln Leu
```

-continued

```
        50                    55                    60

Arg Ala Thr Ile Arg Tyr Lys Ser Gly Val Cys Val Pro Arg Lys Trp
65                    70                    75                    80

Thr Tyr Arg Leu Thr Glu Gly Lys Gly Asn Met Glu Leu Arg Thr Glu
                  85                    90                    95

Gly Arg Pro Asp Met Lys Thr Asp Leu Phe Ser Ser Ser Cys Pro Gly
                  100                   105                   110

Gly Ile Met Leu Lys Glu Thr Gly Gln Gly Tyr Gln Arg Phe Leu Leu
                  115                   120                   125

Tyr Asn Arg Ser Pro His Pro Pro Glu Lys Cys Val Glu Glu Phe Lys
              130                   135                   140

Ser Leu Thr Ser Cys Leu Asp Phe Lys Ala Phe Leu Val Thr Pro Arg
145                   150                   155                   160

Asn Gln Glu Ala Cys Pro Leu Ser Ser Lys
                  165                   170

<210> SEQ ID NO 23
<211> LENGTH: 523
<212> TYPE: PRT
<213> ORGANISM: Artificial Sequence
<220> FEATURE:
<223> OTHER INFORMATION: Synthetic polypeptide

<400> SEQUENCE: 23

Met Tyr Arg Met Gln Leu Leu Ser Cys Ile Ala Leu Ser Leu Ala Leu
1                   5                     10                    15

Val Thr Asn Ser Ile Ser Arg Val Tyr Gln Cys Pro Glu His Ser Gln
                  20                    25                    30

Leu Thr Thr Leu Gly Val Asp Gly Lys Glu Phe Pro Glu Val His Leu
              35                    40                    45

Gly Gln Trp Tyr Phe Ile Ala Gly Ala Ala Pro Thr Lys Glu Glu Leu
          50                    55                    60

Ala Asn Phe Asp Pro Val Asp Asn Ile Val Phe Asn Met Ala Ala Gly
65                    70                    75                    80

Ser Ala Pro Met Gln Leu His Leu Arg Ala Thr Ile Arg Met Lys Asp
                  85                    90                    95

Gly Leu Cys Val Pro Arg Lys Trp Ile Tyr His Leu Thr Glu Gly Ser
                  100                   105                   110

Thr Asp Leu Arg Thr Glu Gly Arg Pro Asp Met Lys Thr Glu Leu Phe
              115                   120                   125

Ser Ser Ser Cys Pro Gly Gly Ile Met Leu Asn Glu Thr Gly Gln Gly
          130                   135                   140

Tyr Gln Arg Phe Leu Leu Tyr Asn Arg Ser Pro His Pro Pro Glu Lys
145                   150                   155                   160

Cys Val Glu Glu Phe Lys Ser Leu Thr Ser Cys Leu Asp Ser Lys Ala
                  165                   170                   175

Phe Leu Leu Thr Pro Arg Asn Gln Glu Ala Cys Glu Leu Ser Asn Asn
                  180                   185                   190

Trp Ala Ser Thr Lys Gly Pro Ser Val Phe Pro Leu Ala Pro Ser Ser
              195                   200                   205

Lys Ser Thr Ser Gly Gly Thr Ala Ala Leu Gly Cys Leu Val Lys Asp
          210                   215                   220

Tyr Phe Pro Glu Pro Val Thr Val Ser Trp Asn Ser Gly Ala Leu Thr
225                   230                   235                   240

Ser Gly Val His Thr Phe Pro Ala Val Leu Gln Ser Ser Gly Leu Tyr
```

-continued

```
              245              250              255
Ser Leu Ser Ser Val Val Thr Val Pro Ser Ser Ser Leu Gly Thr Gln
            260              265              270

Thr Tyr Ile Cys Asn Val Asn His Lys Pro Ser Asn Thr Lys Val Asp
        275              280              285

Lys Lys Val Glu Pro Lys Ser Cys Asp Lys Thr His Thr Cys Pro Pro
    290              295              300

Cys Pro Ala Pro Glu Leu Leu Gly Gly Pro Ser Val Phe Leu Phe Pro
305              310              315              320

Pro Lys Pro Lys Asp Thr Leu Met Ile Ser Arg Thr Pro Glu Val Thr
            325              330              335

Cys Val Val Val Asp Val Ser His Glu Asp Pro Glu Val Lys Phe Asn
            340              345              350

Trp Tyr Val Asp Gly Val Glu Val His Asn Ala Lys Thr Lys Pro Arg
            355              360              365

Glu Glu Gln Tyr Asn Ser Thr Tyr Arg Val Val Ser Val Leu Thr Val
    370              375              380

Leu His Gln Asp Trp Leu Asn Gly Lys Glu Tyr Lys Cys Lys Val Ser
385              390              395              400

Asn Lys Ala Leu Pro Ala Pro Ile Glu Lys Thr Ile Ser Lys Ala Lys
            405              410              415

Gly Gln Pro Arg Glu Pro Gln Val Tyr Thr Leu Pro Pro Ser Arg Glu
            420              425              430

Glu Met Thr Lys Asn Gln Val Ser Leu Thr Cys Leu Val Lys Gly Phe
            435              440              445

Tyr Pro Ser Asp Ile Ala Val Glu Trp Glu Ser Asn Gly Gln Pro Glu
    450              455              460

Asn Asn Tyr Lys Thr Thr Pro Pro Val Leu Asp Ser Asp Gly Ser Phe
465              470              475              480

Phe Leu Tyr Ser Lys Leu Thr Val Asp Lys Ser Arg Trp Gln Gln Gly
            485              490              495

Asn Val Phe Ser Cys Ser Val Met His Glu Ala Leu His Asn His Tyr
            500              505              510

Thr Gln Lys Ser Leu Ser Leu Ser Pro Gly Lys
            515              520
```

<210> SEQ ID NO 24
<211> LENGTH: 523
<212> TYPE: PRT
<213> ORGANISM: Artificial Sequence
<220> FEATURE:
<223> OTHER INFORMATION: Synthetic polypeptide

<400> SEQUENCE: 24

```
Met Tyr Arg Met Gln Leu Leu Ser Cys Ile Ala Leu Ser Leu Ala Leu
1               5               10              15

Val Thr Asn Ser Ile Ser Arg Val Tyr Gln Cys Pro Glu His Ser Gln
            20              25              30

Leu Thr Thr Leu Gly Val Asp Gly Lys Glu Phe Pro Glu Val His Leu
        35              40              45

Gly Gln Trp Tyr Phe Ile Ala Gly Ala Ala Pro Thr Lys Glu Glu Leu
    50              55              60

Ala Thr Phe Asp Pro Lys Asp Asn Ile Val Phe Asn Met Ala Ala Gly
65              70              75              80

Ser Ala Pro Met Gln Leu His Leu Arg Ala Thr Ile Arg Met Lys Asp
```

-continued

```
                      85                        90                        95
Gly Leu Cys Val Pro Arg Lys Trp Ile Tyr His Leu Thr Glu Gly Ser
                100                       105                       110

Thr Asp Leu Arg Thr Glu Gly Arg Pro Asp Met Lys Thr Glu Leu Phe
            115                       120                       125

Ser Ser Ser Cys Pro Gly Gly Ile Met Leu Asn Glu Thr Gly Gln Gly
        130                       135                       140

Tyr Gln Arg Phe Leu Leu Tyr Asn Arg Ser Pro His Pro Pro Glu Lys
145                       150                       155                       160

Cys Val Glu Glu Phe Lys Ser Leu Thr Ser Cys Leu Asp Ser Lys Ala
                165                       170                       175

Phe Leu Leu Thr Pro Arg Asn Gln Glu Ala Cys Glu Leu Ser Asn Asn
            180                       185                       190

Trp Ala Ser Thr Lys Gly Pro Ser Val Phe Pro Leu Ala Pro Ser Ser
            195                       200                       205

Lys Ser Thr Ser Gly Gly Thr Ala Ala Leu Gly Cys Leu Val Lys Asp
        210                       215                       220

Tyr Phe Pro Glu Pro Val Thr Val Ser Trp Asn Ser Gly Ala Leu Thr
225                       230                       235                       240

Ser Gly Val His Thr Phe Pro Ala Val Leu Gln Ser Ser Gly Leu Tyr
                245                       250                       255

Ser Leu Ser Ser Val Val Thr Val Pro Ser Ser Ser Leu Gly Thr Gln
            260                       265                       270

Thr Tyr Ile Cys Asn Val Asn His Lys Pro Ser Asn Thr Lys Val Asp
            275                       280                       285

Lys Lys Val Glu Pro Lys Ser Cys Asp Lys Thr His Thr Cys Pro Pro
        290                       295                       300

Cys Pro Ala Pro Glu Leu Leu Gly Gly Pro Ser Val Phe Leu Phe Pro
305                       310                       315                       320

Pro Lys Pro Lys Asp Thr Leu Met Ile Ser Arg Thr Pro Glu Val Thr
                325                       330                       335

Cys Val Val Val Asp Val Ser His Glu Asp Pro Glu Val Lys Phe Asn
            340                       345                       350

Trp Tyr Val Asp Gly Val Glu Val His Asn Ala Lys Thr Lys Pro Arg
            355                       360                       365

Glu Glu Gln Tyr Asn Ser Thr Tyr Arg Val Val Ser Val Leu Thr Val
        370                       375                       380

Leu His Gln Asp Trp Leu Asn Gly Lys Glu Tyr Lys Cys Lys Val Ser
385                       390                       395                       400

Asn Lys Ala Leu Pro Ala Pro Ile Glu Lys Thr Ile Ser Lys Ala Lys
                405                       410                       415

Gly Gln Pro Arg Glu Pro Gln Val Tyr Thr Leu Pro Pro Ser Arg Glu
            420                       425                       430

Glu Met Thr Lys Asn Gln Val Ser Leu Thr Cys Leu Val Lys Gly Phe
            435                       440                       445

Tyr Pro Ser Asp Ile Ala Val Glu Trp Glu Ser Asn Gly Gln Pro Glu
        450                       455                       460

Asn Asn Tyr Lys Thr Thr Pro Pro Val Leu Asp Ser Asp Gly Ser Phe
465                       470                       475                       480

Phe Leu Tyr Ser Lys Leu Thr Val Asp Lys Ser Arg Trp Gln Gln Gly
                485                       490                       495

Asn Val Phe Ser Cys Ser Val Met His Glu Ala Leu His Asn His Tyr
            500                       505                       510
```

-continued

```
Thr Gln Lys Ser Leu Ser Leu Ser Pro Gly Lys
        515                 520

<210> SEQ ID NO 25
<211> LENGTH: 523
<212> TYPE: PRT
<213> ORGANISM: Artificial Sequence
<220> FEATURE:
<223> OTHER INFORMATION: Synthetic polypeptide

<400> SEQUENCE: 25

Met Tyr Arg Met Gln Leu Leu Ser Cys Ile Ala Leu Ser Leu Ala Leu
1               5                   10                  15

Val Thr Asn Ser Ile Ser Arg Val Tyr Gln Cys Pro Glu His Ser Gln
            20                  25                  30

Leu Thr Thr Leu Gly Val Asp Gly Lys Glu Phe Pro Glu Val His Leu
            35                  40                  45

Gly Gln Trp Tyr Phe Ile Ala Gly Ala Ala Pro Thr Lys Glu Glu Leu
        50                  55                  60

Ala Thr Phe Asp Pro Asn Asp Asn Ile Val Phe Asn Met Ala Ala Gly
65                  70                  75                  80

Ser Ala Pro Met Gln Leu His Leu Arg Ala Thr Ile Arg Met Lys Asp
                85                  90                  95

Gly Leu Cys Val Pro Arg Lys Trp Ile Tyr His Leu Thr Glu Gly Ser
            100                 105                 110

Thr Asp Leu Arg Thr Glu Gly Arg Pro Asp Met Lys Thr Glu Leu Phe
            115                 120                 125

Ser Ser Ser Cys Pro Gly Gly Ile Met Leu Asn Glu Thr Gly Gln Gly
        130                 135                 140

Tyr Gln Arg Phe Leu Leu Tyr Asn Arg Ser Pro His Pro Pro Glu Lys
145                 150                 155                 160

Cys Val Glu Glu Phe Lys Ser Leu Thr Ser Cys Leu Asp Ser Lys Ala
                165                 170                 175

Phe Leu Leu Thr Pro Arg Asn Gln Glu Ala Cys Glu Leu Ser Asn Asn
            180                 185                 190

Trp Ala Ser Thr Lys Gly Pro Ser Val Phe Pro Leu Ala Pro Ser Ser
        195                 200                 205

Lys Ser Thr Ser Gly Gly Thr Ala Ala Leu Gly Cys Leu Val Lys Asp
        210                 215                 220

Tyr Phe Pro Glu Pro Val Thr Val Ser Trp Asn Ser Gly Ala Leu Thr
225                 230                 235                 240

Ser Gly Val His Thr Phe Pro Ala Val Leu Gln Ser Ser Gly Leu Tyr
                245                 250                 255

Ser Leu Ser Ser Val Val Thr Val Pro Ser Ser Ser Leu Gly Thr Gln
            260                 265                 270

Thr Tyr Ile Cys Asn Val Asn His Lys Pro Ser Asn Thr Lys Val Asp
            275                 280                 285

Lys Lys Val Glu Pro Lys Ser Cys Asp Lys Thr His Thr Cys Pro Pro
        290                 295                 300

Cys Pro Ala Pro Glu Leu Leu Gly Gly Pro Ser Val Phe Leu Phe Pro
305                 310                 315                 320

Pro Lys Pro Lys Asp Thr Leu Met Ile Ser Arg Thr Pro Glu Val Thr
            325                 330                 335

Cys Val Val Val Asp Val Ser His Glu Asp Pro Glu Val Lys Phe Asn
            340                 345                 350
```

-continued

```
Trp Tyr Val Asp Gly Val Glu Val His Asn Ala Lys Thr Lys Pro Arg
        355             360             365

Glu Glu Gln Tyr Asn Ser Thr Tyr Arg Val Val Ser Val Leu Thr Val
    370             375             380

Leu His Gln Asp Trp Leu Asn Gly Lys Glu Tyr Lys Cys Lys Val Ser
385             390             395             400

Asn Lys Ala Leu Pro Ala Pro Ile Glu Lys Thr Ile Ser Lys Ala Lys
                405             410             415

Gly Gln Pro Arg Glu Pro Gln Val Tyr Thr Leu Pro Pro Ser Arg Glu
                420             425             430

Glu Met Thr Lys Asn Gln Val Ser Leu Thr Cys Leu Val Lys Gly Phe
            435             440             445

Tyr Pro Ser Asp Ile Ala Val Glu Trp Glu Ser Asn Gly Gln Pro Glu
    450             455             460

Asn Asn Tyr Lys Thr Thr Pro Pro Val Leu Asp Ser Asp Gly Ser Phe
465             470             475             480

Phe Leu Tyr Ser Lys Leu Thr Val Asp Lys Ser Arg Trp Gln Gln Gly
                485             490             495

Asn Val Phe Ser Cys Ser Val Met His Glu Ala Leu His Asn His Tyr
            500             505             510

Thr Gln Lys Ser Leu Ser Leu Ser Pro Gly Lys
        515             520
```

```
<210> SEQ ID NO 26
<211> LENGTH: 523
<212> TYPE: PRT
<213> ORGANISM: Artificial Sequence
<220> FEATURE:
<223> OTHER INFORMATION: Synthetic polypeptide

<400> SEQUENCE: 26
```

```
Met Tyr Arg Met Gln Leu Leu Ser Cys Ile Ala Leu Ser Leu Ala Leu
1               5               10              15

Val Thr Asn Ser Ile Ser Arg Val Tyr Gln Cys Pro Glu His Ser Gln
            20              25              30

Leu Thr Thr Leu Gly Val Asp Gly Lys Glu Phe Pro Glu Val His Leu
        35              40              45

Gly Gln Trp Tyr Phe Ile Ala Gly Ala Ala Pro Thr Lys Glu Glu Leu
    50              55              60

Ala Thr Phe Asp Pro Gln Asp Asn Ile Val Phe Asn Met Ala Ala Gly
65              70              75              80

Ser Ala Pro Met Gln Leu His Leu Arg Ala Thr Ile Arg Met Lys Asp
                85              90              95

Gly Leu Cys Val Pro Arg Lys Trp Ile Tyr His Leu Thr Glu Gly Ser
            100             105             110

Thr Asp Leu Arg Thr Glu Gly Arg Pro Asp Met Lys Thr Glu Leu Phe
        115             120             125

Ser Ser Ser Cys Pro Gly Gly Ile Met Leu Asn Glu Thr Gly Gln Gly
    130             135             140

Tyr Gln Arg Phe Leu Leu Tyr Asn Arg Ser Pro His Pro Pro Glu Lys
145             150             155             160

Cys Val Glu Glu Phe Lys Ser Leu Thr Ser Cys Leu Asp Ser Lys Ala
                165             170             175

Phe Leu Leu Thr Pro Arg Asn Gln Glu Ala Cys Glu Leu Ser Asn Asn
                180             185             190
```

```
Trp Ala Ser Thr Lys Gly Pro Ser Val Phe Pro Leu Ala Pro Ser Ser
        195                 200                 205

Lys Ser Thr Ser Gly Gly Thr Ala Ala Leu Gly Cys Leu Val Lys Asp
        210                 215                 220

Tyr Phe Pro Glu Pro Val Thr Val Ser Trp Asn Ser Gly Ala Leu Thr
225                 230                 235                 240

Ser Gly Val His Thr Phe Pro Ala Val Leu Gln Ser Ser Gly Leu Tyr
                245                 250                 255

Ser Leu Ser Ser Val Val Thr Val Pro Ser Ser Ser Leu Gly Thr Gln
                260                 265                 270

Thr Tyr Ile Cys Asn Val Asn His Lys Pro Ser Asn Thr Lys Val Asp
        275                 280                 285

Lys Lys Val Glu Pro Lys Ser Cys Asp Lys Thr His Thr Cys Pro Pro
        290                 295                 300

Cys Pro Ala Pro Glu Leu Leu Gly Gly Pro Ser Val Phe Leu Phe Pro
305                 310                 315                 320

Pro Lys Pro Lys Asp Thr Leu Met Ile Ser Arg Thr Pro Glu Val Thr
                325                 330                 335

Cys Val Val Val Asp Val Ser His Glu Asp Pro Glu Val Lys Phe Asn
                340                 345                 350

Trp Tyr Val Asp Gly Val Glu Val His Asn Ala Lys Thr Lys Pro Arg
                355                 360                 365

Glu Glu Gln Tyr Asn Ser Thr Tyr Arg Val Val Ser Val Leu Thr Val
        370                 375                 380

Leu His Gln Asp Trp Leu Asn Gly Lys Glu Tyr Lys Cys Lys Val Ser
385                 390                 395                 400

Asn Lys Ala Leu Pro Ala Pro Ile Glu Lys Thr Ile Ser Lys Ala Lys
                405                 410                 415

Gly Gln Pro Arg Glu Pro Gln Val Tyr Thr Leu Pro Pro Ser Arg Glu
                420                 425                 430

Glu Met Thr Lys Asn Gln Val Ser Leu Thr Cys Leu Val Lys Gly Phe
        435                 440                 445

Tyr Pro Ser Asp Ile Ala Val Glu Trp Glu Ser Asn Gly Gln Pro Glu
        450                 455                 460

Asn Asn Tyr Lys Thr Thr Pro Pro Val Leu Asp Ser Asp Gly Ser Phe
465                 470                 475                 480

Phe Leu Tyr Ser Lys Leu Thr Val Asp Lys Ser Arg Trp Gln Gln Gly
                485                 490                 495

Asn Val Phe Ser Cys Ser Val Met His Glu Ala Leu His Asn His Tyr
                500                 505                 510

Thr Gln Lys Ser Leu Ser Leu Ser Pro Gly Lys
        515                 520
```

```
<210> SEQ ID NO 27
<211> LENGTH: 523
<212> TYPE: PRT
<213> ORGANISM: Artificial Sequence
<220> FEATURE:
<223> OTHER INFORMATION: Synthetic polypeptide

<400> SEQUENCE: 27

Met Tyr Arg Met Gln Leu Leu Ser Cys Ile Ala Leu Ser Leu Ala Leu
1               5                   10                  15

Val Thr Asn Ser Ile Ser Arg Val Tyr Gln Cys Pro Glu His Ser Gln
            20                  25                  30
```

```
Leu Thr Thr Leu Gly Val Asp Gly Lys Glu Phe Pro Glu Val His Leu
        35              40              45

Gly Gln Trp Tyr Phe Ile Ala Gly Ala Ala Pro Thr Lys Glu Glu Leu
    50              55              60

Ala Thr Phe Asp Pro Val Asp Asn Ile Val Phe Asn Met Ala Ala Gly
65              70              75              80

Ser Ala Pro Met Gln Leu His Leu Arg Ala Thr Lys Arg Met Lys Asp
            85              90              95

Gly Leu Cys Val Pro Arg Lys Trp Ile Tyr His Leu Thr Glu Gly Ser
            100             105             110

Thr Asp Leu Arg Thr Glu Gly Arg Pro Asp Met Lys Thr Glu Leu Phe
            115             120             125

Ser Ser Ser Cys Pro Gly Gly Ile Met Leu Asn Glu Thr Gly Gln Gly
        130             135             140

Tyr Gln Arg Phe Leu Leu Tyr Asn Arg Ser Pro His Pro Pro Glu Lys
145             150             155             160

Cys Val Glu Glu Phe Lys Ser Leu Thr Ser Cys Leu Asp Ser Lys Ala
            165             170             175

Phe Leu Leu Thr Pro Arg Asn Gln Glu Ala Cys Glu Leu Ser Asn Asn
            180             185             190

Trp Ala Ser Thr Lys Gly Pro Ser Val Phe Pro Leu Ala Pro Ser Ser
        195             200             205

Lys Ser Thr Ser Gly Gly Thr Ala Ala Leu Gly Cys Leu Val Lys Asp
    210             215             220

Tyr Phe Pro Glu Pro Val Thr Val Ser Trp Asn Ser Gly Ala Leu Thr
225             230             235             240

Ser Gly Val His Thr Phe Pro Ala Val Leu Gln Ser Ser Gly Leu Tyr
            245             250             255

Ser Leu Ser Ser Val Val Thr Val Pro Ser Ser Ser Leu Gly Thr Gln
            260             265             270

Thr Tyr Ile Cys Asn Val Asn His Lys Pro Ser Asn Thr Lys Val Asp
            275             280             285

Lys Lys Val Glu Pro Lys Ser Cys Asp Lys Thr His Thr Cys Pro Pro
    290             295             300

Cys Pro Ala Pro Glu Leu Leu Gly Gly Pro Ser Val Phe Leu Phe Pro
305             310             315             320

Pro Lys Pro Lys Asp Thr Leu Met Ile Ser Arg Thr Pro Glu Val Thr
            325             330             335

Cys Val Val Val Asp Val Ser His Glu Asp Pro Glu Val Lys Phe Asn
            340             345             350

Trp Tyr Val Asp Gly Val Glu Val His Asn Ala Lys Thr Lys Pro Arg
            355             360             365

Glu Glu Gln Tyr Asn Ser Thr Tyr Arg Val Val Ser Val Leu Thr Val
    370             375             380

Leu His Gln Asp Trp Leu Asn Gly Lys Glu Tyr Lys Cys Lys Val Ser
385             390             395             400

Asn Lys Ala Leu Pro Ala Pro Ile Glu Lys Thr Ile Ser Lys Ala Lys
            405             410             415

Gly Gln Pro Arg Glu Pro Gln Val Tyr Thr Leu Pro Pro Ser Arg Glu
            420             425             430

Glu Met Thr Lys Asn Gln Val Ser Leu Thr Cys Leu Val Lys Gly Phe
            435             440             445
```

Tyr Pro Ser Asp Ile Ala Val Glu Trp Glu Ser Asn Gly Gln Pro Glu
    450             455             460

Asn Asn Tyr Lys Thr Thr Pro Pro Val Leu Asp Ser Asp Gly Ser Phe
465             470             475             480

Phe Leu Tyr Ser Lys Leu Thr Val Asp Lys Ser Arg Trp Gln Gln Gly
            485             490             495

Asn Val Phe Ser Cys Ser Val Met His Glu Ala Leu His Asn His Tyr
            500             505             510

Thr Gln Lys Ser Leu Ser Leu Ser Pro Gly Lys
        515             520

<210> SEQ ID NO 28
<211> LENGTH: 523
<212> TYPE: PRT
<213> ORGANISM: Artificial Sequence
<220> FEATURE:
<223> OTHER INFORMATION: Synthetic polypeptide

<400> SEQUENCE: 28

Met Tyr Arg Met Gln Leu Leu Ser Cys Ile Ala Leu Ser Leu Ala Leu
1               5               10              15

Val Thr Asn Ser Ile Ser Arg Val Tyr Gln Cys Pro Glu His Ser Gln
            20              25              30

Leu Thr Thr Leu Gly Val Asp Gly Lys Glu Phe Pro Glu Val His Leu
        35              40              45

Gly Gln Trp Tyr Phe Ile Ala Gly Ala Ala Pro Thr Lys Glu Glu Leu
    50              55              60

Ala Thr Phe Asp Pro Val Asp Asn Ile Val Phe Asn Met Ala Ala Gly
65              70              75              80

Ser Ala Pro Met Gln Leu His Leu Arg Ala Thr Asn Arg Met Lys Asp
            85              90              95

Gly Leu Cys Val Pro Arg Lys Trp Ile Tyr His Leu Thr Glu Gly Ser
            100             105             110

Thr Asp Leu Arg Thr Glu Gly Arg Pro Asp Met Lys Thr Glu Leu Phe
        115             120             125

Ser Ser Ser Cys Pro Gly Gly Ile Met Leu Asn Glu Thr Gly Gln Gly
        130             135             140

Tyr Gln Arg Phe Leu Leu Tyr Asn Arg Ser Pro His Pro Pro Glu Lys
145             150             155             160

Cys Val Glu Glu Phe Lys Ser Leu Thr Ser Cys Leu Asp Ser Lys Ala
            165             170             175

Phe Leu Leu Thr Pro Arg Asn Gln Glu Ala Cys Glu Leu Ser Asn Asn
            180             185             190

Trp Ala Ser Thr Lys Gly Pro Ser Val Phe Pro Leu Ala Pro Ser Ser
            195             200             205

Lys Ser Thr Ser Gly Gly Thr Ala Ala Leu Gly Cys Leu Val Lys Asp
        210             215             220

Tyr Phe Pro Glu Pro Val Thr Val Ser Trp Asn Ser Gly Ala Leu Thr
225             230             235             240

Ser Gly Val His Thr Phe Pro Ala Val Leu Gln Ser Ser Gly Leu Tyr
            245             250             255

Ser Leu Ser Ser Val Val Thr Val Pro Ser Ser Ser Leu Gly Thr Gln
            260             265             270

Thr Tyr Ile Cys Asn Val Asn His Lys Pro Ser Asn Thr Lys Val Asp
        275             280             285

-continued

```
Lys Lys Val Glu Pro Lys Ser Cys Asp Lys Thr His Thr Cys Pro Pro
    290                 295                 300

Cys Pro Ala Pro Glu Leu Leu Gly Gly Pro Ser Val Phe Leu Phe Pro
305                 310                 315                 320

Pro Lys Pro Lys Asp Thr Leu Met Ile Ser Arg Thr Pro Glu Val Thr
                325                 330                 335

Cys Val Val Val Asp Val Ser His Glu Asp Pro Glu Val Lys Phe Asn
                340                 345                 350

Trp Tyr Val Asp Gly Val Glu Val His Asn Ala Lys Thr Lys Pro Arg
            355                 360                 365

Glu Glu Gln Tyr Asn Ser Thr Tyr Arg Val Val Ser Val Leu Thr Val
    370                 375                 380

Leu His Gln Asp Trp Leu Asn Gly Lys Glu Tyr Lys Cys Lys Val Ser
385                 390                 395                 400

Asn Lys Ala Leu Pro Ala Pro Ile Glu Lys Thr Ile Ser Lys Ala Lys
                405                 410                 415

Gly Gln Pro Arg Glu Pro Gln Val Tyr Thr Leu Pro Pro Ser Arg Glu
                420                 425                 430

Glu Met Thr Lys Asn Gln Val Ser Leu Thr Cys Leu Val Lys Gly Phe
            435                 440                 445

Tyr Pro Ser Asp Ile Ala Val Glu Trp Glu Ser Asn Gly Gln Pro Glu
    450                 455                 460

Asn Asn Tyr Lys Thr Thr Pro Pro Val Leu Asp Ser Asp Gly Ser Phe
465                 470                 475                 480

Phe Leu Tyr Ser Lys Leu Thr Val Asp Lys Ser Arg Trp Gln Gln Gly
                485                 490                 495

Asn Val Phe Ser Cys Ser Val Met His Glu Ala Leu His Asn His Tyr
                500                 505                 510

Thr Gln Lys Ser Leu Ser Leu Ser Pro Gly Lys
            515                 520
```

```
<210> SEQ ID NO 29
<211> LENGTH: 523
<212> TYPE: PRT
<213> ORGANISM: Artificial Sequence
<220> FEATURE:
<223> OTHER INFORMATION: Synthetic polypeptide

<400> SEQUENCE: 29
```

```
Met Tyr Arg Met Gln Leu Leu Ser Cys Ile Ala Leu Ser Leu Ala Leu
1               5                   10                  15

Val Thr Asn Ser Ile Ser Arg Val Tyr Gln Cys Pro Glu His Ser Gln
                20                  25                  30

Leu Thr Thr Leu Gly Val Asp Gly Lys Glu Phe Pro Glu Val His Leu
            35                  40                  45

Gly Gln Trp Tyr Phe Ile Ala Gly Ala Ala Pro Thr Lys Glu Glu Leu
    50                  55                  60

Ala Thr Phe Asp Pro Val Asp Asn Ile Val Phe Asn Met Ala Ala Gly
65                  70                  75                  80

Ser Ala Pro Met Gln Leu His Leu Arg Ala Thr Ile Arg Tyr Lys Asp
                85                  90                  95

Gly Leu Cys Val Pro Arg Lys Trp Ile Tyr His Leu Thr Glu Gly Ser
            100                 105                 110

Thr Asp Leu Arg Thr Glu Gly Arg Pro Asp Met Lys Thr Glu Leu Phe
            115                 120                 125
```

```
Ser Ser Ser Cys Pro Gly Gly Ile Met Leu Asn Glu Thr Gly Gln Gly
    130             135                 140

Tyr Gln Arg Phe Leu Leu Tyr Asn Arg Ser Pro His Pro Pro Glu Lys
145             150                 155                 160

Cys Val Glu Glu Phe Lys Ser Leu Thr Ser Cys Leu Asp Ser Lys Ala
            165                 170                 175

Phe Leu Leu Thr Pro Arg Asn Gln Glu Ala Cys Glu Leu Ser Asn Asn
            180                 185                 190

Trp Ala Ser Thr Lys Gly Pro Ser Val Phe Pro Leu Ala Pro Ser Ser
            195                 200                 205

Lys Ser Thr Ser Gly Gly Thr Ala Ala Leu Gly Cys Leu Val Lys Asp
    210             215                 220

Tyr Phe Pro Glu Pro Val Thr Val Ser Trp Asn Ser Gly Ala Leu Thr
225             230                 235                 240

Ser Gly Val His Thr Phe Pro Ala Val Leu Gln Ser Ser Gly Leu Tyr
            245                 250                 255

Ser Leu Ser Ser Val Val Thr Val Pro Ser Ser Ser Leu Gly Thr Gln
            260                 265                 270

Thr Tyr Ile Cys Asn Val Asn His Lys Pro Ser Asn Thr Lys Val Asp
    275                 280                 285

Lys Lys Val Glu Pro Lys Ser Cys Asp Lys Thr His Thr Cys Pro Pro
    290                 295                 300

Cys Pro Ala Pro Glu Leu Leu Gly Gly Pro Ser Val Phe Leu Phe Pro
305             310                 315                 320

Pro Lys Pro Lys Asp Thr Leu Met Ile Ser Arg Thr Pro Glu Val Thr
            325                 330                 335

Cys Val Val Val Asp Val Ser His Glu Asp Pro Glu Val Lys Phe Asn
            340                 345                 350

Trp Tyr Val Asp Gly Val Glu Val His Asn Ala Lys Thr Lys Pro Arg
            355                 360                 365

Glu Glu Gln Tyr Asn Ser Thr Tyr Arg Val Val Ser Val Leu Thr Val
    370                 375                 380

Leu His Gln Asp Trp Leu Asn Gly Lys Glu Tyr Lys Cys Lys Val Ser
385             390                 395                 400

Asn Lys Ala Leu Pro Ala Pro Ile Glu Lys Thr Ile Ser Lys Ala Lys
            405                 410                 415

Gly Gln Pro Arg Glu Pro Gln Val Tyr Thr Leu Pro Pro Ser Arg Glu
            420                 425                 430

Glu Met Thr Lys Asn Gln Val Ser Leu Thr Cys Leu Val Lys Gly Phe
            435                 440                 445

Tyr Pro Ser Asp Ile Ala Val Glu Trp Glu Ser Asn Gly Gln Pro Glu
    450                 455                 460

Asn Asn Tyr Lys Thr Thr Pro Pro Val Leu Asp Ser Asp Gly Ser Phe
465                 470                 475                 480

Phe Leu Tyr Ser Lys Leu Thr Val Asp Lys Ser Arg Trp Gln Gln Gly
            485                 490                 495

Asn Val Phe Ser Cys Ser Val Met His Glu Ala Leu His Asn His Tyr
            500                 505                 510

Thr Gln Lys Ser Leu Ser Leu Ser Pro Gly Lys
    515                 520
```

```
<210> SEQ ID NO 30
<211> LENGTH: 523
<212> TYPE: PRT
```

-continued

<213> ORGANISM: Artificial Sequence
<220> FEATURE:
<223> OTHER INFORMATION: Synthetic polypeptide

<400> SEQUENCE: 30

Met Tyr Arg Met Gln Leu Leu Ser Cys Ile Ala Leu Ser Leu Ala Leu
1               5                   10                  15

Val Thr Asn Ser Ile Ser Arg Val Tyr Gln Cys Pro Glu His Ser Gln
                20                  25                  30

Leu Thr Thr Leu Gly Val Asp Gly Lys Glu Phe Pro Glu Val His Leu
            35                  40                  45

Gly Gln Trp Tyr Phe Ile Ala Gly Ala Ala Pro Thr Lys Glu Glu Leu
        50                  55                  60

Ala Asn Phe Asp Pro Val Asp Asn Ile Val Phe Asn Met Ala Ala Gly
65                  70                  75                  80

Ser Ala Pro Met Gln Leu His Leu Arg Ala Thr Ile Arg Met Lys Asp
                85                  90                  95

Gly Leu Cys Val Pro Arg Lys Trp Ile Tyr His Leu Thr Glu Gly Ser
            100                 105                 110

Thr Asp Leu Arg Thr Glu Gly Arg Pro Asp Met Lys Thr Glu Leu Phe
            115                 120                 125

Ser Ser Ser Cys Pro Gly Gly Ile Met Leu Asn Glu Thr Gly Gln Gly
        130                 135                 140

Tyr Gln Arg Phe Leu Leu Tyr Asn Arg Ser Pro His Pro Pro Glu Lys
145                 150                 155                 160

Cys Val Glu Glu Phe Lys Ser Leu Thr Ser Cys Leu Asp Ser Lys Ala
                165                 170                 175

Phe Leu Leu Thr Pro Arg Asn Gln Glu Ala Cys Glu Leu Ser Asn Asn
            180                 185                 190

Trp Ile Ser Ser Ala Ser Ser Ala Lys Thr Thr Pro Pro Ser Val Tyr
        195                 200                 205

Pro Leu Ala Pro Gly Ser Ala Ala Gln Thr Asn Ser Met Val Thr Leu
        210                 215                 220

Gly Cys Leu Val Lys Gly Tyr Phe Pro Glu Pro Val Thr Val Thr Trp
225                 230                 235                 240

Asn Ser Gly Ser Leu Ser Ser Gly Val His Thr Phe Pro Ala Val Leu
            245                 250                 255

Gln Ser Asp Leu Tyr Thr Leu Ser Ser Ser Val Thr Val Pro Ser Ser
            260                 265                 270

Thr Trp Pro Ser Glu Thr Val Thr Cys Asn Val Ala His Pro Ala Ser
        275                 280                 285

Ser Thr Lys Val Asp Lys Lys Ile Val Pro Arg Asp Cys Gly Cys Lys
        290                 295                 300

Pro Cys Ile Cys Thr Val Pro Glu Val Ser Ser Val Phe Ile Phe Pro
305                 310                 315                 320

Pro Lys Pro Lys Asp Val Leu Thr Ile Thr Leu Thr Pro Lys Val Thr
            325                 330                 335

Cys Val Val Val Asp Ile Ser Lys Asp Asp Pro Glu Val Gln Phe Ser
            340                 345                 350

Trp Phe Val Asp Asp Val Glu Val His Thr Ala Gln Thr Gln Pro Arg
            355                 360                 365

Glu Glu Gln Phe Asn Ser Thr Phe Arg Ser Val Ser Glu Leu Pro Ile
    370                 375                 380

Met His Gln Asp Trp Leu Asn Gly Lys Glu Phe Lys Cys Arg Val Asn

```
385              390              395              400

Ser Ala Ala Phe Pro Ala Pro Ile Glu Lys Thr Ile Ser Lys Thr Lys
            405              410              415

Gly Arg Pro Lys Ala Pro Gln Val Tyr Thr Ile Pro Pro Lys Glu
            420              425              430

Gln Met Ala Lys Asp Lys Val Ser Leu Thr Cys Met Ile Thr Asp Phe
            435              440              445

Phe Pro Glu Asp Ile Thr Val Glu Trp Gln Trp Asn Gly Gln Pro Ala
        450              455              460

Glu Asn Tyr Lys Asn Thr Gln Pro Ile Met Asp Thr Asp Gly Ser Tyr
465              470              475              480

Phe Val Tyr Ser Lys Leu Asn Val Gln Lys Ser Asn Trp Glu Ala Gly
                485              490              495

Asn Thr Phe Thr Cys Ser Val Leu His Glu Gly Leu His Asn His His
            500              505              510

Thr Glu Lys Ser Leu Ser His Ser Pro Gly Lys
            515              520

<210> SEQ ID NO 31
<211> LENGTH: 523
<212> TYPE: PRT
<213> ORGANISM: Artificial Sequence
<220> FEATURE:
<223> OTHER INFORMATION: Synthetic polypeptide

<400> SEQUENCE: 31

Met Tyr Arg Met Gln Leu Leu Ser Cys Ile Ala Leu Ser Leu Ala Leu
1               5               10              15

Val Thr Asn Ser Ile Ser Arg Val Tyr Gln Cys Pro Glu His Ser Gln
            20              25              30

Leu Thr Thr Leu Gly Val Asp Gly Lys Glu Phe Pro Glu Val His Leu
            35              40              45

Gly Gln Trp Tyr Phe Ile Ala Gly Ala Ala Pro Thr Lys Glu Glu Leu
        50              55              60

Ala Thr Phe Asp Pro Lys Asp Asn Ile Val Phe Asn Met Ala Ala Gly
65              70              75              80

Ser Ala Pro Met Gln Leu His Leu Arg Ala Thr Ile Arg Met Lys Asp
                85              90              95

Gly Leu Cys Val Pro Arg Lys Trp Ile Tyr His Leu Thr Glu Gly Ser
            100             105             110

Thr Asp Leu Arg Thr Glu Gly Arg Pro Asp Met Lys Thr Glu Leu Phe
            115             120             125

Ser Ser Ser Cys Pro Gly Gly Ile Met Leu Asn Glu Thr Gly Gln Gly
        130             135             140

Tyr Gln Arg Phe Leu Leu Tyr Asn Arg Ser Pro His Pro Pro Glu Lys
145             150             155             160

Cys Val Glu Glu Phe Lys Ser Leu Thr Ser Cys Leu Asp Ser Lys Ala
                165             170             175

Phe Leu Leu Thr Pro Arg Asn Gln Glu Ala Cys Glu Leu Ser Asn Asn
            180             185             190

Trp Ile Ser Ser Ala Ser Ser Ala Lys Thr Thr Pro Pro Ser Val Tyr
            195             200             205

Pro Leu Ala Pro Gly Ser Ala Ala Gln Thr Asn Ser Met Val Thr Leu
        210             215             220

Gly Cys Leu Val Lys Gly Tyr Phe Pro Glu Pro Val Thr Val Thr Trp
```

```
225             230             235             240

Asn Ser Gly Ser Leu Ser Ser Gly Val His Thr Phe Pro Ala Val Leu
            245             250             255

Gln Ser Asp Leu Tyr Thr Leu Ser Ser Ser Val Thr Val Pro Ser Ser
            260             265             270

Thr Trp Pro Ser Glu Thr Val Thr Cys Asn Val Ala His Pro Ala Ser
            275             280             285

Ser Thr Lys Val Asp Lys Lys Ile Val Pro Arg Asp Cys Gly Cys Lys
            290             295             300

Pro Cys Ile Cys Thr Val Pro Glu Val Ser Ser Val Phe Ile Phe Pro
305             310             315             320

Pro Lys Pro Lys Asp Val Leu Thr Ile Thr Leu Thr Pro Lys Val Thr
            325             330             335

Cys Val Val Val Asp Ile Ser Lys Asp Asp Pro Glu Val Gln Phe Ser
            340             345             350

Trp Phe Val Asp Asp Val Glu Val His Thr Ala Gln Thr Gln Pro Arg
            355             360             365

Glu Glu Gln Phe Asn Ser Thr Phe Arg Ser Val Ser Glu Leu Pro Ile
            370             375             380

Met His Gln Asp Trp Leu Asn Gly Lys Glu Phe Lys Cys Arg Val Asn
385             390             395             400

Ser Ala Ala Phe Pro Ala Pro Ile Glu Lys Thr Ile Ser Lys Thr Lys
            405             410             415

Gly Arg Pro Lys Ala Pro Gln Val Tyr Thr Ile Pro Pro Pro Lys Glu
            420             425             430

Gln Met Ala Lys Asp Lys Val Ser Leu Thr Cys Met Ile Thr Asp Phe
            435             440             445

Phe Pro Glu Asp Ile Thr Val Glu Trp Gln Trp Asn Gly Gln Pro Ala
            450             455             460

Glu Asn Tyr Lys Asn Thr Gln Pro Ile Met Asp Thr Asp Gly Ser Tyr
465             470             475             480

Phe Val Tyr Ser Lys Leu Asn Val Gln Lys Ser Asn Trp Glu Ala Gly
            485             490             495

Asn Thr Phe Thr Cys Ser Val Leu His Glu Gly Leu His Asn His His
            500             505             510

Thr Glu Lys Ser Leu Ser His Ser Pro Gly Lys
            515             520
```

<210> SEQ ID NO 32
<211> LENGTH: 523
<212> TYPE: PRT
<213> ORGANISM: Artificial Sequence
<220> FEATURE:
<223> OTHER INFORMATION: Synthetic polypeptide

<400> SEQUENCE: 32

```
Met Tyr Arg Met Gln Leu Leu Ser Cys Ile Ala Leu Ser Leu Ala Leu
1               5               10              15

Val Thr Asn Ser Ile Ser Arg Val Tyr Gln Cys Pro Glu His Ser Gln
            20              25              30

Leu Thr Thr Leu Gly Val Asp Gly Lys Glu Phe Pro Glu Val His Leu
            35              40              45

Gly Gln Trp Tyr Phe Ile Ala Gly Ala Ala Pro Thr Lys Glu Glu Leu
            50              55              60

Ala Thr Phe Asp Pro Asn Asp Asn Ile Val Phe Asn Met Ala Ala Gly
```

```
65                   70                   75                   80

Ser Ala Pro Met Gln Leu His Leu Arg Ala Thr Ile Arg Met Lys Asp
            85                   90                   95

Gly Leu Cys Val Pro Arg Lys Trp Ile Tyr His Leu Thr Glu Gly Ser
            100                  105                  110

Thr Asp Leu Arg Thr Glu Gly Arg Pro Asp Met Lys Thr Glu Leu Phe
            115                  120                  125

Ser Ser Ser Cys Pro Gly Gly Ile Met Leu Asn Glu Thr Gly Gln Gly
    130                  135                  140

Tyr Gln Arg Phe Leu Leu Tyr Asn Arg Ser Pro His Pro Pro Glu Lys
145                  150                  155                  160

Cys Val Glu Glu Phe Lys Ser Leu Thr Ser Cys Leu Asp Ser Lys Ala
                165                  170                  175

Phe Leu Leu Thr Pro Arg Asn Gln Glu Ala Cys Glu Leu Ser Asn Asn
                180                  185                  190

Trp Ile Ser Ser Ala Ser Ser Ala Lys Thr Thr Pro Pro Ser Val Tyr
            195                  200                  205

Pro Leu Ala Pro Gly Ser Ala Ala Gln Thr Asn Ser Met Val Thr Leu
    210                  215                  220

Gly Cys Leu Val Lys Gly Tyr Phe Pro Glu Pro Val Thr Val Thr Trp
225                  230                  235                  240

Asn Ser Gly Ser Leu Ser Ser Gly Val His Thr Phe Pro Ala Val Leu
                245                  250                  255

Gln Ser Asp Leu Tyr Thr Leu Ser Ser Ser Val Thr Val Pro Ser Ser
                260                  265                  270

Thr Trp Pro Ser Glu Thr Val Thr Cys Asn Val Ala His Pro Ala Ser
            275                  280                  285

Ser Thr Lys Val Asp Lys Lys Ile Val Pro Arg Asp Cys Gly Cys Lys
    290                  295                  300

Pro Cys Ile Cys Thr Val Pro Glu Val Ser Ser Val Phe Ile Phe Pro
305                  310                  315                  320

Pro Lys Pro Lys Asp Val Leu Thr Ile Thr Leu Thr Pro Lys Val Thr
                325                  330                  335

Cys Val Val Val Asp Ile Ser Lys Asp Asp Pro Glu Val Gln Phe Ser
                340                  345                  350

Trp Phe Val Asp Asp Val Glu Val His Thr Ala Gln Thr Gln Pro Arg
            355                  360                  365

Glu Glu Gln Phe Asn Ser Thr Phe Arg Ser Val Ser Glu Leu Pro Ile
    370                  375                  380

Met His Gln Asp Trp Leu Asn Gly Lys Glu Phe Lys Cys Arg Val Asn
385                  390                  395                  400

Ser Ala Ala Phe Pro Ala Pro Ile Glu Lys Thr Ile Ser Lys Thr Lys
                405                  410                  415

Gly Arg Pro Lys Ala Pro Gln Val Tyr Thr Ile Pro Pro Pro Lys Glu
                420                  425                  430

Gln Met Ala Lys Asp Lys Val Ser Leu Thr Cys Met Ile Thr Asp Phe
            435                  440                  445

Phe Pro Glu Asp Ile Thr Val Glu Trp Gln Trp Asn Gly Gln Pro Ala
    450                  455                  460

Glu Asn Tyr Lys Asn Thr Gln Pro Ile Met Asp Thr Asp Gly Ser Tyr
465                  470                  475                  480

Phe Val Tyr Ser Lys Leu Asn Val Gln Lys Ser Asn Trp Glu Ala Gly
                485                  490                  495
```

```
Asn Thr Phe Thr Cys Ser Val Leu His Glu Gly Leu His Asn His His
            500             505             510

Thr Glu Lys Ser Leu Ser His Ser Pro Gly Lys
        515             520

<210> SEQ ID NO 33
<211> LENGTH: 523
<212> TYPE: PRT
<213> ORGANISM: Artificial Sequence
<220> FEATURE:
<223> OTHER INFORMATION: Synthetic polypeptide

<400> SEQUENCE: 33

Met Tyr Arg Met Gln Leu Leu Ser Cys Ile Ala Leu Ser Leu Ala Leu
1               5               10              15

Val Thr Asn Ser Ile Ser Arg Val Tyr Gln Cys Pro Glu His Ser Gln
            20              25              30

Leu Thr Thr Leu Gly Val Asp Gly Lys Glu Phe Pro Glu Val His Leu
        35              40              45

Gly Gln Trp Tyr Phe Ile Ala Gly Ala Ala Pro Thr Lys Glu Glu Leu
    50              55              60

Ala Thr Phe Asp Pro Gln Asp Asn Ile Val Phe Asn Met Ala Ala Gly
65              70              75              80

Ser Ala Pro Met Gln Leu His Leu Arg Ala Thr Ile Arg Met Lys Asp
            85              90              95

Gly Leu Cys Val Pro Arg Lys Trp Ile Tyr His Leu Thr Glu Gly Ser
            100             105             110

Thr Asp Leu Arg Thr Glu Gly Arg Pro Asp Met Lys Thr Glu Leu Phe
        115             120             125

Ser Ser Ser Cys Pro Gly Gly Ile Met Leu Asn Glu Thr Gly Gln Gly
    130             135             140

Tyr Gln Arg Phe Leu Leu Tyr Asn Arg Ser Pro His Pro Pro Glu Lys
145             150             155             160

Cys Val Glu Glu Phe Lys Ser Leu Thr Ser Cys Leu Asp Ser Lys Ala
            165             170             175

Phe Leu Leu Thr Pro Arg Asn Gln Glu Ala Cys Glu Leu Ser Asn Asn
            180             185             190

Trp Ile Ser Ser Ala Ser Ser Ala Lys Thr Thr Pro Pro Ser Val Tyr
            195             200             205

Pro Leu Ala Pro Gly Ser Ala Ala Gln Thr Asn Ser Met Val Thr Leu
    210             215             220

Gly Cys Leu Val Lys Gly Tyr Phe Pro Glu Pro Val Thr Val Thr Trp
225             230             235             240

Asn Ser Gly Ser Leu Ser Ser Gly Val His Thr Phe Pro Ala Val Leu
            245             250             255

Gln Ser Asp Leu Tyr Thr Leu Ser Ser Ser Val Thr Val Pro Ser Ser
            260             265             270

Thr Trp Pro Ser Glu Thr Val Thr Cys Asn Val Ala His Pro Ala Ser
        275             280             285

Ser Thr Lys Val Asp Lys Lys Ile Val Pro Arg Asp Cys Gly Cys Lys
        290             295             300

Pro Cys Ile Cys Thr Val Pro Glu Val Ser Ser Val Phe Ile Phe Pro
305             310             315             320

Pro Lys Pro Lys Asp Val Leu Thr Ile Thr Leu Thr Pro Lys Val Thr
            325             330             335
```

```
Cys Val Val Val Asp Ile Ser Lys Asp Asp Pro Glu Val Gln Phe Ser
            340                 345                 350

Trp Phe Val Asp Asp Val Glu Val His Thr Ala Gln Thr Gln Pro Arg
            355                 360                 365

Glu Glu Gln Phe Asn Ser Thr Phe Arg Ser Val Ser Glu Leu Pro Ile
    370                 375                 380

Met His Gln Asp Trp Leu Asn Gly Lys Glu Phe Lys Cys Arg Val Asn
385                 390                 395                 400

Ser Ala Ala Phe Pro Ala Pro Ile Glu Lys Thr Ile Ser Lys Thr Lys
                405                 410                 415

Gly Arg Pro Lys Ala Pro Gln Val Tyr Thr Ile Pro Pro Pro Lys Glu
            420                 425                 430

Gln Met Ala Lys Asp Lys Val Ser Leu Thr Cys Met Ile Thr Asp Phe
            435                 440                 445

Phe Pro Glu Asp Ile Thr Val Glu Trp Gln Trp Asn Gly Gln Pro Ala
    450                 455                 460

Glu Asn Tyr Lys Asn Thr Gln Pro Ile Met Asp Thr Asp Gly Ser Tyr
465                 470                 475                 480

Phe Val Tyr Ser Lys Leu Asn Val Gln Lys Ser Asn Trp Glu Ala Gly
                485                 490                 495

Asn Thr Phe Thr Cys Ser Val Leu His Glu Gly Leu His Asn His His
            500                 505                 510

Thr Glu Lys Ser Leu Ser His Ser Pro Gly Lys
            515                 520

<210> SEQ ID NO 34
<211> LENGTH: 523
<212> TYPE: PRT
<213> ORGANISM: Artificial Sequence
<220> FEATURE:
<223> OTHER INFORMATION: Synthetic polypeptide

<400> SEQUENCE: 34

Met Tyr Arg Met Gln Leu Leu Ser Cys Ile Ala Leu Ser Leu Ala Leu
1               5                   10                  15

Val Thr Asn Ser Ile Ser Arg Val Tyr Gln Cys Pro Glu His Ser Gln
                20                  25                  30

Leu Thr Thr Leu Gly Val Asp Gly Lys Glu Phe Pro Glu Val His Leu
            35                  40                  45

Gly Gln Trp Tyr Phe Ile Ala Gly Ala Ala Pro Thr Lys Glu Glu Leu
    50                  55                  60

Ala Thr Phe Asp Pro Val Asp Asn Ile Val Phe Asn Met Ala Ala Gly
65                  70                  75                  80

Ser Ala Pro Met Gln Leu His Leu Arg Ala Thr Lys Arg Met Lys Asp
                85                  90                  95

Gly Leu Cys Val Pro Arg Lys Trp Ile Tyr His Leu Thr Glu Gly Ser
            100                 105                 110

Thr Asp Leu Arg Thr Glu Gly Arg Pro Asp Met Lys Thr Glu Leu Phe
            115                 120                 125

Ser Ser Ser Cys Pro Gly Gly Ile Met Leu Asn Glu Thr Gly Gln Gly
    130                 135                 140

Tyr Gln Arg Phe Leu Leu Tyr Asn Arg Ser Pro His Pro Pro Glu Lys
145                 150                 155                 160

Cys Val Glu Glu Phe Lys Ser Leu Thr Ser Cys Leu Asp Ser Lys Ala
                165                 170                 175
```

```
Phe Leu Leu Thr Pro Arg Asn Gln Glu Ala Cys Glu Leu Ser Asn Asn
            180                 185                 190

Trp Ile Ser Ser Ala Ser Ser Ala Lys Thr Thr Pro Pro Ser Val Tyr
            195                 200                 205

Pro Leu Ala Pro Gly Ser Ala Ala Gln Thr Asn Ser Met Val Thr Leu
    210                 215                 220

Gly Cys Leu Val Lys Gly Tyr Phe Pro Glu Pro Val Thr Val Thr Trp
225                 230                 235                 240

Asn Ser Gly Ser Leu Ser Ser Gly Val His Thr Phe Pro Ala Val Leu
                245                 250                 255

Gln Ser Asp Leu Tyr Thr Leu Ser Ser Ser Val Thr Val Pro Ser Ser
            260                 265                 270

Thr Trp Pro Ser Glu Thr Val Thr Cys Asn Val Ala His Pro Ala Ser
        275                 280                 285

Ser Thr Lys Val Asp Lys Lys Ile Val Pro Arg Asp Cys Gly Cys Lys
        290                 295                 300

Pro Cys Ile Cys Thr Val Pro Glu Val Ser Ser Val Phe Ile Phe Pro
305                 310                 315                 320

Pro Lys Pro Lys Asp Val Leu Thr Ile Thr Leu Thr Pro Lys Val Thr
                325                 330                 335

Cys Val Val Val Asp Ile Ser Lys Asp Asp Pro Glu Val Gln Phe Ser
                340                 345                 350

Trp Phe Val Asp Asp Val Glu Val His Thr Ala Gln Thr Gln Pro Arg
            355                 360                 365

Glu Glu Gln Phe Asn Ser Thr Phe Arg Ser Val Ser Glu Leu Pro Ile
    370                 375                 380

Met His Gln Asp Trp Leu Asn Gly Lys Glu Phe Lys Cys Arg Val Asn
385                 390                 395                 400

Ser Ala Ala Phe Pro Ala Pro Ile Glu Lys Thr Ile Ser Lys Thr Lys
                405                 410                 415

Gly Arg Pro Lys Ala Pro Gln Val Tyr Thr Ile Pro Pro Pro Lys Glu
                420                 425                 430

Gln Met Ala Lys Asp Lys Val Ser Leu Thr Cys Met Ile Thr Asp Phe
            435                 440                 445

Phe Pro Glu Asp Ile Thr Val Glu Trp Gln Trp Asn Gly Gln Pro Ala
    450                 455                 460

Glu Asn Tyr Lys Asn Thr Gln Pro Ile Met Asp Thr Asp Gly Ser Tyr
465                 470                 475                 480

Phe Val Tyr Ser Lys Leu Asn Val Gln Lys Ser Asn Trp Glu Ala Gly
                485                 490                 495

Asn Thr Phe Thr Cys Ser Val Leu His Glu Gly Leu His Asn His His
            500                 505                 510

Thr Glu Lys Ser Leu Ser His Ser Pro Gly Lys
        515                 520
```

<210> SEQ ID NO 35
<211> LENGTH: 523
<212> TYPE: PRT
<213> ORGANISM: Artificial Sequence
<220> FEATURE:
<223> OTHER INFORMATION: Synthetic polypeptide

<400> SEQUENCE: 35

```
Met Tyr Arg Met Gln Leu Leu Ser Cys Ile Ala Leu Ser Leu Ala Leu
1               5                   10                  15
```

```
Val Thr Asn Ser Ile Ser Arg Val Tyr Gln Cys Pro Glu His Ser Gln
            20              25              30

Leu Thr Thr Leu Gly Val Asp Gly Lys Glu Phe Pro Glu Val His Leu
            35              40              45

Gly Gln Trp Tyr Phe Ile Ala Gly Ala Ala Pro Thr Lys Glu Glu Leu
    50              55              60

Ala Thr Phe Asp Pro Val Asp Asn Ile Val Phe Asn Met Ala Ala Gly
65              70              75              80

Ser Ala Pro Met Gln Leu His Leu Arg Ala Thr Asn Arg Met Lys Asp
                85              90              95

Gly Leu Cys Val Pro Arg Lys Trp Ile Tyr His Leu Thr Glu Gly Ser
            100             105             110

Thr Asp Leu Arg Thr Glu Gly Arg Pro Asp Met Lys Thr Glu Leu Phe
            115             120             125

Ser Ser Ser Cys Pro Gly Gly Ile Met Leu Asn Glu Thr Gly Gln Gly
    130             135             140

Tyr Gln Arg Phe Leu Leu Tyr Asn Arg Ser Pro His Pro Pro Glu Lys
145             150             155             160

Cys Val Glu Glu Phe Lys Ser Leu Thr Ser Cys Leu Asp Ser Lys Ala
                165             170             175

Phe Leu Leu Thr Pro Arg Asn Gln Glu Ala Cys Glu Leu Ser Asn Asn
            180             185             190

Trp Ile Ser Ser Ala Ser Ser Ala Lys Thr Thr Pro Pro Ser Val Tyr
            195             200             205

Pro Leu Ala Pro Gly Ser Ala Ala Gln Thr Asn Ser Met Val Thr Leu
    210             215             220

Gly Cys Leu Val Lys Gly Tyr Phe Pro Glu Pro Val Thr Val Thr Trp
225             230             235             240

Asn Ser Gly Ser Leu Ser Ser Gly Val His Thr Phe Pro Ala Val Leu
            245             250             255

Gln Ser Asp Leu Tyr Thr Leu Ser Ser Ser Val Thr Val Pro Ser Ser
            260             265             270

Thr Trp Pro Ser Glu Thr Val Thr Cys Asn Val Ala His Pro Ala Ser
            275             280             285

Ser Thr Lys Val Asp Lys Lys Ile Val Pro Arg Asp Cys Gly Cys Lys
    290             295             300

Pro Cys Ile Cys Thr Val Pro Glu Val Ser Ser Val Phe Ile Phe Pro
305             310             315             320

Pro Lys Pro Lys Asp Val Leu Thr Ile Thr Leu Thr Pro Lys Val Thr
            325             330             335

Cys Val Val Val Asp Ile Ser Lys Asp Asp Pro Glu Val Gln Phe Ser
            340             345             350

Trp Phe Val Asp Asp Val Glu Val His Thr Ala Gln Thr Gln Pro Arg
            355             360             365

Glu Glu Gln Phe Asn Ser Thr Phe Arg Ser Val Ser Glu Leu Pro Ile
    370             375             380

Met His Gln Asp Trp Leu Asn Gly Lys Glu Phe Lys Cys Arg Val Asn
385             390             395             400

Ser Ala Ala Phe Pro Ala Pro Ile Glu Lys Thr Ile Ser Lys Thr Lys
            405             410             415

Gly Arg Pro Lys Ala Pro Gln Val Tyr Thr Ile Pro Pro Pro Lys Glu
            420             425             430
```

-continued

```
Gln Met Ala Lys Asp Lys Val Ser Leu Thr Cys Met Ile Thr Asp Phe
        435                 440                 445

Phe Pro Glu Asp Ile Thr Val Glu Trp Gln Trp Asn Gly Gln Pro Ala
        450                 455                 460

Glu Asn Tyr Lys Asn Thr Gln Pro Ile Met Asp Thr Asp Gly Ser Tyr
465                 470                 475                 480

Phe Val Tyr Ser Lys Leu Asn Val Gln Lys Ser Asn Trp Glu Ala Gly
                485                 490                 495

Asn Thr Phe Thr Cys Ser Val Leu His Glu Gly Leu His Asn His His
                500                 505                 510

Thr Glu Lys Ser Leu Ser His Ser Pro Gly Lys
        515                 520
```

```
<210> SEQ ID NO 36
<211> LENGTH: 523
<212> TYPE: PRT
<213> ORGANISM: Artificial Sequence
<220> FEATURE:
<223> OTHER INFORMATION: Synthetic polypeptide

<400> SEQUENCE: 36
```

```
Met Tyr Arg Met Gln Leu Leu Ser Cys Ile Ala Leu Ser Leu Ala Leu
1               5                   10                  15

Val Thr Asn Ser Ile Ser Arg Val Tyr Gln Cys Pro Glu His Ser Gln
                20                  25                  30

Leu Thr Thr Leu Gly Val Asp Gly Lys Glu Phe Pro Glu Val His Leu
        35                  40                  45

Gly Gln Trp Tyr Phe Ile Ala Gly Ala Ala Pro Thr Lys Glu Glu Leu
        50                  55                  60

Ala Thr Phe Asp Pro Val Asp Asn Ile Val Phe Asn Met Ala Ala Gly
65                  70                  75                  80

Ser Ala Pro Met Gln Leu His Leu Arg Ala Thr Ile Arg Tyr Lys Asp
                85                  90                  95

Gly Leu Cys Val Pro Arg Lys Trp Ile Tyr His Leu Thr Glu Gly Ser
                100                 105                 110

Thr Asp Leu Arg Thr Glu Gly Arg Pro Asp Met Lys Thr Glu Leu Phe
        115                 120                 125

Ser Ser Ser Cys Pro Gly Gly Ile Met Leu Asn Glu Thr Gly Gln Gly
        130                 135                 140

Tyr Gln Arg Phe Leu Leu Tyr Asn Arg Ser Pro His Pro Pro Glu Lys
145                 150                 155                 160

Cys Val Glu Glu Phe Lys Ser Leu Thr Ser Cys Leu Asp Ser Lys Ala
                165                 170                 175

Phe Leu Leu Thr Pro Arg Asn Gln Glu Ala Cys Glu Leu Ser Asn Asn
                180                 185                 190

Trp Ile Ser Ser Ala Ser Ser Ala Lys Thr Thr Pro Pro Ser Val Tyr
        195                 200                 205

Pro Leu Ala Pro Gly Ser Ala Ala Gln Thr Asn Ser Met Val Thr Leu
        210                 215                 220

Gly Cys Leu Val Lys Gly Tyr Phe Pro Glu Pro Val Thr Val Thr Trp
225                 230                 235                 240

Asn Ser Gly Ser Leu Ser Ser Gly Val His Thr Phe Pro Ala Val Leu
                245                 250                 255

Gln Ser Asp Leu Tyr Thr Leu Ser Ser Ser Val Thr Val Pro Ser Ser
        260                 265                 270
```

```
Thr Trp Pro Ser Glu Thr Val Thr Cys Asn Val Ala His Pro Ala Ser
        275             280             285

Ser Thr Lys Val Asp Lys Lys Ile Val Pro Arg Asp Cys Gly Cys Lys
        290             295             300

Pro Cys Ile Cys Thr Val Pro Glu Val Ser Ser Val Phe Ile Phe Pro
305             310             315             320

Pro Lys Pro Lys Asp Val Leu Thr Ile Thr Leu Thr Pro Lys Val Thr
            325             330             335

Cys Val Val Val Asp Ile Ser Lys Asp Asp Pro Glu Val Gln Phe Ser
            340             345             350

Trp Phe Val Asp Asp Val Glu Val His Thr Ala Gln Thr Gln Pro Arg
        355             360             365

Glu Glu Gln Phe Asn Ser Thr Phe Arg Ser Val Ser Glu Leu Pro Ile
        370             375             380

Met His Gln Asp Trp Leu Asn Gly Lys Glu Phe Lys Cys Arg Val Asn
385             390             395             400

Ser Ala Ala Phe Pro Ala Pro Ile Glu Lys Thr Ile Ser Lys Thr Lys
            405             410             415

Gly Arg Pro Lys Ala Pro Gln Val Tyr Thr Ile Pro Pro Lys Glu
            420             425             430

Gln Met Ala Lys Asp Lys Val Ser Leu Thr Cys Met Ile Thr Asp Phe
            435             440             445

Phe Pro Glu Asp Ile Thr Val Glu Trp Gln Trp Asn Gly Gln Pro Ala
        450             455             460

Glu Asn Tyr Lys Asn Thr Gln Pro Ile Met Asp Thr Asp Gly Ser Tyr
465             470             475             480

Phe Val Tyr Ser Lys Leu Asn Val Gln Lys Ser Asn Trp Glu Ala Gly
            485             490             495

Asn Thr Phe Thr Cys Ser Val Leu His Glu Gly Leu His Asn His His
            500             505             510

Thr Glu Lys Ser Leu Ser His Ser Pro Gly Lys
            515             520
```

```
<210> SEQ ID NO 37
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 37
```

```
Met Tyr Arg Met Gln Leu Leu Ser Cys Ile Ala Leu Ser Leu Ala Leu
1               5               10              15

Val Thr Asn Ser Asn Gln Cys Pro Glu His Ser Gln Leu Thr Ala Leu
            20              25              30

Gly Met Asp Asp Thr Glu Thr Pro Glu Pro His Leu Gly Leu Trp Tyr
        35              40              45

Phe Ile Ala Gly Ala Ala Pro Thr Thr Glu Glu Leu Ala Asn Phe Asp
        50              55              60

Pro Val Asp Asn Ile Val Phe Asn Met Ala Ala Gly Ser Ala Pro Arg
65              70              75              80

Gln Leu Gln Leu Arg Ala Thr Ile Arg Thr Lys Ser Gly Val Cys Val
            85              90              95

Pro Arg Lys Trp Thr Tyr Arg Leu Thr Glu Gly Lys Gly Asn Met Glu
            100             105             110
```

-continued

```
Leu Arg Thr Glu Gly Arg Pro Asp Met Lys Thr Asp Leu Phe Ser Ser
        115                 120                 125

Ser Cys Pro Gly Gly Ile Met Leu Lys Glu Thr Gly Gln Gly Tyr Gln
        130                 135                 140

Arg Phe Leu Leu Tyr Asn Arg Ser Pro His Pro Pro Glu Lys Cys Val
145                 150                 155                 160

Glu Glu Phe Lys Ser Leu Thr Ser Cys Leu Asp Phe Lys Ala Phe Leu
                165                 170                 175

Val Thr Pro Arg Asn Gln Glu Ala Cys Pro Leu Ser Ser Lys Trp Ile
                180                 185                 190

Ser Ser Ala Ser Ser Ala Lys Thr Thr Pro Pro Ser Val Tyr Pro Leu
                195                 200                 205

Ala Pro Gly Ser Ala Ala Gln Thr Asn Ser Met Val Thr Leu Gly Cys
        210                 215                 220

Leu Val Lys Gly Tyr Phe Pro Glu Pro Val Thr Val Thr Trp Asn Ser
225                 230                 235                 240

Gly Ser Leu Ser Ser Gly Val His Thr Phe Pro Ala Val Leu Gln Ser
                245                 250                 255

Asp Leu Tyr Thr Leu Ser Ser Ser Val Thr Val Pro Ser Ser Thr Trp
                260                 265                 270

Pro Ser Glu Thr Val Thr Cys Asn Val Ala His Pro Ala Ser Ser Thr
        275                 280                 285

Lys Val Asp Lys Lys Ile Val Pro Arg Asp Cys Gly Cys Lys Pro Cys
        290                 295                 300

Ile Cys Thr Val Pro Glu Val Ser Ser Val Phe Ile Phe Pro Pro Lys
305                 310                 315                 320

Pro Lys Asp Val Leu Thr Ile Thr Leu Thr Pro Lys Val Thr Cys Val
                325                 330                 335

Val Val Asp Ile Ser Lys Asp Asp Pro Glu Val Gln Phe Ser Trp Phe
                340                 345                 350

Val Asp Asp Val Glu Val His Thr Ala Gln Thr Gln Pro Arg Glu Glu
                355                 360                 365

Gln Phe Asn Ser Thr Phe Arg Ser Val Ser Glu Leu Pro Ile Met His
        370                 375                 380

Gln Asp Trp Leu Asn Gly Lys Glu Phe Lys Cys Arg Val Asn Ser Ala
385                 390                 395                 400

Ala Phe Pro Ala Pro Ile Glu Lys Thr Ile Ser Lys Thr Lys Gly Arg
                405                 410                 415

Pro Lys Ala Pro Gln Val Tyr Thr Ile Pro Pro Pro Lys Glu Gln Met
                420                 425                 430

Ala Lys Asp Lys Val Ser Leu Thr Cys Met Ile Thr Asp Phe Phe Pro
        435                 440                 445

Glu Asp Ile Thr Val Glu Trp Gln Trp Asn Gly Gln Pro Ala Glu Asn
        450                 455                 460

Tyr Lys Asn Thr Gln Pro Ile Met Asp Thr Asp Gly Ser Tyr Phe Val
465                 470                 475                 480

Tyr Ser Lys Leu Asn Val Gln Lys Ser Asn Trp Glu Ala Gly Asn Thr
                485                 490                 495

Phe Thr Cys Ser Val Leu His Glu Gly Leu His Asn His His Thr Glu
                500                 505                 510

Lys Ser Leu Ser His Ser Pro Gly Lys
        515                 520
```

```
<210> SEQ ID NO 38
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 38

Met Tyr Arg Met Gln Leu Leu Ser Cys Ile Ala Leu Ser Leu Ala Leu
1               5                   10                  15

Val Thr Asn Ser Asn Gln Cys Pro Glu His Ser Gln Leu Thr Ala Leu
            20                  25                  30

Gly Met Asp Asp Thr Glu Thr Pro Glu Pro His Leu Gly Leu Trp Tyr
        35                  40                  45

Phe Ile Ala Gly Ala Ala Pro Thr Thr Glu Glu Leu Ala Thr Phe Asp
    50                  55                  60

Pro Lys Asp Asn Ile Val Phe Asn Met Ala Ala Gly Ser Ala Pro Arg
65                  70                  75                  80

Gln Leu Gln Leu Arg Ala Thr Ile Arg Thr Lys Ser Gly Val Cys Val
                85                  90                  95

Pro Arg Lys Trp Thr Tyr Arg Leu Thr Glu Gly Lys Gly Asn Met Glu
            100                 105                 110

Leu Arg Thr Glu Gly Arg Pro Asp Met Lys Thr Asp Leu Phe Ser Ser
        115                 120                 125

Ser Cys Pro Gly Gly Ile Met Leu Lys Glu Thr Gly Gln Gly Tyr Gln
    130                 135                 140

Arg Phe Leu Leu Tyr Asn Arg Ser Pro His Pro Pro Glu Lys Cys Val
145                 150                 155                 160

Glu Glu Phe Lys Ser Leu Thr Ser Cys Leu Asp Phe Lys Ala Phe Leu
                165                 170                 175

Val Thr Pro Arg Asn Gln Glu Ala Cys Pro Leu Ser Ser Lys Trp Ile
            180                 185                 190

Ser Ser Ala Ser Ser Ala Lys Thr Thr Pro Pro Ser Val Tyr Pro Leu
        195                 200                 205

Ala Pro Gly Ser Ala Ala Gln Thr Asn Ser Met Val Thr Leu Gly Cys
    210                 215                 220

Leu Val Lys Gly Tyr Phe Pro Glu Pro Val Thr Val Thr Trp Asn Ser
225                 230                 235                 240

Gly Ser Leu Ser Ser Gly Val His Thr Phe Pro Ala Val Leu Gln Ser
                245                 250                 255

Asp Leu Tyr Thr Leu Ser Ser Ser Val Thr Val Pro Ser Ser Thr Trp
            260                 265                 270

Pro Ser Glu Thr Val Thr Cys Asn Val Ala His Pro Ala Ser Ser Thr
        275                 280                 285

Lys Val Asp Lys Lys Ile Val Pro Arg Asp Cys Gly Cys Lys Pro Cys
    290                 295                 300

Ile Cys Thr Val Pro Glu Val Ser Ser Val Phe Ile Phe Pro Pro Lys
305                 310                 315                 320

Pro Lys Asp Val Leu Thr Ile Thr Leu Thr Pro Lys Val Thr Cys Val
                325                 330                 335

Val Val Asp Ile Ser Lys Asp Asp Pro Glu Val Gln Phe Ser Trp Phe
            340                 345                 350

Val Asp Asp Val Glu Val His Thr Ala Gln Thr Gln Pro Arg Glu Glu
        355                 360                 365

Gln Phe Asn Ser Thr Phe Arg Ser Val Ser Glu Leu Pro Ile Met His
```

-continued

```
            370              375              380

Gln Asp Trp Leu Asn Gly Lys Glu Phe Lys Cys Arg Val Asn Ser Ala
385              390              395              400

Ala Phe Pro Ala Pro Ile Glu Lys Thr Ile Ser Lys Thr Lys Gly Arg
                405              410              415

Pro Lys Ala Pro Gln Val Tyr Thr Ile Pro Pro Pro Lys Glu Gln Met
                420              425              430

Ala Lys Asp Lys Val Ser Leu Thr Cys Met Ile Thr Asp Phe Phe Pro
                435              440              445

Glu Asp Ile Thr Val Glu Trp Gln Trp Asn Gly Gln Pro Ala Glu Asn
        450              455              460

Tyr Lys Asn Thr Gln Pro Ile Met Asp Thr Asp Gly Ser Tyr Phe Val
465              470              475              480

Tyr Ser Lys Leu Asn Val Gln Lys Ser Asn Trp Glu Ala Gly Asn Thr
                485              490              495

Phe Thr Cys Ser Val Leu His Glu Gly Leu His Asn His His Thr Glu
                500              505              510

Lys Ser Leu Ser His Ser Pro Gly Lys
            515              520
```

```
<210> SEQ ID NO 39
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 39

Met Tyr Arg Met Gln Leu Leu Ser Cys Ile Ala Leu Ser Leu Ala Leu
1               5               10               15

Val Thr Asn Ser Asn Gln Cys Pro Glu His Ser Gln Leu Thr Ala Leu
                20              25              30

Gly Met Asp Asp Thr Glu Thr Pro Glu Pro His Leu Gly Leu Trp Tyr
            35              40              45

Phe Ile Ala Gly Ala Ala Pro Thr Thr Glu Glu Leu Ala Thr Phe Asp
        50              55              60

Pro Asn Asp Asn Ile Val Phe Asn Met Ala Ala Gly Ser Ala Pro Arg
65              70              75              80

Gln Leu Gln Leu Arg Ala Thr Ile Arg Thr Lys Ser Gly Val Cys Val
                85              90              95

Pro Arg Lys Trp Thr Tyr Arg Leu Thr Glu Gly Lys Gly Asn Met Glu
            100             105             110

Leu Arg Thr Glu Gly Arg Pro Asp Met Lys Thr Asp Leu Phe Ser Ser
            115             120             125

Ser Cys Pro Gly Gly Ile Met Leu Lys Glu Thr Gly Gln Gly Tyr Gln
    130             135             140

Arg Phe Leu Leu Tyr Asn Arg Ser Pro His Pro Pro Glu Lys Cys Val
145             150             155             160

Glu Glu Phe Lys Ser Leu Thr Ser Cys Leu Asp Phe Lys Ala Phe Leu
                165             170             175

Val Thr Pro Arg Asn Gln Glu Ala Cys Pro Leu Ser Ser Lys Trp Ile
            180             185             190

Ser Ser Ala Ser Ser Ala Lys Thr Thr Pro Pro Ser Val Tyr Pro Leu
            195             200             205

Ala Pro Gly Ser Ala Ala Gln Thr Asn Ser Met Val Thr Leu Gly Cys
```

-continued

```
      210              215              220

Leu Val Lys Gly Tyr Phe Pro Glu Pro Val Thr Val Thr Trp Asn Ser
225                  230                  235                  240

Gly Ser Leu Ser Ser Gly Val His Thr Phe Pro Ala Val Leu Gln Ser
                 245                  250                  255

Asp Leu Tyr Thr Leu Ser Ser Ser Val Thr Val Pro Ser Ser Thr Trp
                 260                  265                  270

Pro Ser Glu Thr Val Thr Cys Asn Val Ala His Pro Ala Ser Ser Thr
                 275                  280                  285

Lys Val Asp Lys Lys Ile Val Pro Arg Asp Cys Gly Cys Lys Pro Cys
                 290                  295                  300

Ile Cys Thr Val Pro Glu Val Ser Ser Val Phe Ile Phe Pro Pro Lys
305                  310                  315                  320

Pro Lys Asp Val Leu Thr Ile Thr Leu Thr Pro Lys Val Thr Cys Val
                 325                  330                  335

Val Val Asp Ile Ser Lys Asp Asp Pro Glu Val Gln Phe Ser Trp Phe
                 340                  345                  350

Val Asp Asp Val Glu Val His Thr Ala Gln Thr Gln Pro Arg Glu Glu
                 355                  360                  365

Gln Phe Asn Ser Thr Phe Arg Ser Val Ser Glu Leu Pro Ile Met His
                 370                  375                  380

Gln Asp Trp Leu Asn Gly Lys Glu Phe Lys Cys Arg Val Asn Ser Ala
385                  390                  395                  400

Ala Phe Pro Ala Pro Ile Glu Lys Thr Ile Ser Lys Thr Lys Gly Arg
                 405                  410                  415

Pro Lys Ala Pro Gln Val Tyr Thr Ile Pro Pro Pro Lys Glu Gln Met
                 420                  425                  430

Ala Lys Asp Lys Val Ser Leu Thr Cys Met Ile Thr Asp Phe Phe Pro
                 435                  440                  445

Glu Asp Ile Thr Val Glu Trp Gln Trp Asn Gly Gln Pro Ala Glu Asn
                 450                  455                  460

Tyr Lys Asn Thr Gln Pro Ile Met Asp Thr Asp Gly Ser Tyr Phe Val
465                  470                  475                  480

Tyr Ser Lys Leu Asn Val Gln Lys Ser Asn Trp Glu Ala Gly Asn Thr
                 485                  490                  495

Phe Thr Cys Ser Val Leu His Glu Gly Leu His Asn His His Thr Glu
                 500                  505                  510

Lys Ser Leu Ser His Ser Pro Gly Lys
                 515                  520
```

```
<210> SEQ ID NO 40
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 40

Met Tyr Arg Met Gln Leu Leu Ser Cys Ile Ala Leu Ser Leu Ala Leu
1                5                  10                  15

Val Thr Asn Ser Asn Gln Cys Pro Glu His Ser Gln Leu Thr Ala Leu
                 20                  25                  30

Gly Met Asp Asp Thr Glu Thr Pro Glu Pro His Leu Gly Leu Trp Tyr
                 35                  40                  45

Phe Ile Ala Gly Ala Ala Pro Thr Thr Glu Glu Leu Ala Thr Phe Asp
```

```
        50                  55                  60

Pro Gln Asp Asn Ile Val Phe Asn Met Ala Ala Gly Ser Ala Pro Arg
65                  70                  75                  80

Gln Leu Gln Leu Arg Ala Thr Ile Arg Thr Lys Ser Gly Val Cys Val
            85                  90                  95

Pro Arg Lys Trp Thr Tyr Arg Leu Thr Glu Gly Lys Gly Asn Met Glu
            100                 105                 110

Leu Arg Thr Glu Gly Arg Pro Asp Met Lys Thr Asp Leu Phe Ser Ser
        115                 120                 125

Ser Cys Pro Gly Gly Ile Met Leu Lys Glu Thr Gly Gln Gly Tyr Gln
        130                 135                 140

Arg Phe Leu Leu Tyr Asn Arg Ser Pro His Pro Pro Glu Lys Cys Val
145                 150                 155                 160

Glu Glu Phe Lys Ser Leu Thr Ser Cys Leu Asp Phe Lys Ala Phe Leu
                165                 170                 175

Val Thr Pro Arg Asn Gln Glu Ala Cys Pro Leu Ser Ser Lys Trp Ile
                180                 185                 190

Ser Ser Ala Ser Ser Ala Lys Thr Thr Pro Pro Ser Val Tyr Pro Leu
                195                 200                 205

Ala Pro Gly Ser Ala Ala Gln Thr Asn Ser Met Val Thr Leu Gly Cys
        210                 215                 220

Leu Val Lys Gly Tyr Phe Pro Glu Pro Val Thr Val Thr Trp Asn Ser
225                 230                 235                 240

Gly Ser Leu Ser Ser Gly Val His Thr Phe Pro Ala Val Leu Gln Ser
                245                 250                 255

Asp Leu Tyr Thr Leu Ser Ser Ser Val Thr Val Pro Ser Ser Thr Trp
                260                 265                 270

Pro Ser Glu Thr Val Thr Cys Asn Val Ala His Pro Ala Ser Ser Thr
            275                 280                 285

Lys Val Asp Lys Lys Ile Val Pro Arg Asp Cys Gly Cys Lys Pro Cys
        290                 295                 300

Ile Cys Thr Val Pro Glu Val Ser Ser Val Phe Ile Phe Pro Pro Lys
305                 310                 315                 320

Pro Lys Asp Val Leu Thr Ile Thr Leu Thr Pro Lys Val Thr Cys Val
                325                 330                 335

Val Val Asp Ile Ser Lys Asp Asp Pro Glu Val Gln Phe Ser Trp Phe
                340                 345                 350

Val Asp Asp Val Glu Val His Thr Ala Gln Thr Gln Pro Arg Glu Glu
            355                 360                 365

Gln Phe Asn Ser Thr Phe Arg Ser Val Ser Glu Leu Pro Ile Met His
    370                 375                 380

Gln Asp Trp Leu Asn Gly Lys Glu Phe Lys Cys Arg Val Asn Ser Ala
385                 390                 395                 400

Ala Phe Pro Ala Pro Ile Glu Lys Thr Ile Ser Lys Thr Lys Gly Arg
                405                 410                 415

Pro Lys Ala Pro Gln Val Tyr Thr Ile Pro Pro Pro Lys Glu Gln Met
            420                 425                 430

Ala Lys Asp Lys Val Ser Leu Thr Cys Met Ile Thr Asp Phe Phe Pro
        435                 440                 445

Glu Asp Ile Thr Val Glu Trp Gln Trp Asn Gly Gln Pro Ala Glu Asn
    450                 455                 460

Tyr Lys Asn Thr Gln Pro Ile Met Asp Thr Asp Gly Ser Tyr Phe Val
465                 470                 475                 480
```

Tyr Ser Lys Leu Asn Val Gln Lys Ser Asn Trp Glu Ala Gly Asn Thr
                485             490                 495

Phe Thr Cys Ser Val Leu His Glu Gly Leu His Asn His His Thr Glu
            500                 505                 510

Lys Ser Leu Ser His Ser Pro Gly Lys
        515             520

<210> SEQ ID NO 41
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 41

Met Tyr Arg Met Gln Leu Leu Ser Cys Ile Ala Leu Ser Leu Ala Leu
1               5                   10                  15

Val Thr Asn Ser Asn Gln Cys Pro Glu His Ser Gln Leu Thr Ala Leu
            20                  25                  30

Gly Met Asp Asp Thr Glu Thr Pro Glu Pro His Leu Gly Leu Trp Tyr
        35                  40                  45

Phe Ile Ala Gly Ala Ala Pro Thr Thr Glu Glu Leu Ala Thr Phe Asp
    50                  55                  60

Pro Val Asp Asn Ile Val Phe Asn Met Ala Ala Gly Ser Ala Pro Arg
65                  70                  75                  80

Gln Leu Gln Leu Arg Ala Thr Lys Arg Thr Lys Ser Gly Val Cys Val
                85                  90                  95

Pro Arg Lys Trp Thr Tyr Arg Leu Thr Glu Gly Lys Gly Asn Met Glu
            100                 105                 110

Leu Arg Thr Glu Gly Arg Pro Asp Met Lys Thr Asp Leu Phe Ser Ser
        115                 120                 125

Ser Cys Pro Gly Gly Ile Met Leu Lys Glu Thr Gly Gln Gly Tyr Gln
    130                 135                 140

Arg Phe Leu Leu Tyr Asn Arg Ser Pro His Pro Pro Glu Lys Cys Val
145                 150                 155                 160

Glu Glu Phe Lys Ser Leu Thr Ser Cys Leu Asp Phe Lys Ala Phe Leu
            165                 170                 175

Val Thr Pro Arg Asn Gln Glu Ala Cys Pro Leu Ser Ser Lys Trp Ile
            180                 185                 190

Ser Ser Ala Ser Ser Ala Lys Thr Thr Pro Pro Ser Val Tyr Pro Leu
        195                 200                 205

Ala Pro Gly Ser Ala Ala Gln Thr Asn Ser Met Val Thr Leu Gly Cys
    210                 215                 220

Leu Val Lys Gly Tyr Phe Pro Glu Pro Val Thr Val Thr Trp Asn Ser
225                 230                 235                 240

Gly Ser Leu Ser Ser Gly Val His Thr Phe Pro Ala Val Leu Gln Ser
            245                 250                 255

Asp Leu Tyr Thr Leu Ser Ser Ser Val Thr Val Pro Ser Ser Thr Trp
            260                 265                 270

Pro Ser Glu Thr Val Thr Cys Asn Val Ala His Pro Ala Ser Ser Thr
        275                 280                 285

Lys Val Asp Lys Lys Ile Val Pro Arg Asp Cys Gly Cys Lys Pro Cys
    290                 295                 300

Ile Cys Thr Val Pro Glu Val Ser Ser Val Phe Ile Phe Pro Pro Lys
305                 310                 315                 320

-continued

```
Pro Lys Asp Val Leu Thr Ile Thr Leu Thr Pro Lys Val Thr Cys Val
            325                 330                 335

Val Val Asp Ile Ser Lys Asp Asp Pro Glu Val Gln Phe Ser Trp Phe
            340                 345                 350

Val Asp Asp Val Glu Val His Thr Ala Gln Thr Gln Pro Arg Glu Glu
            355                 360                 365

Gln Phe Asn Ser Thr Phe Arg Ser Val Ser Glu Leu Pro Ile Met His
        370                 375                 380

Gln Asp Trp Leu Asn Gly Lys Glu Phe Lys Cys Arg Val Asn Ser Ala
385                 390                 395                 400

Ala Phe Pro Ala Pro Ile Glu Lys Thr Ile Ser Lys Thr Lys Gly Arg
                405                 410                 415

Pro Lys Ala Pro Gln Val Tyr Thr Ile Pro Pro Pro Lys Glu Gln Met
            420                 425                 430

Ala Lys Asp Lys Val Ser Leu Thr Cys Met Ile Thr Asp Phe Phe Pro
            435                 440                 445

Glu Asp Ile Thr Val Glu Trp Gln Trp Asn Gly Gln Pro Ala Glu Asn
        450                 455                 460

Tyr Lys Asn Thr Gln Pro Ile Met Asp Thr Asp Gly Ser Tyr Phe Val
465                 470                 475                 480

Tyr Ser Lys Leu Asn Val Gln Lys Ser Asn Trp Glu Ala Gly Asn Thr
                485                 490                 495

Phe Thr Cys Ser Val Leu His Glu Gly Leu His Asn His His Thr Glu
            500                 505                 510

Lys Ser Leu Ser His Ser Pro Gly Lys
            515                 520

<210> SEQ ID NO 42
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 42

Met Tyr Arg Met Gln Leu Leu Ser Cys Ile Ala Leu Ser Leu Ala Leu
1               5                   10                  15

Val Thr Asn Ser Asn Gln Cys Pro Glu His Ser Gln Leu Thr Ala Leu
            20                  25                  30

Gly Met Asp Asp Thr Glu Thr Pro Glu Pro His Leu Gly Leu Trp Tyr
        35                  40                  45

Phe Ile Ala Gly Ala Ala Pro Thr Thr Glu Glu Leu Ala Thr Phe Asp
    50                  55                  60

Pro Val Asp Asn Ile Val Phe Asn Met Ala Ala Gly Ser Ala Pro Arg
65                  70                  75                  80

Gln Leu Gln Leu Arg Ala Thr Asn Arg Thr Lys Ser Gly Val Cys Val
                85                  90                  95

Pro Arg Lys Trp Thr Tyr Arg Leu Thr Glu Gly Lys Gly Asn Met Glu
            100                 105                 110

Leu Arg Thr Glu Gly Arg Pro Asp Met Lys Thr Asp Leu Phe Ser Ser
            115                 120                 125

Ser Cys Pro Gly Gly Ile Met Leu Lys Glu Thr Gly Gln Gly Tyr Gln
        130                 135                 140

Arg Phe Leu Leu Tyr Asn Arg Ser Pro His Pro Pro Glu Lys Cys Val
145                 150                 155                 160
```

```
Glu Glu Phe Lys Ser Leu Thr Ser Cys Leu Asp Phe Lys Ala Phe Leu
            165             170             175

Val Thr Pro Arg Asn Gln Glu Ala Cys Pro Leu Ser Ser Lys Trp Ile
            180             185             190

Ser Ser Ala Ser Ser Ala Lys Thr Thr Pro Pro Ser Val Tyr Pro Leu
            195             200             205

Ala Pro Gly Ser Ala Ala Gln Thr Asn Ser Met Val Thr Leu Gly Cys
            210             215             220

Leu Val Lys Gly Tyr Phe Pro Glu Pro Val Thr Val Thr Trp Asn Ser
225             230             235             240

Gly Ser Leu Ser Ser Gly Val His Thr Phe Pro Ala Val Leu Gln Ser
            245             250             255

Asp Leu Tyr Thr Leu Ser Ser Ser Val Thr Val Pro Ser Ser Thr Trp
            260             265             270

Pro Ser Glu Thr Val Thr Cys Asn Val Ala His Pro Ala Ser Ser Thr
            275             280             285

Lys Val Asp Lys Lys Ile Val Pro Arg Asp Cys Gly Cys Lys Pro Cys
            290             295             300

Ile Cys Thr Val Pro Glu Val Ser Ser Val Phe Ile Phe Pro Pro Lys
305             310             315             320

Pro Lys Asp Val Leu Thr Ile Thr Leu Thr Pro Lys Val Thr Cys Val
            325             330             335

Val Val Asp Ile Ser Lys Asp Asp Pro Glu Val Gln Phe Ser Trp Phe
            340             345             350

Val Asp Asp Val Glu Val His Thr Ala Gln Thr Gln Pro Arg Glu Glu
            355             360             365

Gln Phe Asn Ser Thr Phe Arg Ser Val Ser Glu Leu Pro Ile Met His
            370             375             380

Gln Asp Trp Leu Asn Gly Lys Glu Phe Lys Cys Arg Val Asn Ser Ala
385             390             395             400

Ala Phe Pro Ala Pro Ile Glu Lys Thr Ile Ser Lys Thr Lys Gly Arg
            405             410             415

Pro Lys Ala Pro Gln Val Tyr Thr Ile Pro Pro Pro Lys Glu Gln Met
            420             425             430

Ala Lys Asp Lys Val Ser Leu Thr Cys Met Ile Thr Asp Phe Phe Pro
            435             440             445

Glu Asp Ile Thr Val Glu Trp Gln Trp Asn Gly Gln Pro Ala Glu Asn
            450             455             460

Tyr Lys Asn Thr Gln Pro Ile Met Asp Thr Asp Gly Ser Tyr Phe Val
465             470             475             480

Tyr Ser Lys Leu Asn Val Gln Lys Ser Asn Trp Glu Ala Gly Asn Thr
            485             490             495

Phe Thr Cys Ser Val Leu His Glu Gly Leu His Asn His His Thr Glu
            500             505             510

Lys Ser Leu Ser His Ser Pro Gly Lys
            515             520
```

```
<210> SEQ ID NO 43
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 43
```

-continued

```
Met Tyr Arg Met Gln Leu Leu Ser Cys Ile Ala Leu Ser Leu Ala Leu
1               5                   10                  15

Val Thr Asn Ser Asn Gln Cys Pro Glu His Ser Gln Leu Thr Ala Leu
            20                  25                  30

Gly Met Asp Asp Thr Glu Thr Pro Glu Pro His Leu Gly Leu Trp Tyr
        35                  40                  45

Phe Ile Ala Gly Ala Ala Pro Thr Thr Glu Glu Leu Ala Thr Phe Asp
    50                  55                  60

Pro Val Asp Asn Ile Val Phe Asn Met Ala Ala Gly Ser Ala Pro Arg
65                  70                  75                  80

Gln Leu Gln Leu Arg Ala Thr Ile Arg Tyr Lys Ser Gly Val Cys Val
                85                  90                  95

Pro Arg Lys Trp Thr Tyr Arg Leu Thr Glu Gly Lys Gly Asn Met Glu
            100                 105                 110

Leu Arg Thr Glu Gly Arg Pro Asp Met Lys Thr Asp Leu Phe Ser Ser
        115                 120                 125

Ser Cys Pro Gly Gly Ile Met Leu Lys Glu Thr Gly Gln Gly Tyr Gln
    130                 135                 140

Arg Phe Leu Leu Tyr Asn Arg Ser Pro His Pro Pro Glu Lys Cys Val
145                 150                 155                 160

Glu Glu Phe Lys Ser Leu Thr Ser Cys Leu Asp Phe Lys Ala Phe Leu
            165                 170                 175

Val Thr Pro Arg Asn Gln Glu Ala Cys Pro Leu Ser Ser Lys Trp Ile
            180                 185                 190

Ser Ser Ala Ser Ser Ala Lys Thr Thr Pro Pro Ser Val Tyr Pro Leu
    195                 200                 205

Ala Pro Gly Ser Ala Ala Gln Thr Asn Ser Met Val Thr Leu Gly Cys
    210                 215                 220

Leu Val Lys Gly Tyr Phe Pro Glu Pro Val Thr Val Thr Trp Asn Ser
225                 230                 235                 240

Gly Ser Leu Ser Ser Gly Val His Thr Phe Pro Ala Val Leu Gln Ser
            245                 250                 255

Asp Leu Tyr Thr Leu Ser Ser Ser Val Thr Val Pro Ser Ser Thr Trp
            260                 265                 270

Pro Ser Glu Thr Val Thr Cys Asn Val Ala His Pro Ala Ser Ser Thr
            275                 280                 285

Lys Val Asp Lys Lys Ile Val Pro Arg Asp Cys Gly Cys Lys Pro Cys
    290                 295                 300

Ile Cys Thr Val Pro Glu Val Ser Ser Val Phe Ile Phe Pro Pro Lys
305                 310                 315                 320

Pro Lys Asp Val Leu Thr Ile Thr Leu Thr Pro Lys Val Thr Cys Val
            325                 330                 335

Val Val Asp Ile Ser Lys Asp Asp Pro Glu Val Gln Phe Ser Trp Phe
            340                 345                 350

Val Asp Asp Val Glu Val His Thr Ala Gln Thr Gln Pro Arg Glu Glu
            355                 360                 365

Gln Phe Asn Ser Thr Phe Arg Ser Val Ser Glu Leu Pro Ile Met His
    370                 375                 380

Gln Asp Trp Leu Asn Gly Lys Glu Phe Lys Cys Arg Val Asn Ser Ala
385                 390                 395                 400

Ala Phe Pro Ala Pro Ile Glu Lys Thr Ile Ser Lys Thr Lys Gly Arg
            405                 410                 415
```

-continued

```
Pro Lys Ala Pro Gln Val Tyr Thr Ile Pro Pro Pro Lys Glu Gln Met
            420                 425             430

Ala Lys Asp Lys Val Ser Leu Thr Cys Met Ile Thr Asp Phe Phe Pro
            435                 440             445

Glu Asp Ile Thr Val Glu Trp Gln Trp Asn Gly Gln Pro Ala Glu Asn
            450                 455             460

Tyr Lys Asn Thr Gln Pro Ile Met Asp Thr Asp Gly Ser Tyr Phe Val
465                 470             475             480

Tyr Ser Lys Leu Asn Val Gln Lys Ser Asn Trp Glu Ala Gly Asn Thr
                485             490             495

Phe Thr Cys Ser Val Leu His Glu Gly Leu His Asn His His Thr Glu
            500             505             510

Lys Ser Leu Ser His Ser Pro Gly Lys
            515             520
```

<210> SEQ ID NO 44
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 44

```
Met Tyr Arg Met Gln Leu Leu Ser Cys Ile Ala Leu Ser Leu Ala Leu
1               5                   10              15

Val Thr Asn Ser Asn Gln Cys Pro Glu His Ser Gln Leu Thr Ala Leu
                20                  25              30

Gly Met Asp Asp Thr Glu Thr Pro Glu Pro His Leu Gly Leu Trp Tyr
            35                  40                  45

Phe Ile Ala Gly Ala Ala Pro Thr Thr Glu Glu Leu Ala Asn Phe Asp
        50                  55                  60

Pro Val Asp Asn Ile Val Phe Asn Met Ala Ala Gly Ser Ala Pro Arg
65                  70                  75                  80

Gln Leu Gln Leu Arg Ala Thr Ile Arg Thr Lys Ser Gly Val Cys Val
                85                  90                  95

Pro Arg Lys Trp Thr Tyr Arg Leu Thr Glu Gly Lys Gly Asn Met Glu
            100                 105                 110

Leu Arg Thr Glu Gly Arg Pro Asp Met Lys Thr Asp Leu Phe Ser Ser
            115                 120                 125

Ser Cys Pro Gly Gly Ile Met Leu Lys Glu Thr Gly Gln Gly Tyr Gln
            130                 135                 140

Arg Phe Leu Leu Tyr Asn Arg Ser Pro His Pro Pro Glu Lys Cys Val
145                 150                 155                 160

Glu Glu Phe Lys Ser Leu Thr Ser Cys Leu Asp Phe Lys Ala Phe Leu
                165                 170                 175

Val Thr Pro Arg Asn Gln Glu Ala Cys Pro Leu Ser Ser Lys Trp Ala
            180                 185                 190

Ser Thr Lys Gly Pro Ser Val Phe Pro Leu Ala Pro Ser Ser Lys Ser
            195                 200                 205

Thr Ser Gly Gly Thr Ala Ala Leu Gly Cys Leu Val Lys Asp Tyr Phe
            210                 215                 220

Pro Glu Pro Val Thr Val Ser Trp Asn Ser Gly Ala Leu Thr Ser Gly
225                 230                 235                 240

Val His Thr Phe Pro Ala Val Leu Gln Ser Ser Gly Leu Tyr Ser Leu
                245                 250                 255
```

-continued

```
Ser Ser Val Val Thr Val Pro Ser Ser Ser Leu Gly Thr Gln Thr Tyr
        260             265             270

Ile Cys Asn Val Asn His Lys Pro Ser Asn Thr Lys Val Asp Lys Lys
        275             280             285

Val Glu Pro Lys Ser Cys Asp Lys Thr His Thr Cys Pro Pro Cys Pro
    290             295             300

Ala Pro Glu Leu Leu Gly Gly Pro Ser Val Phe Leu Phe Pro Pro Lys
305             310             315             320

Pro Lys Asp Thr Leu Met Ile Ser Arg Thr Pro Glu Val Thr Cys Val
            325             330             335

Val Val Asp Val Ser His Glu Asp Pro Glu Val Lys Phe Asn Trp Tyr
        340             345             350

Val Asp Gly Val Glu Val His Asn Ala Lys Thr Lys Pro Arg Glu Glu
        355             360             365

Gln Tyr Asn Ser Thr Tyr Arg Val Val Ser Val Leu Thr Val Leu His
    370             375             380

Gln Asp Trp Leu Asn Gly Lys Glu Tyr Lys Cys Lys Val Ser Asn Lys
385             390             395             400

Ala Leu Pro Ala Pro Ile Glu Lys Thr Ile Ser Lys Ala Lys Gly Gln
            405             410             415

Pro Arg Glu Pro Gln Val Tyr Thr Leu Pro Pro Ser Arg Glu Glu Met
            420             425             430

Thr Lys Asn Gln Val Ser Leu Thr Cys Leu Val Lys Gly Phe Tyr Pro
            435             440             445

Ser Asp Ile Ala Val Glu Trp Glu Ser Asn Gly Gln Pro Glu Asn Asn
    450             455             460

Tyr Lys Thr Thr Pro Pro Val Leu Asp Ser Asp Gly Ser Phe Phe Leu
465             470             475             480

Tyr Ser Lys Leu Thr Val Asp Lys Ser Arg Trp Gln Gln Gly Asn Val
            485             490             495

Phe Ser Cys Ser Val Met His Glu Ala Leu His Asn His Tyr Thr Gln
            500             505             510

Lys Ser Leu Ser Leu Ser Pro Gly Lys
            515             520
```

<210> SEQ ID NO 45
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 45

```
Met Tyr Arg Met Gln Leu Leu Ser Cys Ile Ala Leu Ser Leu Ala Leu
1               5               10              15

Val Thr Asn Ser Asn Gln Cys Pro Glu His Ser Gln Leu Thr Ala Leu
            20              25              30

Gly Met Asp Asp Thr Glu Thr Pro Glu Pro His Leu Gly Leu Trp Tyr
            35              40              45

Phe Ile Ala Gly Ala Ala Pro Thr Thr Glu Glu Leu Ala Thr Phe Asp
    50              55              60

Pro Lys Asp Asn Ile Val Phe Asn Met Ala Ala Gly Ser Ala Pro Arg
65              70              75              80

Gln Leu Gln Leu Arg Ala Thr Ile Arg Thr Lys Ser Gly Val Cys Val
            85              90              95
```

-continued

```
Pro Arg Lys Trp Thr Tyr Arg Leu Thr Glu Gly Lys Gly Asn Met Glu
            100                 105                 110

Leu Arg Thr Glu Gly Arg Pro Asp Met Lys Thr Asp Leu Phe Ser Ser
            115                 120                 125

Ser Cys Pro Gly Gly Ile Met Leu Lys Glu Thr Gly Gln Gly Tyr Gln
            130                 135                 140

Arg Phe Leu Leu Tyr Asn Arg Ser Pro His Pro Pro Glu Lys Cys Val
145                 150                 155                 160

Glu Glu Phe Lys Ser Leu Thr Ser Cys Leu Asp Phe Lys Ala Phe Leu
                165                 170                 175

Val Thr Pro Arg Asn Gln Glu Ala Cys Pro Leu Ser Ser Lys Trp Ala
            180                 185                 190

Ser Thr Lys Gly Pro Ser Val Phe Pro Leu Ala Pro Ser Ser Lys Ser
            195                 200                 205

Thr Ser Gly Gly Thr Ala Ala Leu Gly Cys Leu Val Lys Asp Tyr Phe
            210                 215                 220

Pro Glu Pro Val Thr Val Ser Trp Asn Ser Gly Ala Leu Thr Ser Gly
225                 230                 235                 240

Val His Thr Phe Pro Ala Val Leu Gln Ser Ser Gly Leu Tyr Ser Leu
                245                 250                 255

Ser Ser Val Val Thr Val Pro Ser Ser Ser Leu Gly Thr Gln Thr Tyr
            260                 265                 270

Ile Cys Asn Val Asn His Lys Pro Ser Asn Thr Lys Val Asp Lys Lys
            275                 280                 285

Val Glu Pro Lys Ser Cys Asp Lys Thr His Thr Cys Pro Pro Cys Pro
            290                 295                 300

Ala Pro Glu Leu Leu Gly Gly Pro Ser Val Phe Leu Phe Pro Pro Lys
305                 310                 315                 320

Pro Lys Asp Thr Leu Met Ile Ser Arg Thr Pro Glu Val Thr Cys Val
                325                 330                 335

Val Val Asp Val Ser His Glu Asp Pro Glu Val Lys Phe Asn Trp Tyr
            340                 345                 350

Val Asp Gly Val Glu Val His Asn Ala Lys Thr Lys Pro Arg Glu Glu
            355                 360                 365

Gln Tyr Asn Ser Thr Tyr Arg Val Val Ser Val Leu Thr Val Leu His
            370                 375                 380

Gln Asp Trp Leu Asn Gly Lys Glu Tyr Lys Cys Lys Val Ser Asn Lys
385                 390                 395                 400

Ala Leu Pro Ala Pro Ile Glu Lys Thr Ile Ser Lys Ala Lys Gly Gln
                405                 410                 415

Pro Arg Glu Pro Gln Val Tyr Thr Leu Pro Pro Ser Arg Glu Glu Met
            420                 425                 430

Thr Lys Asn Gln Val Ser Leu Thr Cys Leu Val Lys Gly Phe Tyr Pro
            435                 440                 445

Ser Asp Ile Ala Val Glu Trp Glu Ser Asn Gly Gln Pro Glu Asn Asn
            450                 455                 460

Tyr Lys Thr Thr Pro Pro Val Leu Asp Ser Asp Gly Ser Phe Phe Leu
465                 470                 475                 480

Tyr Ser Lys Leu Thr Val Asp Lys Ser Arg Trp Gln Gln Gly Asn Val
                485                 490                 495

Phe Ser Cys Ser Val Met His Glu Ala Leu His Asn His Tyr Thr Gln
                500                 505                 510

Lys Ser Leu Ser Leu Ser Pro Gly Lys
```

-continued

```
            515                520

<210> SEQ ID NO 46
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 46

Met Tyr Arg Met Gln Leu Leu Ser Cys Ile Ala Leu Ser Leu Ala Leu
1               5                   10                  15

Val Thr Asn Ser Asn Gln Cys Pro Glu His Ser Gln Leu Thr Ala Leu
            20                  25                  30

Gly Met Asp Asp Thr Glu Thr Pro Glu Pro His Leu Gly Leu Trp Tyr
        35                  40                  45

Phe Ile Ala Gly Ala Ala Pro Thr Thr Glu Glu Leu Ala Thr Phe Asp
    50                  55                  60

Pro Asn Asp Asn Ile Val Phe Asn Met Ala Ala Gly Ser Ala Pro Arg
65                  70                  75                  80

Gln Leu Gln Leu Arg Ala Thr Ile Arg Thr Lys Ser Gly Val Cys Val
            85                  90                  95

Pro Arg Lys Trp Thr Tyr Arg Leu Thr Glu Gly Lys Gly Asn Met Glu
            100                 105                 110

Leu Arg Thr Glu Gly Arg Pro Asp Met Lys Thr Asp Leu Phe Ser Ser
            115                 120                 125

Ser Cys Pro Gly Gly Ile Met Leu Lys Glu Thr Gly Gln Gly Tyr Gln
        130                 135                 140

Arg Phe Leu Leu Tyr Asn Arg Ser Pro His Pro Pro Glu Lys Cys Val
145                 150                 155                 160

Glu Glu Phe Lys Ser Leu Thr Ser Cys Leu Asp Phe Lys Ala Phe Leu
            165                 170                 175

Val Thr Pro Arg Asn Gln Glu Ala Cys Pro Leu Ser Ser Lys Trp Ala
            180                 185                 190

Ser Thr Lys Gly Pro Ser Val Phe Pro Leu Ala Pro Ser Ser Lys Ser
            195                 200                 205

Thr Ser Gly Gly Thr Ala Ala Leu Gly Cys Leu Val Lys Asp Tyr Phe
        210                 215                 220

Pro Glu Pro Val Thr Val Ser Trp Asn Ser Gly Ala Leu Thr Ser Gly
225                 230                 235                 240

Val His Thr Phe Pro Ala Val Leu Gln Ser Ser Gly Leu Tyr Ser Leu
            245                 250                 255

Ser Ser Val Val Thr Val Pro Ser Ser Ser Leu Gly Thr Gln Thr Tyr
            260                 265                 270

Ile Cys Asn Val Asn His Lys Pro Ser Asn Thr Lys Val Asp Lys Lys
            275                 280                 285

Val Glu Pro Lys Ser Cys Asp Lys Thr His Thr Cys Pro Pro Cys Pro
            290                 295                 300

Ala Pro Glu Leu Leu Gly Gly Pro Ser Val Phe Leu Phe Pro Pro Lys
305                 310                 315                 320

Pro Lys Asp Thr Leu Met Ile Ser Arg Thr Pro Glu Val Thr Cys Val
            325                 330                 335

Val Val Asp Val Ser His Glu Asp Pro Glu Val Lys Phe Asn Trp Tyr
            340                 345                 350

Val Asp Gly Val Glu Val His Asn Ala Lys Thr Lys Pro Arg Glu Glu
```

-continued

```
              355                 360                 365
Gln Tyr Asn Ser Thr Tyr Arg Val Val Ser Val Leu Thr Val Leu His
    370                 375                 380
Gln Asp Trp Leu Asn Gly Lys Glu Tyr Lys Cys Lys Val Ser Asn Lys
385                 390                 395                 400
Ala Leu Pro Ala Pro Ile Glu Lys Thr Ile Ser Lys Ala Lys Gly Gln
                405                 410                 415
Pro Arg Glu Pro Gln Val Tyr Thr Leu Pro Pro Ser Arg Glu Glu Met
                420                 425                 430
Thr Lys Asn Gln Val Ser Leu Thr Cys Leu Val Lys Gly Phe Tyr Pro
                435                 440                 445
Ser Asp Ile Ala Val Glu Trp Glu Ser Asn Gly Gln Pro Glu Asn Asn
    450                 455                 460
Tyr Lys Thr Thr Pro Pro Val Leu Asp Ser Asp Gly Ser Phe Phe Leu
465                 470                 475                 480
Tyr Ser Lys Leu Thr Val Asp Lys Ser Arg Trp Gln Gln Gly Asn Val
                485                 490                 495
Phe Ser Cys Ser Val Met His Glu Ala Leu His Asn His Tyr Thr Gln
                500                 505                 510
Lys Ser Leu Ser Leu Ser Pro Gly Lys
        515                 520

<210> SEQ ID NO 47
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 47

Met Tyr Arg Met Gln Leu Leu Ser Cys Ile Ala Leu Ser Leu Ala Leu
1               5                   10                  15
Val Thr Asn Ser Asn Gln Cys Pro Glu His Ser Gln Leu Thr Ala Leu
                20                  25                  30
Gly Met Asp Asp Thr Glu Thr Pro Glu Pro His Leu Gly Leu Trp Tyr
            35                  40                  45
Phe Ile Ala Gly Ala Ala Pro Thr Thr Glu Glu Leu Ala Thr Phe Asp
        50                  55                  60
Pro Gln Asp Asn Ile Val Phe Asn Met Ala Ala Gly Ser Ala Pro Arg
65                  70                  75                  80
Gln Leu Gln Leu Arg Ala Thr Ile Arg Thr Lys Ser Gly Val Cys Val
                85                  90                  95
Pro Arg Lys Trp Thr Tyr Arg Leu Thr Glu Gly Lys Gly Asn Met Glu
                100                 105                 110
Leu Arg Thr Glu Gly Arg Pro Asp Met Lys Thr Asp Leu Phe Ser Ser
            115                 120                 125
Ser Cys Pro Gly Gly Ile Met Leu Lys Glu Thr Gly Gln Gly Tyr Gln
        130                 135                 140
Arg Phe Leu Leu Tyr Asn Arg Ser Pro His Pro Pro Glu Lys Cys Val
145                 150                 155                 160
Glu Glu Phe Lys Ser Leu Thr Ser Cys Leu Asp Phe Lys Ala Phe Leu
                165                 170                 175
Val Thr Pro Arg Asn Gln Glu Ala Cys Pro Leu Ser Ser Lys Trp Ala
                180                 185                 190
Ser Thr Lys Gly Pro Ser Val Phe Pro Leu Ala Pro Ser Ser Lys Ser
```

-continued

```
              195                 200                 205

Thr Ser Gly Gly Thr Ala Ala Leu Gly Cys Leu Val Lys Asp Tyr Phe
    210                 215                 220

Pro Glu Pro Val Thr Val Ser Trp Asn Ser Gly Ala Leu Thr Ser Gly
225                 230                 235                 240

Val His Thr Phe Pro Ala Val Leu Gln Ser Ser Gly Leu Tyr Ser Leu
                245                 250                 255

Ser Ser Val Val Thr Val Pro Ser Ser Ser Leu Gly Thr Gln Thr Tyr
                260                 265                 270

Ile Cys Asn Val Asn His Lys Pro Ser Asn Thr Lys Val Asp Lys Lys
                275                 280                 285

Val Glu Pro Lys Ser Cys Asp Lys Thr His Thr Cys Pro Pro Cys Pro
    290                 295                 300

Ala Pro Glu Leu Leu Gly Gly Pro Ser Val Phe Leu Phe Pro Pro Lys
305                 310                 315                 320

Pro Lys Asp Thr Leu Met Ile Ser Arg Thr Pro Glu Val Thr Cys Val
                325                 330                 335

Val Val Asp Val Ser His Glu Asp Pro Glu Val Lys Phe Asn Trp Tyr
                340                 345                 350

Val Asp Gly Val Glu Val His Asn Ala Lys Thr Lys Pro Arg Glu Glu
                355                 360                 365

Gln Tyr Asn Ser Thr Tyr Arg Val Val Ser Val Leu Thr Val Leu His
    370                 375                 380

Gln Asp Trp Leu Asn Gly Lys Glu Tyr Lys Cys Lys Val Ser Asn Lys
385                 390                 395                 400

Ala Leu Pro Ala Pro Ile Glu Lys Thr Ile Ser Lys Ala Lys Gly Gln
                405                 410                 415

Pro Arg Glu Pro Gln Val Tyr Thr Leu Pro Pro Ser Arg Glu Glu Met
                420                 425                 430

Thr Lys Asn Gln Val Ser Leu Thr Cys Leu Val Lys Gly Phe Tyr Pro
                435                 440                 445

Ser Asp Ile Ala Val Glu Trp Glu Ser Asn Gly Gln Pro Glu Asn Asn
    450                 455                 460

Tyr Lys Thr Thr Pro Pro Val Leu Asp Ser Asp Gly Ser Phe Phe Leu
465                 470                 475                 480

Tyr Ser Lys Leu Thr Val Asp Lys Ser Arg Trp Gln Gln Gly Asn Val
                485                 490                 495

Phe Ser Cys Ser Val Met His Glu Ala Leu His Asn His Tyr Thr Gln
                500                 505                 510

Lys Ser Leu Ser Leu Ser Pro Gly Lys
    515                 520
```

```
<210> SEQ ID NO 48
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 48

Met Tyr Arg Met Gln Leu Leu Ser Cys Ile Ala Leu Ser Leu Ala Leu
1                 5                 10                 15

Val Thr Asn Ser Asn Gln Cys Pro Glu His Ser Gln Leu Thr Ala Leu
                20                 25                 30

Gly Met Asp Asp Thr Glu Thr Pro Glu Pro His Leu Gly Leu Trp Tyr
```

-continued

```
                  35                  40                  45

Phe Ile Ala Gly Ala Ala Pro Thr Thr Glu Glu Leu Ala Thr Phe Asp
    50                  55                  60

Pro Val Asp Asn Ile Val Phe Asn Met Ala Ala Gly Ser Ala Pro Arg
65                  70                  75                  80

Gln Leu Gln Leu Arg Ala Thr Lys Arg Thr Lys Ser Gly Val Cys Val
                85                  90                  95

Pro Arg Lys Trp Thr Tyr Arg Leu Thr Glu Gly Lys Gly Asn Met Glu
                100                 105                 110

Leu Arg Thr Glu Gly Arg Pro Asp Met Lys Thr Asp Leu Phe Ser Ser
                115                 120                 125

Ser Cys Pro Gly Gly Ile Met Leu Lys Glu Thr Gly Gln Gly Tyr Gln
    130                 135                 140

Arg Phe Leu Leu Tyr Asn Arg Ser Pro His Pro Pro Glu Lys Cys Val
145                 150                 155                 160

Glu Glu Phe Lys Ser Leu Thr Ser Cys Leu Asp Phe Lys Ala Phe Leu
                165                 170                 175

Val Thr Pro Arg Asn Gln Glu Ala Cys Pro Leu Ser Ser Lys Trp Ala
                180                 185                 190

Ser Thr Lys Gly Pro Ser Val Phe Pro Leu Ala Pro Ser Ser Lys Ser
                195                 200                 205

Thr Ser Gly Gly Thr Ala Ala Leu Gly Cys Leu Val Lys Asp Tyr Phe
    210                 215                 220

Pro Glu Pro Val Thr Val Ser Trp Asn Ser Gly Ala Leu Thr Ser Gly
225                 230                 235                 240

Val His Thr Phe Pro Ala Val Leu Gln Ser Ser Gly Leu Tyr Ser Leu
                245                 250                 255

Ser Ser Val Val Thr Val Pro Ser Ser Ser Leu Gly Thr Gln Thr Tyr
                260                 265                 270

Ile Cys Asn Val Asn His Lys Pro Ser Asn Thr Lys Val Asp Lys Lys
                275                 280                 285

Val Glu Pro Lys Ser Cys Asp Lys Thr His Thr Cys Pro Pro Cys Pro
    290                 295                 300

Ala Pro Glu Leu Leu Gly Gly Pro Ser Val Phe Leu Phe Pro Pro Lys
305                 310                 315                 320

Pro Lys Asp Thr Leu Met Ile Ser Arg Thr Pro Glu Val Thr Cys Val
                325                 330                 335

Val Val Asp Val Ser His Glu Asp Pro Glu Val Lys Phe Asn Trp Tyr
                340                 345                 350

Val Asp Gly Val Glu Val His Asn Ala Lys Thr Lys Pro Arg Glu Glu
                355                 360                 365

Gln Tyr Asn Ser Thr Tyr Arg Val Val Ser Val Leu Thr Val Leu His
    370                 375                 380

Gln Asp Trp Leu Asn Gly Lys Glu Tyr Lys Cys Lys Val Ser Asn Lys
385                 390                 395                 400

Ala Leu Pro Ala Pro Ile Glu Lys Thr Ile Ser Lys Ala Lys Gly Gln
                405                 410                 415

Pro Arg Glu Pro Gln Val Tyr Thr Leu Pro Pro Ser Arg Glu Glu Met
                420                 425                 430

Thr Lys Asn Gln Val Ser Leu Thr Cys Leu Val Lys Gly Phe Tyr Pro
                435                 440                 445

Ser Asp Ile Ala Val Glu Trp Glu Ser Asn Gly Gln Pro Glu Asn Asn
    450                 455                 460
```

```
Tyr Lys Thr Thr Pro Pro Val Leu Asp Ser Asp Gly Ser Phe Phe Leu
465             470             475             480

Tyr Ser Lys Leu Thr Val Asp Lys Ser Arg Trp Gln Gln Gly Asn Val
                485             490             495

Phe Ser Cys Ser Val Met His Glu Ala Leu His Asn His Tyr Thr Gln
            500             505             510

Lys Ser Leu Ser Leu Ser Pro Gly Lys
        515             520

<210> SEQ ID NO 49
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 49

Met Tyr Arg Met Gln Leu Leu Ser Cys Ile Ala Leu Ser Leu Ala Leu
1               5               10              15

Val Thr Asn Ser Asn Gln Cys Pro Glu His Ser Gln Leu Thr Ala Leu
            20              25              30

Gly Met Asp Asp Thr Glu Thr Pro Glu Pro His Leu Gly Leu Trp Tyr
        35              40              45

Phe Ile Ala Gly Ala Ala Pro Thr Thr Glu Glu Leu Ala Thr Phe Asp
        50              55              60

Pro Val Asp Asn Ile Val Phe Asn Met Ala Ala Gly Ser Ala Pro Arg
65              70              75              80

Gln Leu Gln Leu Arg Ala Thr Asn Arg Thr Lys Ser Gly Val Cys Val
            85              90              95

Pro Arg Lys Trp Thr Tyr Arg Leu Thr Glu Gly Lys Gly Asn Met Glu
            100             105             110

Leu Arg Thr Glu Gly Arg Pro Asp Met Lys Thr Asp Leu Phe Ser Ser
        115             120             125

Ser Cys Pro Gly Gly Ile Met Leu Lys Glu Thr Gly Gln Gly Tyr Gln
        130             135             140

Arg Phe Leu Leu Tyr Asn Arg Ser Pro His Pro Pro Glu Lys Cys Val
145             150             155             160

Glu Glu Phe Lys Ser Leu Thr Ser Cys Leu Asp Phe Lys Ala Phe Leu
            165             170             175

Val Thr Pro Arg Asn Gln Glu Ala Cys Pro Leu Ser Ser Lys Trp Ala
            180             185             190

Ser Thr Lys Gly Pro Ser Val Phe Pro Leu Ala Pro Ser Ser Lys Ser
        195             200             205

Thr Ser Gly Gly Thr Ala Ala Leu Gly Cys Leu Val Lys Asp Tyr Phe
        210             215             220

Pro Glu Pro Val Thr Val Ser Trp Asn Ser Gly Ala Leu Thr Ser Gly
225             230             235             240

Val His Thr Phe Pro Ala Val Leu Gln Ser Ser Gly Leu Tyr Ser Leu
            245             250             255

Ser Ser Val Val Thr Val Pro Ser Ser Ser Leu Gly Thr Gln Thr Tyr
            260             265             270

Ile Cys Asn Val Asn His Lys Pro Ser Asn Thr Lys Val Asp Lys Lys
        275             280             285

Val Glu Pro Lys Ser Cys Asp Lys Thr His Thr Cys Pro Pro Cys Pro
    290             295             300
```

```
Ala Pro Glu Leu Leu Gly Gly Pro Ser Val Phe Leu Phe Pro Pro Lys
305             310             315             320

Pro Lys Asp Thr Leu Met Ile Ser Arg Thr Pro Glu Val Thr Cys Val
            325             330             335

Val Val Asp Val Ser His Glu Asp Pro Glu Val Lys Phe Asn Trp Tyr
            340             345             350

Val Asp Gly Val Glu Val His Asn Ala Lys Thr Lys Pro Arg Glu Glu
        355             360             365

Gln Tyr Asn Ser Thr Tyr Arg Val Val Ser Val Leu Thr Val Leu His
    370             375             380

Gln Asp Trp Leu Asn Gly Lys Glu Tyr Lys Cys Lys Val Ser Asn Lys
385             390             395             400

Ala Leu Pro Ala Pro Ile Glu Lys Thr Ile Ser Lys Ala Lys Gly Gln
            405             410             415

Pro Arg Glu Pro Gln Val Tyr Thr Leu Pro Pro Ser Arg Glu Glu Met
            420             425             430

Thr Lys Asn Gln Val Ser Leu Thr Cys Leu Val Lys Gly Phe Tyr Pro
        435             440             445

Ser Asp Ile Ala Val Glu Trp Glu Ser Asn Gly Gln Pro Glu Asn Asn
    450             455             460

Tyr Lys Thr Thr Pro Pro Val Leu Asp Ser Asp Gly Ser Phe Phe Leu
465             470             475             480

Tyr Ser Lys Leu Thr Val Asp Lys Ser Arg Trp Gln Gln Gly Asn Val
            485             490             495

Phe Ser Cys Ser Val Met His Glu Ala Leu His Asn His Tyr Thr Gln
            500             505             510

Lys Ser Leu Ser Leu Ser Pro Gly Lys
        515             520
```

```
<210> SEQ ID NO 50
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 50
```

```
Met Tyr Arg Met Gln Leu Leu Ser Cys Ile Ala Leu Ser Leu Ala Leu
1               5               10              15

Val Thr Asn Ser Asn Gln Cys Pro Glu His Ser Gln Leu Thr Ala Leu
            20              25              30

Gly Met Asp Asp Thr Glu Thr Pro Glu Pro His Leu Gly Leu Trp Tyr
        35              40              45

Phe Ile Ala Gly Ala Ala Pro Thr Thr Glu Glu Leu Ala Thr Phe Asp
    50              55              60

Pro Val Asp Asn Ile Val Phe Asn Met Ala Ala Gly Ser Ala Pro Arg
65              70              75              80

Gln Leu Gln Leu Arg Ala Thr Ile Arg Tyr Lys Ser Gly Val Cys Val
            85              90              95

Pro Arg Lys Trp Thr Tyr Arg Leu Thr Glu Gly Lys Gly Asn Met Glu
            100             105             110

Leu Arg Thr Glu Gly Arg Pro Asp Met Lys Thr Asp Leu Phe Ser Ser
        115             120             125

Ser Cys Pro Gly Gly Ile Met Leu Lys Glu Thr Gly Gln Gly Tyr Gln
    130             135             140
```

```
Arg Phe Leu Leu Tyr Asn Arg Ser Pro His Pro Pro Glu Lys Cys Val
145                 150                 155                 160

Glu Glu Phe Lys Ser Leu Thr Ser Cys Leu Asp Phe Lys Ala Phe Leu
                165                 170                 175

Val Thr Pro Arg Asn Gln Glu Ala Cys Pro Leu Ser Ser Lys Trp Ala
                180                 185                 190

Ser Thr Lys Gly Pro Ser Val Phe Pro Leu Ala Pro Ser Ser Lys Ser
                195                 200                 205

Thr Ser Gly Gly Thr Ala Ala Leu Gly Cys Leu Val Lys Asp Tyr Phe
                210                 215                 220

Pro Glu Pro Val Thr Val Ser Trp Asn Ser Gly Ala Leu Thr Ser Gly
225                 230                 235                 240

Val His Thr Phe Pro Ala Val Leu Gln Ser Ser Gly Leu Tyr Ser Leu
                245                 250                 255

Ser Ser Val Val Thr Val Pro Ser Ser Ser Leu Gly Thr Gln Thr Tyr
                260                 265                 270

Ile Cys Asn Val Asn His Lys Pro Ser Asn Thr Lys Val Asp Lys Lys
                275                 280                 285

Val Glu Pro Lys Ser Cys Asp Lys Thr His Thr Cys Pro Pro Cys Pro
                290                 295                 300

Ala Pro Glu Leu Leu Gly Gly Pro Ser Val Phe Leu Phe Pro Pro Lys
305                 310                 315                 320

Pro Lys Asp Thr Leu Met Ile Ser Arg Thr Pro Glu Val Thr Cys Val
                325                 330                 335

Val Val Asp Val Ser His Glu Asp Pro Glu Val Lys Phe Asn Trp Tyr
                340                 345                 350

Val Asp Gly Val Glu Val His Asn Ala Lys Thr Lys Pro Arg Glu Glu
                355                 360                 365

Gln Tyr Asn Ser Thr Tyr Arg Val Val Ser Val Leu Thr Val Leu His
                370                 375                 380

Gln Asp Trp Leu Asn Gly Lys Glu Tyr Lys Cys Lys Val Ser Asn Lys
385                 390                 395                 400

Ala Leu Pro Ala Pro Ile Glu Lys Thr Ile Ser Lys Ala Lys Gly Gln
                405                 410                 415

Pro Arg Glu Pro Gln Val Tyr Thr Leu Pro Pro Ser Arg Glu Glu Met
                420                 425                 430

Thr Lys Asn Gln Val Ser Leu Thr Cys Leu Val Lys Gly Phe Tyr Pro
                435                 440                 445

Ser Asp Ile Ala Val Glu Trp Glu Ser Asn Gly Gln Pro Glu Asn Asn
450                 455                 460

Tyr Lys Thr Thr Pro Pro Val Leu Asp Ser Asp Gly Ser Phe Phe Leu
465                 470                 475                 480

Tyr Ser Lys Leu Thr Val Asp Lys Ser Arg Trp Gln Gln Gly Asn Val
                485                 490                 495

Phe Ser Cys Ser Val Met His Glu Ala Leu His Asn His Tyr Thr Gln
                500                 505                 510

Lys Ser Leu Ser Leu Ser Pro Gly Lys
                515                 520
```

```
<210> SEQ ID NO 51
<211> LENGTH: 1566
<212> TYPE: DNA
<213> ORGANISM: Artificial Sequence
<220> FEATURE:
```

<223> OTHER INFORMATION: Synthetic polynucleotide

<400> SEQUENCE: 51

```
atgtacagga tgcaactcct gtcttgcatt gcactaagtc ttgcacttgt cacgaattcg      60
aatcagtgcc ctgagcacag tcaactaact gcgctgggaa tggacgacac agagaccccca    120 gagcccccacc tgggcctgtg gtactttatt gcgggagcag ccccccaccac ggaagagttg    180 gcaacttttg atccggtgga caatattgtc ttcaacatgg ctgccggctc tgcccccaagg    240 cagctccagc ttcgtgctac catccgcacg aaaagtgggg tctgtgtgcc ccggaagtgg    300
acataccgat tgactgaagg gaaaggaaac atggaactca gaactgaagg gcgcccagac    360
atgaaaacag acctgttctc cagctcgtgc ccaggaggaa tcatgctgaa agagacgggc    420
cagggctacc agcgctttct cctctacaat cggtcaccac accctccaga gaagtgtgtg    480
gaggaattca agtctctgac ctcttgcttg gacttcaaag ccttcttagt gactcccagg    540
aatcaagagg cctgcccgct gtccagcaag tggatctcga gtgctagcag cgctaaaacg    600
acacccccat ctgtctatcc actggcccct ggatctgctg cccaaactaa ctccatggtg    660
accctgggat gcctggtcaa gggctatttc cctgagccag tgacagtgac ctggaactct    720
ggatccctgt ccagcggtgt gcacaccttc ccagctgtcc tgcagtctga cctctacact    780
ctgagcagct cagtgactgt cccctccagc acctggccca gcgagaccgt cacctgcaac    840
gttgcccacc cggccagcag caccaaggtg gacaagaaaa ttgtgcccag ggattgtggt    900
tgtaagcctt gcatatgtac agtcccagaa gtatcatctg tcttcatctt ccccccaaag    960
cccaaggatg tgctcaccat tactctgact cctaaggtca cgtgtgttgt ggtagacatc   1020
agcaaggatg atcccgaggt ccagttcagc tggtttgtag atgatgtgga ggtgcacaca   1080
gctcagacgc aacccccggga ggagcagttc aacagcactt tccgctcagt cagtgaactt   1140
cccatcatgc accaggactg gctcaatggc aaggagttca atgcagggt caacagtgca    1200 gctttccctg cccccatcga gaaaaccatc tccaaaacca aaggcagacc gaaggctccg    1260
caggtgtaca ccattccacc tcccaaggag cagatggcca aggataaagt cagtctgacc   1320
tgcatgataa cagacttctt ccctgaagac attactgtgg agtggcagtg gaatgggcag   1380
ccagcggaga actacaagaa cactcagccc atcatggaca cagatggctc ttacttcgtc   1440
tacagcaagc tcaatgtgca gaagagcaac tgggaggcag gaaatacttt cacctgctct   1500
gtgttacatg agggcctgca caaccaccat actgagaaga gcctctccca ctctcctggt   1560
aaatga                                                               1566
```

<210> SEQ ID NO 52
<211> LENGTH: 1572
<212> TYPE: DNA
<213> ORGANISM: Artificial Sequence
<220> FEATURE:
<223> OTHER INFORMATION: Synthetic polynucleotide

<400> SEQUENCE: 52

```
atgtacagga tgcaactcct gtcttgcatt gcactaagtc ttgcacttgt cacgaattcg      60
atatctcgag tgtaccagtg ccctgagcac agtcaactga caactctggg cgtggatggg    120
aaggagttcc cagaggtcca cttgggccag tggtacttta tcgcaggggc agctcccacc    180
aaggaggagt tggcaacttt tgaccctgtg gacaacattg tcttcaatat ggctgctggc    240
tctgccccga tgcagctcca ccttcgtgct accatccgca tgaaagatgg gctctgtgtg    300
ccccggaaat ggatctacca cctgactgaa gggagcacag atctcagaac tgaaggccgc    360
```

-continued

```
cctgacatga agactgagct cttttccagc tcatgcccag gtggaatcat gctgaatgag        420
acaggccagg gttaccagcg ctttctcctc tacaatcgct caccacatcc tcccgaaaag        480
tgtgtggagg aattcaagtc cctgacttcc tgcctggact ccaaagcctt cttattgact        540
cctaggaatc aagaggcctg tgagctgtcc ataactgggg ctagcaccaa gggcccatcg        600
gtcttccccc tggcaccctc ctccaagagc acctctgggg gcacagcggc cctgggctgc        660
ctggtcaagg actacttccc cgaaccggtg acggtgtcgt ggaactcagg cgccctgacc        720
agcggcgtgc acaccttccc ggctgtccta cagtcctcag gactctactc cctcagcagc        780
gtggtgaccg tgccctccag cagcttgggc acccagacct acatctgcaa cgtgaatcac        840
aagcccagca acaccaaggt ggacaagaaa gttgagccca atcttgtga caaaactcac        900 acatgcccac cgtgcccagc acctgaactc ctggggggac cgtcagtctt cctcttcccc        960
ccaaaaccca aggacaccct catgatctcc cggacccctg aggtcacatg cgtggtggtg       1020
gacgtgagcc acgaagaccc tgaggtcaag ttcaactggt acgtggacgg cgtggaggtg       1080
cataatgcca agacaaagcc gcgggaggag cagtacaaca gcacgtaccg tgtggtcagc       1140
gtcctcaccg tcctgcacca ggactggctg aatggcaagg agtacaagtg caaggtctcc       1200
aacaaagccc tcccagcccc catcgagaaa accatctcca aagccaaagg gcagccccga       1260
gaaccacagg tgtacaccct gcccccatcc cgggaggaga tgaccaagaa ccaggtcagc       1320
ctgacctgcc tggtcaaagg cttctatccc agcgacatcg ccgtggagtg ggagagcaat       1380
gggcagccgg agaacaacta caagaccacg cctcccgtgc tggactccga cggctccttc       1440
ttcctctaca gcaagctcac cgtggacaag agcaggtggc agcaggggaa cgtcttctca       1500
tgctccgtga tgcatgaggc tctgcacaac cactacacgc agaagagcct ctccctgtct       1560
ccgggtaaat ga                                                           1572
```

```
<210> SEQ ID NO 53
<211> LENGTH: 1572
<212> TYPE: DNA
<213> ORGANISM: Artificial Sequence
<220> FEATURE:
<223> OTHER INFORMATION: Synthetic polynucleotide

<400> SEQUENCE: 53
```

```
atgtacagga tgcaactcct gtcttgcatt gcactaagtc ttgcacttgt cacgaattcg         60
atatctcgag tgtaccagtg ccctgagcac agtcaactga caactctggg cgtggatggg        120
aaggagttcc cagaggtcca cttgggccag tggtacttta tcgcaggggc agctcccacc        180
aaggaggagt tggcaacttt tgaccctgtg gacaacattg tcttcaatat ggctgctggc        240
tctgccccga tgcagctcca ccttcgtgct accatccgca tgaaagatgg gctctgtgtg        300
ccccggaaat ggatctacca cctgactgaa gggagcacag atctcagaac tgaaggccgc        360
cctgacatga agactgagct cttttccagc tcatgcccag gtggaatcat gctgaatgag        420
acaggccagg gttaccagcg ctttctcctc tacaatcgct caccacatcc tcccgaaaag        480
tgtgtggagg aattcaagtc cctgacttcc tgcctggact ccaaagcctt cttattgact        540
cctaggaatc aagaggcctg tgagctgtcc ataactgga tctcgagtgc tagcagcgct        600
aaaacgacac ccccatctgt ctatccactg gcccctggat ctgctgccca aactaactcc        660
atggtgaccc tggatgcct ggtcaagggc tatttccctg agccagtgac agtgacctgg        720
aactctggat ccctgtccag cggtgtgcac accttcccag ctgtcctgca gtctgacctc        780
```

-continued

```
tacactctga gcagctcagt gactgtcccc tccagcacct ggcccagcga gaccgtcacc      840
tgcaacgttg cccacccggc cagcagcacc aaggtggaca agaaaattgt gcccagggat      900
tgtggttgta agccttgcat atgtacagtc ccagaagtat catctgtctt catcttcccc      960
ccaaagccca aggatgtgct caccattact ctgactccta aggtcacgtg tgttgtggta     1020
gacatcagca aggatgatcc cgaggtccag ttcagctggt ttgtagatga tgtggaggtg     1080
cacacagctc agacgcaacc ccgggaggag cagttcaaca gcactttccg ctcagtcagt     1140
gaacttccca tcatgcacca ggactggctc aatggcaagg agttcaaatg cagggtcaac     1200
agtgcagctt ccctgccccc catcgagaaa accatctcca aaaccaaagg cagaccgaag     1260
gctccgcagg tgtacaccat tccacctccc aaggagcaga tggccaagga taaagtcagt     1320
ctgacctgca tgataacaga cttcttccct gaagacatta ctgtggagtg gcagtggaat     1380
gggcagccag cggagaacta caagaacact cagcccatca tggacacaga tggctcttac     1440
ttcgtctaca gcaagctcaa tgtgcagaag agcaactggg aggcaggaaa tactttcacc     1500
tgctctgtgt tacatgaggg cctgcacaac caccatactg agaagagcct ctcccactct     1560
cctggtaaat ga                                                         1572
```

<210> SEQ ID NO 54
<211> LENGTH: 1566
<212> TYPE: DNA
<213> ORGANISM: Artificial Sequence
<220> FEATURE:
<223> OTHER INFORMATION: Synthetic polynucleotide

<400> SEQUENCE: 54

```
atgtacagga tgcaactcct gtcttgcatt gcactaagtc ttgcacttgt cacgaattcg       60
aatcagtgcc ctgagcacag tcaactaact gcgctgggaa tggacgacac agagacccca      120
gagccccacc tgggcctgtg gtactttatt gcgggagcag cccccaccac ggaagagttg      180
gcaacttttg atccggtgga caatattgtc ttcaacatgg ctgccggctc tgccccaagg      240
cagctccagc ttcgtgctac catccgcacg aaaagtgggg tctgtgtgcc ccggaagtgg      300
acataccgat tgactgaagg gaaaggaaac atggaactca gaactgaagg gcgcccagac      360
atgaaaacag acctgttctc cagctcgtgc ccaggaggaa tcatgctgaa agagacgggc      420
cagggctacc agcgctttct cctctacaat cggtcaccac accctccaga gaagtgtgtg      480
gaggaattca gtctctgac ctcttgcttg gacttcaaag ccttcttagt gactcccagg      540
aatcaagagg cctgcccgct gtccagcaag tgggctagca ccaagggccc atcggtcttc      600
cccctggcac cctcctccaa gagcacctct ggggggcacag cggccctggg ctgcctggtc      660
aaggactact cccccgaacc ggtgacggtg tcgtggaact caggcgccct gaccagcggc      720
gtgcacacct tccggctgt cctacagtcc tcaggactct actccctcag cagcgtggtg      780
accgtgccct ccagcagctt gggcacccag acctacatct gcaacgtgaa tcacaagccc      840
agcaacacca aggtggacaa gaaagttgag cccaaatctt gtgacaaaac tcacacatgc      900
ccaccgtgcc cagcacctga actcctgggg ggaccgtcag tcttcctctt ccccccaaaa      960
cccaaggaca ccctcatgat ctcccggacc cctgaggtca catgcgtggt ggtggacgtg     1020
agccacgaag accctgaggt caagttcaac tggtacgtgg acggcgtgga ggtgcataat     1080
gccaagacaa agccgcggga ggagcagtac aacagcacgt accgtgtggt cagcgtcctc     1140
accgtcctgc accaggactg gctgaatggc aaggagtaca agtgcaaggt ctccaacaaa     1200
gccctcccag cccccatcga gaaaaccatc tccaaagcca aagggcagcc ccgagaacca     1260
```

```
caggtgtaca ccctgcccc atcccgggag gagatgacca agaaccaggt cagcctgacc   1320
tgcctggtca aaggcttcta tcccagcgac atcgccgtgg agtgggagag caatgggcag   1380
ccggagaaca actacaagac cacgcctccc gtgctggact ccgacggctc cttcttcctc   1440
tacagcaagc tcaccgtgga caagagcagg tggcagcagg ggaacgtctt ctcatgctcc   1500
gtgatgcatg aggctctgca caaccactac acgcagaaga gcctctccct gtctccgggt   1560
aaatga                                                              1566
```

```
<210> SEQ ID NO 55
<211> LENGTH: 90
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (4)..(90)
<223> OTHER INFORMATION: May be absent

<400> SEQUENCE: 55

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45

Gly Gly Ser Gly Gly Ser Gly Gly Ser Gly Gly Ser Gly Gly Ser Gly
        50                  55                  60

Gly Ser Gly Gly Ser Gly Gly Ser Gly Gly Ser Gly Gly Ser Gly Gly
65                  70                  75                  80

Ser Gly Gly Ser Gly Gly Ser Gly Gly Ser
                85                  90
```

```
<210> SEQ ID NO 56
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 56

Met Tyr Arg Met Gln Leu Leu Ser Cys Ile Ala Leu Ser Leu Ala Leu
1               5                   10                  15

Val Thr Asn Ser
            20
```

```
<210> SEQ ID NO 57
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 57

Met Asp Trp Thr Trp Ile Leu Phe Leu Val Ala Ala Ala Thr Arg Val
1               5                   10                  15

His Ser
```

```
<210> SEQ ID NO 58
<211> LENGTH: 20
```

-continued

```
<212> TYPE: PRT
<213> ORGANISM: Artificial Sequence
<220> FEATURE:
<223> OTHER INFORMATION: Synthetic polypeptide

<400> SEQUENCE: 58

Met Glu Thr Pro Ala Gln Leu Leu Phe Leu Leu Leu Leu Trp Leu Pro
1               5                   10                  15

Asp Thr Thr Gly
            20

<210> SEQ ID NO 59
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 59

Ser Gly Ser Glu Thr Pro Gly Thr Ser Glu Ser Ala Thr Pro Glu Ser
1               5                   10                  15

<210> SEQ ID NO 60
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 60

Ser Gly Gly Ser
1

<210> SEQ ID NO 61
<211> LENGTH: 120
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (5)..(120)
<223> OTHER INFORMATION: May be absent

<400> SEQUENCE: 61

Ser Gly Gly Ser Ser Gly Gly Ser Ser Gly Gly Ser Ser Gly Gly Ser
1               5                   10                  15

Ser Gly Gly Ser Ser Gly Gly Ser Ser Gly Gly Ser Ser Gly Gly Ser
            20                  25                  30

Ser Gly Gly Ser Ser Gly Gly Ser Ser Gly Gly Ser Ser Gly Gly Ser
        35                  40                  45

Ser Gly Gly Ser Ser Gly Gly Ser Ser Gly Gly Ser Ser Gly Gly Ser
    50                  55                  60

Ser Gly Gly Ser Ser Gly Gly Ser Ser Gly Gly Ser Ser Gly Gly Ser
65                  70                  75                  80

Ser Gly Gly Ser Ser Gly Gly Ser Ser Gly Gly Ser Ser Gly Gly Ser
                85                  90                  95

Ser Gly Gly Ser Ser Gly Gly Ser Ser Gly Gly Ser Ser Gly Gly Ser
            100                 105                 110

Ser Gly Gly Ser Ser Gly Gly Ser
        115                 120

<210> SEQ ID NO 62
```

```
<211> LENGTH: 120
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (5)..(120)
<223> OTHER INFORMATION: May be absent

<400> SEQUENCE: 62

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

Gly Gly Gly Ser Gly Gly Gly Ser Gly Gly Gly Ser Gly Gly Gly Ser
    50                  55                  60

Gly Gly Gly Ser Gly Gly Gly Ser Gly Gly Gly Ser Gly Gly Gly Ser
65                  70                  75                  80

Gly Gly Gly Ser Gly Gly Gly Ser Gly Gly Gly Ser Gly Gly Gly Ser
            85                  90                  95

Gly Gly Gly Ser Gly Gly Gly Ser Gly Gly Gly Ser Gly Gly Gly Ser
            100                 105                 110

Gly Gly Gly Ser Gly Gly Gly Ser
        115                 120

<210> SEQ ID NO 63
<211> LENGTH: 150
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (6)..(150)
<223> OTHER INFORMATION: May be absent

<400> SEQUENCE: 63

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
            85                  90                  95

Gly Gly Gly Ser Gly Gly Gly Gly Ser Gly Gly Gly Gly Ser Gly Gly
            100                 105                 110

Gly Gly Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser
145                 150
```

```
<210> SEQ ID NO 64
<211> LENGTH: 150
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (6)..(150)
<223> OTHER INFORMATION: May be absent

<400> SEQUENCE: 64

Glu Ala Ala Ala Lys Glu Ala Ala Lys Glu Ala Ala Lys Glu
1               5                   10                  15

Ala Ala Ala Lys Glu Ala Ala Ala Lys Glu Ala Ala Lys Glu Ala
            20                  25                  30

Ala Ala Lys Glu Ala Ala Ala Lys Glu Ala Ala Ala Lys Glu Ala Ala
        35                  40                  45

Ala Lys Glu Ala Ala Ala Lys Glu Ala Ala Ala Lys Glu Ala Ala Ala
    50                  55                  60

Lys Glu Ala Ala Ala Lys Glu Ala Ala Ala Lys Glu Ala Ala Ala Lys
65                  70                  75                  80

Glu Ala Ala Ala Lys Glu Ala Ala Ala Lys Glu Ala Ala Ala Lys Glu
                85                  90                  95

Ala Ala Ala Lys Glu Ala Ala Ala Lys Glu Ala Ala Ala Lys Glu Ala
            100                 105                 110

Ala Ala Lys Glu Ala Ala Ala Lys Glu Ala Ala Ala Lys Glu Ala Ala
        115                 120                 125

Ala Lys Glu Ala Ala Ala Lys Glu Ala Ala Ala Lys Glu Ala Ala Ala
    130                 135                 140

Lys Glu Ala Ala Ala Lys
145                 150

<210> SEQ ID NO 65
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 65

Ser Gly Gly Ser Ser Gly Ser Glu Thr Pro Gly Thr Ser Glu Ser Ala
1               5                   10                  15

Thr Pro Glu Ser Ser Gly Gly Ser
            20

<210> SEQ ID NO 66
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 66

Ser Gly Gly Ser Ser Gly Gly Ser Ser Gly Ser Glu Thr Pro Gly Thr
1               5                   10                  15

Ser Glu Ser Ala Thr Pro Glu Ser Ser Gly Gly Ser Ser Gly Gly Ser
            20                  25                  30

<210> SEQ ID NO 67
```

<211> LENGTH: 104
<212> TYPE: PRT
<213> ORGANISM: Artificial Sequence
<220> FEATURE:
<223> OTHER INFORMATION: Synthetic polypeptide

<400> SEQUENCE: 67

Gly Gly Ser Gly Gly Ser Pro Gly Ser Pro Ala Gly Ser Pro Thr Ser
1               5                   10                  15

Thr Glu Glu Gly Thr Ser Glu Ser Ala Thr Pro Glu Ser Gly Pro Gly
            20                  25                  30

Thr Ser Thr Glu Pro Ser Glu Gly Ser Ala Pro Gly Ser Pro Ala Gly
        35                  40                  45

Ser Pro Thr Ser Thr Glu Glu Gly Thr Ser Thr Glu Pro Ser Glu Gly
    50                  55                  60

Ser Ala Pro Gly Thr Ser Thr Glu Pro Ser Glu Gly Ser Ala Pro Gly
65                  70                  75                  80

Thr Ser Glu Ser Ala Thr Pro Glu Ser Gly Pro Gly Ser Glu Pro Ala
                85                  90                  95

Thr Ser Gly Gly Ser Gly Gly Ser
            100

<210> SEQ ID NO 68
<211> LENGTH: 527
<212> TYPE: PRT
<213> ORGANISM: Artificial Sequence
<220> FEATURE:
<223> OTHER INFORMATION: Synthetic polypeptide

<400> SEQUENCE: 68

Met Tyr Arg Met Gln Leu Leu Ser Cys Ile Ala Leu Ser Leu Ala Leu
1               5                   10                  15

Val Thr Asn Ser Asn Gln Cys Pro Glu His Ser Gln Leu Thr Ala Leu
            20                  25                  30

Gly Met Asp Asp Thr Glu Thr Pro Glu Pro His Leu Gly Leu Trp Tyr
        35                  40                  45

Phe Ile Ala Gly Ala Ala Pro Thr Thr Glu Glu Leu Ala Thr Phe Asp
    50                  55                  60

Pro Val Asp Asn Ile Val Phe Asn Met Ala Ala Gly Ser Ala Pro Arg
65                  70                  75                  80

Gln Leu Gln Leu Arg Ala Thr Ile Arg Thr Lys Ser Gly Val Cys Val
                85                  90                  95

Pro Arg Lys Trp Thr Tyr Arg Leu Thr Glu Gly Lys Gly Asn Met Glu
            100                 105                 110

Leu Arg Thr Glu Gly Arg Pro Asp Met Lys Thr Asp Leu Phe Ser Ser
        115                 120                 125

Ser Cys Pro Gly Gly Ile Met Leu Lys Glu Thr Gly Gln Gly Tyr Gln
    130                 135                 140

Arg Phe Leu Leu Tyr Asn Arg Ser Pro His Pro Pro Glu Lys Cys Val
145                 150                 155                 160

Glu Glu Phe Lys Ser Leu Thr Ser Cys Leu Asp Phe Lys Ala Phe Leu
                165                 170                 175

Val Thr Pro Arg Asn Gln Glu Ala Cys Pro Leu Ser Ser Lys Trp Ile
            180                 185                 190

Ser Ser Ala Ser Ser Ala Lys Thr Thr Pro Pro Ser Val Tyr Pro Leu
        195                 200                 205

Ala Pro Gly Ser Ala Ala Gln Thr Asn Ser Met Val Thr Leu Gly Cys

-continued

```
        210               215               220

Leu Val Lys Gly Tyr Phe Pro Glu Pro Val Thr Val Thr Trp Asn Ser
225               230               235               240

Gly Ser Leu Ser Ser Gly Val His Thr Phe Pro Ala Val Leu Gln Ser
              245               250               255

Asp Leu Tyr Thr Leu Ser Ser Ser Val Thr Val Pro Ser Ser Thr Trp
              260               265               270

Pro Ser Glu Thr Val Thr Cys Asn Val Ala His Pro Ala Ser Ser Thr
              275               280               285

Lys Val Asp Lys Lys Ile Val Pro Arg Asp Cys Gly Cys Lys Pro Cys
          290               295               300

Ile Cys Thr Val Pro Glu Val Ser Ser Val Phe Ile Phe Pro Pro Lys
305               310               315               320

Pro Lys Asp Val Leu Thr Ile Thr Leu Thr Pro Lys Val Thr Cys Val
              325               330               335

Val Val Asp Ile Ser Lys Asp Asp Pro Glu Val Gln Phe Ser Trp Phe
              340               345               350

Val Asp Asp Val Glu Val His Thr Ala Gln Thr Gln Pro Arg Glu Glu
              355               360               365

Gln Phe Asn Ser Thr Phe Arg Ser Val Ser Glu Leu Pro Ile Met His
      370               375               380

Gln Asp Trp Leu Asn Gly Lys Glu Phe Lys Cys Arg Val Asn Ser Ala
385               390               395               400

Ala Phe Pro Ala Pro Ile Glu Lys Thr Ile Ser Lys Thr Lys Gly Arg
              405               410               415

Pro Lys Ala Pro Gln Val Tyr Thr Ile Pro Pro Pro Lys Glu Gln Met
              420               425               430

Ala Lys Asp Lys Val Ser Leu Thr Cys Met Ile Thr Asp Phe Phe Pro
              435               440               445

Glu Asp Ile Thr Val Glu Trp Gln Trp Asn Gly Gln Pro Ala Glu Asn
      450               455               460

Tyr Lys Asn Thr Gln Pro Ile Met Asp Thr Asp Gly Ser Tyr Phe Val
465               470               475               480

Tyr Ser Lys Leu Asn Val Gln Lys Ser Asn Trp Glu Ala Gly Asn Thr
              485               490               495

Phe Thr Cys Ser Val Leu His Glu Gly Leu His Asn His His Thr Glu
              500               505               510

Lys Ser Leu Ser His Ser Pro Gly Lys His His His His His
          515               520               525
```

<210> SEQ ID NO 69
<211> LENGTH: 1584
<212> TYPE: DNA
<213> ORGANISM: Artificial Sequence
<220> FEATURE:
<223> OTHER INFORMATION: Synthetic polynucleotide

<400> SEQUENCE: 69
atgtacagga tgcaactcct gtcttgcatt gcactaagtc ttgcacttgt cacgaattcg      60
aatcagtgcc ctgagcacag tcaactaact gcgctgggaa tggacgacac agagacccca     120
gagccccacc tgggcctgtg gtactttatt gcgggagcag cccccaccac ggaagagttg     180 gcaactttg atccggtgga caatattgtc ttcaacatgg ctgccggctc tgccccaagg     240
cagctccagc ttcgtgctac catccgcacg aaaagtgggg tctgtgtgcc ccggaagtgg     300

-continued

```
acataccgat tgactgaagg gaaaggaaac atggaactca gaactgaagg gcgcccagac    360
atgaaaacag acctgttctc cagctcgtgc ccaggaggaa tcatgctgaa agagacgggc    420
cagggctacc agcgctttct cctctacaat cggtcaccac accctccaga gaagtgtgtg    480
gaggaattca agtctctgac ctcttgcttg gacttcaaag ccttcttagt gactcccagg    540
aatcaagagg cctgcccgct gtccagcaag tggatctcga gtgctagcag cgctaaaacg    600
acacccccat ctgtctatcc actggcccct ggatctgctg cccaaactaa ctccatggtg    660
accctgggat gcctggtcaa gggctatttc cctgagccag tgacagtgac ctggaactct    720
ggatccctgt ccagcggtgt gcacaccttc ccagctgtcc tgcagtctga cctctacact    780
ctgagcagct cagtgactgt cccctccagc acctggccca gcgagaccgt cacctgcaac    840
gttgcccacc cggccagcag caccaaggtg gacaagaaaa ttgtgcccag ggattgtggt    900
tgtaagcctt gcatatgtac agtcccagaa gtatcatctg tcttcatctt cccccccaaag    960 cccaaggatg tgctcaccat tactctgact cctaaggtca cgtgtgttgt ggtagacatc   1020
agcaaggatg atcccgaggt ccagttcagc tggtttgtag atgatgtgga ggtgcacaca   1080
gctcagacgc aacccccggga ggagcagttc aacagcactt ccgctcagt cagtgaactt   1140 cccatcatgc accaggactg gctcaatggc aaggagttca atgcagggt caacagtgca   1200 gctttcctg cccccatcga gaaaaccatc tccaaaacca aaggcagacc gaaggctccg   1260
caggtgtaca ccattccacc tcccaaggag cagatggcca aggataaagt cagtctgacc   1320
tgcatgataa cagacttctt ccctgaagac attactgtgg agtggcagtg gaatgggcag   1380
ccagcggaga actacaagaa cactcagccc atcatggaca cagatggctc ttacttcgtc   1440
tacagcaagc tcaatgtgca gaagagcaac tgggaggcag gaaatacttt cacctgctct   1500
gtgttacatg agggcctgca caaccaccat actgagaaga gcctctccca ctctcctggt   1560
aaacatcacc atcaccatca ctga                                         1584
```

<210> SEQ ID NO 70
<211> LENGTH: 1572
<212> TYPE: DNA
<213> ORGANISM: Artificial Sequence
<220> FEATURE:
<223> OTHER INFORMATION: Synthetic polynucleotide
<400> SEQUENCE: 70

```
atgtacagga tgcaactcct gtcttgcatt gcactaagtc ttgcacttgt cacgaattcg     60
atatctcgag tgtaccagtg ccctgagcac agtcaactga caactctggg cgtggatggg    120
aaggagttcc cagaggtcca cttgggccag tggtacttta tcgcaggggc agctcccacc    180
aaggaggagt tggcaaactt tgaccctgtg dacaacattg tcttcaatat ggctgctggc    240
tctgccccga tgcagctcca ccttcgtgct accatccgca tgaaagatgg gctctgtgtg    300
ccccggaaat ggatctacca cctgactgaa gggagcacag atctcagaac tgaaggccgc    360
cctgacatga agactgagct cttttccagc tcatgcccag gtggaatcat gctgaatgag    420
acaggccagg gttaccagcg ctttctcctc tacaatcgct caccacatcc tcccgaaaag    480
tgtgtggagg aattcaagtc cctgacttcc tgcctggact ccaaagcctt cttattgact    540
cctaggaatc aagaggcctg tgagctgtcc aataactgga tctcgagtgc tagcagcgct    600
aaaacgacac ccccatctgt ctatccactg gcccctggat ctgctgccca aactaactcc    660
atggtgaccc tgggatgcct ggtcaagggc tatttccctg agccagtgac agtgacctgg    720
aactctggat ccctgtccag cggtgtgcac accttcccag ctgtcctgca gtctgacctc    780
```

-continued

```
tacactctga gcagctcagt gactgtcccc tccagcacct ggcccagcga gaccgtcacc      840
tgcaacgttg cccacccggc cagcagcacc aaggtggaca agaaaattgt gcccagggat      900
tgtggttgta agccttgcat atgtacagtc ccagaagtat catctgtctt catcttcccc      960
ccaaagccca aggatgtgct caccattact ctgactccta aggtcacgtg tgttgtggta     1020
gacatcagca aggatgatcc cgaggtccag ttcagctggt ttgtagatga tgtggaggtg     1080
cacacagctc agacgcaacc ccgggaggag cagttcaaca gcactttccg ctcagtcagt     1140
gaacttccca tcatgcacca ggactggctc aatggcaagg agttcaaatg cagggtcaac     1200
agtgcagctt ccctgccccc catcgagaaa accatctcca aaaccaaagg cagaccgaag     1260
gctccgcagg tgtacaccat tccacctccc aaggagcaga tggccaagga taaagtcagt     1320
ctgacctgca tgataacaga cttcttccct gaagacatta ctgtggagtg gcagtggaat     1380
gggcagccag cggagaacta caagaacact cagcccatca tggacacaga tggctcttac     1440
ttcgtctaca gcaagctcaa tgtgcagaag agcaactggg aggcaggaaa tactttcacc     1500
tgctctgtgt tacatgaggg cctgcacaac caccatactg agaagagcct ctcccactct     1560
cctggtaaat ga                                                         1572
```

<210> SEQ ID NO 71
<211> LENGTH: 1572
<212> TYPE: DNA
<213> ORGANISM: Artificial Sequence
<220> FEATURE:
<223> OTHER INFORMATION: Synthetic polynucleotide

<400> SEQUENCE: 71

```
atgtacagga tgcaactcct gtcttgcatt gcactaagtc ttgcacttgt cacgaattcg       60
atatctcgag tgtaccagtg ccctgagcac agtcaactga caactctggg cgtggatggg      120
aaggagttcc cagaggtcca cttgggccag tggtacttta tcgcagggggc agctcccacc     180 aaggaggagt tggcaacttt tgaccctaag gacaacattg tcttcaatat ggctgctggc      240
tctgccccga tgcagctcca ccttcgtgct accatccgca tgaaagatgg gctctgtgtg      300
ccccggaaat ggatctacca cctgactgaa gggagcacag atctcagaac tgaaggccgc      360
cctgacatga agactgagct ctttttccagc tcatgcccag gtggaatcat gctgaatgag      420
acaggccagg gttaccagcg ctttctcctc tacaatcgct caccacatcc tcccgaaaag      480
tgtgtggagg aattcaagtc cctgacttcc tgcctggact ccaaagcctt cttattgact      540
cctaggaatc aagaggcctg tgagctgtcc ataactgga tctcgagtgc tagcagcgct      600
aaaacgacac ccccatctgt ctatccactg gccctggat ctgctgccca aactaactcc      660
atggtgaccc tgggatgcct ggtcaagggc tatttccctg agccagtgac agtgacctgg      720
aactctggat ccctgtccag cggtgtgcac accttccag ctgtcctgca gtctgacctc      780
tacactctga gcagctcagt gactgtcccc tccagcacct ggcccagcga gaccgtcacc      840
tgcaacgttg cccacccggc cagcagcacc aaggtggaca agaaaattgt gcccagggat      900
tgtggttgta agccttgcat atgtacagtc ccagaagtat catctgtctt catcttcccc      960
ccaaagccca aggatgtgct caccattact ctgactccta aggtcacgtg tgttgtggta     1020
gacatcagca aggatgatcc cgaggtccag ttcagctggt ttgtagatga tgtggaggtg     1080
cacacagctc agacgcaacc ccgggaggag cagttcaaca gcactttccg ctcagtcagt     1140
gaacttccca tcatgcacca ggactggctc aatggcaagg agttcaaatg cagggtcaac     1200
```

```
agtgcagctt tccctgcccc catcgagaaa accatctcca aaaccaaagg cagaccgaag      1260
gctccgcagg tgtacaccat tccacctccc aaggagcaga tggccaagga taaagtcagt      1320
ctgacctgca tgataacaga cttcttccct gaagacatta ctgtggagtg gcagtggaat      1380
gggcagccag cggagaacta caagaacact cagcccatca tggacacaga tggctcttac      1440
ttcgtctaca gcaagctcaa tgtgcagaag agcaactggg aggcaggaaa tactttcacc      1500
tgctctgtgt tacatgaggg cctgcacaac caccatactg agaagagcct ctcccactct      1560
cctggtaaat ga                                                          1572
```

<210> SEQ ID NO 72
<211> LENGTH: 1572
<212> TYPE: DNA
<213> ORGANISM: Artificial Sequence
<220> FEATURE:
<223> OTHER INFORMATION: Synthetic polynucleotide

<400> SEQUENCE: 72

```
atgtacagga tgcaactcct gtcttgcatt gcactaagtc ttgcacttgt cacgaattcg        60
atatctcgag tgtaccagtg ccctgagcac agtcaactga caactctggg cgtggatggg       120
aaggagttcc cagaggtcca cttgggccag tggtacttta tcgcaggggc agctcccacc       180
aaggaggagt tggcaacttt tgaccctaac gacaacattg tcttcaatat ggctgctggc       240
tctgccccga tgcagctcca ccttcgtgct accatccgca tgaaagatgg gctctgtgtg       300
ccccggaaat ggatctacca cctgactgaa gggagcacag atctcagaac tgaaggccgc       360
cctgacatga agactgagct cttttccagc tcatgcccag gtggaatcat gctgaatgag       420
acaggccagg gttaccagcg ctttctcctc tacaatcgct caccacatcc tcccgaaaag       480
tgtgtggagg aattcaagtc cctgacttcc tgcctggact ccaaagcctt cttattgact       540
cctaggaatc aagaggcctg tgagctgtcc aataactgga tctcgagtgc tagcagcgct       600
aaaacgacac ccccatctgt ctatccactg gccctggat ctgctgccca aactaactcc        660
atggtgaccc tgggatgcct ggtcaagggc tatttccctg agccagtgac agtgacctgg       720
aactctggat ccctgtccag cggtgtgcac accttcccag ctgtcctgca gtctgacctc       780
tacactctga gcagctcagt gactgtcccc tccagcacct ggcccagcga gaccgtcacc       840
tgcaacgttg cccacccggc cagcagcacc aaggtggaca gaaaaattgt gcccagggat       900
tgtggttgta gccttgcat atgtacagtc ccagaagtat catctgtctt catcttcccc        960
ccaaagccca aggatgtgct caccattact ctgactccta aggtcacgtg tgttgtggta      1020
gacatcagca aggatgatcc cgaggtccag ttcagctggt ttgtagatga tgtggaggtg      1080
cacacagctc agacgcaacc ccgggaggag cagttcaaca gcactttccg ctcagtcagt      1140
gaacttccca tcatgcacca ggactggctc aatggcaagg agttcaaatg cagggtcaac      1200
agtgcagctt tccctgcccc catcgagaaa accatctcca aaaccaaagg cagaccgaag      1260
gctccgcagg tgtacaccat tccacctccc aaggagcaga tggccaagga taaagtcagt      1320
ctgacctgca tgataacaga cttcttccct gaagacatta ctgtggagtg gcagtggaat      1380
gggcagccag cggagaacta caagaacact cagcccatca tggacacaga tggctcttac      1440
ttcgtctaca gcaagctcaa tgtgcagaag agcaactggg aggcaggaaa tactttcacc      1500
tgctctgtgt tacatgaggg cctgcacaac caccatactg agaagagcct ctcccactct      1560
cctggtaaat ga                                                          1572
```

<210> SEQ ID NO 73
<211> LENGTH: 1572
<212> TYPE: DNA
<213> ORGANISM: Artificial Sequence
<220> FEATURE:
<223> OTHER INFORMATION: Synthetic polynucleotide

<400> SEQUENCE: 73
atgtacagga tgcaactcct gtcttgcatt gcactaagtc ttgcacttgt cacgaattcg      60
atatctcgag tgtaccagtg ccctgagcac agtcaactga caactctggg cgtggatggg     120
aaggagttcc cagaggtcca cttgggccag tggtacttta tcgcaggggc agctcccacc     180
aaggaggagt tggcaacttt tgaccctcag gacaacattg tcttcaatat ggctgctggc     240
tctgccccga tgcagctcca ccttcgtgct accatccgca tgaaagatgg gctctgtgtg     300
ccccggaaat ggatctacca cctgactgaa gggagcacag atctcagaac tgaaggccgc     360
cctgacatga agactgagct cttttccagc tcatgcccag gtggaatcat gctgaatgag     420
acaggccagg gttaccagcg ctttctcctc tacaatcgct caccacatcc tcccgaaaag     480
tgtgtggagg aattcaagtc cctgacttcc tgcctggact ccaaagcctt cttattgact     540
cctaggaatc aagaggcctg tgagctgtcc aataactgga tctcgagtgc tagcagcgct     600
aaaacgacac ccccatctgt ctatccactg gcccctggat ctgctgccca aactaactcc     660
atggtgaccc tgggatgcct ggtcaagggc tatttccctg agccagtgac agtgacctgg     720
aactctggat ccctgtccag cggtgtgcac accttcccag ctgtcctgca gtctgacctc     780
tacactctga gcagctcagt gactgtcccc tccagcacct ggcccagcga gaccgtcacc     840
tgcaacgttg cccacccggc cagcagcacc aaggtggaca gaaaaattgt gcccagggat     900
tgtggttgta agccttgcat atgtacagtc ccagaagtat catctgtctt catcttcccc     960
ccaaagccca aggatgtgct caccattact ctgactccta aggtcacgtg tgttgtggta    1020
gacatcagca aggatgatcc cgaggtccag ttcagctggt ttgtagatga tgtggaggtg    1080
cacacagctc agacgcaacc ccgggaggag cagttcaaca gcactttccg ctcagtcagt    1140
gaacttccca tcatgcacca ggactggctc aatggcaagg agttcaaatg cagggtcaac    1200
agtgcagctt tccctgcccc catcgagaaa accatctcca aaaccaaagg cagaccgaag    1260
gctccgcagg tgtacaccat tccacctccc aaggagcaga tggccaagga taaagtcagt    1320
ctgacctgca tgataacaga cttcttccct gaagacatta ctgtggagtg gcagtggaat    1380
gggcagccag cggagaacta caagaacact cagcccatca tggacacaga tggctcttac    1440
ttcgtctaca gcaagctcaa tgtgcagaag agcaactggg aggcaggaaa tactttcacc    1500
tgctctgtgt acatgagggg cctgcacaac caccatactg agaagagcct ctcccactct    1560
cctggtaaat ga                                                       1572

<210> SEQ ID NO 74
<211> LENGTH: 1572
<212> TYPE: DNA
<213> ORGANISM: Artificial Sequence
<220> FEATURE:
<223> OTHER INFORMATION: Synthetic polynucleotide

<400> SEQUENCE: 74
atgtacagga tgcaactcct gtcttgcatt gcactaagtc ttgcacttgt cacgaattcg      60
atatctcgag tgtaccagtg ccctgagcac agtcaactga caactctggg cgtggatggg     120
aaggagttcc cagaggtcca cttgggccag tggtacttta tcgcaggggc agctcccacc     180

-continued

```
aaggaggagt tggcaacttt tgaccctgtg dacaacattg tcttcaatat ggctgctggc      240
tctgccccga tgcagctcca ccttcgtgct accaaacgca tgaaagatgg gctctgtgtg      300
ccccggaaat ggatctacca cctgactgaa gggagcacag atctcagaac tgaaggccgc      360
cctgacatga agactgagct cttttccagc tcatgcccag gtggaatcat gctgaatgag      420
acaggccagg gttaccagcg ctttctcctc tacaatcgct caccacatcc tcccgaaaag      480
tgtgtggagg aattcaagtc cctgacttcc tgcctggact ccaaagcctt cttattgact      540
cctaggaatc aagaggcctg tgagctgtcc aataactgga tctcgagtgc tagcagcgct      600
aaaacgacac ccccatctgt ctatccactg gcccctggat ctgctgccca aactaactcc      660
atggtgaccc tgggatgcct ggtcaagggc tatttccctg agccagtgac agtgacctgg      720
aactctggat ccctgtccag cggtgtgcac accttcccag ctgtcctgca gtctgacctc      780
tacactctga gcagctcagt gactgtcccc tccagcacct ggcccagcga gaccgtcacc      840
tgcaacgttg cccacccggc cagcagcacc aaggtggaca agaaaattgt gcccagggat      900
tgtggttgta agccttgcat atgtacagtc ccagaagtat catctgtctt catcttcccc      960
ccaaagccca aggatgtgct caccattact ctgactccta aggtcacgtg tgttgtggta     1020
gacatcagca aggatgatcc cgaggtccag ttcagctggt ttgtagatga tgtggaggtg     1080
cacacagctc agacgcaacc ccgggaggag cagttcaaca gcactttccg ctcagtcagt     1140
gaacttccca tcatgcacca ggactggctc aatggcaagg agttcaaatg cagggtcaac     1200
agtgcagctt tccctgcccc catcgagaaa accatctcca aaaccaaagg cagaccgaag     1260
gctccgcagg tgtacaccat tccacctccc aaggagcaga tggccaagga taaagtcagt     1320
ctgacctgca tgataacaga cttcttccct gaagacatta ctgtggagtg gcagtggaat     1380
gggcagccag cggagaacta caagaacact cagcccatcg tggacacaga tggctcttac     1440
ttcgtctaca gcaagctcaa tgtgcagaag agcaactggg aggcaggaaa tactttcacc     1500
tgctctgtgt tacatgaggg cctgcacaac caccatactg agaagagcct ctcccactct     1560
cctggtaaat ga                                                        1572
```

<210> SEQ ID NO 75
<211> LENGTH: 1572
<212> TYPE: DNA
<213> ORGANISM: Artificial Sequence
<220> FEATURE:
<223> OTHER INFORMATION: Synthetic polynucleotide

<400> SEQUENCE: 75

```
atgtacagga tgcaactcct gtcttgcatt gcactaagtc ttgcacttgt cacgaattcg       60
atatctcgag tgtaccagtg ccctgagcac agtcaactga caactctggg cgtggatggg      120
aaggagttcc cagaggtcca cttgggccag tggtacttta tcgcaggggc agctcccacc      180
aaggaggagt tggcaacttt tgaccctgtg dacaacattg tcttcaatat ggctgctggc      240
tctgccccga tgcagctcca ccttcgtgct accaaccgca tgaaagatgg gctctgtgtg      300
ccccggaaat ggatctacca cctgactgaa gggagcacag atctcagaac tgaaggccgc      360
cctgacatga agactgagct cttttccagc tcatgcccag gtggaatcat gctgaatgag      420
acaggccagg gttaccagcg ctttctcctc tacaatcgct caccacatcc tcccgaaaag      480
tgtgtggagg aattcaagtc cctgacttcc tgcctggact ccaaagcctt cttattgact      540
cctaggaatc aagaggcctg tgagctgtcc aataactgga tctcgagtgc tagcagcgct      600
aaaacgacac ccccatctgt ctatccactg gcccctggat ctgctgccca aactaactcc      660
```

-continued

```
atggtgaccc tgggatgcct ggtcaagggc tatttccctg agccagtgac agtgacctgg        720
aactctggat ccctgtccag cggtgtgcac accttcccag ctgtcctgca gtctgacctc        780
tacactctga gcagctcagt gactgtcccc tccagcacct ggcccagcga gaccgtcacc        840
tgcaacgttg cccacccggc cagcagcacc aaggtggaca agaaaattgt gcccagggat        900
tgtggttgta agccttgcat atgtacagtc ccagaagtat catctgtctt catcttcccc        960
ccaaagccca aggatgtgct caccattact ctgactccta aggtcacgtg tgttgtggta       1020
gacatcagca aggatgatcc cgaggtccag ttcagctggt ttgtagatga tgtggaggtg       1080
cacacagctc agacgcaacc ccgggaggag cagttcaaca gcactttccg ctcagtcagt       1140
gaacttccca tcatgcacca ggactggctc aatggcaagg agttcaaatg cagggtcaac       1200
agtgcagctt ccctgcccc catcgagaaa accatctcca aaaccaaagg cagaccgaag        1260
gctccgcagg tgtacaccat tccacctccc aaggagcaga tggccaagga taaagtcagt       1320
ctgacctgca tgataacaga cttcttccct gaagacatta ctgtggagtg cagtggaat        1380 gggcagccag cggagaacta caagaacact cagcccatca tggacacaga tggctcttac       1440
ttcgtctaca gcaagctcaa tgtgcagaag agcaactggg aggcaggaaa tactttcacc       1500
tgctctgtgt tacatgaggg cctgcacaac caccatactg agaagagcct ctcccactct       1560
cctggtaaat ga                                                          1572
```

```
<210> SEQ ID NO 76
<211> LENGTH: 1572
<212> TYPE: DNA
<213> ORGANISM: Artificial Sequence
<220> FEATURE:
<223> OTHER INFORMATION: Synthetic polynucleotide

<400> SEQUENCE: 76
```

```
atgtacagga tgcaactcct gtcttgcatt gcactaagtc ttgcacttgt cacgaattcg         60
atatctcgag tgtaccagtg ccctgagcac agtcaactga caactctggg cgtggatggg        120
aaggagttcc cagaggtcca cttgggccag tggtacttta tcgcagggc agctcccacc         180 aaggaggagt tggcaacttt tgaccctgtg gacaacattg tcttcaatat ggctgctggc        240
tctgccccga tgcagctcca ccttcgtgct accatccgct acaaagatgg gctctgtgtg        300
ccccggaaat ggatctacca cctgactgaa gggagcacag atctcagaac tgaaggccgc        360
cctgacatga agactgagct ctttccagc tcatgcccag gtggaatcat gctgaatgag         420
acaggccagg gttaccagcg ctttctcctc tacaatcgct caccacatcc tcccgaaaag        480
tgtgtggagg aattcaagtc cctgacttcc tgcctggact ccaaagcctt cttattgact        540
cctaggaatc aagaggcctg tgagctgtcc aataactgga tctcgagtgc tagcagcgct        600
aaaacgacac ccccatctgt ctatccactg gccctggat ctgctgccca aactaactcc         660
atggtgaccc tgggatgcct ggtcaagggc tatttccctg agccagtgac agtgacctgg        720
aactctggat ccctgtccag cggtgtgcac accttcccag ctgtcctgca gtctgacctc        780
tacactctga gcagctcagt gactgtcccc tccagcacct ggcccagcga gaccgtcacc        840
tgcaacgttg cccacccggc cagcagcacc aaggtggaca agaaaattgt gcccagggat        900
tgtggttgta agccttgcat atgtacagtc ccagaagtat catctgtctt catcttcccc        960
ccaaagccca aggatgtgct caccattact ctgactccta aggtcacgtg tgttgtggta       1020
gacatcagca aggatgatcc cgaggtccag ttcagctggt ttgtagatga tgtggaggtg       1080
```

```
cacacagctc agacgcaacc ccgggaggag cagttcaaca gcactttccg ctcagtcagt    1140
gaacttccca tcatgcacca ggactggctc aatggcaagg agttcaaatg cagggtcaac    1200
agtgcagctt tccctgcccc catcgagaaa accatctcca aaaccaaagg cagaccgaag    1260
gctccgcagg tgtacaccat tccacctccc aaggagcaga tggccaagga taaagtcagt    1320
ctgacctgca tgataacaga cttcttccct gaagacatta ctgtggagtg cagtggaat    1380 gggcagccag cggagaacta caagaacact cagcccatca tggacacaga tggctcttac    1440
ttcgtctaca gcaagctcaa tgtgcagaag agcaactggg aggcaggaaa tactttcacc    1500
tgctctgtgt tacatgaggg cctgcacaac caccatactg agaagagcct ctcccactct    1560
cctggtaaat ga                                                        1572
```

<210> SEQ ID NO 77
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 77

```
tttccatggt taatcagtgc cctgagcaca gtc                                   33
```

<210> SEQ ID NO 78
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 78

```
tttggatccc cacttgctgg acagcgggca                                       30
```

<210> SEQ ID NO 79
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 79

```
ttttctagaa tgtacaggat gcaactcctg tc                                    32
```

<210> SEQ ID NO 80
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 80

```
tttggatcct cagtgatggt gatggtgatg tttaccagga gagtgggaga g              51
```

<210> SEQ ID NO 81
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 81

```
tttctcgagt gtaccagtgc cctgagcaca g                                     31
```

<210> SEQ ID NO 82
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 82
tttgctagcc cagttattgg acagctcaca g                                              31

<210> SEQ ID NO 83
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 83
ttttctagat gtacaggatg caactcctgt c                                              31

<210> SEQ ID NO 84
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 84
tttggatcct catcatttac ccggagacag ggag                                          34

<210> SEQ ID NO 85
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 85
aggagttggc aacctttgac cc                                                        22

<210> SEQ ID NO 86
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 86
ttgaccctaa ggacaacatt                                                           20

<210> SEQ ID NO 87
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 87
ttgaccctaa cgacaacatt                                                           20

<210> SEQ ID NO 88
<211> LENGTH: 20
<212> TYPE: DNA
<213> ORGANISM: Artificial Sequence
<220> FEATURE:
<223> OTHER INFORMATION: Synthetic polynucleotide

```
<400> SEQUENCE: 88
ttgaccctca ggacaacatt                                                    20

<210> SEQ ID NO 89
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 89
cgtgctacca aacgcatgaa a                                                  21

<210> SEQ ID NO 90
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 90
cgtgctacca accgcatgaa a                                                  21

<210> SEQ ID NO 91
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 91
taccatccgc tacaaagatg gg                                                 22

<210> SEQ ID NO 92
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(30)
<223> OTHER INFORMATION: May be absent

<400> SEQUENCE: 92

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
            20                  25                  30

<210> SEQ ID NO 93
<211> LENGTH: 60
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(60)
<223> OTHER INFORMATION: May be absent
<220> FEATURE:
<221> NAME/KEY: misc_feature
<222> LOCATION: (3)..(3)
<223> OTHER INFORMATION: Xaa can be any naturally occurring amino acid
```

```
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(43)
```

```
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 93

Xaa Pro Xaa Pro Xaa Pro Xaa Pro Xaa Pro Xaa Pro Xaa Pro Xaa Pro
1               5                   10                  15

Xaa Pro Xaa Pro Xaa Pro Xaa Pro Xaa Pro Xaa Pro Xaa Pro Xaa Pro
        20                  25                  30

Xaa Pro Xaa Pro Xaa Pro Xaa Pro Xaa Pro Xaa Pro Xaa Pro Xaa Pro
    35                  40                  45

Xaa Pro Xaa Pro Xaa Pro Xaa Pro Xaa Pro Xaa Pro
    50                  55                  60
```

APOM-FC FUSION PROTEINS AND USES THEREOF

RELATED APPLICATIONS

This application is a National Stage filing under 35 U.S.C. § 371 of International Application No. PCT/US2018/000202, filed Aug. 15, 2018, which claims the benefit under 35 U.S.C. § 119(e) to U.S. Provisional Application No. 62/545,629, filed Aug. 15, 2017, and entitled "APOM-FC FUSION PROTEINS AND USES THEREOF," the entire contents of each of which are incorporated herein by reference.

GOVERNMENT LICENSE RIGHTS

This invention was made with government support under Grant Nos. HL100001 and dk092760, awarded by the National Institutes of Health. The government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Sep. 15, 2022, is named C123370125US01-SUBSEQ and is 224,548 bytes in size.

BACKGROUND

Apolipoprotein M (ApoM) binds to a lipid mediator sphingosine-1-phosphate (S1P) and chaperones S1P to activate cell surface G protein-coupled receptors (S1P receptors) to induce cellular responses. ApoM/S1P complex is involved in both acute and chronic disease conditions. Abnormal levels and/or activities of ApoM/S1P complex are observed in various diseases.

SUMMARY

Provided herein are engineered fusion proteins comprising ApoM (e.g., human or murine ApoM) fused to a constant region (Fc) of a immunoglobulin G (IgG, e.g., human IgG or murine IgG), referred to herein as the "ApoM-Fc fusion protein." In some embodiments, the ApoM-Fc fusion protein further comprises a signal peptide (e.g., IL-2 signal peptide) fused to the ApoM, allowing the fusion protein to be secreted. In some embodiments, the fusion protein described herein is able to bind S1P and activate an S1P receptor. In some embodiments, variants of the fusion protein (referred to herein as "sponge variants") that have higher binding affinity to S1P are designed. Methods of using the ApoM-Fc fusion protein or the sponge variants in the treatment of various diseases or disorders are provided.

Accordingly, some aspects of the present disclosure provide fusion proteins comprising an apolipoprotein M (ApoM) fused to a constant region (Fc) of an immunoglobulin (IgG). In some embodiments, the fusion protein further comprises a signal peptide fused to the ApoM. In some embodiments, the immunoglobulin is IgG. In some embodiments, the IgG is IgG1.

In some embodiments, the ApoM is fused at the N-terminus of the Fc. In some embodiments, the ApoM is human ApoM or murine ApoM. In some embodiments, the Fc is human Fc or murine Fc. In some embodiments, the ApoM is human ApoM, and the Fc is human Fc. In some embodiments, the ApoM is murine ApoM, and the Fc is murine Fc.

In some embodiments, the Fc comprises an amino acid sequence that is at least 70% at least 80%, at least 90%, at least 95%, at least 99%, or at least 99.5% identical to SEQ ID NO: 7 or SEQ ID NO: 8. In some embodiments, the Fc comprises the amino acid sequence of SEQ ID NO: 7 or SEQ ID NO: 8. In some embodiments, the Fc consists of the amino acid sequence of SEQ ID NO: 7 or SEQ ID NO: 8.

In some embodiments, the ApoM comprises an amino acid sequence that is at least 70%, at least 80%, at least 90%, at least 95%, or at least 99% identical to SEQ ID NO: 5 or SEQ ID NO: 6. In some embodiments, the ApoM comprises the amino acid sequence of SEQ ID NO: 5 or SEQ ID NO: 6. In some embodiments, the ApoM consists of the amino acid sequence of SEQ ID NO: 5 or SEQ ID NO: 6.

In some embodiments, the fusion protein comprises an amino acid sequence that is at least 70%, at least 80%, at least 90%, at least 95%, or at least 99% identical to SEQ ID NO: 1, SEQ ID NO: 2, or SEQ ID NO: 68. In some embodiments, the fusion protein comprises the amino acid sequence of SEQ ID NO: 1, SEQ ID NO: 2, or SEQ ID NO: 68. In some embodiments, the fusion protein consists of the amino acid sequence of SEQ ID NO: 1, SEQ ID NO: 2, or SEQ ID NO: 68.

In some embodiments, the ApoM comprises at least one amino acid substitution at positions corresponding to positions T42, V46, I68, or M70 in SEQ ID NO: 5. In some embodiments, the ApoM comprises an amino acid substitution at a position corresponding to position T42 in SEQ ID NO: 5.

In some embodiments, the amino acid substitution is T42N. In some embodiments, the ApoM comprises an amino acid substitution at a position corresponding to position V46 in SEQ ID NO: 5. In some embodiments, the amino acid substitution is selected from the group consisting of: V46K, V46N, and V46Q. In some embodiments, the ApoM comprises an amino acid substitution at a position corresponding to position 168 in SEQ ID NO: 5. In some embodiments, the amino acid substitution is selected from the group consisting of: I68K and I68N. In some embodiments, the ApoM comprises an amino acid substitution at a position corresponding to position M70 in SEQ ID NO: 5. In some embodiments, the amino acid substitution is M70Y. In some embodiments, the ApoM comprises an amino acid sequence that is at least 70%, at least 80%, at least 90%, at least 95%, at least 99%, or at least 99.5% identical to SEQ ID NO: 5 or SEQ ID NO: 6, and comprising at least one amino acid substitution at positions corresponding to positions T42, V46, I68, or M70 in SEQ ID NO: 5.

In some embodiments, the ApoM comprises the amino acid sequence of any one of SEQ ID NOs: 9-22. In some embodiments, the ApoM consists of the amino acid sequence of any one of SEQ ID NOs: 9-22.

In some embodiments, the fusion protein comprises an amino acid sequence that is at least 70%, at least 80%, at least 90%, at least 95%, at least 99%, or at least 99.5% identical to any one of SEQ ID NOs: 1-4, and comprising at least one amino acid substitution at positions corresponding to positions T42, V46, I68, or M70 in SEQ ID NO: 5. In some embodiments, the fusion protein comprises the amino acid sequence of any one of SEQ ID NOs.: 23-50. In some embodiments, the fusion protein consists of the amino acid sequence of any one of SEQ ID NOs: 23-50.

In some embodiments, the fusion protein is cross-linked, cyclized, conjugated, acylated, carboxylated, lipidated, acetylated, thioglycolic acid amidated, alkylated, methylated, polyglycylated, glycosylated, polysialylated, phospho-rylated, adenylylated, PEGylated, or combinations thereof. In some embodiments, the fusion protein is conjugated to a polymer. In some embodiments, the fusion protein comprises a chemical modification.

Further provided herein are nucleic acid molecules nucleotide sequence encoding the fusion protein described herein. Cells comprising the fusion protein or the nucleic acid encoding the fusion protein are also provided.

Further provided herein are method of producing the fusion protein described herein, the methods comprising culturing cells comprising the fusion protein or the nucleic acids encoding the fusion protein under conditions that allow the fusion protein to express. In some embodiments, the fusion protein is secreted. In some embodiments, the method further comprises recovering the fusion protein from the culturing media.

Pharmaceutical compositions comprising the fusion protein described herein are provided. In some embodiments, the pharmaceutical composition further comprises a phar-maceutically-acceptable carrier.

Antibodies that bind to the fusion protein described herein are also provided.

Other aspects of the present disclosure provide methods of treating a disease or disorder associated with reduced level of sphingosine-1-phosphate (S1P), the method comprising administering to a subject in need thereof a thera-peutically effective amount of a fusion protein comprising an apolipoprotein M (ApoM) fused to a constant region (Fc) of an immunoglobulin G (IgG).

In some embodiments, the fusion protein further comprises a signal peptide fused to the ApoM. In some embodiments, the IgG is IgG1. In some embodiments, the ApoM is fused at the N-terminus of the Fc. In some embodiments, the ApoM is human ApoM or murine ApoM. In some embodiments, the Fc is human Fc or murine Fc. In some embodiments, the ApoM is human ApoM, and the Fc is human Fc. In some embodiments, the ApoM is murine ApoM, and the Fc is murine Fc. In some embodiments, the ApoM comprises an amino acid sequence that is at least 70%, at least 80%, at least 90%, at least 95%, or at least 99% identical to SEQ ID NO: 5 or SEQ ID NO: 6. In some embodiments, the ApoM comprises the amino acid sequence of SEQ ID NO: 5 or SEQ ID NO: 6. In some embodiments, the ApoM consists of the amino acid sequence of SEQ ID NO: 5 or SEQ ID NO: 6. In some embodiments, the Fc comprises an amino acid sequence that is at least 70%, at least 80%, at least 90%, at least 95%, at least 99%, or at least 99.5% identical to SEQ ID NO: 7 or SEQ ID NO: 8. In some embodiments, the Fc comprises the amino acid sequence of SEQ ID NO: 7 or SEQ ID NO: 8. In some embodiments, the Fc consists of the amino acid sequence of SEQ ID NO:7 or SEQ ID NO: 8. In some embodiments, the fusion protein comprises an amino acid sequence that is at least 70%, at least 80%, at least 90%, at least 95%, or at least 99% identical to SEQ ID NO: 1, SEQ ID NO: 2, or SEQ ID NO: 68. In some embodiments, the fusion protein comprises the amino acid sequence of SEQ ID NO: 1, SEQ ID NO: 2, or SEQ ID NO: 68. In some embodiments, the fusion protein consists of the amino acid sequence of SEQ ID NO: 1, SEQ ID NO: 2, or SEQ ID NO: 68.

In some embodiments, the fusion protein is cross-linked, cyclized, conjugated, acylated, carboxylated, lipidated, acetylated, thioglycolic acid amidated, alkylated, methyl-ated, polyglycylated, glycosylated, polysialylated, phospho-rylated, adenylylated, PEGylated, or combinations thereof. In some embodiments, the fusion protein is conjugated to a polymer. In some embodiments, the fusion protein comprises a chemical modification.

In some embodiments, the fusion protein activates a S1P receptor. In some embodiments, the S1P receptor is S1P1. In some embodiments, the S1P receptor is vascular. In some embodiments, the disease or disorder is selected from the group consisting of: infection, sepsis, diabetes, cardiovas-cular disease, retinal vascular disease, peripheral vascular disease, metabolic syndrome, and respiratory disease. In some embodiments, the disease or disorder is selected from the group consisting of: primary and/or secondary resistant hypertension, neurogenic hypertension, gestational hyper-tension, diabetic hypertension, hypertension of chronic kid-ney disease, cardiac and non-cardiac reperfusion injury, ischemic injury, stroke, pulmonary edema, myocardial infarction, acute coronary syndrome, angina, atherosclero-sis, and age-related macular degeneration. In some embodi-ments, the fusion protein is administered subcutaneously, intracutaneously, intravenously, intramuscularly, intraarticu-larly, intraarterially, intrasynovially, intrasternally, intrathe-cally, intralesionally, or intracranially.

Other aspects of the present disclosure provide methods of treating a disease or disorder associated with excess sphingosine-1-phosphate (S1P), the method comprising administering a therapeutically effective amount of a fusion protein comprising an apolipoprotein M (ApoM) fused to a constant region (Fc) of an immunoglobulin G (IgG) to a subject in need thereof, wherein the ApoM comprises at least one amino acid substitution at positions corresponding to positions T42, V46, I68, or M70 in SEQ ID NO: 5.

In some embodiments, the fusion protein further comprises a signal peptide fused to the ApoM. In some embodiments, the IgG is IgG1. In some embodiments, the ApoM is fused at the N-terminus of the Fc. In some embodiments, the ApoM is human ApoM or murine ApoM. In some embodiments, the Fc is human Fc or murine Fc. In some embodiments, the ApoM is human ApoM, and the Fc is human Fc. In some embodiments, the ApoM is murine ApoM, and the Fc is murine Fc. In some embodiments, the Fc comprises an amino acid sequence that is at least 70%, at least 80%, at least 90%, at least 95%, at least 99%, or at least 99.5% identical to SEQ ID NO: 7 or SEQ ID NO: 8. In some embodiments, the Fc comprises the amino acid sequence of SEQ ID NO: 7 or SEQ ID NO: 8. In some embodiments, the Fc consists of the amino acid sequence of SEQ ID NO: 7 or SEQ ID NO: 8. In some embodiments, the ApoM comprises an amino acid sequence that is at least 70%, at least 80%, at least 90%, at least 95%, at least 99%, or at least 99.5% identical to SEQ ID NO: 5 or SEQ ID NO: 6, and comprising at least one amino acid substitution at positions correspond-ing to positions T42, V46, I68, or M70 in SEQ ID NO: 5. In some embodiments, the ApoM comprises an amino acid substitution at a position corresponding to position T42 in SEQ ID NO: 5. In some embodiments, the amino acid substitution is T42N. In some embodiments, the ApoM comprises an amino acid substitution at a position corre-sponding to position V46 in SEQ ID NO: 5. In some embodiments, the amino acid substitution is selected from the group consisting of: V46K, V46N, and V46Q. In some embodiments, the ApoM comprises an amino acid substitu-tion at a position corresponding to position 168 in SEQ ID NO: 5. In some embodiments, the amino acid substitution is selected from the group consisting of: I68K and I68N. In some embodiments, the ApoM comprises an amino acid substitution at a position corresponding to position M70 in SEQ ID NO: 5. In some embodiments, the amino acid substitution is M70Y. In some embodiments, the ApoM comprises the amino acid sequence of any one of SEQ ID NOs: 9-22. In some embodiments, the ApoM consists of the amino acid sequence of any one of SEQ ID NOs: 9-22. In some embodiments, the fusion protein comprising an amino acid sequence that is at least 70%, at least 80%, at least 90%, at least 95%, at least 99%, or at least 99.5% identical to any one of SEQ ID NOs: 1-4, and comprising at least one amino acid substitution at positions corresponding to positions T42, V46, I68, or M70 in SEQ ID NO: 5. In some embodiments, the fusion protein comprises the amino acid sequence of any one of SEQ ID NOs.: 23-50. In some embodiments, the fusion protein consists of the amino acid sequence of any one of SEQ ID NOs: 23-50.

In some embodiments, the fusion protein is cross-linked, cyclized, conjugated, acylated, carboxylated, lipidated, acetylated, thioglycolic acid amidated, alkylated, methylated, polyglycylated, glycosylated, polysialylated, phosphorylated, adenylylated, PEGylated, or combinations thereof. In some embodiments, the fusion protein is conjugated to a polymer. In some embodiments, the fusion protein comprises a chemical modification. In some embodiments, the fusion protein sequesters the excess S1P.

In some embodiments, the disease or disorder is cancer, an inflammatory disease, or an autoimmune disease. In some embodiments, the cancer is metastatic cancer. In some embodiments, the inflammatory disease is rheumatoid arthritis.

In some embodiments, the fusion protein is administered subcutaneously, intracutaneously, intravenously, intramuscularly, intraarticularly, intraarterially, intrasynovially, intrasternally, intrathecally, intralesionally, or intracranially.

Yet other aspect of the present disclosure provide methods comprising contacting the fusion protein described herein with sphingosine-1-phosphate (S1P). In some embodiments, the contacting is carried out in a cell.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

(FIG. 1A) CHO cells or CHO cells stably transduced with $S1P_1$, $S1P_2$, or $S1P_3$ were treated for 5-30 minutes using Albumin-S1P, ApoM-$F_c$-S1P (both 100 nM S1P) or ApoM-$F_c$-TM (12 µg/ml) (Top panels) or by a dose-response with Albumin-S1P or ApoM-$F_c$-S1P diluted to 0-200 nM S1P, or ApoM-Fc-TM (12 µg/ml) (Bottom panels). Samples were analyzed for phospho-p44/42 ERK (pERK) and total p42/44 ERK (tERK) by immunoblotting. (FIG. 1B) HUVECs were treated with Albumin (A1b)-S1P (333 nM S1P), ApoM-$F_c$-S1P (20 µg/ml; 240 nM S1P) or ApoM-$F_c$-TM (20 mg/ml) for indicated times and analyzed by immunoblotting for activation of p44/42 ERK, AKT and eNOS. (FIG. 1C) CRISPR/Cas9 derived $S1P_1$, $S1P_3$, or $S1P_{1,3}$ KO HUVECs were treated with ApoM-$F_c$-S1P (12 µg/ml; 10 0 nM S1P) and analyzed by immunoblotting for activation of p44/42 ERK. For all western blot experiments, N=3 independent experiments; with a representative blot shown.

FIGS. 3A to 3C. Effect of ApoM-Fc on retinal pathological neovascularization. C57B1/6 mice were subjected to Oxygen-induced retinopathy (OIR) (1). Mice were maintained in hyperoxia (75%02) from p7-p12 and re-introduced to normoxia. At p12, p14 and p16, mice were injected with either saline or Apom-Fc (4 mg/Kg) re-suspended in saline. Mice were sacrificed at p17, retina were isolated by standard methods (1) and stained with Isolectin B4-alexa 564. Retina were visualized by confocal microscopy and multiple digital images were obtained and analyzed by ImageJ. Presented are representative samples from the experiment. Data are presented as (FIG. 3A) Vaso-obliteration (measurement of the area of vascular loss/total area of the retina) resulting from OIR. (FIG. 3B) Neovascularization (Measurement of vascular regrowth) resulting from OIR. (FIG. 3C) Lesion size (measurement of overgrowth of pathological vascular tufts) resulting from OIR at p17. Neovascularization and Lesion size are key determinants of pathological disease and the main metrics for determining the efficacy of any therapeutic targeting retinopathies. N=5 for each experiment and data were analyzed by 2-way ANOVA, comparing treated vs. untreated retinal tissues.

(FIG. 4A) Western blot analysis of HEK293T cell lysates containing mApoM-mFc-His (pFUSE-mApoM-mFc-His) and Coomassie Blue stained SDS-PAGE gel (Right) of 5 µg of purified mApoM-mFc-His. (FIG. 4B) Western blot analysis (Left) of HEK293T cell lysates containing hApoM-hFc (pFUSE-hApoM-hFc;) and Coomassie Blue stained SDS-PAGE gel (Right) of 8 µg of purified hApoM-hFc. (FIG. 4C) Measurement of endothelial barrier function using TEER analysis of 10 µg of purified mApoM-mFc-His or saline control. (FIG. 4D) Measurement of endothelial barrier function using TEER analysis of 10 µg of purified hApoM-hFc or saline control.

DETAILED DESCRIPTION OF CERTAIN EMBODIMENTS

Figure 1A:
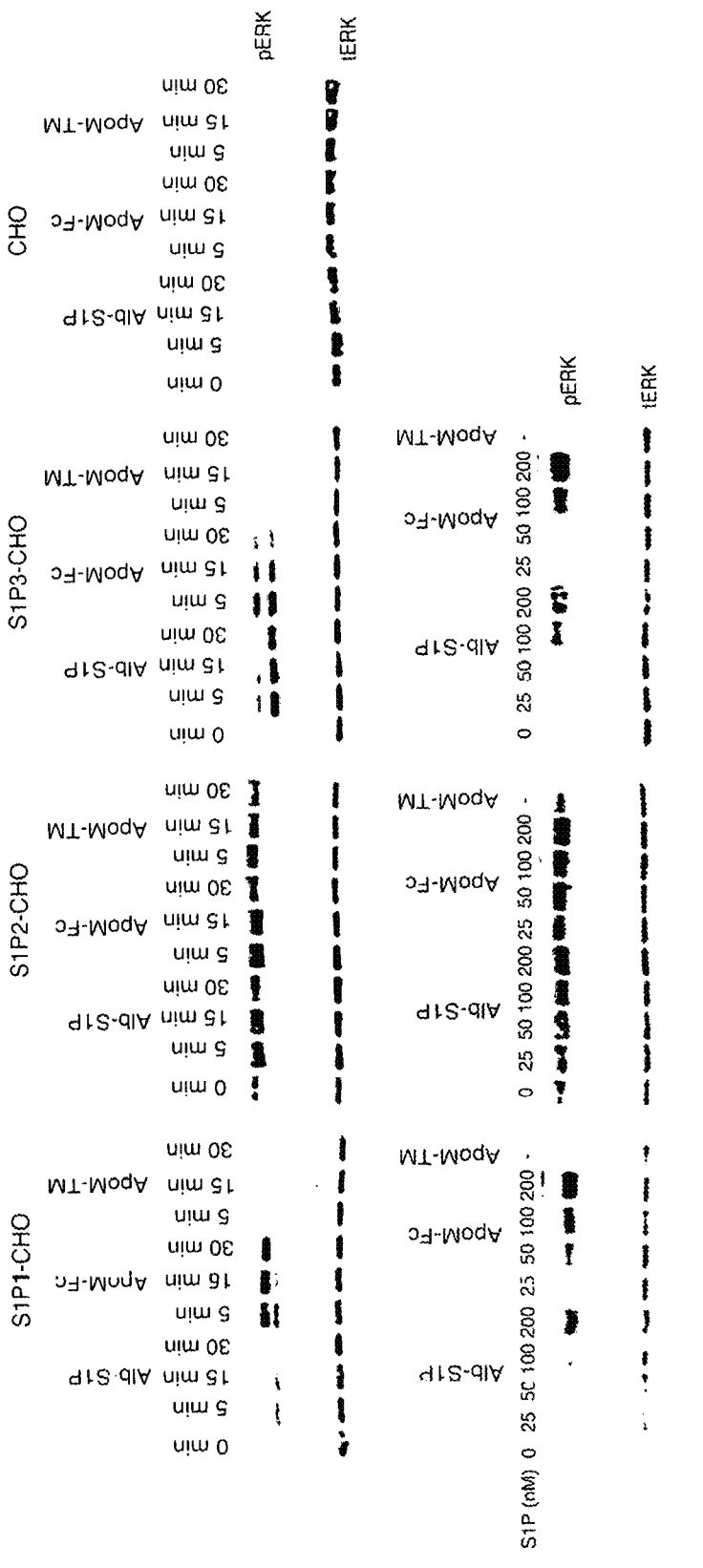
FIGS. 1A to 1C. ApoM-Fc activates SIP receptors.
Figure 1B:
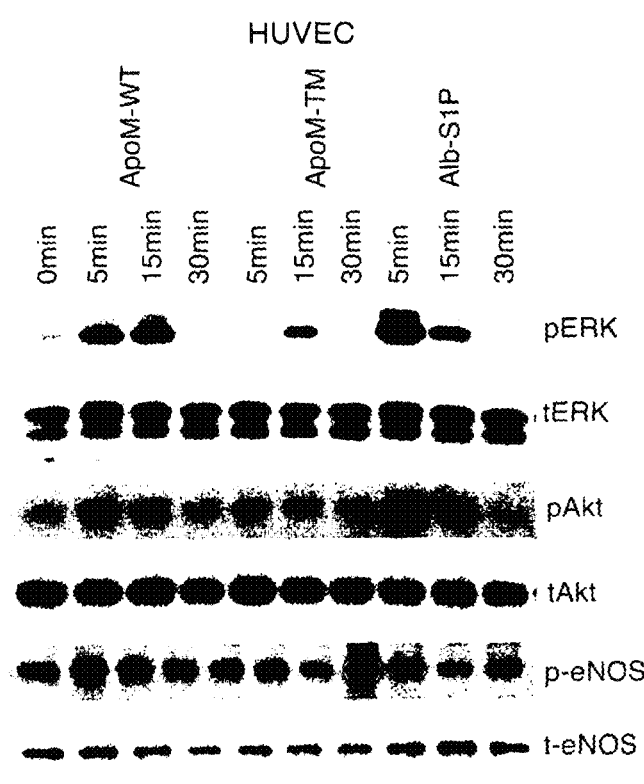
Figure 1C:
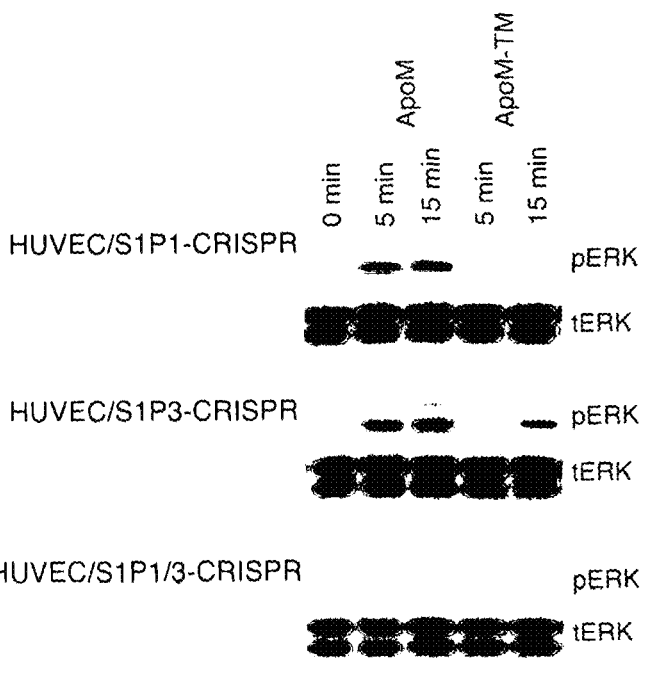

Endothelial cell function is essential for normal cardiovascular homeostasis. Many environmental and intrinsic risk factors for cardiovascular and cerebrovascular diseases cause endothelial dysfunction. Indeed, dysfunctional endothelium is implicated in the development of vascular diseases (e.g., as described in Girouard et al., *Journal of Applied Physiology* 100, 328-335, 2006, incorporated herein by reference). On the other hand, various endogenous factors promote optimal endothelial function and counteract the risk factors (e.g., as described in Libby et al., *Journal of the American College of Cardiology* 54, 2129-2138, 2009, incorporated herein by reference). Among such factors is the high-density lipoprotein (HDL), a multifunctional circulating nanoparticle. Plasma HDL concentrations are shown to be correlated with reduced risk from cardiovascular and cerebrovascular diseases(e.g., as described in Libby et al., *Journal of the American College of Cardiology* 54, 2129-2138, 2009, incorporated herein by reference) as well as improved outcomes after an ischemic event (e.g., as described in Makihara et al., *Cerebrovascular Diseases* 33, 240-247, 2012; and Olsson et al., *European Heart Journal* 26, 890-896, 2005, incorporated herein by reference). HDL particles are heterogeneous, contain numerous bioactive factors and regulate vascular, metabolic and immune functions, suggesting that specific HDL particle subtypes regulate unique functions in the cardiovascular system.

It was previously shown that plasma apolipoprotein M (ApoM)-containing HDL (ApoM$^+$HDL) is a physiological carrier of the bioactive lipid sphingosine 1-phosphate (S1P). ApoM-S1P complexes activate G protein-coupled S1P receptors, suppressing inflammatory responses and maintains vascular barrier function. Mice that lack ApoM have alterations in lipoprotein metabolism and exhibit enhanced atherosclerosis in the LDL receptor null background. Various pathological conditions, including type I and II diabetes, cardiovascular diseases, infection, and conditions associated with endothelial injury, are associated with reduced level or activity of ApoM/S1P.

Provided herein are strategies of modulating the ApoM-S1P signaling pathway for promoting endothelial function and restoring homeostasis. Such strategies involve providing recombinant ApoM to bind to S1P and form ApoM-S1P complexes. In some embodiments, the S1P-ApoM complex activates the S1P receptors and downstream signaling pathways. In some embodiments, ApoM variants that sequester excess S1P are provided. In some embodiments, the recombinant ApoM may be provided during pathological conditions.

Free ApoM that is not associated with HDL has an extremely short half-life (e.g., as described in Faber et al., *Molecular Endocrinology* 20, 212-218, 2006, incorporated herein by reference). As demonstrated herein, fusing the ApoM to a constant region of an immunoglobulin stabilize the ApoM in plasma. In some embodiments, a signal peptide is fused to the ApoM that is fused to the Fc, allowing the fusion protein to be secreted, e.g., into the culturing media, and purified.

Accordingly, some aspects of the present provide a fusion protein comprising an apolipoprotein M (ApoM) fused to a constant region (Fc) of an immunoglobulin G (IgG). A "fusion protein" as used herein, refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. A fusion protein may comprise different domains, for example, an ApoM domain and a Fc domain. In some embodiments, the ApoM is fused at the N-terminus of the Fc. In some embodiments, the ApoM is fused at the C-terminus of the Fc.

A "constant region (Fc) of an immunoglobulin (Ig)" refers to a carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and in some embodiments, lacks the CH1 domain.

In some embodiments, the Fc is derived from a heavy chain constant region of an IgG (Igγ) (γ subclasses 1, 2, 3, or 4). In some embodiments, the Fc is derived from a heavy chain constant region of IgG1. Other classes of immunoglobulin, IgA (Igα), IgD (Igδ), IgE (Igε) and IgM (Ig), may also be used. The choice of appropriate immunoglobulin heavy chain constant region is described in the art, e.g., in U.S. Pat. Nos. 5,541,087, and 5,726,044, incorporated herein by reference. The choice of particular immunoglobulin heavy chain constant region sequences from certain immunoglobulin classes and subclasses to achieve a particular result is considered to be within the level of skill in the art. In some embodiments, The portion of the DNA construct encoding the immunoglobulin Fc region preferably comprises at least a portion of a hinge domain, and preferably at least a portion of a CH3 domain of Fc γ or the homologous domains in any of IgA, IgD, IgE, or IgM. The immunoglobulin may be from any mammal (e.g., a human or a murine such as a mouse or a rat). In some embodiments, the Fc is from a human IgG (e.g., human IgG1) is used. In some embodiments, the Fc is from a murrain IgG (e.g., murine IgG1). The amino acid sequences of Fc from human or murine IgG1, and nucleotide sequences encoding such are provided in Table 1. It is to be understood that the sequences provided are for illustration purpose only and are not meant to be limiting. Substitution or deletion of amino acids within the immunoglobulin heavy chain constant regions are also contemplated herein. A non-limiting example would be to introduce amino acid substitutions in the upper CH2 region to create an Fc variant with reduced affinity for Fc receptors (e.g., as described in Cole et al. (1997) *J. Immunol.* 159: 3613, incorporated herein by reference).

In some embodiments, the Fc comprises an amino acid sequence that is at least 70% identical to SEQ ID NO: 7 or SEQ ID NO: 8. For example, the Fc may comprise an amino acid sequence that is at least 70%, at least 80%, at least 90%, at least 95%, at least 99%, or at least 99.5% identical to SEQ ID NO: 7 or SEQ ID NO: 8. In some embodiments, the Fc comprises an amino acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO: 7 or SEQ ID NO: 8. In some embodiments, the Fc comprises the amino acid sequence of SEQ ID NO: 7 or SEQ ID NO 8. In some embodiments, the Fc consists of the amino acid sequence of SEQ ID NO: 7 or SEQ ID NO 8.

"Apolipoprotein M (ApoM)" is a 26-kDa protein that is mainly associated with high-density lipoprotein (HDL) in mammalian (e.g., human) plasma, with a small proportion present in triglyceride-rich lipoproteins (TGRLP) and low-density lipoproteins (LDL). It belongs to lipocalin protein superfamily. ApoM is only expressed in liver and in kidney and small amounts are found in fetal liver and kidney. Expression of native ApoM could be regulated by platelet activating factor (PAF), transforming growth factors (TGF), insulin-like growth factor (IGF) and leptin in vivo and/or in vitro. The ApoM may be from any mammal (e.g., a human or a murine such as a mouse or a rat). The amino acid sequences of wild-type human and mouse ApoM, and nucleotide sequences encoding such are provided in Table 1. It is to be understood that the sequences provided are for illustration purpose only and are not meant to be limiting.

In some embodiments, the ApoM comprises an amino acid sequence that is at least 70% identical to SEQ ID NO: 5 or SEQ ID NO: 6. For example, the ApoM may comprise an amino acid sequence that is at least 70%, at least 80%, at least 90%, at least 95%, or at least 99% identical to SEQ ID NO: 5 or SEQ ID NO: 6. In some embodiments, the ApoM comprises an amino acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 5 or SEQ ID NO: 6. In some embodiments, the ApoM comprises the amino acid sequence of SEQ ID NO: 5 or SEQ ID NO 6. In some embodiments, the ApoM consists of the amino acid sequence of SEQ ID NO: 5 or SEQ ID NO 6.

In some embodiments, the fusion protein described herein comprises a human ApoM fused to a human Fc. In some embodiments, the fusion protein described herein comprises a murine ApoM fused to a murine Fc. In some embodiments, the fusion protein described herein comprises a human ApoM fused to a murine Fc. In some embodiments, the fusion protein described herein comprises a murine ApoM fused to a human Fc. While any of the fusion proteins described herein may be used in any subject (e.g., a human or a murine such as a mouse or a rat), using a fusion protein comprising domains that are from the same origin (e.g., species) as the subject may reduce unwanted immune response against the fusion protein in the subject. As such, in some embodiments, a fusion protein comprising a human ApoM fused to a human Fc is used in a human subject (e.g., for chronic administration for treating a disease or disorder). In some embodiments, a fusion protein comprising a murine (e.g., mouse) ApoM fused to a murine (e.g., mouse) Fc is used in a mouse (e.g., in a mouse model of a disease or disorder).

In some embodiments, the fusion protein further comprises a signal peptide. For example, in some embodiments, the signal peptide is fused at the N-terminus of ApoM. A "signal peptide" refers to a short peptide (e.g., 16-30 amino acids long) present at the N-terminus of a large number of newly synthesized proteins that are destined towards the secretory pathway. Signal peptides are typically needed for the translocation across the membrane on the secretory pathway and thus universally control the entry of most proteins both in eukaryotes and prokaryotes to the secretory pathway. Signal peptides generally include three regions: an N-terminal region of differing length, which usually comprises positively charged amino acids; a hydrophobic region; and a short carboxy-terminal peptide region. In eukaryotes, the signal peptide of a nascent precursor protein (pre-protein) directs the ribosome to the rough endoplasmic reticulum (ER) membrane and initiates the transport of the growing peptide chain across it. The signal peptide is not responsible for the final destination of the mature protein, however. Secretory proteins devoid of further address tags in their sequence are by default secreted to the external environment. Signal peptides are cleaved from precursor proteins by an endoplasmic reticulum (ER)-resident signal peptidase or they remain uncleaved and function as a membrane anchor.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide may have a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

In some embodiments, the fusion protein of the present disclosure contains a signal peptide at the either the N- or C-terminus to facilitate secretion of the fusion protein. In some embodiments, the signal peptide is at the N-terminus of the fusion protein. For example, the fusion protein may have a signal peptide-ApoM-Fc structure. In some embodiments, the signal peptide fused to the fusion protein is an artificial signal peptide, e.g., an IL-2 signal peptide, an IgE signal peptide or an IgG signal peptide. In some embodiments, the signal peptide is an IL-2 signal peptide comprising the amino acid sequence of MYRMQLLSCIALSLA-LVTNS (SEQ ID NO: 56). In some embodiments, the signal peptide is an Ig heavy chain epsilon-1 signal peptide (IgE HC SP) comprising the amino acid sequence of MDWTWILFLVAAATRVHS (SEQ ID NO: 57). In some embodiments, a signal peptide is an IgGk chain V-III region HAH signal peptide (IgGk SP) comprising the amino acid sequence of METPAQLLFLLLLWLPDTTG (SEQ ID NO: 58).

In some embodiments, the fusion protein of the present disclosure comprises an amino acid sequence that is at least 70% identical to any one of SEQ ID NOs: 1-4 and 68. For example, the fusion protein may comprise an amino acid sequence that is at least 70%, at least 80%, at least 90%, at least 95%, at least 99%, or at least 99.5% identical to any one of SEQ ID NOs: 1-4 and 68. In some embodiments, the fusion protein comprises an amino acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to any one of SEQ ID NOs: 1-4 and 68. In some embodiments, the fusion protein comprises the amino acid sequence of any one of SEQ ID NOs: 1-4 and 68. In some embodiments, the fusion protein consists of the amino acid sequence of any one of SEQ ID NOs: 1-4 and 68.

Further provided herein are ApoM variants and fusion proteins comprising such ApoM variants. As described herein, amino acids in ApoM that are involved in binding to S1P may be substituted with another amino acid that enhances the binding of the ApoM variant to S1P. In some embodiments, the amino acids in ApoM that are involved in binding to S1P are those that interact with the phosphate of S1P. In some embodiments, the amino acids in ApoM that are involved in binding to S1P are substituted with positively charged or hydrogen-bonding amino acids for enhanced interaction with the phosphate in S1P and thus tighter binding to S1P. Such ApoM variants are referred to herein as "ApoM sponge variants." Fusion proteins comprising the ApoM sponge variants may also be referred to as "sponge variants." ApoM that does not contain the mutations in the sponge variants may be referred to as "non-sponge ApoM."

In some embodiments, the ApoM sponge variant binds to S1P with enhanced affinity. In some embodiments, the affinity between an ApoM sponge variant and S1P is enhanced by at least 20%, compared to the affinity between a non-sponge ApoM and S1P. For example, the affinity between an ApoM sponge variant and S1P may be enhanced by the at least 20%, at least 30%, at least 40%, at least 50%, at least 60%, at least 70%, at least 80%, at least 90%, at least 100%, at least 2-fold, at least 5-fold, at least 10-fold, at least 50-fold, at least 100-fold, at least 1000 fold, or more, compared to the affinity between a non-sponge ApoM and S1P. In some embodiments, the affinity between an ApoM sponge variant and S1P is enhanced by 20%, 30%, 40%, 50%, 60%, 70%, 80%, 90%, 100%, 2-fold, 5-fold, 10-fold, 50-fold, 100-fold, 1000 fold, or more, compared to the affinity between a non-sponge ApoM and S1P.

In some embodiments, the amino acids in ApoM that are substituted are T42, V46, I68, and/or M70 in human ApoM (SEQ ID NO: 5). These amino acid positions correspond to T42, V46, I68, and/or T70 in mouse ApoM (SEQ ID NO: 6), which may also be substituted. An "amino acid substitution" without the reference to a specific amino acid, may include any amino acid other than the wild type residue normally found at that position. Such substitutions may be replacement with non-polar (hydrophobic) amino acids, such as glycine, alanine, valine, leucine, isoleucine, methionine, phenylalanine, tryptophan, and proline. Substitutions may be replacement with polar (hydrophylic) amino acids such as serine, threonine, cysteine, tyrosine, asparagine, and glutamine. Substitutions may be replacement with electrically charged amino acids, e.g., negatively electrically charged amino acids such as aspartic acid and glutamic acid and positively electrically charged amino acids such as lysine, arginine, and histidine.

The substitution mutations described herein will typically be replacement with a different naturally occurring amino acid residue, but in some cases non-naturally occurring amino acid residues may also be substituted. Non-natural amino acids, as the term is used herein, are non-proteinogenic (i.e., non-protein coding) amino acids that either occur naturally or are chemically synthesized. Examples include but are not limited to β-amino acids (β3 and β2), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, and N-methyl amino acids. In some embodiments, the amino acid can be substituted or unsubstituted. The substituted amino acid or substituent can be a halogenated aromatic or aliphatic amino acid, a halogenated aliphatic or aromatic modification on the hydrophobic side chain, or an aliphatic or aromatic modification.

In some embodiments, the ApoM sponge variant described comprises at least one amino acid substitution at positions corresponding to positions T42, V46, I68, or M70 in SEQ ID NO: 5. For example, the ApoM sponge variant may comprise 1, 2, 3, or 4 amino acid substitutions at positions corresponding to positions T42, V46, I68, or M70 in SEQ ID NO: 5. For ApoM sponge variant that comprises more than one amino acid substitution, the amino acid substitutions may be any combination at positions corresponding to positions T42, V46, I68, or M70 in SEQ ID NO: 5, e.g., at T42 and V46, at T42 and I68, at T42 and M70, at V46 and I68, at V46 and M70, at I68 and M70, at T42, V46, V46 and I68, at T42, V46, and M70, at T42, I68, and M70, at V46, I68, and M70, and at T42, V46, I68, and M70.

In some embodiments, the ApoM sponge variant comprises an amino acid substitution at a position corresponding to position T42 in SEQ ID NO: 5. As described herein, in some embodiments, the amino acid at a position corresponding to position T42 of SEQ ID No: 5 may be substituted with an positively charged or hydrogen-bonding amino acid. In some embodiments, the amino acid substitution at the position corresponding to T42 is T42N.

In some embodiments, the ApoM sponge variant comprises an amino acid substitution at a position corresponding to position V46 in SEQ ID NO: 5. As described herein, in some embodiments, the amino acid at a position corresponding to position V46 in SEQ ID No: 5 may be substituted with an positively charged or hydrogen-bonding amino acid. In some embodiments, the amino acid substitution at the position corresponding to V46 in SEQ ID NO: 5 is V46K, V46N, or V46Q.

In some embodiments, the ApoM sponge variant comprises an amino acid substitution at a position corresponding to position 168 in SEQ ID NO: 5. As described herein, in some embodiments, the amino acid at a position corresponding to position 168 in SEQ ID No: 5 may be substituted with an positively charged or hydrogen-bonding amino acid. In some embodiments, the amino acid substitution at the position corresponding to 168 in SEQ ID NO: 5 is I68K or I68N.

In some embodiments, the ApoM sponge variant comprises an amino acid substitution at a position corresponding to position M70 in SEQ ID NO: 5. As described herein, in some embodiments, the amino acid at a position corresponding to position M70 of SEQ ID No: 5 may be substituted with an positively charged or hydrogen-bonding amino acid. In some embodiments, the amino acid substitution at the position corresponding to M70 in SEQ ID NO: 5 is M70Y. In some embodiments, the amino acid substitution at the position corresponding to M70 in SEQ ID NO: 5 is I70Y (e.g., in SEQ ID NO: 6).

In some embodiments, the ApoM sponge variant comprises an amino acid sequence that is at least 70% identical to SEQ ID NO: 5 or SEQ ID NO: 6, and comprising at least one amino acid substitution at positions corresponding to positions T42, V46, I68, or M70 in SEQ ID NO: 5. For example, the ApoM sponge variant may comprise an amino acid sequence that is at least 70%, at least 80%, at least 90%, at least 95%, at least 99%, or at least 99.5% identical to SEQ ID NO: 5 or SEQ ID NO: 6, and comprising at least one amino acid substitution at positions corresponding to positions T42, V46, I68, or M70 in SEQ ID NO: 5. In some embodiments, the ApoM sponge variant comprises an amino acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 5 or SEQ ID NO: 6, and comprising at least one amino acid substitution at positions corresponding to positions T42, V46, I68, or M70 in SEQ ID NO: 5. In some embodiments, the ApoM sponge variant comprises the amino acid sequence of any one of SEQ ID NOs: 9-22. In some embodiments, the ApoM sponge variant consists of the amino acid sequence of any one of SEQ ID NOs: 9-22.

The fusion proteins of the present disclosure may comprise any of the ApoM sponge variant described herein. In some embodiments, the fusion protein comprising the ApoM sponge mutant further comprises a signal peptide, e.g., fused to the N-terminus of ApoM sponge mutant. In some embodiments, in a fusion protein comprising the ApoM sponge variant, the amino acid substitutions that corresponding to T42, V46, I68, or M70 in SEQ ID NO: 5 are at positions T66, V70, I92, or M94 of the fusion protein (e.g., in SEQ ID NO: 1), or at positions T66, V70, I92, or 194 of the fusion protein (e.g., in SEQ ID NO: 2).

In some embodiments, the fusion protein comprising an ApoM sponge variant comprises an amino acid sequence that is at least 70% identical to any one of SEQ ID NOs: 1-4, and comprising at least one amino acid substitution at positions corresponding to positions T42, V46, I68, or M70 in SEQ ID NO: 5. In some embodiments, the fusion protein comprising an ApoM sponge variant comprises an amino acid sequence that is at least 70%, at least 80%, at least 90%, at least 95%, at least 99%, or at least 99.5% identical to any one of SEQ ID NOs: 1-4, and comprising at least one amino acid substitution at positions corresponding to positions T42, V46, I68, or M70 in SEQ ID NO: 5. In some embodiments, the fusion protein comprising an ApoM sponge variant comprises an amino acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to any one of SEQ ID NOs: 1-4, and comprising at least one amino acid substitution at positions corresponding to positions T42, V46, I68, or M70 in SEQ ID NO: 5. In some embodiments, the fusion protein comprising the ApoM sponge variant comprises the amino acid sequence of any one of SEQ ID Nos: 23-50. In some embodiments, the fusion protein comprising the ApoM sponge variant consists of the amino acid sequence of any one of SEQ ID NOs: 23-50.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

Amino acid substitution can be achieved during chemical synthesis of the peptide by adding the desired substitute amino acid at the appropriate sequence in the synthesis process. Alternatively, molecular biology methods can be used. Non-conservative substitutions are also encompassed to the extent that they substantially retain the activities of those peptides described herein.

In some embodiments, the amino acid substituted fusion protein will substantially retain the activity of the non-substituted fusion protein. By "substantially retain" means one or more activity of the variant is at least 50% compared to the activity of the original polypeptide in a similar assay, under similar conditions. In some embodiments, the activity is at least 60%, at least 70%, at least 80%, at least 90%, at least 95%, at least 99%, at least 100%, at least 2-fold, at least 5-fold, at least 10-fold, at least 100-fold or higher activity compared to the original fusion protein.

In some embodiments, a linker may be used to fuse the ApoM (e.g., wild type or variant) to the Fc, and/or to fuse signal peptide to the rest of the fusion protein. A "linker" refers to a chemical group or a molecule linking two molecules or moieties, e.g., two domains of a fusion protein. Typically, the linker is positioned between, or flanked by, two groups, molecules, domains, or other moieties and connected to each one via a covalent bond, thus connecting the two. The linker may be as simple as a covalent bond, or it may be a polymeric linker many atoms in length. In some embodiments, the linker is a polypeptide or based on amino acids. In some embodiments, the linker is not peptide-like. In some embodiments, the linker is a covalent bond (e.g., a carbon-carbon bond, disulfide bond, carbon-heteroatom bond, etc.). In some embodiments, the linker is a carbon-nitrogen bond of an amide linkage. In some embodiments, the linker is a cyclic or acyclic, substituted or unsubstituted, branched or unbranched aliphatic or heteroaliphatic linker. In some embodiments, the linker is polymeric (e.g., poly-ethylene, polyethylene glycol, polyamide, polyester, etc.). In some embodiments, the linker comprises a monomer, dimer, or polymer of aminoalkanoic acid. In some embodiments, the linker comprises an aminoalkanoic acid (e.g., glycine, ethanoic acid, alanine, beta-alanine, 3-aminopropanoic acid, 4-aminobutanoic acid, 5-pentanoic acid, etc.). In some embodiments, the linker comprises a monomer, dimer, or polymer of aminohexanoic acid (Ahx). In some embodiments, the linker is based on a carbocyclic moiety (e.g., cyclopentane, cyclohexane). In other embodiments, the linker comprises a polyethylene glycol moiety (PEG). In other embodiments, the linker comprises amino acids. In some embodiments, the linker comprises a peptide. In some embodiments, the linker comprises an aryl or heteroaryl moiety. In some embodiments, the linker is based on a phenyl ring. The linker may include functionalized moieties to facilitate attachment of a nucleophile (e.g., thiol, amino) from the peptide to the linker. Any electrophile may be used as part of the linker. Exemplary electrophiles include, but are not limited to, activated esters, activated amides, Michael acceptors, alkyl halides, aryl halides, acyl halides, and isothiocyanates.

In some embodiments, the linker is an amino acid or a plurality of amino acids (e.g., a peptide or protein). In some embodiments, the linker is a bond (e.g., a covalent bond), an organic molecule, group, polymer, or chemical moiety. In some embodiments, the linker is 1-100 amino acids in length, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-110, 110-120, 120-130, 130-140, 140-150, or 150-200 amino acids in length. Longer or shorter linkers are also contemplated.

In some embodiments, a linker comprises the amino acid sequence SGSETPGTSESATPES (SEQ ID NO: 59), which may also be referred to as the XTEN linker. In some embodiments, a linker comprises the amino acid sequence SGGS (SEQ ID NO: 60). In some embodiments, a linker comprises $(SGGS)_n$(SEQ ID NO: 61), $(GGGS)_n$ (SEQ ID NO: 62), $(GGGGS)_n$ (SEQ ID NO: 63), $(G)_n$ (SEQ ID NO: 92), $(EAAAK)_n$ (SEQ ID NO: 64), $(GGS)_n$(SEQ ID NO: 55), SGSETPGTSESATPES (SEQ ID NO: 59), or $(XP)_n$ (SEQ ID NO: 93) motif, or a combination of any of these, wherein n is independently an integer between 1 and 30, and wherein X is any amino acid. In some embodiments, n is 1, 2, 3, 4, 5, 6, 7, 8, 9, 10, 11, 12, 13, 14, or 15. In some embodiments, a linker comprises SGSETPGTSESATPES (SEQ ID NO: 59), and SGGS (SEQ ID NO: 60). In some embodiments, a linker comprises SGGSSGSETPGTSESAT-PESSGGS (SEQ ID NO: 65). In some embodiments, a linker comprises SGGSSGGSSGSETPGTSESAT-PESSGGSSGGS (SEQ ID NO: 66). In some embodiments, a linker comprises (SEQ ID NO: 67)

GGSGGSPGSPAGSPTSTEEGTSESATPESGPGTSTEPSEGSAPGSPAGSP

TSTEEGTSTEPSEGSAPGTSTEPSEGSAPGTSESATPESGPGSEPATSGG

SGGS.

In some embodiments, the fusion protein described herein comprises a modification. When the fusion protein is referred to herein, it encompasses all its variants and derivatives. Polypeptides comprising modifications have additional features other than amino acid contents. As used herein, a "modification" or "derivative" of a protein or polypeptide (e.g., the fusion protein described herein) produces a modified or derivatized polypeptide, which is a form of a given peptide that is chemically modified relative to the reference peptide, the modification including, but not limited to, oligomerization or polymerization, modifications of amino acid residues or peptide backbone, cross-linking, cyclization, conjugation, PEGylation, glycosylation, acetylation, phosphorylation, acylation, carboxylation, lipidation, thioglycolic acid amidation, alkylation, methylation, polyglycylation, glycosylation, polysialylation, adenylylation, PEGylation, fusion to additional heterologous amino acid sequences, or other modifications that substantially alter the stability, solubility, or other properties of the peptide while substantially retaining the activity of the polypeptides described herein. It is to be understood that the fusion protein comprising such modifications, are cross-linked, cyclized, conjugated, acylated, carboxylated, lipidated, acetylated, thioglycolic acid amidated, alkylated, methylated, polyglycylated, glycosylated, polysialylated, phosphorylated, adenylylated, PEGylated, or combination thereof. In some embodiments, the modified fusion protein of the present disclosure may contain non-amino acid elements, such as polyethylene glycols, lipids, poly- or monosaccharide, and phosphates. The fusion protein of the present disclosure, may comprise the modifications disclosed herein at the C-terminus (e.g., C-terminal amidation), N-terminus (e.g., N-terminal acetylation). Terminal modifications are useful, and are well known, to reduce susceptibility to proteinase digestion, and therefore serve to prolong half-life of the polypeptides in solutions, particularly biological fluids where proteases may be present. In some embodiments, the fusion proteins described herein are further modified within the sequence, such as, modification by terminal-NH$_2$ acylation, e.g., acetylation, or thioglycolic acid amidation, by terminal-carboxylamidation, e.g., with ammonia, methylamine, and the like terminal modifications.

Terminal modifications are useful, to reduce susceptibility by proteinase digestion, and therefore can serve to prolong half-life of the polypeptides in solution, particularly in biological fluids where proteases may be present. Amino terminus modifications include methylation (e.g., —NHCH3 or —N(CH3)2), acetylation (e.g., with acetic acid or a halogenated derivative thereof such as a-chloroacetic acid, a-bromoacetic acid, or a-iodoacetic acid), adding a benzyloxycarbonyl (Cbz) group, or blocking the amino terminus with any blocking group containing a carboxylate functionality defined by RCOO—or sulfonyl functionality defined by R—SO2—, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the polypeptide. In certain embodiments, the N-terminus is acetylated with acetic acid or acetic anhydride.

Carboxy terminus modifications include replacing the free acid with a carboxamide group or forming a cyclic lactam at the carboxy terminus to introduce structural constraints. One can also cyclize the peptides described herein, or incorporate a desamino or descarboxy residue at the termini of the peptide, so that there is no terminal amino or carboxyl group, to decrease susceptibility to proteases or to restrict the conformation of the peptide. Methods of circular peptide synthesis are known in the art, for example, in U.S. Patent Application No. 20090035814; Muralidharan and Muir, 2006, Nat Methods, 3:429-38; and Lockless and Muir, 2009, Proc Natl Acad Sci USA. Jun 18, Epub. C-terminal functional groups of the peptides described herein include amide, amide lower alkyl, amide di(lower alkyl), lower alkoxy, hydroxy, and carboxy, and the lower ester derivatives thereof, and the pharmaceutically acceptable salts thereof.

In some embodiments, the fusion proteins described herein are phosphorylated. One can also readily modify peptides by phosphorylation, and other methods (e.g., as described in Hruby, et al. (1990) Biochem J. 268:249-262). In some embodiments, one can also replace the naturally occurring side chains of the genetically encoded amino acids (or the stereoisomeric D amino acids) with other side chains, for instance with groups such as alkyl, lower (C1-6) alkyl, cyclic 4-, 5-, 6-, to 7-membered alkyl, amide, amide lower alkyl amide di(lower alkyl), lower alkoxy, hydroxy, carboxy and the lower ester derivatives thereof, and with 4-, 5-, 6-, to 7-membered heterocycles. For example, proline analogues in which the ring size of the proline residue is changed from 5 members to 4, 6, or 7 members can be employed.

Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl groups. These heterocyclic groups can be substituted or unsubstituted. Where a group is substituted, the substituent can be alkyl, alkoxy, halogen, oxygen, or substituted or unsubstituted phenyl.

In some embodiments, the fusion proteins described herein may be attached to one or more polymer moieties. In some embodiments, these polymers are covalently attached to the fusion proteins of the disclosure. In some embodiments, for therapeutic use of the end product preparation, the polymer is pharmaceutically acceptable. One skilled in the art will be able to select the desired polymer based on such considerations as whether the polymer-peptide conjugate will be used therapeutically, and if so, the desired dosage, circulation time, resistance to proteolysis, and other considerations.

Suitable polymers include, for example, polyethylene glycol (PEG), polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. Such a polymer may or may not have its own biological activity. The polymers can be covalently or non-covalently conjugated to the fusion protein. Methods of conjugation for increasing serum half-life and for radiotherapy are known in the art, for example, in U.S. Pat. Nos. 5,180,816, 6,423,685, 6,884,780, and 7,022,673, which are hereby incorporated by reference in their entirety.

In some embodiments, the fusion protein described herein may be attached to one or more water soluble polymer moieties. The water soluble polymer may be, for example, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl-pyrrolidone)polyethylene glycol, propropylene glycol homopolymers, polypropylene oxide/ethylene oxide copolymers, and polyoxyethylated polyols. A preferred water soluble polymer is PEG.

The polymer may be of any molecular weight, and may be branched or unbranched. The average molecular weight of the reactant PEG is preferably between about 3,000 and about 50,000 daltons (the term "about" indicating that in preparations of PEG, some molecules will weigh more, and some less, than the stated molecular weight). More preferably, the PEG has a molecular weight of from about 10 kDa to about 40 kDa, and even more preferably, the PEG has a molecular weight from 15 to 30 kDa. Other sizes may be used, depending on the desired therapeutic profile (e.g., duration of sustained release desired; effects, if any, on biological activity; ease in handling; degree or lack of antigenicity; and other effects of PEG on a therapeutic peptide known to one skilled in the art).

The number of polymer molecules attached may vary; for example, one, two, three, or more water-soluble polymers may be attached to a peptide of the disclosure. The multiple attached polymers may be the same or different chemical moieties (e.g., PEGs of different molecular weight).

In certain embodiments, PEG may be attached to at least one terminus (N-terminus or C-terminus) of the fusion protein described herein. In some embodiments, PEG may be attached to a linker moiety of the fusion protein. In some embodiments, the linker contains more than one reactive amine capable of being derivatized with a suitably activated PEG species.

PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity), and increase the hydrodynamic size (size in solution) of the agent which prolongs its circulatory time by reducing renal clearance. PEGylation can also provide water solubility to hydrophobic drugs and proteins. PEGylation, by increasing the molecular weight of a molecule, can impart several significant pharmacological advantages over the unmodified form, such as: improved drug solubility, reduced dosage frequency, without diminished efficacy with potentially reduced toxicity, extended circulating life, increased drug stability, and enhanced protection from proteolytic degradation. In addition, PEGylated drugs are have wider opportunities for new delivery formats and dosing regimens. Methods of PEGylating molecules, proteins and peptides are well known in the art, e.g., as described in U.S. Pat. Nos. 5,766,897; 7,610,156; 7,256,258 and the International Application No. WO/1998/032466.

Encompassed herein are conjugates of the fusion protein herein. The fusion proteins can be conjugated to other polymers in addition to polyethylene glycol (PEG). The polymer may or may not have its own biological activity. Further examples of polymer conjugation include but are not limited to polymers such as polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. Conjugation to a polymer can improve serum half-life, among other effects. A variety of chelating agents can be used to conjugate the peptides described herein. These chelating agents include but are not limited to ethylenediaminetetraacetic acid (EDTA), diethylenetriaminopentaacetic acid (DTPA), ethyleneglycol-0,0'-bis(2-aminoethyl)-N,N,N',N'-tetraacetic acid (EGTA), N,N'-bis(hydroxybenzyl)ethylenediamine-N,N'-diacetic acid (HBED), triethylenetetraminehexaacetic acid (TTHA), 1,4,7,10-tetra-azacyclododecane-N,N',N'',N'''-tetraacetic acid (DOTA), 1,4,7,10-tetraazacyclotridecane-1,4,7,10-tetraacetic acid (TITRA), 1,4,8,11-tetraazacyclotetradecane-N,N',N'',N'''-tetraacetic acid (TETA), and 1,4,8,11-tetraazacyclotetradecane (TETRA). Methods of conjugation are well known in the art, for example, P. E. Thorpe, et. al, 1978, Nature 271, 752-755; Harokopakis E., et. al., 1995, Journal of Immunological Methods, 185:31-42; S. F. Atkinson, et. al., 2001, J. Biol. Chem., 276:27930-27935; and U. S Pat. Nos.: 5,601,825, 5,180,816, 6,423,685, 6,706,252, 6,884, 780, and 7,022,673, which are hereby incorporated by reference in their entirety.

Other methods for stabilizing peptides known in the art may be used with the methods and compositions described herein. For example, using D-amino acids, using reduced amide bonds for the peptide backbone, and using non-peptide bonds to link the side chains, including, but not limited to, pyrrolinone and sugar mimetics can each provide stabilization. The design and synthesis of sugar scaffold peptide mimetics are described by Hirschmann et al. (J. Med. Chem., 1996, 36, 2441-2448, which is incorporated herein by reference in its entirety). Further, pyrrolinone-based peptide mimetics present the peptide pharmacophore on a stable background that has improved bioavailability characteristics (see, for example, Smith et al., J. Am. Chem. Soc. 2000, 122, 11037-11038), which is incorporated herein by reference in its entirety.

All combinations of the different modifications and derivatizations are envisioned for the fusion protein described herein. Modifications, derivatives and methods of reprivatizing polypeptides are described in Published International Application WO 2010/014616, the contents of which are incorporated herein by reference.

Other aspects of the present disclosure provide methods of producing the fusion protein. The fusion protein will generally be produced by expression form recombinant nucleic acids in appropriate cells (e.g., bacterial cell or eukaryotic cells) and isolated. To produce the fusion protein, nucleic acids encoding the fusion protein may be introduced to a cell (e.g., a bacterial cell or a eukaryotic cell such as a yeast cell or an insect cell. The cells may be cultured under conditions that allow the fusion protein to express from the nucleic acids encoding the fusion protein. Fusion proteins comprising a signal peptide can be secreted, e.g., into the culturing media and can subsequently be recovered. The fusion protein may be isolated using any methods of purifying a protein known in the art.

The nucleic acids encoding the fusion protein described herein may be obtained, and the nucleotide sequence of the nucleic acids determined, by any method known in the art. Non-limiting, exemplary nucleotide sequence encoding the fusion protein or variants described herein are provided in Table 1 and Table 2, e.g., SEQ ID NOs: 51-54. One skilled in the art is able to identify the nucleotide sequence encoding the fusion protein from the amino acid sequence of the fusion protein. The nucleic acids encoding the fusion protein of the present disclosure, may be DNA or RNA, double-stranded or single stranded. In some embodiments, the nucleotide sequence encoding the fusion protein may be codon optimized to adapt to different expression systems (e.g., for mammalian expression).

In some embodiments, the nucleic acid is comprised within a vector, such as an expression vector. In some embodiments, the vector comprises a promoter operably linked to the nucleic acid.

A variety of promoters can be used for expression of the fusion proteins described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *Escherichia coli* can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used (Yao et al., Human Gene Therapy; Gossen et al., Natl. Acad. Sci. USA, 89:5547-5551 (1992); Shockett et al., Proc. Natl. Acad. Sci. USA, 92:6522-6526 (1995)).

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

An expression vector comprising the nucleic acid can be transferred to a host cell by conventional techniques (e.g., electroporation, liposomal transfection, and calcium phosphate precipitation) and the transfected cells are then cultured by conventional techniques to produce the fusion proteins described herein. In some embodiments, the expression of the fusion proteins described herein is regulated by a constitutive, an inducible or a tissue-specific promoter.

The host cells used to express the fusion proteins described herein may be either bacterial cells such as *Escherichia coli*, or, preferably, eukaryotic cells. In particular, mammalian cells, such as Chinese hamster ovary cells (CHO), in conjunction with a vector such as the major intermediate early gene promoter element from human cytomegalovirus is an effective expression system for immunoglobulins (Foecking et al. (1986) "Powerful And Versatile Enhancer-Promoter Unit For Mammalian Expression Vectors," Gene 45:101-106; Cockett et al. (1990) "High Level Expression Of Tissue Inhibitor Of Metalloproteinases In Chinese Hamster Ovary Cells Using Glutamine Synthetase Gene Amplification," Biotechnology 8:662-667).

A variety of host-expression vector systems may be utilized to express the fusion proteins described herein. Such host-expression systems represent vehicles by which the coding sequences of the isolated fusion proteins described herein may be produced and subsequently purified, but also represent cells which may, when transformed or transfected with the appropriate nucleotide coding sequences, express the fusion proteins described herein in situ. These include, but are not limited to, microorganisms such as bacteria (e.g., *E. coli* and *B. subtilis*) transformed with recombinant bacteriophage DNA, plasmid DNA or cosmid DNA expression vectors containing coding sequences for the fusion proteins described herein; yeast (e.g., *Saccharomyces pichia*) transformed with recombinant yeast expression vectors containing sequences encoding the fusion proteins described herein; insect cell systems infected with recombinant virus expression vectors (e.g., baclovirus) containing the sequences encoding the fusion proteins described herein; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding the fusion proteins described herein; or mammalian cell systems (e.g., COS, CHO, BHK, 293, 293T, 3T3 cells, lymphotic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the fusion proteins being expressed. For example, when a large quantity of such a protein is to be produced, for the generation of pharmaceutical compositions of fusion proteins described herein, vectors which direct the expression of high levels of fusion protein products that are readily purified may be desirable. Such vectors include, but are not limited, to the *E. coli* expression vector pUR278 (Ruther et al. (1983) "Easy Identification Of cDNA Clones," EMBO J. 2:1791-1794), in which the coding sequence may be ligated individually into the vector in frame with the lac Z coding region so that a fusion protein is produced; pIN vectors (Inouye et al. (1985) "Up-Promoter Mutations In The 1pp Gene Of *Escherichia Coli*," Nucleic Acids Res. 13:3101-3110; Van Heeke et al. (1989) "Expression Of Human Asparagine Synthetase In *Escherichia Coli*," J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts (e.g., see Logan et al. (1984) "Adenovirus Tripartite Leader Sequence Enhances Translation Of mRNAs Late After Infection," Proc. Natl. Acad. Sci. USA 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al. (1987) "Expression And Secretion Vectors For Yeast," Methods in Enzymol. 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Purification and modification of recombinant proteins is well known in the art such that the design of the polyprotein precursor could include a number of embodiments readily appreciated by a skilled worker. Any known proteases or peptidases known in the art can be used for the described modification of the precursor molecule, e.g., thrombin or factor Xa (Nagai et al. (1985) "Oxygen Binding Properties Of Human Mutant Hemoglobins Synthesized In *Escherichia Coli*," Proc. Nat. Acad. Sci. USA 82:7252-7255, and reviewed in Jenny et al. (2003) "A Critical Review Of The Methods For Cleavage Of Fusion Proteins With Thrombin And Factor Xa," Protein Expr. Purif. 31:1-11, each of which is incorporated by reference herein in its entirety)), enterokinase (Collins-Racie et al. (1995) "Production Of Recombinant Bovine Enterokinase Catalytic Subunit In *Escherichia Coli* Using The Novel Secretory Fusion Partner DsbA," Biotechnology 13:982-987 hereby incorporated by reference herein in its entirety)), furin, and AcTEV (Parks et al. (1994) "Release Of Proteins And Peptides From Fusion Proteins Using A Recombinant Plant Virus Proteinase," Anal. Biochem. 216:413-417 hereby incorporated by reference herein in its entirety)) and the Foot and Mouth Disease Virus Protease C3.

Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express fusion proteins described herein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the fusion proteins described herein. Such engineered cell lines may be particularly useful in screening and evaluation of fusion proteins that interact directly or indirectly with the fusion proteins described herein.

A number of selection systems may be used, including but not limited to the herpes simplex virus thymidine kinase (Wigler et al. (1977) "Transfer Of Purified Herpes Virus Thymidine Kinase Gene To Cultured Mouse Cells," Cell 11: 223-232), hypoxanthine-guanine phosphoribosyltransferase (Szybalska et al. (1992) "Use Of The HPRT Gene And The HAT Selection Technique In DNA-Mediated Transformation Of Mammalian Cells First Steps Toward Developing Hybridoma Techniques And Gene Therapy," Bioessays 14: 495-500), and adenine phosphoribosyltransferase (Lowy et al. (1980) "Isolation Of Transforming DNA: Cloning The Hamster aprt Gene," Cell 22: 817-823) genes can be employed in tk-, hgprt- or aprt-cells, respectively. Also, antimetabolite resistance can be used as the basis of selection for the following genes: dhfr, which confers resistance to methotrexate (Wigler et al. (1980) "Transformation Of Mammalian Cells With An Amplifiable Dominant-Acting Gene," Proc. Natl. Acad. Sci. USA 77:3567-3570; O'Hare et al. (1981) "Transformation Of Mouse Fibroblasts To Methotrexate Resistance By A Recombinant Plasmid Expressing A Prokaryotic Dihydrofolate Reductase," Proc. Natl. Acad. Sci. USA 78: 1527-1531); gpt, which confers resistance to mycophenolic acid (Mulligan et al. (1981) "Selection For Animal Cells That Express The *Escherichia coli* Gene Coding For Xanthine-Guanine Phosphoribosyltransferase," Proc. Natl. Acad. Sci. USA 78: 2072-2076); neo, which confers resistance to the aminoglycoside G-418 (Tolstoshev (1993) "Gene Therapy, Concepts, Current Trials And Future Directions," Ann. Rev. Pharmacol. Toxicol. 32:573-596; Mulligan (1993) "The Basic Science Of Gene Therapy," Science 260:926-932; and Morgan et al. (1993) "Human Gene Therapy," Ann. Rev. Biochem. 62:191-217) and hygro, which confers resistance to hygromycin (Santerre et al. (1984) "Expression Of Prokaryotic Genes For Hygromycin B And G418 Resistance As Dominant-Selection Markers In Mouse L Cells," Gene 30:147-156). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al. (1981) "A New Dominant Hybrid Selective Marker For Higher Eukaryotic Cells," J. Mol. Biol. 150:1-14.

The expression levels of the fusion described herein can be increased by vector amplification (for a review, see Bebbington and Hentschel, The use of vectors based on gene amplification for the expression of cloned genes in mammalian cells in DNA cloning, Vol. 3 (Academic Press, New York, 1987). When a marker in the vector system expressing a fusion protein described herein is amplifiable, increase in the level of inhibitor present in culture of host cell will increase the number of copies of the marker gene. Since the amplified region is associated with the nucleotide sequence of a fusion protein described herein or a fusion protein described herein, production of the fusion protein will also increase (Crouse et al. (1983) "Expression And Amplification Of Engineered Mouse Dihydrofolate Reductase Mini-genes," Mol. Cell. Biol. 3:257-266).

Once a fusion described herein has been recombinantly expressed, it may be purified by any method known in the art for purification of polypeptides, polyproteins or antibodies (e.g., analogous to antibody purification schemes based on antigen selectivity) for example, by chromatography (e.g., ion exchange, affinity, particularly by affinity for the specific antigen (optionally after Protein A selection where the polypeptide comprises an Fc domain (or portion thereof)), and sizing column chromatography), centrifugation, differential solubility, or by any other standard technique for the purification of polypeptides or antibodies.

In some embodiments, to facilitate purification, e.g., by affinity chromatography, the fusion protein described herein further contains a fusion domain. Well known examples of such fusion domains include, without limitation, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS6) fusion partners.

Other aspects of the present disclosure provide antibodies that bind to the fusion protein described herein. An "antibody" or "immunoglobulin (Ig)" is a large, Y-shaped protein produced mainly by plasma cells that is used by the immune system to neutralize an exogenous substance (e.g., a pathogens such as bacteria and viruses). Antibodies are classified as IgA, IgD, IgE, IgG, and IgM. "Antibodies" and "antibody fragments" include whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. An antibody may be a polyclonal antibody or a monoclonal antibody.

The basic 4-chain antibody unit is a heterotetrameric glycoprotein composed of two identical L chains and two H chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for and F isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, (e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6, incorporated herein by reference).

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated a, 6, F, 7 and, respectively. The γ and α classes are further divided into subclasses on the basis of relatively minor differences in CH sequence and function, e.g., humans express the following subclasses: IgG1, IgG2, IgG3, IgG4, IgA1, and IgA2.

The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a j-sheet configuration, connected by three hypervariable regions, which form loops connecting, and in some cases forming part of, the j-sheet structure. The hypervariable regions in each chain are held together in close proximity by the FRs and, with the hypervariable regions from the other chain, contribute to the formation of the antigen-binding site of antibodies (see, e.g., Kabat et al., Sequences of Proteins of Immunological Interest, 5th Ed. Public Health Service, National Institutes of Health, Bethesda, Md. (1991), incorporated herein by reference). The constant domains are not involved directly in binding an antibody to an antigen, but exhibit various effector functions, such as participation of the antibody in antibody dependent cellular cytotoxicity (ADCC).

An "antibody fragment" for use in accordance with the present disclosure contains the antigen-binding portion of an antibody. The antigen-binding portion of an antibody refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (e.g., as described in Ward et al., (1989) Nature 341:544-546, incorporated herein by reference), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883, incorporated herein by reference). Such single chain antibodies are also intended to be encompassed within the term "antigen-binding portion" of an antibody. These antibody fragments are obtained using conventional techniques known to those with skill in the art, and the fragments are screened for utility in the same manner as are full-length antibodies.

In some embodiments, an antibody fragment may be a Fc fragment, a Fv fragment, or a single-change Fv fragment. The Fc fragment comprises the carboxy-terminal portions of both H chains held together by disulfides. The effector functions of antibodies are determined by sequences in the Fc region, which region is also the part recognized by Fc receptors (FcR) found on certain types of cells.

The Fv fragment is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

Single-chain Fv also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding (e.g., as described in Pluckthun in The Pharmacology of Monoclonal Antibodies, vol. 113, Rosenburg and Moore eds., Springer-Verlag, New York, pp. 269-315 (1994); Borrebaeck 1995, incorporated herein by reference).

Antibodies may be isolated. An isolated antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

In some embodiments, the antibody of the present disclosure is a monoclonal antibody. A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). Monoclonal antibodies may also be isolated from phage antibody libraries, e.g., using the techniques described in Clackson et al., Nature, 352:624-628 (1991) and Marks et al., J. Mol. Biol., 222: 581-597 (1991), incorporated herein by reference.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc.), and human constant region sequences.

In some embodiments, the antibody of the present disclosure is a polyclonal antibody. A "polyclonal antibody" a mixture of different antibody molecules which react with more than one immunogenic determinant of an antigen. Polyclonal antibodies may be isolated or purified from mammalian blood, secretions, or other fluids, or from eggs. Polyclonal antibodies may also be recombinant. A recombinant polyclonal antibody is a polyclonal antibody generated by the use of recombinant technologies. Recombinantly generated polyclonal antibodies usually contain a high concentration of different antibody molecules, all or a majority of (e.g., more than 80%, more than 85%, more than 90%, more than 95%, more than 99%, or more) which are displaying a desired binding activity towards an antigen composed of more than one epitope.

Methods of producing antibodies (e.g., monoclonal antibodies or polyclonal antibodies) are known in the art. For example, a polyclonal antibody may be prepared by immunizing an animal, preferably a mammal, with an allergen of choice followed by the isolation of antibody-producing B-lymphocytes from blood, bone marrow, lymph nodes, or spleen. Alternatively, antibody-producing cells may be isolated from an animal and exposed to an allergen in vitro against which antibodies are to be raised. The antibody-producing cells may then be cultured to obtain a population of antibody-producing cells, optionally after fusion to an immortalized cell line such as a myeloma. In some embodiments, as a starting material B-lymphocytes may be isolated from the tissue of an allergic patient, in order to generate fully human polyclonal antibodies. Antibodies may be produced in mice, rats, pigs (swine), sheep, bovine material, or other animals transgenic for the human immunoglobulin genes, as starting material in order to generate fully human polyclonal antibodies. In some embodiments, mice or other animals transgenic for the human immunoglobulin genes (e.g. as disclosed in U.S. Pat. No. 5,939,598), the animals may be immunized to stimulate the in vivo generation of specific antibodies and antibody producing cells before preparation of the polyclonal antibodies from the animal by extraction of B lymphocytes or purification of polyclonal serum.

Monoclonal antibodies are typically made by cell culture that involves fusing myeloma cells with mouse spleen cells immunized with the desired antigen (i.e., hyrbidoma technology). The mixture of cells is diluted and clones are grown from single parent cells on microtitre wells. The antibodies secreted by the different clones are then assayed for their ability to bind to the antigen (with a test such as ELISA or Antigen Microarray Assay) or immuno-dot blot. The most productive and stable clone is then selected for future use.

In some embodiments, the antibodies described herein are "humanized" for use in human (e.g., as therapeutics). "Humanized" forms of non-human (e.g., rodent) antibodies are chimeric antibodies that contain minimal sequence derived from the non-human antibody. Humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

In some embodiments, an antibody may bind to the fusion protein with a $K_D$ of less than $5\times10^{-8}$ M, and optionally between $5\times10^{-8}$ and $1\times10^{-10}$. In some embodiments, binding of the antibody to the fusion protein inhibits its biological activity. In some embodiments, binding of the antibody to the fusion protein stimulates its biological activity.

Further provided herein are methods of using the fusion proteins (e.g., in therapeutic applications). For example, in some embodiments, the fusion protein described herein is formulated in a pharmaceutical composition. Methods of treating a disease or disorder using the fusion protein described herein or the pharmaceutical composition comprising such are also provided. In some embodiments, the method using the fusion protein described herein comprises contacting the fusion protein with S1P. Contacting the fusion protein described herein with S1P results in the formation of a complex between the fusion protein and S1P. In some embodiments, such contacting is carried out in a cell.

In some embodiments, the "non-sponge" fusion protein is used in methods of treating a disease or disorder associated with reduced level of sphingosine-1-phosphate (S1P), the method comprising administering to a subject in need thereof a therapeutically effective amount of the "non-sponge ApoM" fusion protein. Such fusion protein binds to S1P and activates a S1P receptor, triggering downstream signaling pathway. In some embodiments, the S1P receptor is S1P1. It is demonstrated herein that the fusion protein-S1P complex specifically activates the S1P1 receptor, compared to other types of S1P receptors, e.g., S1P2 or S1P3. In some embodiments, the S1P receptor (e.g., S1P1) is vascular, i.e., found on the surface of an endothelial cell in a blood vessel.

A disease or disorder "associated with reduced level of S1P" refers to an abnormal condition where the level or activity of S1P, or S1P-triggered signaling pathway is reduced in a subject that has the disease or disorder, compared to a healthy subject. In some embodiments, the level or activity of S1P, or S1P-triggered signaling pathway is reduced by at least 20% in a subject that has the disease or disorder, compared to a healthy subject. For example, the level or activity of S1P, or S1P-triggered signaling pathway may be reduced by at least 20%, at least 30%, at least 40%, at least 50%, at least 60%, at least 70%, at least 80%, at least 90%, or 100% in a subject that has the disease or disorder, compared to a healthy subject. In some embodiments, the level or activity of S1P, or S1P-triggered signaling pathway is reduced by 20%, 30%, 40%, 50%, 60%, 70%, 80%, 90%, or 100% in a subject that has the disease or disorder, compared to a healthy subject.

Administering the "non-sponge" fusion protein or the composition comprising such fusion protein described herein to a subject having a disease or disorder associated with reduced level of S1P increased S1P signaling, e.g., by activating S1P receptor such as S1P1. In some embodiments, the S1P signaling is increases by at least 20%, in the presence of the fusion protein, compared to without the fusion protein. For example, the S1P signaling may be increased by at least 20%, at least 30%, at least 40%, at least 50%, at least 60%, at least 70%, at least 80%, at least 90%, at least 100%, at least 2-fold, at least 5-fold, at least 10-fold, at least 50-fold, at least 100-fold, at least 1000 fold, or more, in the presence of the fusion protein, compared to without the fusion protein. In some embodiments, the S1P signaling is increased by 20%, 30%, 40%, 50%, 60%, 70%, 80%, 90%, 100%, 2-fold, 5-fold, 10-fold, 50-fold, 100-fold, 1000 fold, or more, in the presence of the fusion protein, compared to without the fusion protein.

In some embodiments, the diseases or disorders associated with reduced level of S1P include, without limitation: infection, sepsis, diabetes, cardiovascular diseases, retinal vascular diseases, peripheral vascular diseases, metabolic syndromes, and respiratory diseases.

In some embodiments, the diseases or disorders associated with reduced level of S1P include, without limitation: primary and/or secondary resistant hypertension, neurogenic hypertension, gestational hypertension, diabetic hypertension, hypertension of chronic kidney disease, cardiac and non-cardiac reperfusion injury, ischemic injury, stroke, pulmonary edema, myocardial infarction, acute coronary syndrome, angina, atherosclerosis, and age-related macular degeneration.

In some embodiments, the fusion protein comprising the ApoM "sponge variant" fused to a Fc is used in methods of treating a disease or disorder associated with excess sphingosine-1-phosphate (S1P), the method comprising administering to a subject in need thereof a therapeutically effective amount of the fusion protein comprising the ApoM "sponge variant" fused to an Fc. Such fusion protein binds to S1P with increased affinity, thus sequestering the excess S1P. "Sequester" means to remove the excess amount of free S1P.

A disease or disorder "associated with excess of S1P" refers to an abnormal condition where the level or activity of S1P, or S1P-triggered signaling pathway is increased in a subject that has the disease or disorder, compared to a healthy subject. In some embodiments, the level or activity of S1P, or S1P-triggered signaling pathway is increased by at least 20% in a subject that has the disease or disorder, compared to a healthy subject. For example, the level or activity of S1P, or S1P-triggered signaling pathway may be increased by at least 20%, at least 30%, at least 40%, at least 50%, at least 60%, at least 70%, at least 80%, at least 90%, at least 100%, at least 2-fold, at least 5-fold, at least 10-fold, at least 50-fold, at least 100-fold, at least 1000 fold, or more, in a subject that has the disease or disorder, compared to a healthy subject. In some embodiments, the level or activity of S1P, or S1P-triggered signaling pathway is increased by 20%, 30%, 40%, 50%, 60%, 70%, 80%, 90%, 100%, 2-fold, 5-fold, 10-fold, 50-fold, 100-fold, 1000 fold, or more, in a subject that has the disease or disorder, compared to a healthy subject.

Administering the "sponge variant" fusion protein or the composition comprising such fusion protein described herein to a subject having a disease or disorder associated with excess S1P decreases S1P signaling, e.g., by sequestering excess S1P. In some embodiments, the S1P signaling is decreased by at least 20%, in the presence of the fusion protein, compared to without the fusion protein. For example, the S1P signaling may be decreased by at least 20%, at least 30%, at least 40%, at least 50%, at least 60%, at least 70%, at least 80%, at least 90%, or 100% in the presence of the fusion protein, compared to without the fusion protein. In some embodiments, the S1P signaling is decreased by 20%, 30%, 40%, 50%, 60%, 70%, 80%, 90%, or 100% in the presence of the fusion protein, compared to without the fusion protein.

In some embodiments, the diseases or disorders associated with excess S1P include, without limitation: cancer, inflammatory diseases, and autoimmune diseases. In some embodiments, the cancer is metastatic cancer. In some embodiments, the inflammatory disease is rheumatoid arthritis. Non-limiting, exemplary cancers include: neoplasms, malignant tumors, metastases, or any disease or disorder characterized by uncontrolled cell growth such that it would be considered cancerous. The cancer may be a primary or metastatic cancer. Cancers include, but are not limited to, adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, biliary tract cancer, osteosarcoma, fibrous histiocytoma, brain cancer, brain stem glioma, cerebellar astrocytoma, malignant glioma, glioblastoma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, acute lymphocytic and myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, choriocarcinoma, hematological neoplasm, adult T-cell leukemia, lymphoma, lymphocytic lymphoma, stromal tumors and germ cell tumors, or Wilms tumor. In some embodiments, the cancer is lung cancer, breast cancer, prostate cancer, colorectal cancer, gastric cancer, liver cancer, pancreatic cancer, brain and central nervous system cancer, skin cancer, ovarian cancer, leukemia, endometrial cancer, bone, cartilage and soft tissue sarcoma, lymphoma, neuroblastoma, nephroblastoma, retinoblastoma, or gonadal germ cell tumor.

A "pharmaceutical composition," as used herein, refers to the formulation of the fusion protein described herein in combination with a pharmaceutically acceptable carrier. The pharmaceutical composition can further comprise additional agents (e.g. for specific delivery, increasing half-life, or other therapeutic agents).

The term "pharmaceutically-acceptable carrier", as used herein, means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the fusion protein from one site (e.g., the delivery site) of the body, to another site (e.g., organ, tissue or portion of the body). A pharmaceutically acceptable carrier is "acceptable" in the sense of being compatible with the other ingredients of the formulation and not injurious to the tissue of the subject (e.g., physiologically compatible, sterile, physiologic pH, etc.). Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21)

polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

In some embodiments, an fusion protein of the present disclosure in a composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the fusion protein of the disclosure does not absorb are used.

In other embodiments, the fusion protein of the present disclosure are delivered in a controlled release system. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

The fusion protein of the present disclosure can be administered as pharmaceutical compositions comprising a therapeutically effective amount of a binding agent and one or more pharmaceutically compatible ingredients.

In some embodiments, the pharmaceutical composition is formulated in accordance with routine procedures as a pharmaceutical composition adapted for intravenous or subcutaneous administration to a subject, e.g., a human being. Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

A pharmaceutical composition for systemic administration may be a liquid, e.g., sterile saline, lactated Ringer's or Hank's solution. In addition, the pharmaceutical composition can be in solid forms and re-dissolved or suspended immediately prior to use. Lyophilized forms are also contemplated.

The pharmaceutical composition can be contained within a lipid particle or vesicle, such as a liposome or microcrystal, which is also suitable for parenteral administration. The particles can be of any suitable structure, such as unilamellar or plurilamellar, so long as compositions are contained therein. The fusion proteins of the present disclosure can be entrapped in 'stabilized plasmid-lipid particles' (SPLP) containing the fusogenic lipid dioleoylphosphatidyletha-nolamine (DOPE), low levels (5-10 mol %) of cationic lipid, and stabilized by a polyethyleneglycol (PEG) coating (Zhang Y. P. et al., Gene Ther. 1999, 6:1438-47). Positively charged lipids such as N-[1-(2,3-dioleoyloxi)propyl]-N,N,N-trimethyl-amoniummethylsulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757.

The pharmaceutical compositions of the present disclosure may be administered or packaged as a unit dose, for example. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

In some embodiments, the pharmaceutical composition can be provided as a pharmaceutical kit comprising (a) a container containing a fusion protein of the disclosure in lyophilized form and (b) a second container containing a pharmaceutically acceptable diluent (e.g., sterile water) for injection. The pharmaceutically acceptable diluent can be used for reconstitution or dilution of the lyophilized fusion protein of the disclosure. Optionally associated with such container(s) can be a notice in the form prescribed by a governmental agency regulating the manufacture, use or sale of pharmaceuticals or biological products, which notice reflects approval by the agency of manufacture, use or sale for human administration.

In another aspect, an article of manufacture containing materials useful for the treatment of the diseases described above is included. In some embodiments, the article of manufacture comprises a container and a label. Suitable containers include, for example, bottles, vials, syringes, and test tubes. The containers may be formed from a variety of materials such as glass or plastic. In some embodiments, the container holds a composition that is effective for treating a disease described herein and may have a sterile access port. For example, the container may be an intravenous solution bag or a vial having a stopper pierceable by a hypodermic injection needle. The active agent in the composition is an fusion protein of the disclosure. In some embodiments, the label on or associated with the container indicates that the composition is used for treating the disease of choice. The article of manufacture may further comprise a second container comprising a pharmaceutically-acceptable buffer, such as phosphate-buffered saline, Ringer's solution, or dextrose solution. It may further include other materials desirable from a commercial and user standpoint, including other buffers, diluents, filters, needles, syringes, and package inserts with instructions for use.

The terms "treatment" or "to treat" refer to both therapeutic and prophylactic treatments. If the subject is in need of treatment of cancer (as a disease associated with excess S1P), then "treating the condition" refers to ameliorating, reducing or eliminating one or more symptoms associated with the cancer or the severity of cancer or preventing any further progression of cancer. If the subject in need of treatment is one who is at risk of having cancer, then treating the subject refers to reducing the risk of the subject having cancer or preventing the subject from developing cancer.

A subject shall mean a human or vertebrate animal or mammal including but not limited to a rodent, e.g., a rat or a mouse, dog, cat, horse, cow, pig, sheep, goat, turkey, chicken, and primate, e.g., monkey. The methods of the present disclosure are useful for treating a subject in need thereof. A subject in need thereof can be a subject who has a risk of developing a disease or disorder associated with reduced to excess S1P, or a subject who has such a disease or disordered.

Pharmaceutically compositions that may be used in accordance with the present disclosure may be directly administered to the subject or may be administered to a subject in need thereof in a therapeutically effective amount. The term "therapeutically effective amount" refers to the amount necessary or sufficient to realize a desired biologic effect. For example, a therapeutically effective amount of a cancer-target liposome associated with the present disclosure may be that amount sufficient to ameliorate one or more symptoms of the disease or disorder. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular pharmaceutically compositions being administered the size of the subject, or the severity of the disease or condition. One of ordinary skill in the art can empirically determine the effective amount of a particular therapeutic compound associated with the present disclosure without necessitating undue experimentation.

Subject doses of the fusion protein described herein for delivery typically range from about 0.1 μg to 10 mg per administration, which depending on the application could be given daily, weekly, or monthly and any other amount of time there between. In some embodiments a single dose is administered during the critical consolidation or reconsolidation period. The doses for these purposes may range from about 10 μg to 5 mg per administration, and most typically from about 100 μg to 1 mg, with 2-4 administrations being spaced, for example, days or weeks apart, or more. In some embodiments, however, parenteral doses for these purposes may be used in a range of 5 to 10,000 times higher than the typical doses described above.

In some embodiments, a fusion protein of the present disclosure is administered at a dosage of between about 1 and 10 mg/kg of body weight of the mammal. In other embodiments, a fusion protein of the present disclosure is administered at a dosage of between about 0.001 and 1 mg/kg of body weight of the mammal. In yet other embodiments, a fusion protein of the present disclosure is administered at a dosage of between about 10-100 ng/kg, 100-500 ng/kg, 500 ng/kg-1 mg/kg, or 1-5 mg/kg of body weight of the mammal, or any individual dosage therein.

The formulations of the present disclosure are administered in pharmaceutically acceptable solutions, which may routinely contain pharmaceutically acceptable concentrations of salt, buffering agents, preservatives, compatible carriers, and optionally other therapeutic ingredients.

For use in therapy, an effective amount of the fusion protein of the present disclosure can be administered to a subject by any mode that delivers the fusion protein to the desired location, e.g., mucosal, injection, systemic, etc.. Administering the pharmaceutical composition of the present disclosure may be accomplished by any means known to the skilled artisan. In some embodiments, the fusion protein is administered subcutaneously, intracutaneously, intravenously, intramuscularly, intraarticularly, intraarterially, intrasynovially, intrasternally, intrathecally, intralesionally, or intracranially.

For oral administration, the fusion protein of the present disclosure can be formulated readily by combining the active compound(s) with pharmaceutically acceptable carriers well known in the art. Such carriers enable the compounds of the present disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers, i.e., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline (Abuchowski and Davis, 1981, "Soluble Polymer-Enzyme Adducts" In: Enzymes as Drugs, Hocenberg and Roberts, eds., Wiley-Interscience, New York, NY, pp. 367-383; Newmark, et al., 1982, J. Appl. Biochem. 4:185-189). Other polymers that could be used are poly-1,3-dioxolane and poly-1,3,6-tioxocane. Preferred for pharmaceutical usage, as indicated above, are polyethylene glycol moieties.

The location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the therapeutic agent or by release of the biologically active material beyond the stomach environment, such as in the intestine.

To ensure full gastric resistance a coating impermeable to at least pH 5.0 is preferred. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e., powder; for liquid forms, a soft gelatin shell may be used. The shell material of cachets could be thick starch or other edible paper. For pills, lozenges, molded tablets or tablet triturates, moist massing techniques can be used.

The fusion protein can be included in the formulation as fine multi particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the therapeutic agent may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the therapeutic agent either alone or as a mixture in different ratios.

Pharmaceutical preparations which can be used orally include push fit capsules made of gelatin, as well as soft, sealed capsules made of gelatin and a plasticizer, such as glycerol or sorbitol. The push fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The pharmaceutical compositions of the present disclosure, when desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the fusion protein may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, 1990, which is incorporated herein by reference.

The pharmaceutical compositions of the present disclosure and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

Example 1: Design and Production of Mouse and Human ApoM-Fc Fusion Proteins for Chronic Studies and Clinical Studies, Respectively ApoM, which binds to S1P, chaperones this lipid mediator and activates cell surface G protein-coupled receptors to induce cellular responses[1]. ApoM/S1P complex is involved in both acute and chronic disease conditions. For example, during sepsis and septic shock, ApoM and S1P levels are reduced[2]. In addition, during type I and II diabetes, and cardiovascular disease, ApoM/S1P levels are reduced or less active[1,3-5]. Thus it is desirable to restore ApoM/S1P levels during these disease conditions as a therapy.

An engineered fusion protein of human ApoM fused to the murine IgG1 constant region (Fc) was developed and the protein was constructed for rapid secretion in the recombinant system. This protein was named as ApoM-Fc. A triple mutant form of ApoM, which does not bind to S1P, was also fused to Fc to form a variant fusion protein, termed ApoM-Fc-TM. However, in order to develop ApoM-Fc molecules suitable for chronic administration in mouse models of acute and chronic human diseases without inducing an immune response, a construct containing mouse ApoM fused to murine IgG1Fc was designed herein to develop a nonimmunogenic derivative for mouse models. Another construct containing a humanized ApoM-Fc, fusing human ApoM and human IgG1Fc, was also designed herein for clinical administration in human clinical trials. The design of the DNA constructs and the translated polypeptides of both mouse and human versions are shown below in Table 1. In short, IL-2 signal peptide is fused to mouse and human ApoM cDNAs. The C-terminus of the fusion protein is then fused to mouse and human Fc polypeptides, respectively. In some instances, due to structural differences in the fusion and for ease of purification, six histidines were added to the carboxy-terminus of murine ApoM-mFc fusion, allowing purification of the fusion proteins with affinity purification using Nickel-NTA affinity resin. These proteins are designed to be efficiently secreted into the conditioned medium of eukaryotic cells, for example, CHO cells or Baculovirus transfected Sf9 cells, so that sufficient quantities of the fusion protein may be purified.

TABLE 1

Mouse and Human ApoM, Fc (IgG1 constant region) and ApoM-Fc fusion protein Sequences

| Name | Sequence | SEQ ID NO: |
|---|---|---|
| Domain Sequences | | |
| Human ApoM | YQCPEHSQLTTLGVDGKEFPEVHLGQWYFIAGAAPTKEELATFDP VDNIVFNMAAGSAPMQLHLRATIRMKDGLCVPRKWIYHLTEGST DLRTEGRPDMKTELFSSSCPGGIMLNETGQGYQRFLLYNRSPHPP EKCVEEFKSLTSCLDSKAFLLTPRNQEACELSNN | 5 |
| Mouse ApoM | NQCPEHSQLTALGMDDTETPEPHLGLWYFIAGAAPTTEELATFDP VDNIVFNMAAGSAPRQLQLRATIRTKSGVCVPRKWTYRLTEGKG NMELRTEGRPDMKTDLFSSSCPGGIMLKETGQGYQRFLLYNRSP HPPEKCVEEFKSLTSCLDFKAFLVTPRNQEACPLSSK | 6 |
| Human IgG1Fc | WASTKGPSVFPLAPSSKSTSGGTAALGCLVKDYFPEPVTVSWNSG ALTSGVHTFPAVLQSSGLYSLSSVVTVPSSSLGTQTYICNVNHKPS NTKVDKKVEPKSCDKTHTCPPCPAPELLGGPSVFLFPPKPKDTLM ISRTPEVTCVVVDVSHEDPEVKFNWYVDGVEVHNAKTKPREEQY NSTYRVVSVLTVLHQDWLNGKEYKCKVSNKALPAPIEKTISKAK GQPREPQVYTLPPSREEMTKNQVSLTCLVKGFYPSDIAVEWESNG QPENNYKTTPPVLDSDGSFFLYSKLTVDKSRWQQGNVFSCSVMH EALHNHYTQKSLSLSPGK | 7 |
| Mouse IgG1Fc | WISSASSAKTTPPSVYPLAPGSAAQTNSMVTLGCLVKGYFPEPVT VTWNSGSLSSGVHTFPAVLQSDLYTLSSSVTVPSSTWPSETVTCN VAHPASSTKVDKKIVPRDCGCKPCICTVPEVSSVFIFPPPKPKDVLTI TLTPKVTCVVVDISKDDPEVQFSWFVDDVEVHTAQTQPREEQFN STFRSVSELPIMHQDWLNGKEFKCRVNSAAFPAPIEKTISKTKGRP KAPQVYTIPPPKEQMAKDKVSLTCMITDFFPEDITVEWQWNGQP AENYKNTQPIMDTDGSYFVYSKLNVQKSNWEAGNTFTCSVLHE GLHNHHTEKSLSHSPGK | 8 |
| Fusion protein Sequences | | |
| Amino acid sequence of Human ApoM-human IgG1Fc Fusion (hApoM-Fc) | MYRMOLLSCIALSLALVTNSISRVYQCPEHSQLTTLGVDGKEFP EVHLGQWYFIAGAAPTKEELATFDPVDNIVFNMAAGSAPMQL HLRATIRMKDGLCVPRKWIYHLTEGSTDLRTEGRPDMKTEL FSSSCPGGIMLNETGQGYQRFLLYNRSPHPPEKCVEEFKSLTS CLDSKAFLLTPRNQEACELSNN*WASTKGPSVFPLAPSSKSTSGGTA ALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLG GPSVFLFPPKPKDTLMISRTPEVTCVVVDVSHEDPEVKFNWYVDGVE VHNAKTKPREEQYNSTYRVVSVLTVLHQDWLNGKEYKCKVSNKALPA PIEKTISKAKGQPREPQVYTLPPSREEMTKNQVSLTCLVKGFYPSDIAV EWESNGQPENNYKTTPPVLDSDGSFFLYSKLTVDKSRWQQGNVFSCS VMHEALHNHYTQKSLSLSPGK**** | 1 |
| Amino acid sequence of Mouse ApoM-mouse IgG1Fc fusion (mApoM-Fc) | MYRMQLLSCIALSLALVTNSNQCPEHSQLTALGMDDTETPEPH LGLWYFIAGAAPTTEELATFDPVDNIVFNMAAGSAPRQLQLR ATIRTKSGVCVPRKWTYRLTEGKGNMELRTEGRPDMKTDLF SSSCPGGIMLKETGQGYQRFLLYNRSPHPPEKCVEEFKSLTSC LDFKAFLVTPRNQEACPLSSK*WISSASSAKTTPPSVYPLAPGSAAQT* | 2 |

TABLE 1-continued

Mouse and Human ApoM, Fc (IgG1 constant region) and ApoM-Fc fusion
protein Sequences

| Name | Sequence | SEQ ID NO: |
|---|---|---|
| | *NSMVTLGCLVKGYFPEPVTVTWNSGSLSSGVHTFPAVLQSDLYTLSSS*<br>*VTVPSSTWPSETVTCNVAHPASSTKVDKKIVPRDCGCKPCICTVPEVSS*<br>*VFIFPPKPKDVLTITLTPKVTCVVVDISKDDPEVQFSWFVDDVEVHTA*<br>*QTQPREEQFNSTFRSVSELPIMHQDWLNGKEFKCRVNSAAFPAPIEK*<br>*TISKTKGRPKAPQVYTIPPPKEQMAKDKVSLTCMITDFFPEDITVEWQ*<br>*WNGQPAENYKNTQPIMDTDGSYFVYSKLNVQKSNWEAGNTFTCSVL*<br>*HEGLHNHHTEKSLSHSPGK\** | |
| Amino acid sequence of human ApoM-mouse IgG1Fc fusion | MYRMQLLSCIALSLALVTNSISRVYQCPEHSQLTTLGVDGKEFP<br>EVHLGQWYFIAGAAPTKEELATFDPVDNIVFNMAAGSAPMQL<br>HLRATIRMKDGLCVPRKWIYHLTEGSTDLRTEGRPDMKTEL<br>FSSSCPGGIMLNETGQGYQRFLLYNRSPHPPEKCVEEFKSLTS<br>CLDSKAFLLTPRNQEACELSNN*WISSASSAKTTPPSVYPLAPGSAA*<br>*QTNSMVTLGCLVKGYFPEPVTVTWNSGSLSSGVHTFPAVLQSDLYTLS*<br>*SSVTVPSSTWPSETVTCNVAHPASSTKVDKKIVPRDCGCKPCICTVPEV*<br>*SSVFIFPPKPKDVLTITLTPKVTCVVVDISKDDPEVQFSWFVDDVEVH*<br>*TAQTQPREEQFNSTFRSVSELPIMHQDWLNGKEFKCRVNSAAFPAPI*<br>*EKTISKTKGRPKAPQVYTIPPPKEQMAKDKVSLTCMITDFFPEDITVE*<br>*WQWNGQPAENYKNTQPIMDTDGSYFVYSKLNVQKSNWEAGNTFTCS*<br>*VLHEGLHNHHTEKSLSHSPGK\** | 3 |
| Amino acid sequence of mouse ApoM-human IgG1Fc fusion (mApoM-hFc) | MYRMQLLSCIALSLALVTNSNQCPEHSQLTALGMDDTETPEPH<br>LGLWYFIAGAAPTTEELATFDPVDNIVFNMAAGSAPRQLQLR<br>ATIRTKSGVCVPRKWTYRLTEGKGNMELRTEGRPDMKTDLF<br>SSSCPGGIMLKETGQGYQRFLLYNRSPHPPEKCVEEFKSLTSC<br>LDFKAFLVTPRNQEACPLSSK*WASTKGPSVFPLAPSSKSTSGGTAA*<br>*LGCLVKDYFPEPVTVSWNSGALTSGVHTFPAVLQSSGLYSLSSVVTVPS*<br>*SSLGTQTYICNVNHKPSNTKVDKKVEPKSCDKTHTCPPCPAPELLGG*<br>*PSVFLFPPKPKDTLMISRTPEVTCVVVDVSHEDPEVKFNWYVDGVEV*<br>*HNAKTKPREEQYNSTYRVVSVLTVLHQDWLNGKEYKCKVSNKALPAP*<br>*IEKTISKAKGQPREPQVYTLPPSREEMTKNQVSLTCLVKGFYPSDIAVE*<br>*WESNGQPENNYKTTPPVLDSDGSFFLYSKLTVDKSRWQQGNVFSCSV*<br>*MHEALHNHYTQKSLSLSPGK\** | 4 |
| Amino acid sequence of Mouse ApoM-mouse IgG1Fc-His6 fusion (mApoM-mFc) | MYRMQLLSCIALSLAINTNSNQCPEHSQLTALGMDDTETPEPH<br>LGLWYFIAGAAPTTEELATFDPVDNIVFNMAAGSAPRQLQLR<br>ATIRTKSGVCVPRKWTYRLTEGKGNMELRTEGRPDMKTDLF<br>SSSCPGGIMLKETGQGYQRFLLYNRSPHPPEKCVEEFKSLTSC<br>LDFKAFLVTPRNQEACPLSSK*WISSASSAKTTPPSVYPLAPGSAAQT*<br>*NSMVTLGCLVKGYFPEPVTVTWNSGSLSSGVHTFPAVLQSDLYTISSS*<br>*VTVPSSTWPSETVTCNVAHPASSTKVDKKIVPRDCGCKPCICTVPEVSS*<br>*VFIFPPKPKDVLTITLTPKVTCVVVDISKDDPEVQFSWFVDDVEVHTA*<br>*QTQPREEQFNSTFRSVSELPIMHQDWLNGKEFKCRVNSAAFPAPIEK*<br>*TISKTKGRPKAPQVYTIPPPKEQMAKDKVSLTCMITDFFPEDITVEWQ*<br>*WNGQPAENYKNTQPIMDTDGSYFVYSKLNVQKSNWEAGNTFTCSVL*<br>*HEGLHNHHTEKSLSHSPGKHHHHHH\** | 68 |

Nucleotide Sequences Encoding the Fusion Proteins

| | | |
|---|---|---|
| Polynucleotide sequence of Murine ApoM-mouse IgG1 Fc Fusion (mApoM-mFc) | *Atg*tacaggatgcaactcctgtcttgcattgcactaagtcttgcacttgtcac<u>gaattc</u>aatcagtgccc<br>tgagcacagtcaactaactgcgctgggaatggacgacacagagaccccagagcccacctggg<br>cctgtggtactttattgcggagcagcccccaccacggaagagttggcaactttttgatccggtgga<br>caatattgtcttcaacatggctgccggctctgcccaaggcagctccagcttcgtgctaccatccgc<br>acgaaaagtggggtctgtgtgccccggaagtggacataccgattgactgaagggaaaggaaac<br>atggaactcagaactgaagggcgcccagacatgaaaacagacctgttctccagctcgtgcccag<br>gaggaatcatgctgaaagagacgggccagggctaccagcgcttttctcctctacaatcggtcacca<br>caccctccagagaagtgtgtggaggaattcaagtctctgacctcttgcttggacttcaaagccttct<br>tagtgactcccaggaatcaagaggcctgcccgctgtccagcaagtgga<u>t</u><u>ctcgag</u>tgctagcagcg<br>ctaaaacgacacccccatctgtctatccactggccctggatctgctgcccaaactaactccatggtgac<br>cctgggatgcctggtcaaggtctatccctgatgcagtgacagtgacctggaactctggatccctgtcc<br>agcggtgtgcacaccttcccagctgtcctgcagtctgacctctacactctgagcagctcagtgactgtcc<br>cctccagcacctggcccagcgagaccgtcacctgcaacgttgcccacccggccagcagcaccaaggt<br>ggacaagaaaattgtgcccagggattgtggttgtaagccttgcatatgtacagtcccagaagtatcatctg<br>tcttcatcttccccccaaagcccaaggatgtgctcaccattactctgactcctaaggtcacgtgtgttgtggt<br>agacatcagcaaggatgatcccgaggtccagttcagctggtttgtagatgatgtggaggtgcacacagc<br>tcagacgcaaccccgggaggagcagttcaacagcactaccgctcagtcagtgaacttccatcatgca<br>ccaggactggctcaatggcaaggagttcaaatgcagggtcaacagtgcagctccctgcccccatcga<br>gaaaaccatctccaaaaccaaaggcagaccgaaggctccgcaggtgtacaccattccacctcccaag<br>gagcagatggccaaggataaagtcagtctgacctgcatgataacagacttcttccctgaagacattactg<br>tggagtggcagtggaatgggcagccagcggagaactacaagaacactcagcccatcatggacacag<br>atggctcaacttcgtctacagcaagctcaatgtgcagaagagcaactgggaggcaggaaatactttcac<br>ctgctctgtgttacatgagggcctgcacaaccaccatactgagaagagcctctcccactctcctggtaaat<br>*ga* | 51 |

TABLE 1-continued

Mouse and Human ApoM, Fc (IgG1 constant region) and ApoM-Fc fusion
protein Sequences

| Name | Sequence | SEQ ID NO: |
|---|---|---|
| Polynucleotide sequence of Human ApoM-human IgG1Fc Fusion (hApoM-hFc) | Atgtacaggatgcaactcctgtcttgcattgcactaagtcttgcacttgtcacgaattcgatatctcgagtgt accagtgccctgagcacagtcaactgacaactctgggcgtggatgggaaggagttcccagaggt ccacttgggccagtggtactttatcgcaggggcagctcccaccaaggaggagttggcaactttg accctgtggacaacattgtcttcaatatggctgctggctctgccccgatgcagctccaccttcgtgct accatccgcatgaaagatgggctctgtgtgccccggaaatggatctaccacctgactgaaggga gcacagatctcagaactgaaggccgccctgacatgaagactgagctcttttccagctcatgccca ggtggaatcatgctgaatgagacaggccagggttaccagcggctttctcctctacaatcgctcacca catcctcccgaaaagtgtgtggaggaattcaagtccctgacttcctgcctggactccaaagccttct tattgactcctaggaatcaagaggcctgtgagctgtccaataactgggctagcaccaagggcccat cggtcttccccctggcaccctcctccaagagcacctctggggggcacagcggccctgggctgcctggtc aaggactacttccccgaaccggtgacggtgtcgtggaactcaggcgccctgaccagcggcgtgcaca ccttcccggctgtcctacagtcctcaggactctactccctcagcagcgtggtgaccgtgccctccagcag cttgggcacccagacctacatctgcaacgtgaatcacaagcccagcaacaccaaggtggacaagaaa gttgagcccaaatcttgtgacaaaactcacacatgcccaccgtgcccagcacctgaactcctgggggga ccgtcagtcttcctcttccccccaaaacccaaggacaccctcatgatctcccggacccctgaggtcacat gcgtggtggtggacgtgagccacgaagaccctgaggtcaagttcaactggtacgtggacggcgtgga ggtgcataatgccaagacaaagccgcgggaggagcagtacaacagcacgtaccgtgtggtcagcgtc ctcaccgtcctgcaccaggactggctgaatggcaaggagtacaagtgcaaggtctccaacaaagccct cccagcccccatcgagaaaaccatctccaaagccaaaggcagccccgagaaccacaggtgtacac cctgcccccatcccgggaggagatgaccaagaaccaggtcagcctgacctgcctggtcaaaggcttct atcccagcgacatcgccgtggagtgggagagcaatgggcagccggagaacaactacaagaccacgc ctcccgtgctggactccgacggctccttcttcctctacagcaagctcaccgtggacaagagcaggtggc agcaggggaacgtcttctcatgctccgtgatgcatgaggctctgcacaaccactacacgcagaagagc ctctccctgtctccgggtaaatga | 52 |
| Polynucleotide sequence of Human ApoM-mouse IgG1Fc Fusion (hApoM-mFc) | Atgtacaggatgcaactcctgtcttgcattgcactaagtcttgcacttgtcacgaattcgatatctcgagtgt accagtgccctgagcacagtcaactgacaactctgggcgtggatgggaaggagttcccagaggt ccacttgggccagtggtactttatcgcaggggcagctcccaccaaggaggagttggcaactttg accctgtggacaacattgtcttcaatatggctgctggctctgccccgatgcagctccaccttcgtgct accatccgcatgaaagatgggctctgtgtgccccggaaatggatctaccacctgactgaaggga gcacagatctcagaactgaaggccgccctgacatgaagactgagctcttttccagctcatgccca ggtggaatcatgctgaatgagacaggccagggttaccagcggctttctcctctacaatcgctcacca catcctcccgaaaagtgtgtggaggaattcaagtccctgacttcctgcctggactccaaagccttct tattgactcctaggaatcaagaggcctgtgagctgtccaataactggatctcgagtgctagcagcagc taaaacgacaccccatctgtctatccactggccctggatctgctgcccaaactaactccatggtgacc ctgggatgcctggtcaagggctattccctgagccagtgacagtgacctggaactctggatccctgtcca gcggtgtgcacaccttcccagctgtcctgcagtctgacctctacactctgagcagctcagtgactgtccc ctccagcacctggcccagcgagaccgtcacctgcaacgttgcccacccggccagcagcaccaaggtg gacaagaaaattgtgcccagggattgtggttgtaagccttgcatatgtacagtcccagaagtatcatctgt cttcatcttcccccaaagcccaaggatgtgctcaccattactctgactcctaaggtcacgtgtgttgtggt agacgcaacccgggaggagcagttcaacagcacttccgtcagtcagtgaacttcccatcatgca ccaggactggctcaatggcaaggagttcaaatgcagggtcaacagtgcagcttttcctgcccccatcga gaaaaccatctccaaaaccaaaggcagaccgaaggctccgcaggtgtacaccattccacctcccaag gagcagatggccaaggataaagtcagtctgacctgcatgataacagacttcttccctgaagacattactg tggagtggcagtggaatgggcagccagcggagaactacaagaacactcagcccatcatggacacag atggctcttacttcgtctacagcaagctcaatgtgcagaagagcaactgggaggcaggaaatactttcac ctgctctgtgttacatgagggcctgcacaaccaccatactgagaagagcctctcccactctcctggtaaat ga | 53 |
| Polynucleotide sequence of mouse ApoM-human IgG1Fc Fusion (mApoM-hFc) | Atgtacaggatgcaactcctgtcttgcattgcactaagtcttgcacttgtcacgaattcgaatcagtgccc tgagcacagtcaactaactgcgctgggaatggacgacacagagaccccagagccccacctggg cctgtggtactttattgcgggagcagccccaccacggaagagttggcaacttttgatccggtgga caatattgtcttcaacatggctgccggctctgcccaaggcagctccagcttcgtgctaccatccgc acgaaaagtggggtctgtgtgccccggaagtggacataccgattgactgaagggaaaggaaac atggaactcagaactgaagggcgcccagacatgaaaacagacctgttctccagctcgtgcccag gaggaatcatgctgaaagagacgggccagggctaccagcgctttctcctctacaatcggtcacca caccctccagagaagtgtgtggaggaattcaagtctctgacctcttgcttggacttcaaagccttct tagtgactcccaggaatcaagaggcctgcccgctgtccaacaatgtgggctagcaccaagggcccat cggtcttccccctggcaccctcctccaagagcacctctggggggcacagcggccctgggctgcctggt caaggactacttccccgaaccggtgacggtgtcgtggaactcaggcgccctgaccagcggcgtgcac accttcccggctgtcctacagtcctcaggactctactccctcagcagcgtggtgaccgtgccctccagca gcttgggcacccagacctacatctgcaacgtgaatcacaagcccagcaacaccaaggtggacaagaa agttgagcccaaatcttgtgacaaaactcacacatgcccaccgtgcccagcacctgaactcctgggggg accgtcagtcttcctcttccccccaaaacccaaggacaccctcatgatctcccggacccctgaggtcaca tgcgtggtggtggacgtgagccacgaagaccctgaggtcaagttcaactggtacgtggacggcgtgga ggtgcataatgccaagacaaagccgcgggaggagcagtacaacagcacgtaccgtgtggtcagcgtc ctcaccgtcctgcaccaggactggctgaatggcaaggagtacaagtgcaaggtctccaacaaagccct cccagcccccatcgagaaaaccatctccaaagccaaaggcagccccgagaaccacaggtgtacac cctgcccccatcccgggaggagatgaccaagaaccaggtcagcctgacctgcctggtcaaaggcttct atcccagcgacatcgccgtggagtgggagagcaatgggcagccggagaacaactacaagaccacgc ctcccgtgctggactccgacggctccttcttcctctacagcaagctcaccgtggacaagagcaggtggc | 54 |

TABLE 1-continued

Mouse and Human ApoM, Fc (IgG1 constant region) and ApoM-Fc fusion
protein Sequences

| Name | Sequence | SEQ ID NO: |
|---|---|---|
| | agcaggggaacgtcttctcatgctccgtgatgcatgaggctctgcacaaccactacacgcagaagagc<br>ctctccctgtctccgggtaaa*tga* | |
| Polynucleotide sequence of murine ApoM-mouseIgG1Fc-His Fusion (mApoM-mFc-His) | *Atg*tacaggatgcaactcctgtcttgcattgcactaagtcttgcacttgtcac<u>gaattc</u>aatcagtgccc<br>tgagcacagtcaactaactgcgctgggaatggacgacacagagaccccagagccccacctggg<br>cctgtggtactttattgcgggagcagcccccaccacggaagagttggcaacttttgatccggtgga<br>caatattgtcttcaacatggctgccggctctgccccaaggcagctccagcttcgtgctaccatccgc<br>acgaaaagtggggtctgtgtgccccggaagtggacataccgattgactgaagggaaaggaaac<br>atggaactcagaactgaagggcgcccagacatgaaaacagacctgttctccagctcgtgcccag<br>gaggaatcatgctgaaagagacgggccagggctaccagcgctttctcctctacaatcggtcacca<br>caccctccagagaagtgtgtggaggaattcaagtctctgacctcttgcttggacttcaaagccttct<br>tagtgactcccaggaatcaagaggcctgcccgctgtccagcaagtggatctcgagtgctagcagcg<br>ctaaaacgacacccccatctgtctatccactggccctggatctgctgcccaaactaactccatggtgac<br>cctgtggatgcctggtcaaggcctatttccctgagccagtgacagtgacctggaactctggatccctgtcc<br>agcggtgtgcacaccttcccagctgtcctgcagtctgacctctacactctgagcagctcagtgactgtcc<br>cctccagcacctggcccagcgagaccgtcacctgcaacgttgcccacccggccagcagcaccaaggt<br>ggacaagaaaattgtgcccagggattgtggttgtaagccttgcatatgtacagtcccagaagtatcatctg<br>tcttcatcttcccccaaagcccaaggatgtgctcaccattactctgactcctaaggtcacgtgtgttgtggt<br>agacatcagcaaggatgatcccgaggtccagttcagctggtttgtagatgatgtggaggtgcacacagc<br>tcagacgcaacccgggaggagcagttcaacagcactttccgctcagtcagtgaacttcccatcatgca<br>ccaggactggctcaatggcaaggagttcaaatgcagggtcaacagtgcagctttccctgcccccatcga<br>gaaaaccatctccaaaaccaaaggcagaccgaaggctccgcaggtgtacaccattccacctcccaag<br>gagcagatggccaaggataaagtcagtctgacctgcatgataacagacttcttccctgaagacattactg<br>tggagtggcagtggaatgggcagccagcggagaactacaagaacactcagcccatcatggacacag<br>atggctcttacttcgtctacagcaagctcaatgtgcagaagagcaactgggaggcaggaaatactttcac<br>ctgctctgtgttacatgagggcctgcacaaccaccatactgagaagagcctctcccactctcctggtaaa<br>catcaccatcaccatcac*tga* | 69 |

For SEQ ID NO: 51, the open reading frame of mouse Apolipoprotein M (GenBank: BC021597.1) encoding amino acids 21-190 (boldface) was generated by PCR and cloned into the EcoRI (gaattc) and XhoI (ctcgag) cloning sites of the pFUSEss-CHIg-mG1 vector, encoding the human IL-2 signal peptide and the mouse IgG1 constant region (Catalog #pfusess-mchg1; Invivogen). The Start (ATG) and Stop (TGA) codons are in italics.

The predicted polypeptide sequence of the Mouse ApoM-mouse IgG1Fc fusion is given by SEQ ID NO: 1. The signal peptide of human interleukin-2 is underlined, the mouse ApoM Amino acids 21-190 are in bold, and the mouse IgG1 constant region (Fc) is in italics.

For SEQ ID NO: 52, the open reading frame of Human Apolipoprotein M (GenBank: BC020683.1) encoding amino acids 21-188 (boldface) was generated by PCR and cloned into the XHOI (ctcgag) and NHEI cloning sites of the pFUSEss-CHIg-hG1 vector (Catalog #pfusess-hchg1; Invivogen), encoding the human IL-2 signal peptide and the human IgG1 constant region. The Start (ATG) and Stop (TGA) codons are in italics.

The predicted polypeptide sequence of the Human ApoM-human IgG1Fc fusion is given by SEQ ID NO: 2. The signal peptide of human interleukin-2 is underlined, the Human ApoM Amino acids 21-188 are in bold, and the Human IgG1 constant region (Fc) is in italics.

In SEQ ID NO: 53, the open reading frame of Human Apolipoprotein M (GenBank: BC020683.1) encoding amino acids 21-188 (boldface) was generated by PCR and cloned into the XHOI (ctcgag) and NHEI cloning sites of the pFUSEss-CHIg-mG1 vector (Catalog #pfusess-mchg1; Invivogen), encoding the human 11-2 signal peptide and the mouse IgG1 constant region. The mutations were created by primer-based site directed mutagenesis. The Start (ATG) and Stop (TGA) codons are in italics.

The predicted polypeptide sequence of the Human ApoM mouse IgG1Fc fusion is given by SEQ ID NO: 3. The signal peptide of human interleukin-2 is underlined, the Human ApoM Amino acids 21-188 are in bold, and the mouse IgG1 constant region (Fc) is in italics.

For SEQ ID NO: 69, the open reading frame of mouse Apolipoprotein M (GenBank: BC021597.1) encoding Amino acids 21-190 (bolded in SEQ ID NO: 68) was generated by PCR and cloned into the NcoI (ccatgg) and BglII (ctcgag) cloning sites of the pFUSE-mIgG1-Fc2 vector, encoding the human IL-2 signal peptide and the mouse IgG1 constant region (Catalog #pfusemg1fc1; Invivogen). The six histidine tag is underlined. Start (Atg) and Stop (tga) codons are in italics. Polypeptide sequence of the Mouse ApoM-mouse IgG1Fc-His fusion is shown as SEQ ID NO: 68. Signal peptide of human interleukin-2 (underlined). Mouse ApoM Amino acids 21-190 (Bold). Mouse IgG1 constant region (Fc; Italics).

The plasmid constructs for mApoM-mFc-His (pFUSE-mApoM-mFc-His) and human ApoM-Fc (pFUSE-hApoM-hFc) were tested for protein expression by transfection into HEK293T cells and specific ApoM Western blot analysis. The proteins mApoM-mFc-His and human ApoM-hFc were expressed in CHO-S suspension cell cultures and purified in milligram quantities from CHO-S culture supernatant CHO-S suspension cell cultures. The purified mApoM-mFc-His and human ApoM-hFc proteins were then tested for functional activity using transendothelial electrical resistance (TEER) analysis of endothelial cells, which demonstrates specific S1P receptor activation, by showing increasing barrier resistance and thus enhanced Eendothelial Ccell function (FIGS. 4A-4D).

Figure 2:
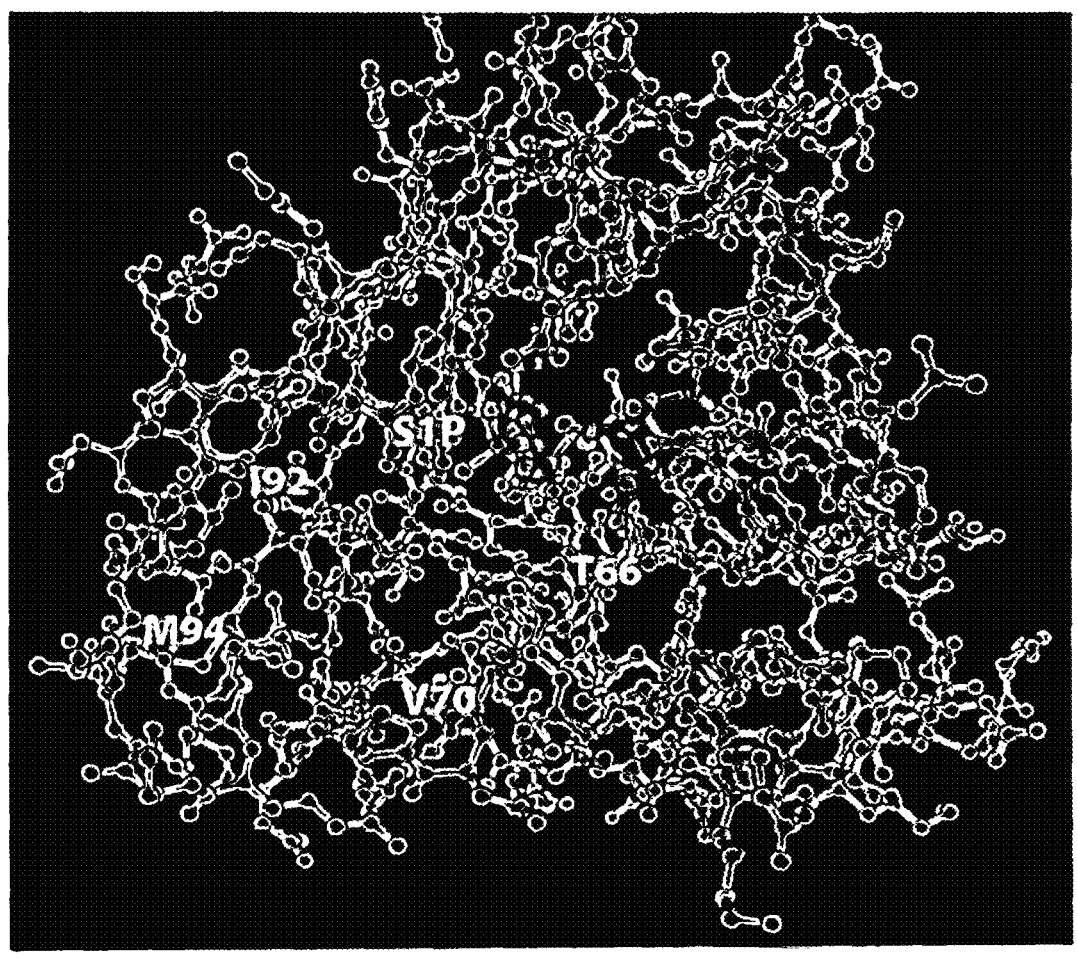
FIG. 2. Crystal Structure of ApoM[2]. The hydrophobic binding pocket of ApoM and an open, unfilled cleft surrounding the S1P lipid-phosphate moiety were identified. Further analysis revealed that four amino acids immediately surrounding the cleft (T66, V70, I92, and M94 in ApoM-$F_c$) might be permissive for mutation and alteration of the protein-lipid moiety interaction. Furthermore, given the negative charge of the phosphate ($PO_3$) group of S1P (Phosphate (Green); Oxygen (red)), introduction of either positively charged amino acid side-chains (i.e., Lysine (K)) or amino acid side chains capable of hydrogen bonding (i.e., Aspagine (N), Glutamine (Q), or tyrosine (Y)) into the cleft would be predicted to increase interaction of the cleft with phospholipid and increase the affinity of ApoM for S1P by enhancing or stabilizing lipid binding.
Figures 4A, 4B:
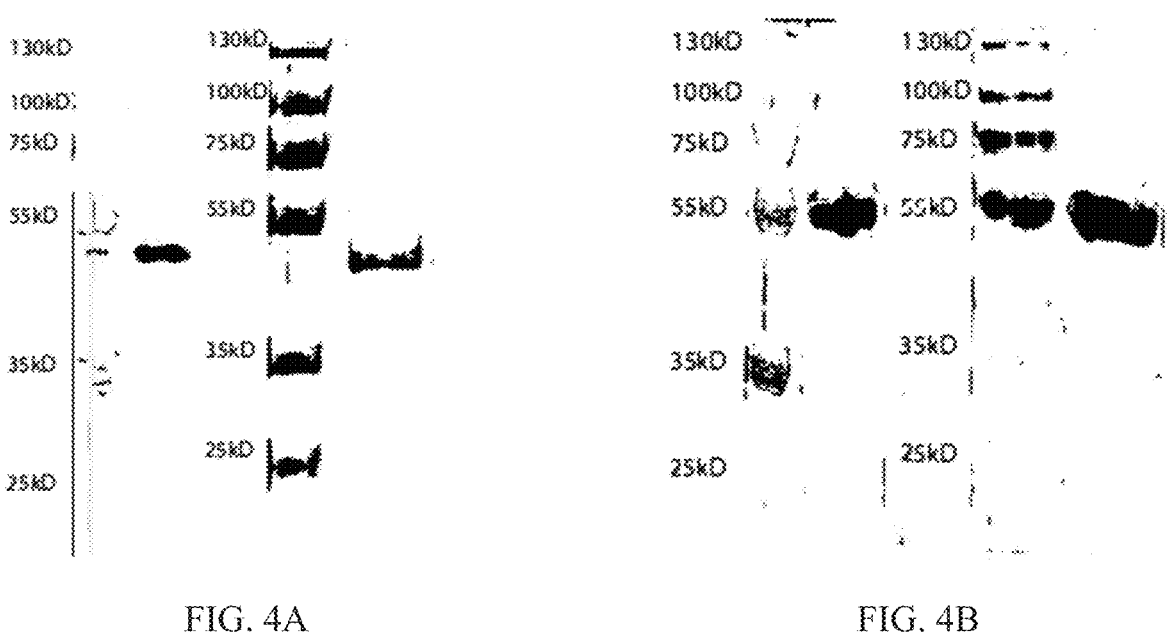
FIGS. 4A-4D. Expression and Characterization of mApoM-mFc-His and hApoM-hFc.
Figure 4C:
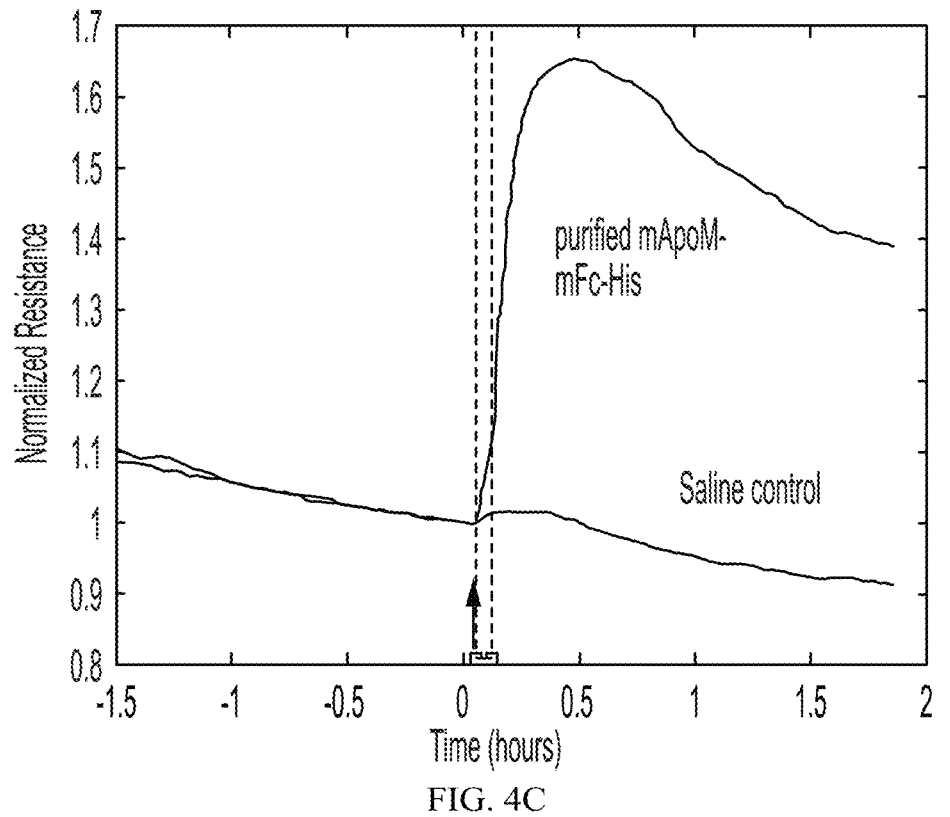
Figure 4D:
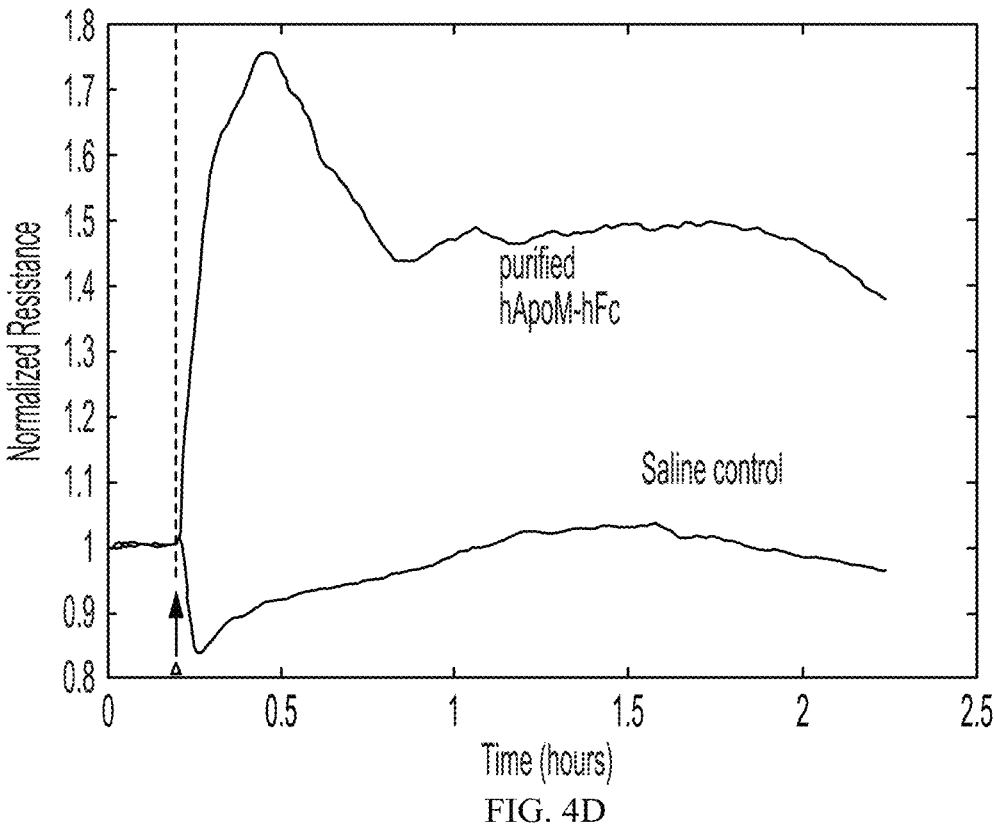

In order to determine which S1P receptors interact with ApoM-Fc, S1P receptors 1, 2 or 3 were expressed in CHO cells. Control CHO cells or CHO cells expressing S1P receptors were then stimulated with ApoM-Fc and the receptor-dependent cellular signal transduction pathways were examined. As shown in FIGS. 2A to 2C, ApoM-Fc activated S1P receptors-1, -2 and -3. However, it activated S1P receptor-1 much more efficiently than the other two receptors. This shows that ApoM-Fc can be used to examine receptor signaling and discovery of specific receptor agonists and antagonists.

Materials and Methods for Example 1

Creation of Mouse ApoM-$F_c$-his

The open reading frame of mouse Apolipoprotein M (GenBank: BC021597.1) encoding Amino acids 21-190 was generated by PCR using the primers: Forward: 5'-tttccatggt-taatcagtgccctgagcacagtc-3' (SEQ ID NO: 77); Reverse: 5'-tttggatccccacttgctggacagcgggca-3' (SEQ ID NO: 78).

The PCR product was digested using NcoI (ggatcc) and BamHI (ggatcc) and cloned into the NcoI (ccatgg) and BglII (ctcgag) cloning sites of the pFUSE-mIgG1-Fc2 vector, encoding the human IL-2 signal peptide and the mouse IgG1 constant region (Catalog #pfusemg1fc1; Invivogen) to create pFUSE-mApoM-mFc.

A six histidine carboxyl-terminal tag (underlined) was added to the fusion open reading frame using the primers: forward 5'-ttttctagaatgtacaggatgcaactcctgtc-3' (SEQ ID NO: 79); reverse: 5'-tttggatcctcagtgatggtgatggtgatgtttaccag-gagagtgggagag-3' (SEQ ID NO: 80). The PCR product was digested using XbaI (tctaga) and BamHI (ggatcc) and cloned into the XbaI and BamHI cloning sites of the pcdh-cmv-mcs-ef1-puro vector to create pCDH-mApoM-Fc-His.

Creation of Human ApoM-hFc

The open reading frame of human Apolipoprotein M (GenBank: BC020683.1) encoding Amino acids 21-190 (boldface) was generated by PCR using the primers: forward 5'-tttctcgagtgtaccagtgccctgagcacag-3' (SEQ ID NO: 81); reverse: 5'-tttgctagcccagttattggacagctcacag-3' (SEQ ID NO: 82). The PCR product was digested using XHOI (ctcgag) and NHEI (gctagc) and cloned into the cloning sites of the pFUSEss-CHIg-hG1 vector (Catalog #pfusess-hchg1; Invivogen), and cloned into the XHOI (ctcgag) and NHEI (gctagc) cloning sites of the pFUSEss-CHIg-hG1 vector (Catalog #pfusess-hchg1; Invivogen), to create pFUSE-hApoM-hFc.

The fusion open reading frame was subjected to a second round of PCR using the primers: forward: 5'-ttttctagatgta-caggatgcaactcctgtc-3' (SEQ ID NO: 83); reverse: 5'-tttg-gatcctcatcatttacccggagacagggag-3' (SEQ ID NO: 84). The PCR product was digested using XbaI (tctaga) and BamHI (ggatcc) and cloned into the XbaI and BamHI cloning sites of the pcdh-cmv-mcs-ef1-puro vector to create pCDH-hA-poM-hFc.

Expression of mApoM-mFc in HEK293T Cells

HEK293T cells (3×100 mm plate) were transfected with 5 μg of pCDH-mApoM-mFc-His or pCDH-hApoM-hFc per plate using Turbofect (Thermo Fisher Scientific). After 24 hours, cell lysate was run on SDS-PAGE and analyzed for ApoM expression using an anti-ApoM rabbit monoclonal antibody (Abcam; Catalog #ab91656) by western blot.

Expression and Purification of mApoM-mFc-his from CHO-S Cells

CHO-S cells (100 mm plate) (ThermoFisher) were transfected with 5 μg of pCDH-mApoM-mFc-His using Turbofect (Thermo Fisher Scientific). Cells were selected for 5 days using puromycin (30 ug/ml; Thermo Fisher Scientific). Selected cells were adapted to suspension culture in Free-Style CHO Expression Medium (Catalog #12651014;

Thermo Fisher Scientific) and grown to a density of $3×10^{\hat{}}$cells/ml (500 ml). Supernatant were clarified by centrifugation and the resulting supernatant was subjected to affinity chromatography using 1 ml of Ni-NTA Superflow beads (Qiagen). Protein was eluted, concentrated, and resuspended in saline using Amicon Ultra-15 Centrifugal Filters. 5 μg of purified protein was analyzed by SDS-PAGE and stained with Coomassie Blue.

Expression and Purification of hApoM-hFc from CHO-S Cells

CHO-S cells (100 mm plate) (ThermoFisher) were transfected with 5 μg of pCDH-hApoM-Fc using Turbofect (Thermo Fisher Scientific). Cells were selected for 5 days using puromycin (30 μg/ml; Thermo Fisher Scientific). Selected cells were adapted to suspension culture in Free-Style CHO Expression Medium (Catalog #12651014; Thermo Fisher Scientific) and grown to a density of $3×10^6$ cells/ml (500 ml). Supernatant were clarified by centrifugation and the resulting supernatant was subjected to affinity chromatography using 1 ml of Protein G sepharose (Catalog #101241; ThermoFisher Scientific). Protein was eluted, concentrated, and resuspended in saline using Amicon Ultra-15 Centrifugal Filters. 8 μg of purified protein was analyzed by SDS-PAGE and stained with Coomassie Blue.

Measurement of Endothelial Barrier Function In Vitro Using TEER Analysis with ECIS HUVECs were analyzed between passages 4 and 8. Endothelial barrier function was evaluated by measuring the resistance of a cell-covered electrode by using an endothelial cell impedance system (ECIS) instrument (Applied Bio-Physics). HUVECs were plated on 0.1% fibronectin-coated electrodes (8W10E plates) at a density of $1×10^5$ cells per well. Confluent cells were starved for 2 to 6 hours in endothelial basal medium (EBM-2; Lonza) and treated with either mApoM-mFc-His or hApoM-hFc at the concentrations indicated. Resistance was monitored and expressed as fractional resistance, normalizing to the baseline at the initiation of the assay. The assay was performed in triplicate.

Example 2: Development of ApoM-Fc Fusion Proteins that are Designed to "Sponge" SIP to Inhibit Excessive SIP Signaling in Metastatic Cancer and Chronic Inflammatory Diseases The examination of the crystal structure of ApoM bound to S1P[6] suggests the presence of a tight ligand binding pocket which contains amino acid residues that ion pair with the phosphate head group of S1P (FIG. 3). In addition, several residues of ApoM form a ligand binding pocket that interacts with the hydrophobic sphingosine moiety. Four amino acids of ApoM were identified to have a potential for altering the binding pocket. By substituting positively charged or hydrogen-bonding amino acids to interact with the negatively charged phosphate of S1P, the mutated ApoM would be predicted to bind to S1P tighter than the wild-type ApoM molecule and therefore lead to a "S1P sponge"-like molecule, which would bind S1P and not release it efficiently (FIG. 3). A total of seven amino-acid substitution mutants (Table 4) were prepared using site-directed mutagenesis of pFUSE-hApoM-mIgG1Fc backbone and the resulting plasmids were transfected into CHO cells. ApoM-Fc protein representing each mutant was purified and evaluated for S1P content by mass spectroscopy Table 3 (and Material and Methods section). Such molecules, termed as S1P "sponges", are expected to block free S1P that is released from activated cells by competing with the interaction with receptors. They would thus act as antagonists of S1P in environments in which S1P is less abundant. For example, in the inflammatory milieu, vascular permeability is needed to have S1P-dependent responses in tissue cells which express S1P receptors.

The potential application for ApoM-Fc sponges are in the treatment of tumor metastasis and the chronic inflammatory disease of rheumatoid Arthritis. Both conditions are known for the production of excess S1P.

ApoM-Fc Sponge for the Treatment of Metastatic Cancer

Tumor growth, expansion and metastasis are multivariate processes dependent on a number of bioactive factors including sphingolipids. Multiple studies have observed that tumor cells have increased amounts of S1P[7]. In addition, it has been observed that some tumors use S1P as a growth/survival factor during the course of disease pathology, have increased S1P-dependent migration and metastasis, and that S1P contributes to tumor chemoresistance[7]. Given these observations, a biologic that binds to S1P and blocks possible S1P-dependent signaling in tumors would provide a means to dampen S1P-dependent tumor growth, metastasis and chemoresistance. Using a B16 lung metastasis model, mice were treated with candidate ApoM-Fc mutant "sponge" proteins, and the resulting tumors were evaluated for size and number to determine the effect of this approach on the growth of tumors. Subsequent studies could include evaluation of synergistic approaches using ApoM-Fc mutant "sponge" in conjunction with established chemotherapeutic agents, such as cis-platinum or Doxirubicin, or immunotherapeutic agents, such as anti-PD-1 or anti-PD-L1 or anti-CTLA-4 antibodies, or anti-angiogenics such as anti-VEGF antibody to determine if removal of S1P sensitizes tumors to other therapies.

ApoM-Fc Sponge for the Treatment of Chronic Inflammatory Diseases Such as Rheumatoid Arthritis (RA)

Chronic inflammatory diseases including Rheumatoid Arthritis (RA) are characterized by excessive infiltration of the synovia of articular joints with inflammatory leukocytes. As a result of the infiltration, these cells produce excessive quantities of inflammatory cytokines such as Il-1$\beta$, TNF$\alpha$ and IL-6[8]. One consequence of excessive cytokine signaling is the direct activation of sphingosine kinase and the resultant excess production of S1P in inflamed synovia, which is detectable in synovial fluid[8]. The excessive S1P has the potential to further activate infiltrating leukocytes as well as affect the tissues composing the synovium. The efficacy of the ApoM-Fc mutant "sponge" molecules in absorbing SP from inflamed synovial fluid were directly tested through mixing experiments. S P concentration of the fluid and the ApoM-Fc would be determined by mass spectroscopy before and after incubation. As a second approach, mice would be induced to the arthritic state with the established Collagen-induced Arthritis model[9] and then treated with ApoM-Fc mutant "sponge" or appropriate controls.

Similar to the approaches described herein, for chronic administration studies, S1P sponge variants of ApoM in human and mouse versions were designed and produced. These are given in Table 2.

TABLE 2

| Mutation positions for S1P sponge variants of (Relative to SEQ ID NO: 3) | | | |
|---|---|---|---|
| Name | Sequence | SEQ ID NO: | Mutations (Bold, Italics) |
| Polynucleotide sequence showing mutation positions of S1P sponge mutant ApoM-IgG1Fc Fusion (ApoM-Fc-Sponge) | Atg*gt*acaggatgcaactcctgtcttgcattgcactaagtcttgcacagtcacgaattcg atat<u>ctcgagt</u>gtaccagtgccctgagcacagtcaactgacaactctgggcgtgg atgggaaggagttcccagaggtccacttgggccagtggtactttatcgcaggg cagctcccaccaaggaggagttggca*act*ttgaccct*gtg*gacaacattgtctt caatatggctgctggctctgccccgatgcagctccaccttcgtgctaco*at*ccgc *atg*aaagatgggctctgtgtgccccggaaatggatctaccacctgactgaaggg agcacagatctcagaactgaaggccgcutgacatgaagactgagctcttttcc agctcatgcccaggtggaatcatgctgaatgagacaggccagggttaccagcg cttttctcctctacaatcgctcaccacatcctcccgaaaagtgtgtggaggaattca agtccctgacttcctgcctggactccaaagccttcttattgactcctaggaatcaa gaggcctgtgagagtccaataactggatc<u>ctcgagt</u>gctagcagcgctaaaacga caccccatctgtctatccactggccctggatctgctgcccaaactaactccatggtg accctgggatgcctggtcaagggctatttccctgagccagtgacagtgacctggaac tctggatccctgtccagcggtgtgcacaccttcccagctgtcctgcagtctgacctcta cactctgagcagctcagtgactgtcccctccagcacctggcccagcgagaccgtca cctgcaacgttgcccacccggccagcagcaccaaggtggacaagaaaattgtgccc agggattgtgtggttgtaagccttgcatatgtacagtcccagaagtatcatctgtcttcatct tccccccaaagcccaaggatgtgctcaccattactctgactcctaaggtcacgtgtgtt gtggtagacatcagcaaggatgatcccgaggtccagttcagctggtttgtagatgatg tggaggtgcacacagctcagacgcaaccccgggaggagcagttcaacagcactttc cgctcagtcagtgaacttcccatcatgcaccaggactggctcaatggcaaggagttc aaatgcaggqtcaacagtgcagctttccctgcccccatcgagaaaaccatctccaaa accaaaggcagaccgaaggctccgcaggtgtacaccattccacctcccaaggagc agatggccaaggataaagtcagtctgacctgcatgataacagacttcttccctgaaga cattactgtggagtggcagtggaatgggcagccagcggagaactacaagaacactc agcccatcatggacacagatggctcttacttcgtctacagcaagctcaatgtgcagaa gagcaactgggaggcaggaaatacttttcacctgactgtgttacatgagggcctgca caaccaccatactgagaagagcctctcccactctcctggtaaa*tga* | 53 | Mutation 1 T66N; act > aac<br><br>Mutation 2 V70K; gtg > aag<br><br>Mutation 3 V70N; gtg > aac<br><br>Mutation 4 V70Q; gtg > cag<br><br>Mutation 5 I92K; atc > aaa<br><br>Mutation 6 I92N; atc > aac<br><br>Mutation 7 M94Y; atg > tac |
| Polypeptide sequence showing mutation positions of Human ApoM-mouse IgG1Fc Fusion(ApoM-Fc-Sponge) | <u>MYRMQLLSCIALSLALVTNSISRV</u>YQCPEHSQLTTLG VDGKEFPEVHLGQWYFIAGAAPTKEELA*T*FDP*V*DN IVFNMAAGSAPMQLHLRAT*I*R*M*KDGLCVPRKWIY HLTEGSTDLRTEGRPDMKTELFSSSCPGGIMLNET GQGYQRFLLYNRSPHPPEKCVEEFKSLTSCLDSKA FLLTPRNQEACELSNN*WISSASSAKTTPPSVYPLAPGSA AQTNSMVTLGCLVKGYFPEPVTVTWNSGSLSSGVHTFPA VLQSDLYTLSSSVTVPSSTWPSETVTCNVAHPASSTKVDKK* | 3 | Mutation 1 T66N<br>Mutation 2 V70K<br>Mutation 3 V70N<br>Mutation 4 V70Q<br>Mutation 5 I92K<br>Mutation 6 I92N<br>Mutation 7 M94Y |

TABLE 2-continued

Mutation positions for S1P sponge variants of (Relative to SEQ ID NO: 3)

| Name | Sequence | SEQ ID NO: | Mutations (Bold, Italics) |
|------|----------|------------|---------------------------|
| | *IVPRDCGCKPCICTVPEVSSVFIFPPKPKDVLTITLTPKVT CVVVDISKDDPEVQFSWFVDDVEVHTAQTQPREEQFNS TFRSVSELPIMHQDWLNGKEFKCRVNSAAFPAPIEKTISK TKGRPKAPQVYTIPPPKEQMAKDKVSLTCMITDFFPEDI TVEWQWNGQPAENYKNTQPIMDTDGSYFVYSKLNVQKS NWEAGNTFTCSVLHEGLHNHHTEKSLSHSPGK** | | |

SIP-Binding Analysis of ApoM-Fc Sponge Mutants

The effect of each mutation on the binding of S1P was determined. Individual cultures of CHO cells were transfected with plasmids for each mutant clone and recombinant cells were expanded. The ApoM-Fc sponge mutants were purified from supernatants from each cell line (see materials and methods) and proteins were mixed with S1P, re-purified and subjected to Mass Spectrometry analysis to determine S1P content.

For binding analysis, 500 μg of each ApoM-Fc (sponge) mutant was purified and mixed with S1P (Avanti Polar Lipids; Cat No. 860492) resuspended in methanol at a 10:1 (M/M) ratio and incubated at 4° C. for 24 hours. Each protein was repurified to separate free protein from S1P using a Biorad NGC FPLC on a Superose 6 10/300 chromatography column. 25 micrograms of each purified protein was analyzed for sphingolipid content by LC-mass spectrometry (LC-MS). The results were shown in Table 3. When compared to WT ApoM-Fc, Clone 4 V70Q retained comparable S1P binding.

TABLE 3

Sphingolipid content and species.

| Sponge Clone ID | S1P(nM) |
|-----------------|---------|
| 1. T66N | 97.76 |
| 2. V70K | 41.33 |
| 3. V70N | 14.26 |
| 4. V70Q | 209.20 |
| 5. I92K | 28.86 |
| 6. I92N | 39.82 |
| 7. M94Y | 22.33 |
| 8. WT hApoM-mFc | 256 |

TABLE 4

Amino Acid Sequences of "Sponge" Variants

| Variants | Amino Acid Sequence | SEQ ID NO |
|----------|---------------------|-----------|
| | ApoM | |
| Human ApoM T42N | YQCPEHSQLTTLGVDGKEFPEVHLGQWYFIAGAAPTKEELANFDPVDNIVFN MAAGSAPMQLHLRATIRMKDGLCVPRKWIYHLTEGSTDLRTEGRPDMKTEL FSSSCPGGIMLNETGQGYQRFLLYNRSPHPPEKCVEEFKSLTSCLDSKAFLLTP RNQEACELSNN | 9 |
| Human ApoM V46K | YQCPEHSQLTTLGVDGKEFPEVHLGQWYFIAGAAPTKEELATFDPKDNIVFN MAAGSAPMQLHLRATIRMKDGLCVPRKWIYHLTEGSTDLRTEGRPDMKTEL FSSSCPGGIMLNETGQGYQRFLLYNRSPHPPEKCVEEFKSLTSCLDSKAFLLTP RNQEACELSNN | 10 |
| Human ApoM V46N | YQCPEHSQLTTLGVDGKEFPEVHLGQWYFIAGAAPTKEELATFDPNDNIVFN MAAGSAPMQLHLRATIRMKDGLCVPRKWIYHLTEGSTDLRTEGRPDMKTEL FSSSCPGGIMLNETGQGYQRFLLYNRSPHPPEKCVEEFKSLTSCLDSKAFLLTP RNQEACELSNN | 11 |
| Human ApoM V46Q | YQCPEHSQLTTLGVDGKEFPEVHLGQWYFIAGAAPTKEELATFDPQDNIVFN MAAGSAPMQLHLRATIRMKDGLCVPRKWIYHLTEGSTDLRTEGRPDMKTEL FSSSCPGGIMLNETGQGYQRFLLYNRSPHPPEKCVEEFKSLTSCLDSKAFLLTP RNQEACELSNN | 12 |
| Human ApoM I68K | YQCPEHSQLTTLGVDGKEFPEVHLGQWYFIAGAAPTKEELATFDPVDNIVFN MAAGSAPMQLHLRATKRMKDGLCVPRKWIYHLTEGSTDLRTEGRPDMKTE LFSSSCPGGIMLNETGQGYQRFLLYNRSPHPPEKCVEEFKSLTSCLDSKAFLLT PRNQEACELSNN | 13 |
| Human ApoM I68N | YQCPEHSQLTTLGVDGKEFPEVHLGQWYFIAGAAPTKEELATFDPVDNIVFN MAAGSAPMQLHLRATNRMKDGLCVPRKWIYHLTEGSTDLRTEGRPDMKTE LFSSSCPGGIMLNETGQGYQRFLLYNRSPHPPEKCVEEFKSLTSCLDSKAFLLT PRNQEACELSNN | 14 |

TABLE 4-continued

Amino Acid Sequences of "Sponge" Variants

| Variants | Amino Acid Sequence | SEQ ID NO |
|---|---|---|
| Human ApoM M70Y | YQCPEHSQLTTLGVDGKEFPEVHLGQWYFIAGAAPTKEELATFDPVDNIVFN MAAGSAPMQLHLRATIRYKDGLCVPRKWIYHLTEGSTDLRTEGRPDMKTEL FSSSCPGGIMLNETGQGYQRFLLYNRSPHPPEKCVEEFKSLTSCLDSKAFLLTP RNQEACELSNN | 15 |
| Mouse ApoM T42N | NQCPEHSQLTALGMDDTETPEPHLGLWYFIAGAAPTTEELANFDPVDNIVFN MAAGSAPRQLQLRATIRTKSGVCVPRKWTYRLTEGKGNMELRTEGRPDMKT DLFSSSCPGGIMLKETGQGYQRFLLYNRSPHPPEKCVEEFKSLTSCLDFKAFL VTPRNQEACPLSSK | 16 |
| Mouse ApoM V46K | NQCPEHSQLTALGMDDTETPEPHLGLWYFIAGAAPTTEELATFDPKDNIVFN MAAGSAPRQLQLRATIRTKSGVCVPRKWTYRLTEGKGNMELRTEGRPDMKT DLFSSSCPGGIMLKETGQGYQRFLLYNRSPHPPEKCVEEFKSLTSCLDFKAFL VTPRNQEACPLSSK | 17 |
| Mouse ApoM V46N | NQCPEHSQLTALGMDDTETPEPHLGLWYFIAGAAPTTEELATFDPNDNIVFN MAAGSAPRQLQLRATIRTKSGVCVPRKWTYRLTEGKGNMELRTEGRPDMKT DLFSSSCPGGIMLKETGQGYQRFLLYNRSPHPPEKCVEEFKSLTSCLDFKAFL VTPRNQEACPLSSK | 18 |
| Mouse ApoM V46Q | NQCPEHSQLTALGMDDTETPEPHLGLWYFIAGAAPTTEELATFDPQDNIVFN MAAGSAPRQLQLRATIRTKSGVCVPRKWTYRLTEGKGNMELRTEGRPDMKT DLFSSSCPGGIMLKETGQGYQRFLLYNRSPHPPEKCVEEEKSLTSCLDFKAFL VTPRNQEACPLSSK | 19 |
| Mouse ApoM I68K | NQCPEHSQLTALGMDDTETPEPHLGLWYFIAGAAPTTEELATFDPVDNIVFN MAAGSAPRQLQLRATKRTKSGVCVPRKWTYRLTEGKGNMELRTEGRPDMK TDLFSSSCPGGIMLKETGQGYQRFLLYNRSPHPPEKCVEEFKSLTSCLDFKAFL VTPRNQEACPLSSK | 20 |
| Mouse ApoM I68N | NQCPEHSQLTALGMDDTETPEPHLGLWYFIAGAAPTTEELATFDPVDNIVFN MAAGSAPRQLQLRATNRTKSGVCVPRKWTYRLTEGKGNMELRTEGRPDMK TDLFSSSCPGGIMLKETGQGYQRFLLYNRSPHPPEKCVEEFKSLTSCLDFKAFL VTPRNQEACPLSSK | 21 |
| Mouse ApoM T70Y | NQCPEHSQLTALGMDDTETPEPHLGLWYFIAGAAPTTEELATFDPVDNIVFN MAAGSAPRQLQLRATIRYKSGVCVPRKWTYRLTEGKGNMELRTEGRPDMK TDLFSSSCPGGIMLKETGQGYQRFLLYNRSPHPPEKCVEEFKSLTSCLDFKAFL VTPRNQEACPLSSK | 22 |

Fusion Protein

| Variants | Amino Acid Sequence | SEQ ID NO |
|---|---|---|
| Human ApoM T42N-human IgG1Fc (T66N) | MYRMQLLSCIALSLALVTNSISRVYQCPEHSQLTTLGVDGKEFPEVHLGQWY FIAGAAPTKEELANFDPVDNIVFNMAAGSAPMQLHLRATIRMKDGLCVPRK WIYHLTEGSTDLRTEGRPDMKTELFSSSCPGGIMLNETGQGYQRFLLYNRSPH PPEKCVEEFKSLTSCLDSKAFLLTPRNQEACELSNNWASTKGPSVFPLAPSSKS TSGGTAALGCLVKDYFPEPVTVSWNSGALTSGVHTFPAVLQSSGLYSLSSVV TVPSSSLGTQTYICNVNHKPSNTKVDKKVEPKSCDKTHTCPPCPAPELLGGPS VFLFPPKPKDTLMISRTPEVTCVVVDVSHEDPEVKFNWYVDGVEVHNAKTK PREEQYNSTYRVVSVLTVLHQDWLNGICEYKCKVSNKALPAPIEKTISKAKGQ PREPQVYTLPPSREEMTKNQVSLTCLVKGFYPSDIAVEWESNGQPENNYKTT PPVLDSDGSFFLYSKLTVDKSRWQQGNVFSCSVMHEALHNHYTQKSLSLSPG K* | 23 |
| Human ApoM V46K-human IgG1Fc (V70K) | MYRMQLLSCIALSLALVTNSISRVYQCPEHSQLTTLGVDGKEFPEVHLGQWY FIAGAAPTICEELATFDPKDNIVFNMAAGSAPMQLHLRATIRMICDGLCVPRK WIYHLTEGSTDLRTEGRPDMKTELFSSSCPGGIMLNETGQGYQRFLLYNRSPH PPEKCVEEFKSLTSCLDSKAFLLTPRNQEACELSNNWASTKGPSVFPLAPSSKS TSGGTAALGCLVKDYFPEPVTVSWNSGALTSGVHTFPAVLQSSGLYSLSSVV TVPSSSLGTQTYICNVNHKPSNTKVDKKVEPKSCDKTHTCPPCPAPELLGGPS VFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQ PREPQVYTLPPSREEMTKNQVSLTCLVKGFYPSDIAVEWESNGQPENNYKTT PPVLDSDGSFFLYSKLTVDKSRWQQGNVFSCSVMHEALHNHYTQKSLSLSPG K* | 24 |
| Human ApoM V46N-human IgG1Fc (V70N) | MYRMQLLSCIALSLALVTNSISRVYQCPEHSQLTTLGVDGKEFPEVHLGQWY FIAGAAPTKEELATFDPNDNIVFNMAAGSAPMQLHLRATIRMKDGLCVPRK WIYHLTEGSTDLRTEGRPDMKTELFSSSCPGGIMLNETGQGYQRFLLYNRSPH PPEKCVEEFKSLTSCLDSKAFLLTPRNQEACELSNNWASTKGPSVFPLAPSSKS TSGGTAALGCLVKDYFPEPVTVSWNSGALTSGVHTFPAVLQSSGLYSLSSVV TVPSSSLGTQTYICNVNHKPSNTKVDKKVEPKSCDKTHTCPPCPAPELLGGPS VFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQ | 25 |

TABLE 4-continued

| Amino Acid Sequences of "Sponge" Variants | | |
|---|---|---|
| Variants | Amino Acid Sequence | SEQ ID NO |
| | PREPQVYTLPPSREEMTKNQVSLTCLVKGFYPSDIAVEWESNGQPENNYKTT PPVLDSDGSFFLYSKLTVDKSRWQQGNVFSCSVMHEALHNHYTQKSLSLSPG K* | |
| Human ApoM V46Q-human IgG1Fc (V70Q) | MYRMQLLSCIALSLALVTNSISRVYQCPEHSQLTTLGVDGKEFPEVHLGQWY FIAGAAPTKEELATFDPQDNIVFNMAAGSAPMQLHLRATIRMKDGLCVPRK WIYHLTEGSTDLRTEGRPDMKTELFSSSCPGGIMLNETGQGYQRFLLYNRSPH PPEKCVEEFKSLTSCLDSKAFLLTPRNQEACELSNNWASTKGPSVFPLAPSSKS TSGGTAALGCLVKDYFPEPVTVSWNSGALTSGVHTFPAVLQSSGLYSLSSVV TVPSSSLGTQTYICNVNHKPSNTKVDKKVEPKSCDKTHTCPPCPAPELLGGPS VFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQ PREPQVYTLPPSREEMTKNQVSLTCLVKGFYPSDIAVEWESNGQPENNYKTT PPVLDSDGSFFLYSKLTVDKSRWQQGNVESCSVMHEALHNHYTQKSLSLSPG K* | 26 |
| Human ApoM I68K-human IgG1Fc (I92K) | MYRMQLLSCIALSLALVTNSISRVYQCPEHSQLTTLGVDGKEFPEVHLGQWY FIAGAAPTKEELATFDPVDNIVFNMAAGSAPMQLHLRATKRMKDGLCVPRK WIYHLTEGSTDLRTEGRPDMKTELFSSSCPGGIMLNETGQGYQRFLLYNRSPH PPEKCVEEFKSLTSCLDSKAFLLTPRNQEACELSNNWASTKGPSVFPLAPSSKS TSGGTAALGCLVKDYFPEPVTVSWNSGALTSGVHTFPAVLQSSGLYSLSSVV TVPSSSLGTQTYICNVNHKPSNTKVDKKVEPKSCDKTHTCPPCPAPELLGGPS VFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQ PREPQVYTLPPSREEMTKNQVSLTCLVKGFYPSDIAVEWESNGQPENNYKTT PPVLDSDGSFFLYSKLTVDKSRWQQGNVFSCSVMHEALHNHYTQKSLSLSPG K* | 27 |
| Human ApoM I68N-human IgG1Fc (I92N) | MYRMQLLSCIALSLALVTNSISRVYQCPEHSQLTTLGVDGKEFPEVHLGQWY FIAGAAPTKEELATFDPVDNIVFNMAAGSAPMQLHLRATNRMKDGLCVPRK WIYHLTEGSTDLRTEGRPDMKTELFSSSCPGGIMLNETGQGYQRFLLYNRSPH PPEKCVEEFKSLTSCLDSKAFLLTPRNQEACELSNNWASTKGPSVFPLAPSSKS TSGGTAALGCLVKDYFPEPVTVSWNSGALTSGVHTFPAVLQSSGLYSLSSVV TVPSSSLGTQTYICNVNHKPSNTKVDKKVEPKSCDKTHTCPPCPAPELLGGPS VFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQ PREPQVYTLPPSREEMTKNQVSLTCLVKGFYPSDIAVEWESNGQPENNYKTT PPVLDSDGSFFLYSKLTVDKSRWQQGNVFSCSVMHEALHNHYTQKSLSLSPG K* | 28 |
| Human ApoM M70Y-human IgG1Fc (M94Y) | MYRMQLLSCIALSLALVTNSISRVYQCPEHSQLTTLGVDGKEFPEVHLGQWY FIAGAAPTKEELATFDPVDNIVFNMAAGSAPMQLHLRATIRYKDGLCVPRKW IYHLTEGSTDLRTEGRPDMKTELFSSSCPGGIMLNETGQGYQRFLLYNRSPHP PEKCVEEFKSLTSCLDSKAFLLTPRNQEACELSNNWASTKGPSVFPLAPSSKS TSGGTAALGCLVKDYFPEPVTVSWNSGALTSGVHTFPAVLQSSGLYSLSSVV TVPSSSLGTQTYICNVNHKPSNTKVDKKVEPKSCDKTHTCPPCPAPELLGGPS VFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQ PREPQVYTLPPSREEMTKNQVSLTCLVKGFYPSDIAVEWESNGQPENNYKTT PPVLDSDGSFFLYSKLTVDKSRWQQGNVFSCSVMHEALHNHYTQKSLSLSPG K* | 29 |
| Human ApoM T42N-mouse IgG1Fc (T66N) | MYRMQLLSCIALSLALVTNSISRVYQCPEHSQLTTLGVDGKEFPEVHLGQWY FIAGAAPTKEELANFDPVDNIVFNMAAGSAPMQLHLRATIRMKDGLCVPRK WIYHLTEGSTDLRTEGRPDMKTELFSSSCPGGIMLNETGQGYQRFLLYNRSPH PPEKCVEEEKSLTSCLDSKAFLLTPRNQEACELSNNWISSASSAKTTPPSVYPL APGSAAQTNSMVTLGCLVKGYFPEPVTVTWNSGSLSSGVHTFPAVLQSDLYT LSSSVTVPSSTWPSETVTCNVAHPASSTKVDKKIVPRDCGCKPCICTVPEVSSV FIFPPKPKDVLTITLTPKVTCVVVDISKDDPEVQFSWFVDDVEVHTAQTQPRE EQFNSTFRSVSELPIMHQDWLNGKEFKCRVNSAAFPAPIEKTISKTKGRPKAP QVYTIPPPKEQMAKDKVSLTCMITDFFPEDITVEWQWNGQPAENYKNTQPIM DTDGSYFVYSKLNVQKSNWEAGNTFTCSVLHEGLHNHHTEKSLSHSPGK* | 30 |
| Human ApoM V46K-mouse IgG1Fc (V70K) | MYRMQLLSCIALSLALVTNSISRVYQCPEHSQLTTLGVDGKEFPEVHLGQWY FIAGAAPTKEELATFDPKDNIVFNMAAGSAPMQLHLRATIRMKDGLCVPRK WIYHLTEGSTDLRTEGRPDMKTELFSSSCPGGIMLNETGQGYQRFLLYNRSPH PPEKCVEEFKSLTSCLDSKAFLLTPRNQEACELSNNWISSASSAKTTPPSVYPL APGSAAQTNSMVTLGCLVKGYFPEPVTVTWNSGSLSSGVHTFPAVLQSDLYT LSSSVTVPSSTWPSETVTCNVAHPASSTKVDKKIVPRDCGCKPCICTVPEVSSV FIFPPKPKDVLTITLTPKVTCVVVDISKDDPEVQFSWFVDDVEVHTAQTQPRE EQFNSTFRSVSELPIMHQDWLNGKEFKCRVNSAAFPAPIEKTISKTKGRPKAP QVYTIPPPKEQMAKDKVSLTCMITDFFPEDITVEWQWNGQPAENYKNTQPIM DTDGSYFVYSKLNVQKSNWEAGNTFTCSVLHEGLHNHHTEKSLSHSPGK* | 31 |

TABLE 4-continued

Amino Acid Sequences of "Sponge" Variants

| Variants | Amino Acid Sequence | SEQ ID NO |
|---|---|---|
| Human ApoM V46N-mouse IgG1Fc (V70N) | MYRMQLLSCIALSLALVTNSISRVYQCPEHSQLTTLGVDGKEFPEVHLGQWY FIAGAAPTKEELATFDPNDNIVFNMAAGSAPMQLHLRATIRMKDGLCVPRK WIYHLTEGSTDLRTEGRPDMKTELFSSSCPGGIMLNETGQGYQRFLLYNRSPH PPEKCVEEFKSLTSCLDSKAFLLTPRNQEACELSNNWISSASSAKTTPPSVYPL APGSAAQTNSMVTLGCLVKGYFPEPVTVTWNSGSLSSGVHTFPAVLQSDLYT LSSSVTVPSSTWPSETVTCNVAHPASSTKVDKKIVPRDCGCKPCICTVPEVSSV FIFPPKPKDVLTITLTPKVTCVVVDISKDDPEVQFSWFVDDVEVHTAQTQPRE EQFNSTFRSVSELPIMHQDWLNGKEFKCRVNSAAFPAPIEKTISKTKGRPKAP QVYTIPPPKEQMAKDKVSLTCMITDFFPEDITVEWQWNGQPAENYKNTQPIM DTDGSYFVYSKLNVQKSNWEAGNTFTCSVLHEGLHNHHTEKSLSHSPGK* | 32 |
| Human ApoM V46Q-mouse IgG1Fc (V70Q) | MYRMQLLSCIALSLALVTNSISRVYQCPEHSQLTTLGVDGKEEPEVHLGQWY FIAGAAPTKEELATFDPQDNIVFNMAAGSAPMQLHLRATIRMKDGLCVPRK WIYHLTEGSTDLRTEGRPDMKTELFSSSCPGGIMLNETGQGYQRFLLYNRSPH PPEKCVEEFKSLTSCLDSKAFLLTPRNQEACELSNNWISSASSAKTTPPSVYPL APGSAAQTNSMVTLGCLVKGYFPEPVTVTWNSGSLSSGVHTFPAVLQSDLYT LSSSVTVPSSTWPSETVTCNVAHPASSTKVDKKIVPRDCGCKPCICTVPEVSSV FIFPPKPKDVLTITLTPKVTCVVVDISKDDPEVQFSWFVDDVEVHTAQTQPRE EQFNSTFRSVSELPIMHQDWLNGKEFKCRVNSAAFPAPIEKTISKTKGRPKAP QVYTIPPPKEQMAKDKVSLTCMITDFFPEDITVEWQWNGQPAENYKNTQPIM DTDGSYFVYSKLNVQKSNWEAGNTFTCSVLHEGLHNHHTEKSLSHSPGK* | 33 |
| Human ApoM I68K-mouse IgG1Fc (I92K) | MYRMQLLSCIALSLALVTNSISRVYQCPEHSQLTTLGVDGKEFPEVHLGQWY FIAGAAPTKEELATFDPVDNIVFNMAAGSAPMQLHLRATKRMKDGLCVPRK WIYHLTEGSTDLRTEGRPDMKTELFSSSCPGGIMLNETGQGYQRFLLYNRSPH PPEKCVEEFKSLTSCLDSKAFLLTPRNQEACELSNNWISSASSAKTTPPSVYPL APGSAAQTNSMVTLGCLVKGYFPEPVTVTWNSGSLSSGVHTFPAVLQSDLYT LSSSVTVPSSTWPSETVTCNVAHPASSTKVDKKIVPRDCGCKPCICTVPEVSSV FIFPPKPKDVLTITLTPKVTCVVVDISKDDPEVQFSWFVDDVEVHTAQTQPRE EQFNSTFRSVSELPIMHQDWLNGKEFKCRVNSAAFPAPIEKTISKTKGRPKAP QVYTIPPPKEQMAKDKVSLTCMITDFFPEDITVEWQWNGQPAENYKNTQPIM DTDGSYFVYSKLNVQKSNWEAGNTFTCSVLHEGLHNHHTEKSLSHSPGK* | 34 |
| Human ApoM I68N-mouse IgG1Fc (I92N) | MYRMQLLSCIALSLALVTNSISRVYQCPEHSQLTTLGVDGKEFPEVHLGQWY FIAGAAPTKEELATFDPVDNIVFNMAAGSAPMQLHLRATNRMKDGLCVPRK WIYHLTEGSTDLRTEGRPDMKTELFSSSCPGGIMLNETGQGYQRFLLYNRSPH PPEKCVEEFKSLTSCLDSKAFLLTPRNQEACELSNNWISSASSAKTTPPSVYPL APGSAAQTNSMVTLGCLVKGYFPEPVTVTWNSGSLSSGVHTFPAVLQSDLYT LSSSVTVPSSTWPSETVTCNVAHPASSTKVDKKIVPRDCGCKPCICTVPEVSSV FIFPPKPKDVLTITLTPKVTCVVVDISKDDPEVQFSWFVDDVEVHTAQTQPRE EQFNSTFRSVSELPIMHQDWLNGKEFKCRVNSAAFPAPIEKTISKTKGRPKAP QVYTIPPPKEQMAKDKVSLTCMITDFFPEDITVEWQWNGQPAENYKNTQPIM DTDGSYFVYSKLNVQKSNWEAGNTFTCSVLHEGLHNHHTEKSLSHSPGK* | 35 |
| Human ApoM M70Y-mouse IgG1Fc (M94Y) | MYRMQLLSCIALSLALVTNSISRVYQCPEHSQLTTLGVDGKEFPEVHLGQWY FIAGAAPTKEELATFDPVDNIVFNMAAGSAPMQLHLRATIRYKDGLCVPRKW IYHLTEGSTDLRTEGRPDMKTELFSSSCPGGIMLNETGQGYQRFLLYNRSPHP PEKCVEEFKSLTSCLDSKAFLLTPRNQEACELSNNWISSASSAKTTPPSVYPLA PGSAAQTNSMVTLGCLVKGYFPEPVTVTWNSGSLSSGVHTFPAVLQSDLYTL SSSVTVPSSTWPSETVTCNVAHPASSTKVDKKIVPRDCGCKPCICTVPEVSSVF IFPPKPKDVLTITLTPKVTCVVVDISKDDPEVQFSWFVDDVEVHTAQTQPREE QFNSTFRSVSELPIMHQDWLNGKEFKCRVNSAAFPAPIEKTISKTKGRPKAPQ VYTIPPPKEQMAKDKVSLTCMITDFFPEDITVEWQWNGQPAENYKNTQPIMD TDGSYFVYSKLNVQKSNWEAGNTFTCSVLHEGLHNHHTEKSLSHSPGK* | 36 |
| Mouse ApoM T42N-mouse IgG1Fc (T66N) | MYRMQLLSCIALSLALVTNSNQCPEHSQLTALGMDDTETPEPHLGLWYFIAG AAPTTEELANFDPVDNIVFNMAAGSAPRQLQLRATIRTKSGVCVPRKWTYRL TEGKGNMELRTEGRPDMKTDLFSSSCPGGIMLKETGQGYQRFLLYNRSPHPP EKCVEEFKSLTSCLDFKAFLVTPRNQEACPLSSKWISSASSAKTTPPSVYPLAP GSAAQTNSMVTLGCLVKGYFPEPVTVTWNSGSLSSGVHTFPAVLQSDLYTLS SSVTVPSSTWPSETVTCNVAHPASSTKVDKKIVPRDCGCKPCICTVPEVSSVFI FPPKPKDVLTITLTPKVTCVVVDISKDDPEVQFSWFVDDVEVHTAQTQPREEQ FNSTFRSVSELPIMHQDWLNGKEFKCRVNSAAFPAPIEKTISKTKGRPKAPQV YTIPPPKEQMAKDKVSLTCMITDFFPEDITVEWQWNGQPAENYKNTQPIMDT DGSYFVYSKLNVQKSNWEAGNTFTCSVLHEGLHNHHTEKSLSHSPGK* | 37 |
| Mouse ApoM V46K-mouse IgG1Fc (V70K) | MYRMQLLSCIALSLALVTNSNQCPEHSQLTALGMDDTETPEPHLGLWYFIAG AAPTTEELATFDPKDNIVFNMAAGSAPRQLQLRATIRTKSGVCVPRKWTYRL TEGKGNMELRTEGRPDMKTDLFSSSCPGGIMLKETGQGYQRFLLYNRSPHPP EKCVEEFKSLTSCLDFKAFLVTPRNQEACPLSSKWISSASSAKTTPPSVYPLAP GSAAQTNSMVTLGCLVKGYFPEPVTVTWNSGSLSSGVHTFPAVLQSDLYTLS SSVTVPSSTWPSETVTCNVAHPASSTKVDKKIVPRDCGCKPCICTVPEVSSVFI FPPKPKDVLTITLTPKVTCVVVDISKDDPEVQFSWFVDDVEVHTAQTQPREEQ FNSTFRSVSELPIMHQDWLNGKEFKCRVNSAAFPAPIEKTISKTKGRPKAPQV | 38 |

TABLE 4-continued

Amino Acid Sequences of "Sponge" Variants

| Variants | Amino Acid Sequence | SEQ ID NO |
|---|---|---|
| | YTIPPPKEQMAKDKVSLTCMITDFFPEDITVEWQWNGQPAENYKNTQPIMDT<br>DGSYFVYSKLNVQKSNWEAGNTFTCSVLHEGLHNHHTEKSLSHSPGK* | |
| Mouse ApoM<br>V46N-mouse<br>IgG1Fc<br>(V70N) | MYRMQLLSCIALSLALVTNSNQCPEHSQLTALGMDDTETPEPHLGLWYFIAG<br>AAPTTEELATFDPNDNIVFNMAAGSAPRQLQLRATIRTKSGVCVPRKWTYRL<br>TEGKGNMELRTEGRPDMKTDLFSSSCPGGIMLKETGQGYQRFLLYNRSPHPP<br>EKCVEEFKSLTSCLDFKAFLVTPRNQEACPLSSKWISSASSAKTTPPSVYPLAP<br>GSAAQTNSMVTLGCLVKGYFPEPVTVTWNSGSLSSGVHTFPAVLQSDLYTLS<br>SSVTVPSSTWPSETVTCNVAHPASSTKVDKKIVPRDCGCKPCICTVPEVSSVFI<br>FPPKPKDVLTITLTPKVTCVVVDISKDDPEVQFSWFVDDVEVHTAQTQPREEQ<br>FNSTFRSVSELPIMHQDWLNGKEFKCRVNSAAFPAPIEKTISKTKGRPKAPQV<br>YTIPPPKEQMAKDKVSLTCMITDFFPEDITVEWQWNGQPAENYKNTQPIMDT<br>DGSYFVYSKLNVQKSNWEAGNTFTCSVLHEGLHNHHTEKSLSHSPGK* | 39 |
| Mouse ApoM<br>V46Q-mouse<br>IgG1Fc<br>(V70Q) | MYRMQLLSCIALSLALVTNSNQCPEHSQLTALGMDDTETPEPHLGLWYFIAG<br>AAPTTEELATFDPQDNIVFNMAAGSAPRQLQLRATIRTKSGVCVPRKWTYRL<br>TEGKGNMELRTEGRPDMKTDLFSSSCPGGIMLKETGQGYQRFLLYNRSPHPP<br>EKCVEEFKSLTSCLDFKAFLVTPRNQEACPLSSKWISSASSAKTTPPSVYPLAP<br>GSAAQTNSMVTLGCLVKGYFPEPVTVTWNSGSLSSGVHTFPAVLQSDLYTLS<br>SSVTVPSSTWPSETVTCNVAHPASSTKVDKKIVPRDCGCKPCICTVPEVSSVFI<br>FPPKPKDVLTITLTPKVTCVVVDISKDDPEVQFSWFVDDVEVHTAQTQPREEQ<br>FNSTFRSVSELPIMHQDWLNGKEFKCRVNSAAFPAPIEKTISKTKGRPKAPQV<br>YTIPPPKEQMAKDKVSLTCMITDFFPEDITVEWQWNGQPAENYKNTQPIMDT<br>DGSYFVYSKLNVQKSNWEAGNTFTCSVLHEGLHNHHTEKSLSHSPGK* | 40 |
| Mouse ApoM<br>I68K-mouse<br>IgG1Fc (I92K) | MYRMQLLSCIALSLALVTNSNQCPEHSQLTALGMDDTETPEPHLGLWYFIAG<br>AAPTTEELATFDPVDNIVFNMAAGSAPRQLQLRATKRTKSGVCVPRKWTYRL<br>LTEGKGNMELRTEGRPDMKTDLFSSSCPGGIMLKETGQGYQRFLLYNRSPHP<br>PEKCVEEFKSLTSCLDFKAFLVTPRNQEACPLSSKWISSASSAKTTPPSVYPLA<br>PGSAAQTNSMVTLGCLVKGYFPEPVTVTWNSGSLSSGVHTFPAVLQSDLYTL<br>SSSVTVPSSTWPSETVTCNVAHPASSTKVDKKIVPRDCGCKPCICTVPEVSSVF<br>IFPPKPKDVLTITLTPKVTCVVVDISKDDPEVQFSWFVDDVEVHTAQTQPREE<br>QFNSTFRSVSELPIMHQDWLNGKEFKCRVNSAAFPAPIEKTISKTKGRPKAPQ<br>VYTIPPPKEQMAKDKVSLTCMITDFFPEDITVEWQWNGQPAENYKNTQPIMD<br>TDGSYFVYSKLNVQKSNWEAGNTFTCSVLHEGLHNHHTEKSLSHSPGK* | 41 |
| Mouse ApoM<br>I68N-mouse<br>IgG1Fc (I92N) | MYRMQLLSCIALSLALVTNSNQCPEHSQLTALGMDDTETPEPHLGLWYFIAG<br>AAPTTEELATFDPVDNIVFNMAAGSAPRQLQLRATNRTKSGVCVPRKWTYR<br>LTEGKGNMELRTEGRPDMKTDLFSSSCPGGIMLKETGQGYQRFLLYNRSPHP<br>PEKCVEEFKSLTSCLDFKAFLVTPRNQEACPLSSKWISSASSAKTTPPSVYPLA<br>PGSAAQTNSMVTLGCLVKGYFPEPVTVTWNSGSLSSGVHTFPAVLQSDLYTL<br>SSSVTVPSSTWPSETVTCNVAHPASSTKVDKKIVPRDCGCKPCICTVPEVSSVF<br>IFPPKPKDVLTITLTPKVTCVVVDISKDDPEVQFSWFVDDVEVHTAQTQPREE<br>QFNSTFRSVSELPIMHQDWLNGKEFKCRVNSAAFPAPIEKTISKTKGRPKAPQ<br>VYTIPPPKEQMAKDKVSLTCMITDFFPEDITVEWQWNGQPAENYKNTQPIMD<br>TDGSYFVYSKLNVQKSNWEAGNTFTCSVLHEGLHNHHTEKSLSHSPGK* | 42 |
| Mouse ApoM<br>T70Y-mouse<br>IgG1Fc<br>(T94Y) | MYRMQLLSCIALSLALVTNSNQCPEHSQLTALGMDDTETPEPHLGLWYFIAG<br>AAPTTEELATFDPVDNIVFNMAAGSAPRQLQLRATIRYKSGVCVPRKWTYRL<br>TEGKGNMELRTEGRPDMKTDLFSSSCPGGIMLIKETGQGYQRFLLYNRSPHPP<br>EKCVEEFKSLTSCLDFKAFLVTPRNQEACPLSSKWISSASSAKTTPPSVYPLAP<br>GSAAQTNSMVTLGCLVKGYFPEPVTVTWNSGSLSSGVHTFPAVLQSDLYTLS<br>SSVTVPSSTWPSETVTCNVAHPASSTKVDKKIVPRDCGCKPCICTVPEVSSVFI<br>FPPKPKDVLTITLTPKVTCVVVDISKDDPEVQFSWFVDDVEVHTAQTQPREEQ<br>FNSTFRSVSELPIMHQDWLNGKEFKCRVNSAAFPAPIEKTISKTKGRPKAPQV<br>YTIPPPKEQMAKDKVSLTCMITDFFPEDITVEWQWNGQPAENYKNTQPIMDT<br>DGSYFVYSKLNVQKSNWEAGNTFTCSVLHEGLHNHHTEKSLSHSPGK* | 43 |
| Mouse ApoM<br>T42N-human<br>IgG1Fc<br>(T66N) | MYRMQLLSCIALSLALVTNSNQCPEHSQLTALGMDDTETPEPHLGLWYFIAG<br>AAPTTEELANFDPVDNIVFNMAAGSAPRQLQLRATIRTKSGVCVPRKWTYRL<br>TEGKGNMELRTEGRPDMKTDLFSSSCPGGIMLKETGQGYQRFLLYNRSPHPP<br>EKCVEEFKSLTSCLDFKAFLVTPRNQEACPLSSKWASTKGPSVFPLAPSSKSTS<br>GGTAALGCLVKDYFPEPVTVSWNSGALTSGVHTFPAVLQSSGLYSLSSVVTV<br>PSSSLGTQTYICNVNHKPSNTKVDKKVEPKSCDKTHTCPPCPAPELLGGPSVF<br>LFPPKPKDTLMISRTPEVTCVVVDVSHEDPEVKFNWYVDGVEVHNAKTKPR<br>EEEQYNSTYRVVSVLTVLHQDWLNGKEYKCKVSNKALPAPIEKTISKAKGQPR<br>EPQVYTLPPSREEMTKNQVSLTCLVKGFYPSDIAVEWESNGQPENNYKTTPP<br>VLDSDGSFFLYSKLTVDKSRWQQGNVFSCSVMHEALHNHYTQKSLSLSPGK* | 44 |
| Mouse ApoM<br>V46K-human<br>IgG1Fc<br>(V70K) | MYRMQLLSCIALSLALVTNSNQCPEHSQLTALGMDDTETPEPHLGLWYFIAG<br>AAPTTEELATFDPKDNIVFNMAAGSAPRQLQLRATIRTKSGVCVPRKWTYRL<br>TEGKGNMELRTEGRPDMKTDLFSSSCPGGIMLKETGQGYQRFLLYNRSPHPP<br>EKCVEEFKSLTSCLDFKAFLVTPRNQEACPLSSKWASTKGPSVFPLAPSSKSTS<br>GGTAALGCLVKDYFPEPVTVSWNSGALTSGVHTFPAVLQSSGLYSLSSVVTV | 45 |

TABLE 4-continued

| Amino Acid Sequences of "Sponge" Variants | | |
|---|---|---|
| Variants | Amino Acid Sequence | SEQ ID NO |
| | PSSSLGTQTYICNVNHKPSNTKVDKKVEPKSCDKTHTCPPCPAPELLGGPSVF LFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPGK* | |
| Mouse ApoM V46N-human IgG1Fc (V70N) | MYRMQLLSCIALSLALVTNSNQCPEHSQLTALGMDDTETPEPHLGLWYFIAG AAPTTEELATFDPNDNIVFNMAAGSAPRQLQLRATIRTKSGVCVPRKWTYRL TEGKGNMELRTEGRPDMKTDLFSSSCPGGIMLKETGQGYQRFLLYNRSPHPP EKCVEEFKSLTSCLDFKAFLVTPRNQEACPLSSKWASTKGPSVFPLAPSSKSTS GGTAALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGPSVF LFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPGK* | 46 |
| Mouse ApoM V46Q-human IgG1Fc (V70Q) | MYRMQLLSCIALSLALVTNSNQCPEHSQLTALGMDDTETPEPHLGLWYFIAG AAPTTEELATFDPQDNIVFNMAAGSAPRQLQLRATIRTKSGVCVPRKWTYRL TEGKGNMELRTEGRPDMKTDLFSSSCPGGIMLKETGQGYQRFLLYNRSPHPP EKCVEEFKSLTSCLDFKAFLVTPRNQEACPLSSKWASTKGPSVFPLAPSSKSTS GGTAALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGPSVF LFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPGK* | 47 |
| Mouse ApoM I68K-human IgG1Fc (I92K) | MYRMQLLSCIALSLALVTNSNQCPEHSQLTALGMDDTETPEPHLGLWYFIAG AAPTTEELATFDPVDNIVFNMAAGSAPRQLQLRATKRTKSGVCVPRKWTYR LTEGKGNMELRTEGRPDMKTDLFSSSCPGGIMLKETGQGYQRFLLYNRSPHP PEKCVEEFKSLTSCLDFKAFLVTPRNQEACPLSSKWASTKGPSVFPLAPSSKST SGGTAALGCLVKDYFPEPVTVSWNSGALTSGVHTFPAVLQSSGLYSLSSVVT VPSSSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPGK* | 48 |
| Mouse ApoM I68N-human IgG1Fc (I92N) | MYRMQLLSCIALSLALVTNSNQCPEHSQLTALGMDDTETPEPHLGLWYFIAG AAPTTEELATFDPVDNIVFNMAAGSAPRQLQLRATNRTKSGVCVPRKWTYR LTEGKGNMELRTEGRPDMKTDLFSSSCPGGIMLKETGQGYQRFLLYNRSPHP PEKCVEEFKSLTSCLDFKAFLVTPRNQEACPLSSKWASTKGPSVFPLAPSSKST SGGTAALGCLVKDYFPEPVTVSWNSGALTSGVHTFPAVLQSSGLYSLSSVVT VPSSSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPGK* | 49 |
| Mouse ApoM T70Y-human IgG1Fc (T94Y) | MYRMQLLSCIALSLALVTNSNQCPEHSQLTALGMDDTETPEPHLGLWYFIAG AAPTTEELATFDPVDNIVFNMAAGSAPRQLQLRATIRYKSGVCVPRKWTYRL TEGKGNMELRTEGRPDMKTDLFSSSCPGGIMLKETGQGYQRFLLYNRSPHPP EKCVEEFKSLTSCLDFKAFLVTPRNQEACPLSSKWASTKGPSVFPLAPSSKSTS GGTAALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGPSVF LFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPGK* | 50 |

*mutated amino acids are underlined; all fusion protein sequences contains a N-terminal signal peptide. The mutation positions using the fusion protein sequence as the reference sequences are shown in parentheses after the name of the variant.

TABLE 5

Exemplary nucleotide sequences of the ApoM-Fc sponge mutants

| hApoM-mFc sponge mutant | Nucleotide sequence |
|---|---|
| T66N | Atgtacaggatgcaactcctgtcttgcattgcactaagtcttgcacttgtcacgaattcgatatctcgagtgtaccagtgccctgagcac agtcaactgacaactctgggcgtggatgggaaggagttcccagaggtccacttgggccagtggtactttatcgcaggggcagc tcccaccaaggaggagttggcaaactttgaccctgtggacaacattgtcttcaatatggctgctggctctgccccgatgcagctc caccttcgtgctaccatccgcatgaaagatgggctctgtgtgccccggaaatggatctaccacctgactgaagggagcacaga tctcagaactgaaggccgccctgacatgaagactgagctcttttccagctcatgcccaggtggaatcatgctgaatgagacag gccagggttaccagcggctttctcctctacaatcgctcaccacatcctcccgaaaagtgtgtggaggaattcaagtccctgacttc ctgcctggactccaaagccttcttattgactcctaggaatcaagaggcctgtgagctgtccaataactggatctcgagtgctagca gcgctaaaacgacaccccatctgtctatccactggcccctggatctgctgcccaaactaactccatggtgaccctgggatgcctggtc aagggctatttccctgagccagtgacagtgacctggaactctggatccctgtccagcggtgtgtgcacaccttcccagctgtcctgcagtct gacctctacactctgagcagctcagtgactgtcccctccagcacctggcccagcgagaccgtcacctgcaacgttgcccacccggcc agcagcaccaaggtggacaagaaaattgtgcccagggattgtggttgtaagccttgcatatgtacagtcccagaagtatcatctgtcttc atcttcccccaaagcccaaggatgtgctcaccattactctgactcctaaggtcacgtgtgttgtggtagacatcagcaaggatgatccc gaggtccagttcagctggtttgtagatgatgtggaggtgcacacagctcagacgcaaccccgggaggagcagttcaacagcactttcc gctcagtcagtgaacttcccatcatgcaccaggactggctcaatggcaaggagttcaaatgcagggtcaacagtgcagctttccctgcc cccatcgagaaaaccatctccaaaaccaaaggcagaccgaaggctccgcaggtgtacaccattccacctcccaaggagcagatggc caaggataaagtcagtctgacctgcatgataacagacttcttccctgaagacattactgtggagtggcagtggaatgggcagccagcg gagaactacaagaacactcagcccatcatggacacagatggctcttacttcgtctacagcaagctcaatgtgcagaagagcaactggg aggcaggaaatactttcacctgctctgtgttacatgagggcctgcacaaccaccatactgagaagagcctctcccactctcctggtaaat ga (SEQ ID NO: 70) |
| V70K | Atgtacaggatgcaactcctgtcttgcattgcactaagtcttgcacttgtcacgaattcgatatctcgagtgtaccagtgccctgagcac agtcaactgacaactctgggcgtggatgggaaggagttcccagaggtccacttgggccagtggtactttatcgcaggggcagc tcccaccaaggaggagttggcaaactttgaccctaaggacaacattgtcttcaatatggctgctggctctgccccgatgcagctc caccttcgtgctaccatccgcatgaaagatgggctctgtgtgccccggaaatggatctaccacctgactgaagggagcacaga tctcagaactgaaggccgccctgacatgaagactgagctcttttccagctcatgcccaggtggaatcatgctgaatgagacag gccagggttaccagcggctttctcctctacaatcgctcaccacatcctcccgaaaagtgtgtggaggaattcaagtccctgacttc ctgcctggactccaaagccttcttattgactcctaggaatcaagaggcctgtgagctgtccaataactggatctcgagtgctagca gcgctaaaacgacaccccatctgtctatccactggcccctggatctgctgcccaaactaactccatggtgaccctgggatgcctggtc aagggctatttccctgagccagtgacagtgacctggaactctggatccctgtccagcggtgtgtgcacaccttcccagctgtcctgcagtct gacctctacactctgagcagctcagtgactgtcccctccagcacctggcccagcgagaccgtcacctgcaacgttgcccacccggcc agcagcaccaaggtggacaagaaaattgtgcccagggattgtggttgtaagccttgcatatgtacagtcccagaagtatcatctgtcttc atcttcccccaaagcccaaggatgtgctcaccattactctgactcctaaggtcacgtgtgttgtggtagacatcagcaaggatgatccc gaggtccagttcagctggtttgtagatgatgtggaggtgcacacagctcagacgcaaccccgggaggagcagttcaacagcactttcc gctcagtcagtgaacttcccatcatgcaccaggactggctcaatggcaaggagttcaaatgcagggtcaacagtgcagctttccctgcc cccatcgagaaaaccatctccaaaaccaaaggcagaccgaaggctccgcaggtgtacaccattccacctcccaaggagcagatggc caaggataaagtcagtctgacctgcatgataacagacttcttccctgaagacattactgtggagtggcagtggaatgggcagccagcg gagaactacaagaacactcagcccatcatggacacagatggctcttacttcgtctacagcaagctcaatgtgcagaagagcaactggg aggcaggaaatactttcacctgctctgtgttacatgagggcctgcacaaccaccatactgagaagagcctctcccactctcctggtaaat ga (SEQ ID NO: 71) |
| V70N | Atgtacaggatgcaactcctgtcttgcattgcactaagtcttgcacttgtcacgaattcgatatctcgagtgtaccagtgccctgagcac agtcaactgacaactctgggcgtggatgggaaggagttcccagaggtccacttgggccagtggtactttatcgcaggggcagc tcccaccaaggaggagttggcaactttgaccctaacgacaacattgtcttcaatatggctgctggctctgccccgatgcagctc caccttcgtgctaccatccgcatgaaagatgggctctgtgtgccccggaaatggatctaccacctgactgaagggagcacaga tctcagaactgaaggccgccctgacatgaagactgagctcttttccagctcatgcccaggtggaatcatgctgaatgagacag gccagggttaccagcgctttctcctctacaatcgctcaccacatcctcccgaaaagtgtgtggaggaattcaagtccctgacttc ctgcctggactccaaagccttcttattgactcctaggaatcaagaggcctgtgagctgtccaataactggatctcgagtgctagca gcgctaaaacgacaccccatctgtctatccactggcccctggatctgctgcccaaactaactccatggtgaccctgggatgcctggtc aagggctatttccctgagccagtgacagtgacctggaactctggatccctgtccagcggtgtgtgcacaccttcccagctgtcctgcagtct gacctctacactctgagcagctcagtgactgtcccctccagcacctggcccagcgagaccgtcacctgcaacgttgcccacccggcc agcagcaccaaggtggacaagaaaattgtgcccagggattgtggttgtaagccttgcatatgtacagtcccagaagtatcatctgtcttc atcttcccccaaagcccaaggatgtgctcaccattactctgactcctaaggtcacgtgtgttgtggtagacatcagcaaggatgatccc gaggtccagttcagctggtttgtagatgatgtggaggtgcacacagctcagacgcaaccccgggaggagcagttcaacagcactttcc gctcagtcagtgaacttcccatcatgcaccaggactggctcaatggcaaggagttcaaatgcagggtcaacagtgcagctttccctgcc cccatcgagaaaaccatctccaaaaccaaaggcagaccgaaggctccgcaggtgtacaccattccacctcccaaggagcagatggc caaggataaagtcagtctgacctgcatgataacagacttcttccctgaagacattactgtggagtggcagtggaatgggcagccagcg gagaactacaagaacactcagcccatcatggacacagatggctcttacttcgtctacagcaagctcaatgtgcagaagagcaactggg aggcaggaaatactttcacctgctctgtgttacatgagggcctgcacaaccaccatactgagaagagcctctcccactctcctggtaaat ga (SEQ ID NO: 72) |
| V70Q | Atgtacaggatgcaactcctgtcttgcattgcactaagtcttgcacttgtcacgaattcgatatctcgagtgtaccagtgccctgagcac agtcaactgacaactctgggcgtggatgggaaggagttcccagaggtccacttgggccagtggtactttatcgcaggggcagc tcccaccaaggaggagttggcaactttgaccctcaggacaacattgtcttcaatatggctgctggctctgccccgatgcagctc caccttcgtgctaccatccgcatgaaagatgggctctgtgtgccccggaaatggatctaccacctgactgaagggagcacaga tctcagaactgaaggccgccctgacatgaagactgagctcttttccagctcatgcccaggtggaatcatgctgaatgagacag gccagggttaccagcggctttctcctctacaatcgctcaccacatcctcccgaaaagtgtgtggaggaattcaagtccctgacttc ctgcctggactccaaagccttcttattgactcctaggaatcaagaggcctgtgagctgtccaataactggatctcgagtgctagca gcgctaaaacgacaccccatctgtctatccactggcccctggatctgctgcccaaactaactccatggtgaccctgggatgcctggtc aagggctatttccctgagccagtgacagtgacctggaactctggatccctgtccagcggtgtgtgcacaccttcccagctgtcctgcagtct gacctctacactctgagcagctcagtgactgtcccctccagcacctggcccagcgagaccgtcacctgcaacgttgcccacccggcc agcagcaccaaggtggacaagaaaattgtgcccagggattgtggttgtaagccttgcatatgtacagtcccagaagtatcatctgtcttc atcttcccccaaagcccaaggatgtgctcaccattactctgactcctaaggtcacgtgtgttgtggtagacatcagcaaggatgatccc gaggtccagttcagctggtttgtagatgatgtggaggtgcacacagctcagacgcaaccccgggaggagcagttcaacagcactttcc |

TABLE 5-continued

Exemplary nucleotide sequences of the ApoM-Fc sponge mutants

| hApoM-mFc sponge mutant | Nucleotide sequence |
|---|---|
| | gctcagtcagtgaacttcccatcatgcaccaggactggctcaatggcaaggagttcaaatgcagggtcaacagtgcagctttccctgcc<br>cccatcgagaaaaccatctccaaaaccaaaggcagaccgaaggctccgcaggtgtacaccattccacctcccaaggagcagatggc<br>caaggataaagtcagtctgacctgcatgataacagacttcttccctgaagacattactgtggagtggcagtggaatgggcagccagcg<br>gagaactacaagaacactcagcccatcatggacacagatggctcttacttcgtctacagcaagctcaatgtgcagaagagcaactggg<br>aggcaggaaatactttcacctgctctgtgttacatgagggcctgcacaaccaccatactgagaagagcctctcccactctcctggtaaat<br>ga (SEQ ID NO: 73) |
| 192K | Atgtacaggatgcaactcctgtcttgcattgcactaagtcttgcacttgtcacgaattcgatatctcgagtgtaccagtgccctgagcac<br>agtcaactgacaactctgggcgtggatgggaaggagttcccagaggtccacttgggccagtggtactttatcgcaggggcagc<br>tcccaccaaggaggagttggcaacttttgaccctgtggacaacattgtcttcaatatggctgctggctctgccccgatgcagctc<br>caccttcgtgctaccaaacgcatgaaagatgggctctgtgtgccccggaaatggatctaccacctgactgaagggagcacag<br>atctcagaactgaaggccgccctgacatgaagactgagctctttccagctcatgcccaggtggaatcatgctgaatgagaca<br>ggccagggttaccagcgctttctcctctacaatcgctcaccacatcctcccgaaaagtgtgtggaggaattcaagtccctgactt<br>cctgcctggactccaaagccttcttattgactcctaggaatcaagaggcctgtgagctgtccaataactggatctcgagtgctagc<br>agcgctaaaacgacaccccatctgtctatccactggccctggatctgctgcccaaactaactccatggtgaccctgggatgcctggt<br>caagggctatttccctgagccagtgacagtgacctggaactctggatccctgtccagcggtgtgcacaccttcccagctgtcctgcagt<br>ctgacctctacactctgagcagctcagtgactgtcccctccagcacctggcccagcgagaccgtcacctgcaacgttgcccacccgg<br>ccagcagcaccaaggtggacaagaaaattgtgcccagggattgtggttgtaaggccttgcatatgtacagtcccagaagtatcatctgtct<br>tcatcttcccccaaagcccaaggatgtgctcaccattactctgactcctaaggtcacgtgtgttggtagacatcagcaaggatgatc<br>ccgaggtccagttcagctggtttgtagatgatgtggaggtgcacacagctcagacgcaaccccgggaggagcagttcaacagcacttt<br>ccgctcagtcagtgaacttcccatcatgcaccaggactggctcaatggcaaggagttcaaatgcagggtcaacagtgcagctttccctg<br>ccccatcgagaaaaccatctccaaaaccaaaggcagaccgaaggctccgcaggtgtacaccattccacctcccaaggagcagatg<br>gccaaggataaagtcagtctgacctgcatgataacagacttcttccctgaagacattactgtggagtggcagtggaatgggcagccag<br>cggagaactacaagaacactcagcccatcatggacacagatggctcttacttcgtctacagcaagctcaatgtgcagaagagcaactg<br>ggaggcaggaaatactttcacctgctctgtgttacatgagggcctgcacaaccaccatactgagaagagcctctcccactctcctggta<br>aatga (SEQ ID NO: 74) |
| 192N | Atgtacaggatgcaactcctgtcttgcattgcactaagtcttgcacttgtcacgaattcgatatctcgagtgtaccagtgccctgagcac<br>agtcaactgacaactctgggcgtggatgggaaggagttcccagaggtccacttgggccagtggtactttatcgcaggggcagc<br>tcccaccaaggaggagttggcaacttttgaccctgtggacaacattgtcttcaatatggctgctggctctgccccgatgcagctc<br>caccttcgtgctaccaaccgcatgaaagatgggctctgtgtgccccggaaatggatctaccacctgactgaagggagcacaga<br>tctcagaactgaaggccgccctgacatgaagactgagctctttccagctcatgcccaggtggaatcatgctgaatgagacag<br>gccagggttaccagcgctttctcctctacaatcgctcaccacatcctcccgaaaagtgtgtggaggaattcaagtccctgacttc<br>ctgcctggactccaaagccttcttattgactcctaggaatcaagaggcctgtgagctgtccaataactggatctcgagtgctagca<br>gcgctaaaacgacaccccatctgtctatccactggccctggatctgctgcccaaactaactccatggtgaccctgggatgcctggtc<br>aagggctatttccctgagccagtgacagtgacctggaactctggatccctgtccagcggtgtgcacaccttcccagctgtcctgcagtct<br>gacctctacactctgagcagctcagtgactgtcccctccagcacctggcccagcgagaccgtcacctgcaacgttgcccacccggcc<br>agcagcaccaaggtggacaagaaaattgtgcccagggattgtggttgtaaggccttgcatatgtacagtcccagaagtatcatctgtcttc<br>atcttcccccaaagcccaaggatgtgctcaccattactctgactcctaaggtcacgtgtgttggtagacatcagcaaggatgatccc<br>gaggtccagttcagctggtttgtagatgatgtggaggtgcacacagctcagacgcaaccccgggaggagcagttcaacagcactttcc<br>gctcagtcagtgaacttcccatcatgcaccaggactggctcaatggcaaggagttcaaatgcagggtcaacagtgcagctttccctgcc<br>cccatcgagaaaaccatctccaaaaccaaaggcagaccgaaggctccgcaggtgtacaccattccacctcccaaggagcagatggc<br>caaggataaagtcagtctgacctgcatgataacagacttcttccctgaagacattactgtggagtggcagtggaatgggcagccagcg<br>gagaactacaagaacactcagcccatcatggacacagatggctcttacttcgtctacagcaagctcaatgtgcagaagagcaactggg<br>aggcaggaaatactttcacctgctctgtgttacatgagggcctgcacaaccaccatactgagaagagcctctcccactctcctggtaaat<br>ga (SEQ ID NO: 75) |
| M94Y | Atgtacaggatgcaactcctgtcttgcattgcactaagtcttgcacttgtcacgaattcgatatctcgagtgtaccagtgccctgagcac<br>agtcaactgacaactctgggcgtggatgggaaggagttcccagaggtccacttgggccagtggtactttatcgcaggggcagc<br>tcccaccaaggaggagttggcaacttttgaccctgtggacaacattgtcttcaatatggctgctggctctgccccgatgcagctc<br>caccttcgtgctaccatccgctacaaagatgggctctgtgtgccccggaaatggatctaccacctgactgaagggagcacaga<br>tctcagaactgaaggccgccctgacatgaagactgagctctttccagctcatgcccaggtggaatcatgctgaatgagacag<br>gccagggttaccagcgctttctcctctacaatcgctcaccacatcctcccgaaaagtgtgtggaggaattcaagtccctgacttc<br>ctgcctggactccaaagccttcttattgactcctaggaatcaagaggcctgtgagctgtccaataactggatctcgagtgctagca<br>gcgctaaaacgacaccccatctgtctatccactggccctggatctgctgcccaaactaactccatggtgaccctgggatgcctggtc<br>aagggctatttccctgagccagtgacagtgacctggaactctggatccctgtccagcggtgtgcacaccttcccagctgtcctgcagtct<br>gacctctacactctgagcagctcagtgactgtcccctccagcacctggcccagcgagaccgtcacctgcaacgttgcccacccggcc<br>agcagcaccaaggtggacaagaaaattgtgcccagggattgtggttgtaaggccttgcatatgtacagtcccagaagtatcatctgtcttc<br>atcttcccccaaagcccaaggatgtgctcaccattactctgactcctaaggtcacgtgtgttgtggtagacatcagcaaggatgatccc<br>gaggtccagttcagctggtttgtagatgatgtggaggtgcacacagctcagacgcaaccccgggaggagcagttcaacagcactttcc<br>gctcagtcagtgaacttcccatcatgcaccaggactggctcaatggcaaggagttcaaatgcagggtcaacagtgcagctttccctgcc<br>cccatcgagaaaaccatctccaaaaccaaaggcagaccgaaggctccgcaggtgtacaccattccacctcccaaggagcagatggc<br>caaggataaagtcagtctgacctgcatgataacagacttcttccctgaagacattactgtggagtggcagtggaatgggcagccagcg<br>gagaactacaagaacactcagcccatcatggacacagatggctcttacttcgtctacagcaagctcaatgtgcagaagagcaactggg<br>aggcaggaaatactttcacctgctctgtgttacatgagggcctgcacaaccaccatactgagaagagcctctcccactctcctggtaaat<br>ga (SEQ ID NO: 76) |

Activation of S1P receptor 1 using ApoM-Fc sponge mutants

Figure 5:
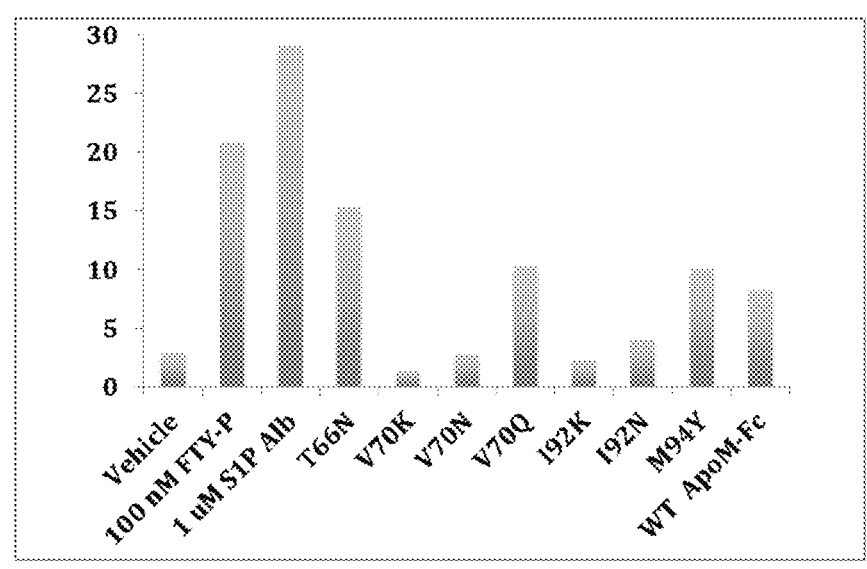
FIG. 5. A poM-Fc mutants T66N, V70Q, and M94Y activate S1P receptor-1 signaling in MEF reporter cells. MEF S1Pr1 reporter cells were seeded in 384 well plates and treated with either saline vehicle, 100 nM FTY-P, 1 µM S1P Albumin, 5 µg of purified ApoM-Fc sponge mutants (clones 1-7), or 5 µg of WT purified ApoM-Fc for 24 hours. GFP-positive nuclei were imaged and quantitated by an ArrayScan VTI at ×10 using the spot detector software. Data are presented as the mean of triplicate wells.

Each purified ApoM-Fc sponge mutant was analyzed for activation of the S1P receptor 1 using a recently developed receptor-specific in vitro reporter system described in Kono et al. (Sphingosine-1-phosphate receptor 1 reporter mice reveal receptor activation sites in vivo. J. Clin. Invest. 2014; 124:2076-2086). Activation of the S1P receptor 1 leads to transcription and accumulation of a GFP-Histone protein in the nucleus of an MEF cell line. Increases in nuclear Green-Fluorescence intensity is proportional to the degree of S1P receptor 1 activation by an S1P chaperone such as ApoM-Fc. The resulting fluorescence intensity is quantified by digital spectrophotometry. Using this system it was observed that ApoM-Fc (sponge) mutants T66N, V70Q, and M94Y activate S1P1 receptor more efficiently than WT ApoM-Fc (FIG. 5). When combined with the results in Table 1, these results suggest that while the ApoM-Fc sponge mutants T66N and M94Y bind decreased quantities of S1P on a molar basis, these mutants are more efficient at activating the S1P receptor 1 in this assay.

Materials and Methods for Example 2

Site-Directed Mutagenesis of ApoM-F$_c$

The previously constructed pFUSE-hApoM-mIgG1-Fc was subjected to site-directed mutagenesis using the QuikChange II kit (Agilent) and manufacturer's instructions. The DNA Primers used for mutagenesis are given in Table 5.

TABLE 5

DNA Primers for mutagenesis.

| Mutation | | Primer |
|---|---|---|
| Mutation 1 | T66N | 5'-aggagttggca*ACC*ttttgaccc-3' (SEQ ID NO: 85) |
| Mutation 2 | V70K | 5'-ttgaccct*AAg*gacaacatt-3' (SEQ ID NO: 86) |
| Mutation 3 | V70N | 5'-ttgaccct*AAC*gacaacatt-3' (SEQ ID NO: 87) |
| Mutation 4 | V70Q | 5'-ttgaccct*CAg*gacaacatt-3' (SEQ ID NO: 88) |
| Mutation 5 | 192K | 5'-cgtgctacc*AAA*cgcatgaaa-3' (SEQ ID NO: 89) |
| Mutation 6 | 192N | 5'-cgtgctacc*AAC*cgcatgaaa-3' (SEQ ID NO: 90) |
| Mutation 7 | M94Y | 5'-taccatccgc*tAC*aaagatggg-3' (SEQ ID NO: 91) |

Mutant plasmids were transformed into competent DH5a and selected on LB Ampicillin (100 mg/ml) Agar plates. Recombinant clones were subjected to DNA sequence analysis to confirm mutations.

Production of CHO Cells Expressing ApoM-Fc Mutants

Each confirmed mutant clone plasmid was prepared for transfection by Midi-prep (Qiagen) and transfected onto a fresh culture of Chinese Hamster Ovary (CHO) cells using Turbofect (Thermo Fisher Scientific). Transfected cells were selected for 7 days in Geneticin (500 mg/ml) and expanded.

Production and Purification of ApoM-Fc Mutants

Recombinant CHO cells from each clone were cultured for 24 hours in Ham's F12 media supplemented with Bovine Serum Albumin (10 μg/ml). ApoM-Fc mutant containing media was clarified by centrifugation (15,000 g) and resulting supernatant was incubated overnight with Concanavalin-A Sepharose Beads (GE Healthcare) and washed with 20 volumes of Lectin binding buffer (LBB; 20 mM Tris, pH 7.5, 450 mM NaCl, 1 mM MnCl2) and eluted with LBB supplemented with 2 volumes of 250 mM β-methylmannoside (Sigma). Purified protein was quantified by Bradford assay (Biorad). 500 μg of each ApoM-Fc (sponge) mutant was mixed with S1P (Avanti Polar Lipids; Cat No. 860492) resuspended in methanol at a 10:1 S1P/Protein (M/M) ratio and incubated at 4° C. for 24 hours. Each protein was re-purified to separate protein from free S1P using a Biorad NGC FPLC on a Superose 6 10/300 chromatography column.

SIP Content of ApoM-Fc Mutants

25 μg of purified protein was analyzed for sphingolipid content and species by liquid chromatography/mass spectroscopy (LC/MS) using the Stony Brook University Lipidomics Core Facility. (Table 3).

In Vitro Analysis of SIP-Dependent Signal Transduction in SIP$_1$ Reporter Cells Kono et al. (J. Clin. Invest. 2014; 124:2076-2086) established a mouse strain based on the β-arrestin signaling to record S1P$_1$ signaling (called the S1P$_1$-GFP signaling mouse). Essentially, activation of the S1P$_1$ receptor by S1P results in accumulation of a histone-GFP fusion protein in the nuclei of activated cells. A MEF line was established from day 10.5 embryos. With standard protocols, embryos were dissociated, and MEFs were isolated and transformed with SV40 large T antigen. The resulting transformed cells were selected for low endogenous GFP expression and maintained in DMEM supplemented with 10% charcoal-stripped FBS, which contains very low amounts of S1P. For functional assays, we determined that the addition of fatty acid-free (FAF) albumin-S1P results in nuclear GFP accumulation, appearing as early as 6 hours with maximum signal at 24 hours after stimulus.

Cells were seeded into 384 well plates, allowed to adhere for 24 hours and then supplemented with either FTY-P (Cayman Chemical; 402615-91-2), S1P (Avanti Polar Lipids; Catalog #860492) resuspended in Fatty-acid free albumin (Millipore-Sigma; Catalog #9048-46-8), or 5 μg/well of purified sponge mutant clones 1-7 or WT ApoM-Fc. GFP-positive nuclei were imaged and quantitated by an Array-Scan VTI at ×10 using the spot detector software. Data are presented as the mean of triplicate wells.

Tumor Metastasis Assay

In order to evaluate the efficacy of ApoM-Fc mutant "Sponge" entities, a tumor metastasis assay will be performed using B16 melanoma cells obtained from the ATCC and tested for *mycoplasma*. 500,000 cells will be injected intravenously. Tumor growth will be allowed to proceed for 2-3 weeks. Mice will receive 4 mg/kg of ApoM-Fc WT or Mutant every 4 days for the duration of the experiment. Mice will be sacrificed and lungs excised and tumor size and number will be determined.

Rheumatic Synovial Joint Fluid Assay

Synovial fluid from human or mouse controls or pathologically affected joints will be obtained and assayed for S1P content by mass spectroscopy. ApoM-Fc mutant proteins (1-100 μg/ml) is mixed with fluid for 2-24 hours and purified by size exclusion chromatography on an FPLC. S1P content of both mutant protein before incubation and mutant protein after exposure to synovial fluid is measured for S1P content by mass spectroscopy and the relative S1P binding capacity of each mutant protein will be determined. Candidate ApoM-Fc mutants are injected at 1-50 µg/ml into affected and control joints in mouse models for Rheumatoid Arthritis, such as the collagen induced arthritis (CIA) model2, and histology analysis is performed to evaluate the efficacy of the treatment regimen.

Example 3: Development of ApoM-Fc to Treat Retinal Vascular Diseases

Abnormal vascular proliferation occurs in many ophthalmic diseases, including diabetic retinopathy and age-related macular degeneration (wet form) (wet AMD). A mouse model for these diseases has been developed[10]. In this model, inhibitors of retinal vascular tuft formation were effective in clinical trials of wet AMD. It has been shown that ApoM-Fc treatment inhibits pathological retinal vascular tuft formation, as shown in FIGS. 3A to 3C. This indicates that ApoM-Fc can be useful in the treatment of diabetic retinopathy and wet AMD.

REFERENCES

1. Proia, R. L. & Hla, T. Emerging biology of sphingosine-1-phosphate: its role in pathogenesis and therapy. The Journal of clinical investigation 125, 1379-1387, doi:10.1172/JC176369 (2015).
2. Frej, C. et al. Sphingosine 1-phosphate and its carrier apolipoprotein M in human sepsis and in *Escherichia coli* sepsis in baboons. Journal of cellular and molecular medicine 20, 1170-1181, doi:10.1111/jcmm.12831 (2016).
3. Ruiz, M. et al. High-Density Lipoprotein-Associated Apolipoprotein M Limits Endothelial Inflammation by Delivering Sphingosine-1-Phosphate to the Sphingosine-1-Phosphate Receptor 1. Arteriosclerosis, thrombosis, and vascular biology 37, 118-129, doi:10.1161/ATVBAHA.116.308435 (2017).
4. Levkau, B. HDL-S1P: cardiovascular functions, disease-associated alterations, and therapeutic applications. Frontiers in pharmacology 6, 243, doi:10.3389/fphar.2015.00243 (2015).
5. Sattler, K. et al. Defects of High-Density Lipoproteins in Coronary Artery Disease Caused by Low Sphingosine-1-Phosphate Content: Correction by Sphingosine-1-Phosphate-Loading. Journal of the American College of Cardiology 66, 1470-1485, doi:10.1016/j.jacc.2015.07.057 (2015).
6. Christoffersen, C. et al. Endothelium-protective sphingosine-1-phosphate provided by HDL-associated apolipoprotein M. Proceedings of the National Academy of Sciences of the United States of America 108, 9613-9618, doi:10.1073/pnas.1103187108 (2011).
7. Pyne, N. J. & Pyne, S. Sphingosine 1-phosphate and cancer. Nat Rev Cancer 10, 489-503, doi:10.1038/nrc2875 (2010).
8. Kitano, M. et al. Sphingosine 1-phosphate/sphingosine 1-phosphate receptor 1 signaling in rheumatoid synovium: regulation of synovial proliferation and inflammatory gene expression. Arthritis Rheum 54, 742-753, doi:10.1002/art.21668 (2006).
9. Michaud, J., Kohno, M., Proia, R. L. & Hla, T. Normal acute and chronic inflammatory responses in sphingosine kinase 1 knockout mice. FEBS Lett 580, 4607-4612, doi:10.1016/j.febslet.2006.07.035 (2006).
10. Smith, L. E. et al. Oxygen-induced retinopathy in the mouse. Investigative ophthalmology & visual science 35, 101-111 (1994).

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

What is claimed is:

1. A fusion protein comprising an apolipoprotein M (ApoM) fused to a constant region (Fc) of an immunoglobulin (IgG), wherein the fusion protein comprises an amino acid sequence that is at least 99.5% identical to SEQ ID NO: 1.

2. The fusion protein of claim 1, wherein the ApoM comprises one or two amino acid substitutions at positions selected from the group consisting of positions T42, V46, I68, and M70 in SEQ ID NO: 5.

3. The fusion protein of claim 1, wherein the ApoM comprises an amino acid sequence that is at least 99% identical to SEQ ID NO: 5.

4. The fusion protein of claim 2, wherein the ApoM comprises the amino acid sequence of any one of SEQ ID NOs: 9-15.

5. The fusion protein of claim 1, wherein the fusion protein comprises the amino acid sequence of any one of SEQ ID NOs: 23-29.

6. The fusion protein of claim 1, comprising the amino acid sequence of SEQ ID NO: 1.

7. A nucleic acid molecule comprising a nucleotide sequence encoding the fusion protein of claim 1.

8. A method of producing a fusion protein, comprising culturing a cell comprising the nucleic acid molecule of claim 7 in a culturing media, under conditions that allow the fusion protein to express.

* * * * *